(12) United States Patent
Liang et al.

(10) Patent No.: US 7,977,372 B2
(45) Date of Patent: Jul. 12, 2011

(54) ORTHO AMINOAMIDES FOR THE TREATMENT OF CANCER

(75) Inventors: Chungen Liang, Shanghai (CN); Guozhi Tang, Shanghai (CN); Jason Christopher Wong, Shanghai (CN); Xihan Wu, Shanghai (CN); Zhenshan Zhang, Shanghai (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/708,581

(22) Filed: Feb. 19, 2010

(65) Prior Publication Data

US 2010/0216806 A1 Aug. 26, 2010

(30) Foreign Application Priority Data

Feb. 23, 2009 (EP) .................................. 09153445
Apr. 2, 2009 (EP) .................................. 09157150

(51) Int. Cl.
*C07D 207/00* (2006.01)
*A01N 43/36* (2006.01)

(52) U.S. Cl. ........................ 514/423; 548/530
(58) Field of Classification Search ................ None
See application file for complete search history.

(56) References Cited

U.S. PATENT DOCUMENTS

| 3,810,910 A | 5/1974 | Meyer et al. |
| 2005/0245518 A1 | 11/2005 | Delorme et al. |

FOREIGN PATENT DOCUMENTS

| DE | 2062265 | 5/1972 |
| FR | 2167954 | 8/1973 |
| WO | 0138322 | 5/2001 |
| WO | 2005/092899 | 10/2005 |
| WO | 2006115845 | 11/2006 |
| WO | 2007087130 | 8/2007 |
| WO | 2007100657 | 9/2007 |

OTHER PUBLICATIONS

WO 2009/095324, Hoffmann-La Roche [CH]; Chen Li; He Yun; Wong Jason Christop, Aug. 6, 2009, table 2, compounds 9-6, 9-17, 9-3.
Office Action, U.S. Appl. No. 12/358,348, First Named Inventor: Li Chen, filed Jan. 23, 2009, Mail Date: Mar. 12, 2010.
Koyama et al., Blood, vol. 96 (2000) pp. 1490-1495.
Martin et al., Oncogene (2007) vol. 26, pp. 5450-5467.
Matsuoka et al., Biochemical Pharmacology (2007) vol. 74 pp. 465-476.
Rastogi et al., Indian J. Chem. Section B, 21B (1982) pp. 485-487.
Moll et al., Z. Chem. vol. 17 (1977) pp. 133-134.
Hassan et al., Indian J. Chem. 39B (2000) pp. 764-768.
Bastin et al., Organic Process Research & Development (2000) vol. 4 pp. 427-435.
Ansel et al., Pharmaceutical Dosage Forms and Drug Delivery Systems (1995) pp. 456-457.
Zhang et al., Mol Cell. Bio (2004) vol. 24 pp. 5106-5118.
English Language Abstract corresponding to Foreign document No. 3 (DE2062265), 2010.
Jordan, V. C., Nature Reviews Drug Discovery vol. 2, (2003), pp. 205-213.
Dorwald, Z. F., Side Reactions in Organic Synthesis: A Guide to Successful Synthesis Design, Weinheim, Wiley-VCH Verlag GmbH & Co., KGaA, (2005), Preface.
Golub et al. Science, vol. 286 (1999) pp. 531-537.

*Primary Examiner* — Sun Jae Y Loewe
(74) *Attorney, Agent, or Firm* — George W. Johnston; Patricia S. Rocha-Tramaloni; David E. Wildman

(57) ABSTRACT

Compounds of formula

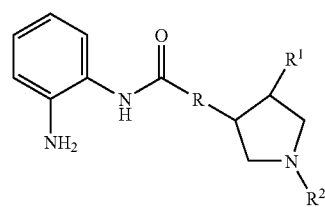

(I)

are HDAC inhibitors. These compounds are useful for the treatment of diseases such as cancer in humans or animals.

12 Claims, No Drawings

ORTHO AMINOAMIDES FOR THE TREATMENT OF CANCER

PRIORITY TO RELATED APPLICATION(S)

This application claims the benefit of European Patent Application No. 09153445.3, filed Feb. 23, 2009, which is hereby incorporated by reference in its entirety.

FIELD OF THE INVENTION

The invention relates to novel antitumor agents and pharmaceutically acceptable salts thereof, and processes for the manufacture of these novel compounds and medicaments containing them. The compounds of the invention have antiproliferative and differentiation-inducing activity, which results in inhibition of tumor cell proliferation, induction of apoptosis and inhibition of invasion. The invention concerns thus also the use of such compounds for the treatment of diseases such as cancer and for the manufacture of corresponding medicaments.

The compounds according to this invention are inhibitors of histone deacetylase (HDAC) and therefore show antiproliferative and differentiation-inducing activity, which results in inhibition of tumor cell proliferation, induction of apoptosis and inhibition of invasion. These compounds are thus useful for the treatment of cancer.

Background of Invention Transcriptional regulation is a major event in cell differentiation, proliferation, and apoptosis. Transcriptional activation of a set of genes determines cell destination and for this reason transcription is tightly regulated by a variety of factors. One of its regulatory mechanisms involved in the process is an alteration in the tertiary structure of DNA, which affects transcription by modulating the accessibility of transcription factors to their target DNA segments. Nucleosomal integrity is regulated by the acetylation status of the core histones. In a hypoacetylated state, nucleosomes are tightly compacted and thus are nonpermissive for transcription. On the other hand, nucleosomes are relaxed by acetylation of the core histones, with the result being permissiveness to transcription. The acetylation status of the histones is governed by the balance of the activities of histone acetyl transferase (HAT) and histone deacetylase (HDAC). Recently, HDAC inhibitors have been found to arrest growth and induce apoptosis in several types of cancer cells, including colon cancer cells, T-cell lymphoma cells, and erythroleukemic cells. Given that apoptosis is a crucial factor for cancer progression, HDAC inhibitors are promising reagents for cancer therapy as effective inducers of apoptosis (Koyama, Y., et al., Blood 96 (2000) 1490-1495).

Histone deacetylases (HDACs) are the key enzymatic components of multiprotein complexes responsible for deacetylation of lysine residues in histone and nonhistone protein substrates. HDACs can be subdivided into three major classes according to their sequence homology to the yeast HDACs, Rpd3, Hda1, and Sir2. The class I HDACs (HDACs 1, 2, 3, and 8), homologous to Rpd3, localize primarily in the nucleus and appear to be expressed in most tissues. The class II HDACs (HDACs 4, 5, 6, 7, 9, 10), homologous to Hda1, are able to shuttle between the nucleus and the cytoplasm depending on a variety of regulatory signals and cellular state, and have tissue-specific expression patterns. These HDACs can be further subdivided into class IIa (HDACs 4, 5, 7, 9), and class IIb (HDACs 6, 10). The class III HDACs, homologous to Sir2, are $NAD^+$-dependent deacetylases that are mechanistically distinct from the class I and II HDACs and are not inhibited by classical HDAC inhibitors such as trichostatin A, trapoxin B, or SNDX-275. The HDACs can thus be divided into three classes on the basis of sequence similarity, cellular localization tendencies, tissue expression patterns, and enzymatic mechanism.

The class I HDACs in particular have been closely associated with antiproliferative effects against tumor cells. For example, pharmacological inhibition of HDACs 1-3 leads to induction of the cyclin-dependent kinase inhibitor p21 and concommitant cell cycle arrest. The class IIa HDACs are known to associate with the HDAC3/SMRT/N-CoR complex and MEF2 and as such have important roles in regulating muscle cell gene expression (reviewed in *Oncogene* 2007, 26, 5450-5467) and the immune response (*Biochemical Pharmacology* 2007, 74, 465-476). Due to their specific antiproliferative function, selective inhibition of the class I HDACs may be desirable to achieve antitumor efficacy with lower toxicity.

WO 2007/100657 describes o-phenylendiamine derivatives as cell differentiation inducers. The same type of compounds is also the subject of WO2007/087130. The compounds described in these applications are exclusively o-phenylene derivatives monoacylated with derivatives of benzoic acid. However there remains a need for new compounds with improved therapeutic properties, such as enhanced activity, decreased toxicity, better solubility and/or improved pharmacokinetic profile, to name only a few.

Monoacylated o-phenylendiamines are known in the art as precursors for the preparation of the corresponding benzimidazoles, such preparation methods are e.g. described in DE-A 2 062 265; FR 2 167 954; Rastogi, R., and Sharma, S., Indian J. Chem., Sect. B, 21B (5) (1982) 485-487; Moll, R., et al., Z. Chem. 17 (1977) 133-134; and Hassan, H., et al., Indian J. Chem. 39B (2000) 764-768.

SUMMARY OF THE INVENTION

In an embodiment, the present invention is directed to the trans-isomers, most preferably 3,4-trans-isomers, of compounds of formula (I)

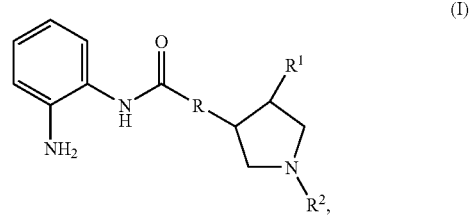

wherein
R is

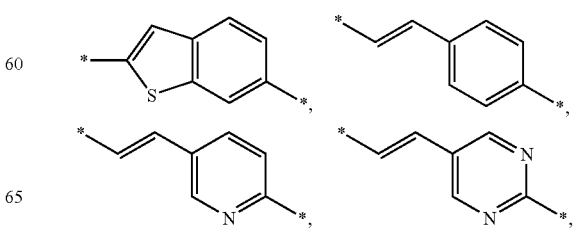

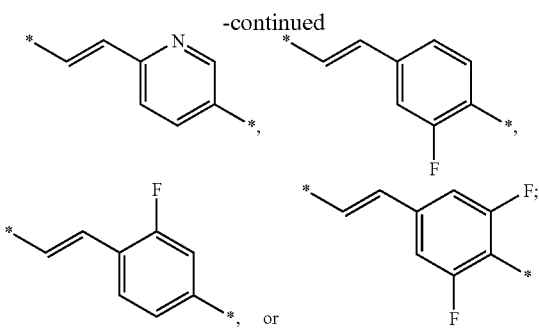

R¹ is benzoimidazolyl, unsubstituted or substituted by halogen, lower alkyl, lower alkoxy, cyano, —OCF₂H, —OCF₃, trifluoromethyl, or cycloalkyl;
—CO—NH—R³, wherein R³ is aryl or heteroaryl, unsubstituted or substituted once, twice or three times by halogen, lower alkyl, lower alkoxy, cyano, —OCF₂H, —OCF₃, trifluoromethyl, or cycloalkyl;
or

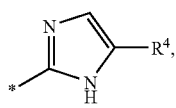

wherein R⁴ is aryl, unsubstituted or substituted by halogen, lower alkyl, lower alkoxy, cyano, —OCF₂H, —OCF₃, trifluoromethyl, or cycloalkyl; and
R² is lower alkyl, heterocyclyl, or heteroaryl, unsubstituted, or once, twice or three times substituted by halogen, phenyl, cyano, hydroxy, or lower alkoxy;
or a pharmaceutically acceptable salt, racemic mixture, enantiomer, or tautomeric form thereof.

The present invention is also directed to pharmaceutical compositions containing the compounds of formula I or a pharmaceutically acceptable salt thereof.

The compounds of the present invention show enhanced potency toward class I HDACs and enhanced antiproliferative efficacy versus cancer cells as compared to SNDX-275, a structurally-related HDAC inhibitor in clinical trials. Class I HDAC inhibitory potency is evaluated by a reporter gene assay that evaluates HDAC subtype activity in the context of relevant multiprotein complexes present in the cell that are typically absent in enzyme activity assays. Thus, the compounds of the present invention possess in-cell inhibitory potency toward class I HDACs that correlates to their improved anticancer efficacy in comparison to SNDX-275.

DETAILED DESCRIPTION OF THE INVENTION

The following definitions of general terms used herein apply irrespective of whether the terms appear alone or in combination. As used in this specification and the appended claims, the singular forms "a", "an" and "the" include plural forms unless the context clearly dictates otherwise.

The term "lower alkyl" as used herein denotes a saturated, linear- or branched chain hydrocarbon group containing 1 to 8, preferably 1 to 6, more preferably 1 to 4 carbon-atoms, for example methyl, ethyl, propyl, isopropyl, 1-butyl, 2-butyl, tert-butyl and the like. Preferred "$C_1$-$C_8$-alkyl" groups have 1, 2, 3 or 4 carbon-atoms.

The term "lower alkoxy" as used herein denotes a group —O-alkyl, wherein the "alkyl" is as defined above; for example, methoxy, ethoxy, propoxy, isopropoxy, n-butoxy, i-butoxy, 2-butoxy, t-butoxy and the like. Preferred alkoxy groups are groups with 1-4 carbon atoms.

The term "cycloalkyl" as used herein means a saturated, cyclic hydrocarbon consisting of one or two rings, which may be fused or attached via a single bond, and containing from 3 to 8, preferably from 3 to 6 carbon atoms. Examples of such 3 to 8 membered cycloalkyl rings are cyclopropyl, cyclobutyl, cyclopentyl, cyclohexyl, cyclooctyl, octahydro-indene, bicyclo[2.2.1]heptane, bicyclohexyl and the like.

The term "heterocyclyl" as used herein means a 3 to 8 membered mono- or bicyclic cycloalkyl as defined above, wherein up to four carbon atoms, preferably one, two or three ring carbon atoms are replaced by oxygen, nitrogen or sulphur. Examples include but are not limited to morpholinyl, thiomorpholinyl, piperidinyl, piperazinyl, tetrahydro-pyranyl, 2-Oxa-5-aza-bicyclo[2.2.1]heptanyl, [1,4]oxathianyl, azepanyl, [1,4]diazepanyl, pyrrolidinyl, pyrazolidinyl, [1,2,3]triazolidinyl, imidazolidinyl, thiazolidinyl, azetidinyl. Preferred examples are tetrahydropyranyl, oxetanyl.

The term "aryl" means an aromatic, or partially aromatic hydrocarbon containing 6 to 10 carbon atoms and consisting of one or two rings, which may be fused or attached via a single bond. Examples are phenyl, biphenyl, indenyl or naphthyl. Preferred example is phenyl.

The term "heteroaryl" means an aromatic or partially aromatic hydrocarbon containing 5 to 10 carbon atoms and consisting of one or two rings, which may be fused or attached via a single bond, and wherein up to four, preferably one, two or three carbon atoms can be replaced by oxygen, nitrogen or sulphur. Examples of such heteroaromatic rings include but are not limited to pyrrolyl, thiophenyl, furanyl, imidazolyl, pyrazolyl, triazolyl, oxazolyl, isoxazolyl, isothiazolyl, pyridinyl, pyrazinyl, pyridazinyl, triazinyl, tetrazinyl, quinolinyl, quinoxalinyl, chromanyl, benzoimidazolyl, indolyl, benzo[b]thiophenyl. Preferred examples are pyridinyl, pyridazinyl.

The term "halogen" means fluorine, chlorine, bromine or iodine.

"Pharmaceutically acceptable", such as pharmaceutically acceptable carrier, excipient, etc., means pharmacologically acceptable and substantially non-toxic to the subject to which the particular compound is administered.

The term "several times substituted" as used herein means up to 5 times substituted, preferably up to 4 times, most preferably 2 or 3 times substituted and unless otherwise indicated, the substituents at each substitution site are independently selected from the specified options.

"Therapeutically effective amount" means an amount that is effective to prevent, alleviate or ameliorate symptoms of disease or prolong the survival of the subject being treated.

As is pointed out herein, the compounds of the present invention are HDAC inhibitors having anti-proliferative and differentiation-inducing activity, which results in inhibition of tumor cell proliferation, induction of apoptosis and inhibition of invasion. These compounds are therefore useful for the treatment of diseases such as cancer in humans or animals.

Compounds of the general formula (I) which contain one or several chiral centers can either be present in a racemic or in an optically active form. The racemates can be separated according to known methods into the enantiomers. Preferably, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

More particularly, the present 3,4-disubstituted pyrrolidines are synthesized from a [2+3] cycloaddition reaction (see reaction schemes below), which leads to the trans-orientation of the substituent groups attached to the carbon atoms at the 3- and 4-positions of said pyrrolidines. Since the cycloaddition reaction is not enantioselective, a mixture of the two possible trans-enantiomers (3R, 4S and 3S, 4R) is obtained. Usually said mixture will contain the two trans-enantiomers in a ratio of about 1:1, however other ratios shall not be excluded. Therefore, the term "racemic" as used in "racemic-trans" ("rac-trans" or "rac-( trans-3,4)") herein refers to such mixture, while the term "trans" in "racemic-trans" refers to the above-described orientation at the 3,4-carbon atoms. The presence of any cis-isomers (3R, 4R) or (3S, 4S) of the present compounds, when prepared according to the methods disclosed herein, could not be detected.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et. al., Organic Process Research & Development 2000, 4, 427-435; or in Ansel, H., et. al., In: Pharmaceutical Dosage Forms and Drug Delivery Systems, 6th ed. (1995), pp. 196 and 1456-1457.

In one preferred embodiment the present invention provides the compounds of formula (I) as described above in the specific configuration according to formula (Ia),

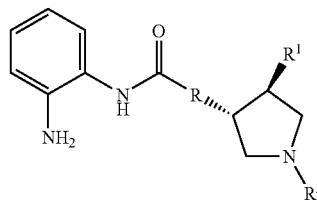

(Ia)

wherein R¹, R² and R have the meanings given above.

In another preferred embodiment the present invention provides the compounds of formula (I) as described above in the specific configuration according to formula (Ib),

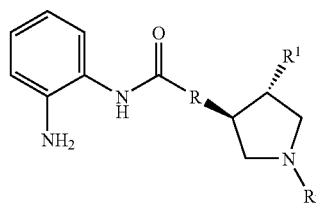

(Ib)

wherein R¹, R² and R have the meanings given above.

In still another preferred embodiment the present invention is directed to compounds of formula (I) wherein
R¹ is —CO—NH—R³, wherein R³ is phenyl, unsubstituted or substituted once, twice or three times by halogen, lower alkyl, lower alkoxy, cyano, —OCF₂H, —OCF₃, trifluoromethyl, or cycloalkyl; and all remaining substituents have the meanings given above.

In another preferred embodiment, the present invention is directed to compounds of formula (I) as defined above, wherein R⁴ is phenyl; and all remaining substituents have the meanings given above.

In another preferred embodiment, the present invention is directed to compounds of formula (I) wherein R is

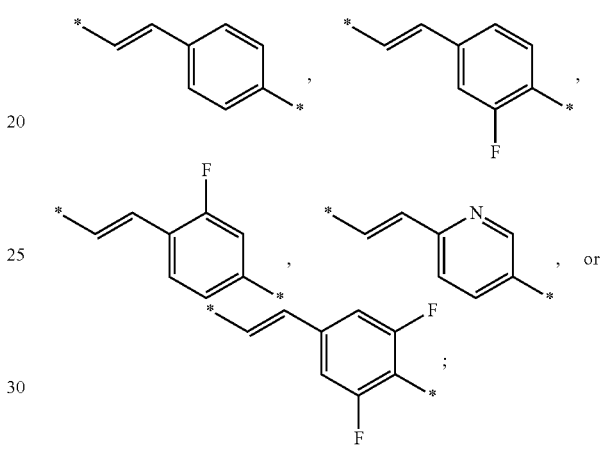

and
all remaining substituents have the meanings given above.

In still another embodiment, the present invention is directed to compounds of formula (I) wherein
R² is lower alkyl, unsubstituted or substituted by cyano, halogen, hydroxyl;
or

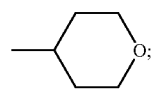

and
all remaining substituents have the significances given herein before.

The following specific compounds are especially preferred according to the present invention:
rac-(trans-3,4)-4-{4-[(E)-2-(2-Amino-phenylcarbamoyl)-vinyl]-2-fluoro-phenyl}-1-(2-hydroxy-1,1-dimethyl-ethyl)-pyrrolidine-3-carboxylic acid (4-chloro-phenyl)-amide;
rac-(trans-3,4)-4-{4-[(E)-2-(2-Amino-phenylcarbamoyl)-vinyl]-2-fluoro-phenyl}-1-methyl-pyrrolidine-3-carboxylic acid (4-fluoro-phenyl)-amide;
rac-(trans-3,4)-4-{4-[(E)-2-(2-Amino-phenylcarbamoyl)-vinyl]-2-fluoro-phenyl}-1-(tetrahydro-pyran-4-yl)-pyrrolidine-3-carboxylic acid (4-chloro-phenyl)-amide;
rac-(trans-3,4)-4-{4-[(E)-2-(2-Amino-phenylcarbamoyl)-vinyl]-2-fluoro-phenyl}-1-methyl-pyrrolidine-3-carboxylic acid (4-chloro-phenyl)-amide;
rac-(trans-3,4)-4-{4-[(E)-2-(2-Amino-phenylcarbamoyl)-vinyl]-2-fluoro-phenyl}-1-methyl-pyrrolidine-3-carboxylic acid (4-chloro-phenyl)-amide;

rac-(trans-3,4)-4-{4-[(E)-2-(2-Amino-phenylcarbamoyl)-vinyl]-3-fluoro-phenyl}-1-methyl-pyrrolidine-3-carboxylic acid (4-chloro-phenyl)-amide;

rac-(trans-3,4)-4-{6-[(E)-2-(2-Amino-phenylcarbamoyl)-vinyl]-pyridin-3-yl}-1-methyl-pyrrolidine-3-carboxylic acid (4-fluoro-phenyl)-amide;

rac-(trans-3,4)-4-{6-[(E)-2-(2-Amino-phenylcarbamoyl)-vinyl]-pyridin-3-yl}-1-methyl-pyrrolidine-3-carboxylic acid (4-chloro-phenyl)-amide;

rac-(trans-3,4)-4-{4-[(E)-2-(2-Amino-phenylcarbamoyl)-vinyl]-phenyl}-1-methyl-pyrrolidine-3-carboxylic acid (4-fluoro-3-methyl-phenyl)-amide;

rac-(trans-3,4)-4-{4-[(E)-2-(2-Amino-phenylcarbamoyl)-vinyl]-phenyl}-1-methyl-pyrrolidine-3-carboxylic acid m-tolylamide;

rac-(trans-3,4)-4-{4-[(E)-2-(2-Amino-phenylcarbamoyl)-vinyl]-phenyl}-1-methyl-pyrrolidine-3-carboxylic acid (4-chloro-3-methyl-phenyl)-amide;

rac-(trans-3,4)-4-{4-[(E)-2-(2-Amino-phenylcarbamoyl)-vinyl]-phenyl}-1-methyl-pyrrolidine-3-carboxylic acid (3-chloro-4-fluoro-phenyl)-amide;

rac-(trans-3,4)-4-{4-[(E)-2-(2-Amino-phenylcarbamoyl)-vinyl]-phenyl}-1-methyl-pyrrolidine-3-carboxylic acid (3-bromo-phenyl)-amide;

rac-(trans-3,4)-4-{4-[(E)-2-(2-Amino-phenylcarbamoyl)-vinyl]-phenyl}-1-methyl-pyrrolidine-3-carboxylic acid (4-fluoro-phenyl)-amide;

rac-(trans-3,4)-4-{4-[(E)-2-(2-Amino-phenylcarbamoyl)-vinyl]-phenyl}-1-methyl-pyrrolidine-3-carboxylic acid phenylamide;

rac-(trans-3,4)-4-{4-[(E)-2-(2-Amino-phenylcarbamoyl)-vinyl]-phenyl}-1-methyl-pyrrolidine-3-carboxylic acid (4-methoxy-phenyl)-amide;

rac-(trans-3,4)-4-{4-[(E)-2-(2-Amino-phenylcarbamoyl)-vinyl]-phenyl}-1-methyl-pyrrolidine-3-carboxylic acid p-tolylamide;

rac-(trans-3,4)-4-{4-[(E)-2-(2-Amino-phenylcarbamoyl)-vinyl]-phenyl}-1-methyl-pyrrolidine-3-carboxylic acid (4-bromo-phenyl)-amide;

rac-(trans-3,4)-4-{4-[(E)-2-(2- Amino-phenylcarbamoyl)-vinyl]-phenyl}-1-methyl-pyrrolidine-3-carboxylic acid (4-cyclopropyl-phenyl)-amide;

rac-(trans-3,4)-4-{4-[(E)-2-(2-Amino-phenylcarbamoyl)-vinyl]-phenyl}-1-methyl-pyrrolidine-3-carboxylic acid (4-difluoromethoxy-phenyl)-amide;

rac-(trans-3,4)-4-{4-[(E)-2-(2-Amino-phenylcarbamoyl)-vinyl]-phenyl}-1-methyl-pyrrolidine-3-carboxylic acid (3-methoxy-phenyl)-amide;

rac-(trans-3,4)-4-{4-[(E)-2-(2-Amino-phenylcarbamoyl)-vinyl]-phenyl}-1-methyl-pyrrolidine-3-carboxylic acid (3-bromo-4-fluoro-phenyl)-amide;

rac-(trans-3,4)-4-{4-[(E)-2-(2-Amino-phenylcarbamoyl)-vinyl]-phenyl}-1-methyl-pyrrolidine-3-carboxylic acid (2-fluoro-phenyl)-amide;

rac-(trans-3,4)-4-{4-[(E)-2-(2-Amino-phenylcarbamoyl)-vinyl]-phenyl}-1-methyl-pyrrolidine-3-carboxylic acid (4-chloro-3-methoxy-phenyl)-amide;

rac-(trans-3,4)-4-{4-[(E)-2-(2-Amino-phenylcarbamoyl)-vinyl]-phenyl}-1-methyl-pyrrolidine-3-carboxylic acid (2,4-difluoro-phenyl)-amide;

rac-(trans-3,4)-4-{4-[(E)-2-(2-Amino-phenylcarbamoyl)-vinyl]-phenyl}-1-methyl-pyrrolidine-3-carboxylic acid (3-cyano-phenyl)-amide;

rac-(trans-3,4)-4-{4-[(E)-2-(2-Amino-phenylcarbamoyl)-vinyl]-phenyl}-1-methyl-pyrrolidine-3-carboxylic acid (4-isopropyl-phenyl)-amide;

rac-(trans-3,4)-4-{4-[(E)-2-(2-Amino-phenylcarbamoyl)-vinyl]-phenyl}-1-methyl-pyrrolidine-3-carboxylic acid (3-chloro-4-methoxy-phenyl)-amide;

rac-(trans-3,4)-4-{4-[(E)-2-(2-Amino-phenylcarbamoyl)-vinyl]-phenyl}-1-methyl-pyrrolidine-3-carboxylic acid (3-fluoro-4-methoxy-phenyl)-amide;

(3R,4S)-4-{4-[(E)-2-(2-Amino-phenylcarbamoyl)-vinyl]-phenyl}-1-methyl-pyrrolidine-3-carboxylic acid (4-chloro-phenyl)-amide;

(3R,4S)-4-{4-[(E)-2-(2-Amino-phenylcarbamoyl)-vinyl]-phenyl}-1-methyl-pyrrolidine-3-carboxylic acid (4-fluoro-phenyl)-amide;

rac-(trans-3,4)-4-{4-[(E)-2-(2-Amino-phenylcarbamoyl)-vinyl]-phenyl}-1-cyanomethyl-pyrrolidine-3-carboxylic acid (4-chloro-phenyl)-amide;

rac-(trans-3,4)-4-{4-[(E)-2-(2-Amino-phenylcarbamoyl)-vinyl]-phenyl}-1-ethyl-pyrrolidine-3-carboxylic acid (4-chloro-phenyl)-amide;

rac-(trans-3,4)-4-{4-[(E)-2-(2-Amino-phenylcarbamoyl)-vinyl]-phenyl}-1-(2-fluoro-ethyl)-pyrrolidine-3-carboxylic acid (4-chloro-phenyl)-amide;

rac-(trans-3,4)-4-{4-[(E)-2-(2-Amino-phenylcarbamoyl)-vinyl]-phenyl}-1-(2-hydroxy-ethyl)-pyrrolidine-3-carboxylic acid (4-chloro-phenyl)-amide;

rac-(trans-3,4)-4-{4-[(E)-2-(2-Amino-phenylcarbamoyl)-vinyl]-phenyl}-1-(2-fluoro-ethyl)-pyrrolidine-3-carboxylic acid (4-fluoro-phenyl)-amide;

rac-(trans-3,4)-4-{4-[(E)-2-(2-Amino-phenylcarbamoyl)-vinyl]-phenyl}-1-(2-methoxy-ethyl)-pyrrolidine-3-carboxylic acid (4-chloro-phenyl)-amide;

rac-(trans-3,4)-4-{4-[(E)-2-(2-Amino-phenylcarbamoyl)-vinyl]-phenyl}-1-isopropyl-pyrrolidine-3-carboxylic acid (4-fluoro-phenyl)-amide;

rac-(trans-3,4)-4-{4-[(E)-2-(2-Amino-phenylcarbamoyl)-vinyl]-phenyl}-1-isopropyl-pyrrolidine-3-carboxylic acid (4-bromo-phenyl)-amide;

rac-(trans-3,4)-4-{4-[(E)-2-(2-Amino-phenylcarbamoyl)-vinyl]-phenyl}-1-isopropyl-pyrrolidine-3-carboxylic acid (4-chloro-phenyl)-amide;

rac-(trans-3,4)-4-{4-[(E)-2-(2-Amino-phenylcarbamoyl)-vinyl]-phenyl}-1-isopropyl-pyrrolidine-3-carboxylic acid (3-bromo-phenyl)-amide;

rac-(trans-3,4)-4-{4-[(E)-2-(2-Amino-phenylcarbamoyl)-vinyl]-phenyl}-1-tert-butyl-pyrrolidine-3-carboxylic acid (4-chloro-2-fluoro-phenyl)-amide;

rac-(trans-3,4)-4-{4-[(E)-2-(2-Amino-phenylcarbamoyl)-vinyl]-phenyl}-1-tert-butyl-pyrrolidine-3-carboxylic acid (4-bromo-phenyl)-amide;

rac-(trans-3,4)-4-{4-[(E)-2-(2-Amino-phenylcarbamoyl)-vinyl]-phenyl}-1-tert-butyl-pyrrolidine-3-carboxylic acid (4-difluoromethoxy-phenyl)-amide;

rac-(trans-3,4)-4-{4-[(E)-2-(2-Amino-phenylcarbamoyl)-vinyl]-phenyl}-1-tert-butyl-pyrrolidine-3-carboxylic acid (4-fluoro-phenyl)-amide;

rac-(trans-3,4)-4-{4-[(E)-2-(2-Amino-phenylcarbamoyl)-vinyl]-phenyl}-1-tert-butyl-pyrrolidine-3-carboxylic acid (4-chloro-phenyl)-amide;

rac-(trans-3,4)-4-{4-[(E)-2-(2-Amino-phenylcarbamoyl)-vinyl]-phenyl}-1-tert-butyl-pyrrolidine-3-carboxylic acid (4-cyano-phenyl)-amide;

rac-(trans-3,4)-4-{4-[(E)-2-(2-Amino-phenylcarbamoyl)-vinyl]-phenyl}-1-(2-hydroxy-1,1-dimethyl-ethyl)-pyrrolidine-3-carboxylic acid (4-chloro-phenyl)-amide;

(3R,4S)-4-{4-[(E)-2-(2-Amino-phenylcarbamoyl)-vinyl]-phenyl}-1-(2-hydroxy-1,1-dimethyl-ethyl)-pyrrolidine-3-carboxylic acid (4-chloro-phenyl)-amide;

rac-(trans-3,4)-4-{4-[(E)-2-(2-Amino-phenylcarbamoyl)-vinyl]-phenyl}-1-(2-hydroxy-1,1-dimethyl-ethyl)-pyrrolidine-3-carboxylic acid (4-difluoromethoxy-phenyl)-amide;

rac-(trans-3,4)-4-{4-[(E)-2-(2-Amino-phenylcarbamoyl)-vinyl]-phenyl}-1-(2-hydroxy-2-methyl-propyl)-pyrrolidine-3-carboxylic acid (4-chloro-phenyl)-amide;

rac-(trans-3,4)-4-{4-[(E)-2-(2-Amino-phenylcarbamoyl)-vinyl]-phenyl}-1-(2-hydroxy-2-methyl-propyl)-pyrrolidine-3-carboxylic acid (4-bromo-phenyl)-amide;

rac-(trans-3,4)-4-{4-[(E)-2-(2-Amino-phenylcarbamoyl)-vinyl]-phenyl}-1-(2-hydroxy-2-methyl-propyl)-pyrrolidine-3-carboxylic acid (4-difluoromethoxy-phenyl)-amide;

rac-(trans-3,4)-4-{4-[(E)-2-(2-Amino-phenylcarbamoyl)-vinyl]-phenyl}-1-(2-hydroxy-2-methyl-propyl)-pyrrolidine-3-carboxylic acid (4-chloro-phenyl)-amide;

rac-(trans-3,4)-4-{4-[(E)-2-(2-Amino-phenylcarbamoyl)-vinyl]-phenyl}-1-(tetrahydro-pyran-4-yl)-pyrrolidine-3-carboxylic acid (4-chloro-phenyl)-amide;

rac-(trans-3,4)-4-{4-[(E)-2-(2-Amino-phenylcarbamoyl)-vinyl]-phenyl}-1-(tetrahydro-pyran-4-yl)-pyrrolidine-3-carboxylic acid (4-bromo-phenyl)-amide;

rac-(trans-3,4)-4-{4-[(E)-2-(2-Amino-phenylcarbamoyl)-vinyl]-phenyl}-1-(tetrahydro-pyran-4-yl)-pyrrolidine-3-carboxylic acid (3-difluoromethoxy-phenyl)-amide;

rac-(trans-3,4)-4-{4-[(E)-2-(2-Amino-phenylcarbamoyl)-vinyl]-phenyl}-1-(tetrahydro-pyran-4-yl)-pyrrolidine-3-carboxylic acid (4-fluoro-phenyl)-amide;

rac-(trans-3,4)-4-{4-[(E)-2-(2-Amino-phenylcarbamoyl)-vinyl]-phenyl}-1-(tetrahydro-pyran-4-yl)-pyrrolidine-3-carboxylic acid (4-difluoromethoxy-phenyl)-amide;

(3S,4R)-4-{4-[(E)-2-(2-Amino-phenylcarbamoyl)-vinyl]-phenyl}-1-methyl-pyrrolidine-3-carboxylic acid (4-chloro-phenyl)-amide;

(3S,4R)-4-{4-[(E)-2-(2-Amino-phenylcarbamoyl)-vinyl]-phenyl}-1-methyl-pyrrolidine-3-carboxylic acid (4-fluoro-phenyl)-amide; and (3S,4R)-4-{4-[(E)-2-(2-Amino-phenylcarbamoyl)-vinyl]-phenyl}-1-(2-hydroxy-1,1-dimethyl-ethyl)-pyrrolidine-3-carboxylic acid (4-chloro-phenyl)-amide.

In another preferred embodiment the present invention provides the specific compounds listed in the tables of examples 5, 11, 16, 21, 26, 31, 36, 42, 64, 73, 80, 85 and 94. These compounds are preferably in the trans-configuration (3R, 4S or 3S, 4R) or a mixture thereof (rac-(trans-3,4)).

The compounds according to the present invention have valuable pharmaceutical properties, in particular as anti-proliferative or anti-cancer agents, more specifically as agents for the treatment of solid tumors and hematological tumors. Accordingly, another embodiment according to the present invention provides pharmaceutical compositions comprising at least one compound of formula (I), together with one or more pharmaceutically acceptable carriers and/or adjuvant.

The pharmaceutical compositions of the invention can be administered orally, e.g. in the form of tablets, coated tablets, dragées, hard and soft gelatine capsules, solutions, emulsions or suspensions. They also can be administered rectally, e.g. in the form of suppositories, or parenterally, e.g. in the form of injection solutions.

The above-mentioned pharmaceutical preparations can be obtained by processing the compounds according to this invention with pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, masking agents or antioxidants. They can also contain other therapeutically valuable substances, including additional active ingredients other than those of formula (I).

Dosages

Another embodiment according to the present invention is directed to a method of treatmenting or ameliorating cancer, in particular solid tumors and hematological tumors, more particularly leukemia, lymphoma, colon, liver, or gastric cancer.

The therapeutically effective amount or dosage of a compound according to this invention can vary but may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 5-400 mg/kg, preferably about 10-100 mg/kg is appropriate. The daily dosage can be administered as a single dose or in divided doses, or for parenteral administration, it may be given as continuous infusion.

General Synthesis of Compounds According to the Invention

The compounds of the present invention can be prepared by any conventional means. Suitable processes for synthesizing these compounds are provided in the examples. Generally, the compounds of the present invention as well as their starting materials can be synthesized according to the following general reaction schemes 1 to 18, respectively. In said reaction schemes 1 to 18, all substituents, in particular R, and $R^1$ to $R^4$, have the meanings given above unless explicitly otherwise stated. In particular, the predominant conformations in the schemes are the ones which lead to the racemic trans stereoisomers as depicted in formulas (Ia) and (Ib). Furthermore, and unless explicitly otherwise stated, all reactions, reaction conditions, abbreviations and symbols have the meanings well known to a person of ordinary skill in organic chemistry.

| Abbreviations as used herein comprise: | |
|---|---|
| bp: | boiling point |
| dba: | dibenzylidene acetone |
| DIPEA: | diisopropylethylamine |
| DMEM: | Dulbecco's Modified Eagle Medium |
| DMF: | dimethylformamide |
| DMSO: | dimethylsulfoxide |
| DNA: | deoxyribonucleic acid |
| EDCI: | 1-ethyl-3-(3-dimethylaminopropyl)carbodiimide |

| Abbreviations as used herein comprise: | |
|---|---|
| ELISA: | enzyme-linked immunosorbent assay |
| EtOAc: | ethyl acetate |
| FBS: | fetal bovine serum |
| g: | gram |
| GFP: | green fluorescent protein |
| $GI_{50}$: | concentration required for 50% growth inhibition |
| $GI_{90}$: | concentration required for 90% growth inhibition |
| h: | hour |
| HATU: | O-(7-azabenzotriazol-1-yl)-N,N,N',N'-tetramethyluronium hexafluorophosphate |
| HDAC: | histone deacetylase |
| HOAc: | acetic acid |
| HOBt: | 1-hydroxybenzotriazole |
| HPLC: | high performance liquid chromatography |
| Hz: | Hertz |
| MeOD: | deuterated methanol |
| MeOH: | methanol |
| mg: | milligram |
| MHz: | megahertz |
| mL: | milliliter |
| mmol: | millimole |
| MsCl: | methanesulfonyl chloride |
| MTS: | 3-(4,5-dimethylthiazol-2-yl)-5-(3-carboxymethoxyphenyl)-2-(4-sulfophenyl)-2H-tetrazolium) |
| MW: | molecular weight |
| nL: | nanoliter |
| NMR: | nuclear magnetic resonance |
| O/N or o/n: | overnight |
| PET or Pet: | petroleum ether |
| PyBrop: | bromo-tris-pyrrolidino-phosphoniumhexafluorophosphate |
| rt: | room temperature |
| TBS: | tert-butyldimethylsilyl |
| t-BuOK: | potassium tert-butoxide |
| TEA: | triethylamine |
| THF: | tetrahydrofuran |
| TLC: | thin layer chromatography |
| uL: | microliter |
| WST: | 4-[3-(4-iodophenyl)-2-(4-nitrophenyl)-2H-5-tetrazolio]-1,3-benzene disulfonate |

A. General Synthetic Route for $R^1$ Amide-Based Analogues (Scheme 1)

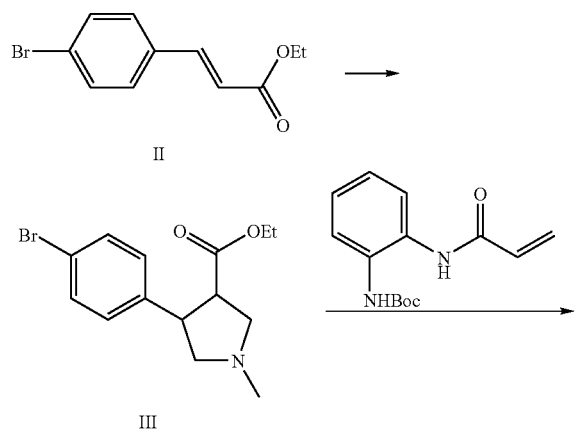

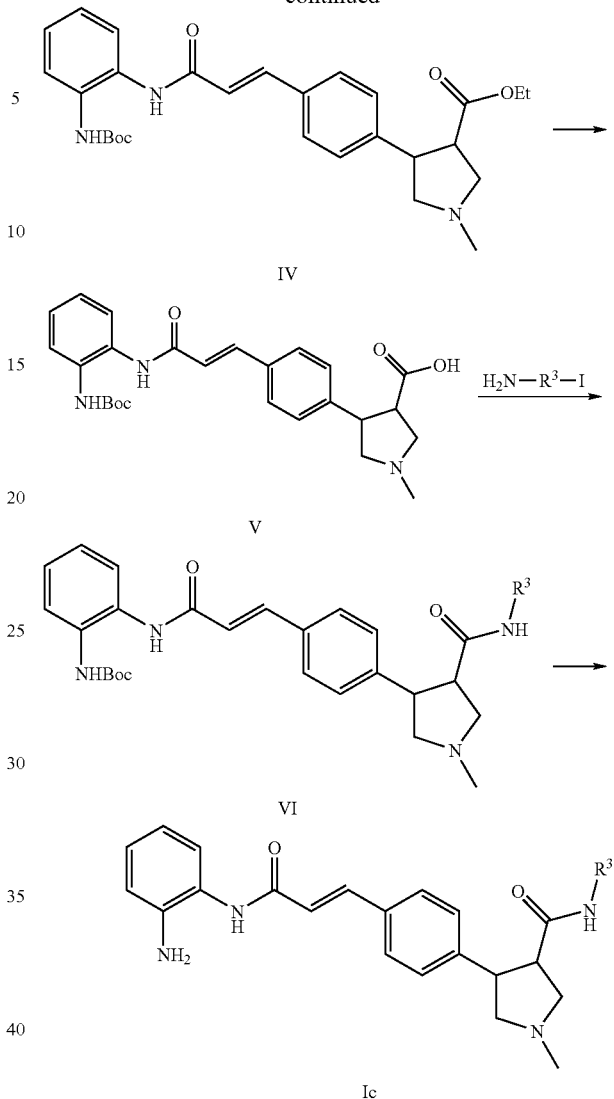

Compounds of interest Ic can be prepared according to Scheme 1. Starting with ester II, imminium ylide cycloaddition with sarcosine and paraformaldehyde gives pyrrolidine III. Heck reaction coupling of (2-acryloylamino-phenyl)-carbamic acid tert-butyl ester with III provides cinnamide IV. Basic hydrolysis of cinnamide IV to V followed by coupling of various amines to V furnishes amides VI. Acidic deprotection of the Boc protecting group generates compounds of interest Ic.

3-(4-Bromo-phenyl)-acrylic acid ethyl ester (II) can be prepared from condensation of 4-bromobenzaldehyde with malonic acid monoethyl ester. The reaction can be carried out in a suitable organic solvent such as dimethylformamide, typically at 100 degrees Celsius over several hours.

4-(4-Bromo-phenyl)-1-methyl-pyrrolidine-3-carboxylic acid ethyl ester (III) can be prepared from imminium ylide cycloaddition of sarcosine and paraformaldehyde with II. The reaction can be carried out in a suitable organic solvent such as toluene, typically at refluxing conditions over several hours in the presence of 3 Angstrom molecular sieves.

4-{4-[2-(2-tert-Butoxycarbonylamino-phenylcarbamoyl)-vinyl]-phenyl}-1-methyl-pyrrolidine-3-carboxylic acid ethyl ester (IV) can be prepared by Heck coupling of III with (2-acryloylamino-phenyl)-carbamic acid tert-butyl ester. The reaction is typically performed in deoxygenated dimethylformamide with triethylamine, tri-ortho-tolyl-phosphine, $Pd_2(dba)_3$, at 80-100 degrees Celsius for about four to ten hours under inert atmosphere.

4-{4-[2-(2-tert-Butoxycarbonylamino-phenylcarbamoyl)-vinyl]-phenyl}-1-methyl-pyrrolidine-3-carboxylic acid (V) can be prepared by hydrolysis of IV. The reaction is typically carried out with a suitable base such as sodium or lithium hydroxide in a suitable solvent mixture such as tetrahydrofuran and water or methanol and water at room temperature over several hours.

Amide compounds VI can be prepared from coupling various amines with 4-{4-[2-(2-tert-butoxycarbonylamino-phenylcarbamoyl)-vinyl]-phenyl}-1-methyl-pyrrolidine-3-carboxylic acid (V). The reaction is typically performed with standard peptide coupling reagents such as EDCI and HOBt, PyBrop and diisopropylethylamine, or HATU and triethylamine in a suitable inert solvent such as dichloromethane or dimethylformamide or mixtures thereof at room temperature for several hours.

Compounds of interest Ic are obtained by deprotection of compounds VI. The reaction is typically performed in methanolic hydrogen chloride at room temperature over several hours.

B. General Synthetic Route for Synthesis of $R^1$ Benzoimidazoles (Scheme 2)

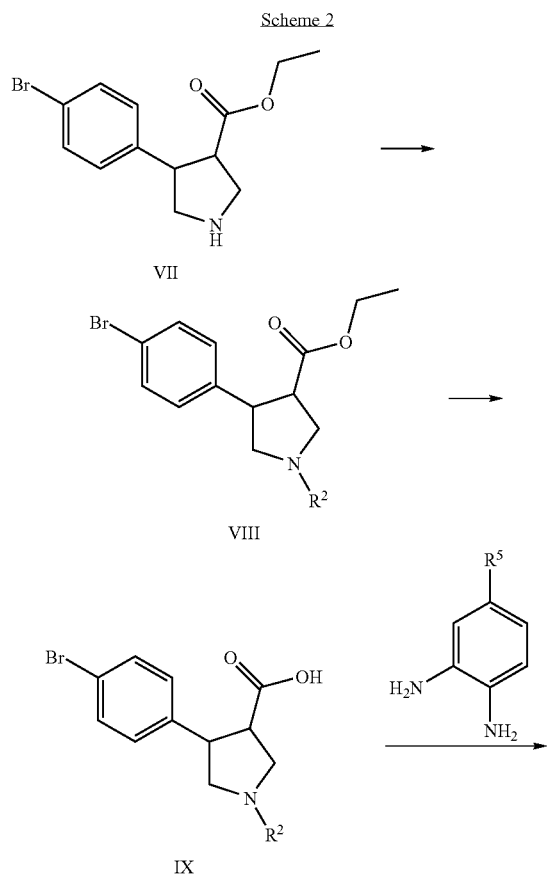

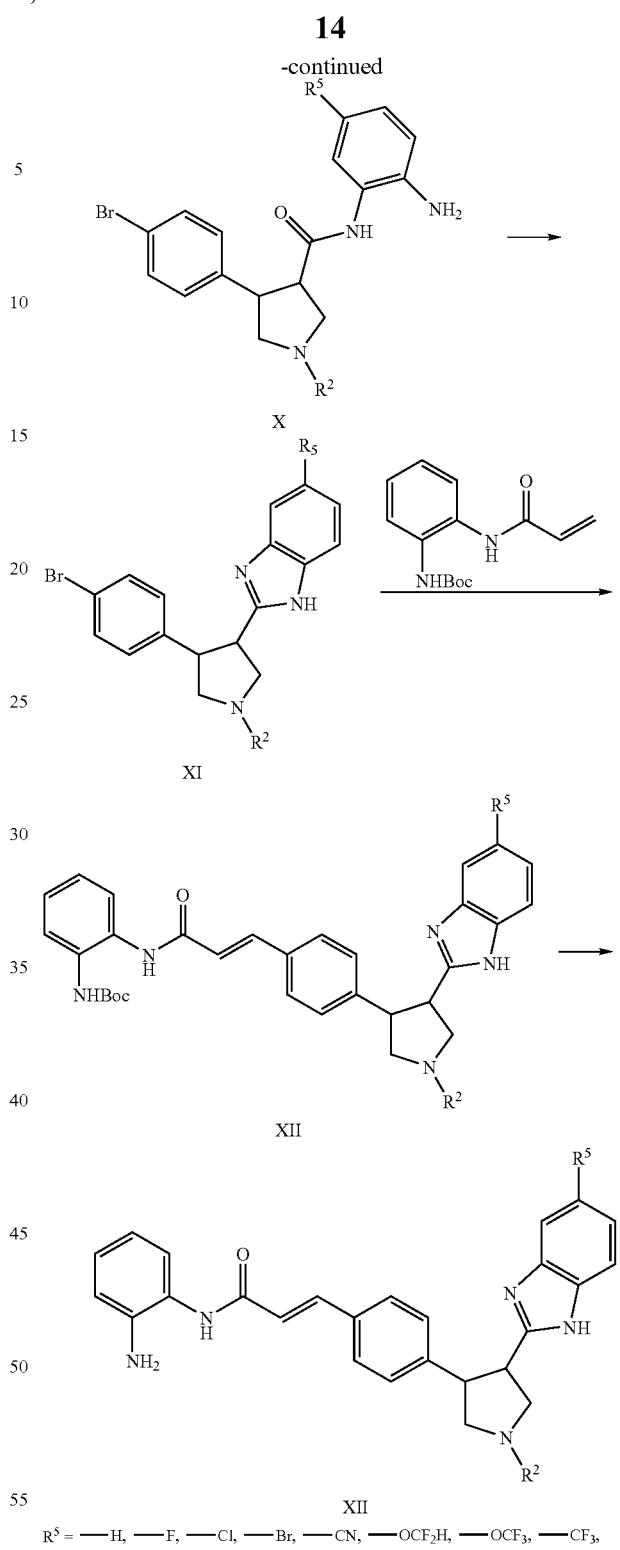

$R^5$ = —H, —F, —Cl, —Br, —CN, —$OCF_2H$, —$OCF_3$, —$CF_3$, lower alkyl, lower alkoxy, cycloalkyl Compounds of interest Id can be prepared according to Scheme 2. Starting with pyrrolidine VII, reductive amination with various aldehydes or ketones provides substituted pyrrolidines VIII. Hydrolysis of compounds VIII leads to acids IX, which are in turn coupled with various 1,2-phenylenediamine analogues to give amides X. Amides X are then converted to benzoimidazoles XI via acid-mediated intramolecular cyclization. Heck reaction coupling of (2-acryloylaminophenyl)-carbamic acid tert-butyl ester with XI provides cinnamides XII. Acidic deprotection of the Boc protecting group in cinnamides XII generates compounds of interest Id.

4-(4-Bromo-phenyl)-pyrrolidine-3-carboxylic acid ethyl ester (VII) can be prepared in racemic form according to the synthetic route described in Scheme 17 or in enantioselective fashion according to the synthetic route described in Scheme 18.

Substituted pyrrolidines VIII can be prepared from reductive amination of various aldehydes or ketones with compound VII. The reaction can be carried out with a suitable reducing agent such as sodium triacetoxyborohydride in an inert organic solvent such as dichloromethane, typically at room temperature for twelve to sixteen hours.

Acids IX can be prepared by hydrolysis of compounds VIII. The reaction is typically carried out with a suitable base such as sodium or lithium hydroxide in a suitable solvent mixture such as tetrahydrofuran and water or methanol and water at room temperature over several hours.

Amides X can be prepared by coupling of various 1,2-phenylenediamine analogues to acids IX. The reaction is typically performed by converting the acids IX to their corresponding acid chlorides in situ using oxalyl chloride and catalytic DMF, followed by addition to a 1,2-phenylenediamine dissolved in a suitable inert organic solvent, typically at zero degrees Celsius, followed by stirring at room temperature for several hours.

Benzoimidazoles XI can be prepared via intramolecular cyclization/condensation of amides X. The reaction is typically performed by heating amides X with sodium acetate in acetic acid, usually at reflux temperature for eight hours.

Cinnamides XII can be prepared by Heck coupling of benzoimidazoles XI with (2-acryloylamino-phenyl)-carbamic acid tert-butyl ester. The reaction is typically performed in deoxygenated dimethylformamide with triethylamine, tri-ortho-tolyl-phosphine, $Pd_2(dba)_3$, at 80-100 degrees Celsius for about four to ten hours under inert atmosphere.

Compounds of interest Id are obtained by deprotection of compounds XII. The reaction is typically performed in methanolic hydrogen chloride at room temperature over several hours.

C. General Synthetic Route for Synthesis of $R^1$ Imidazoles (Scheme 3)

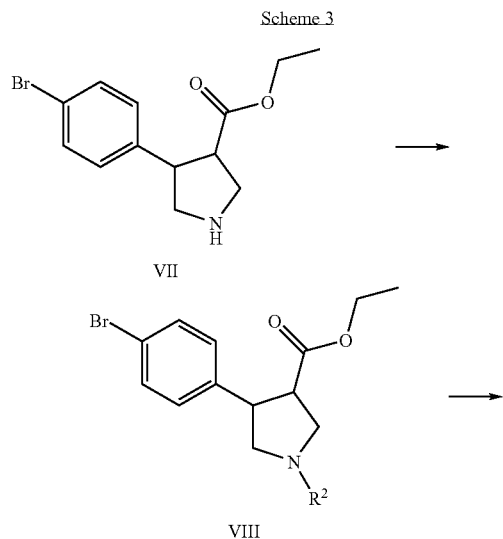

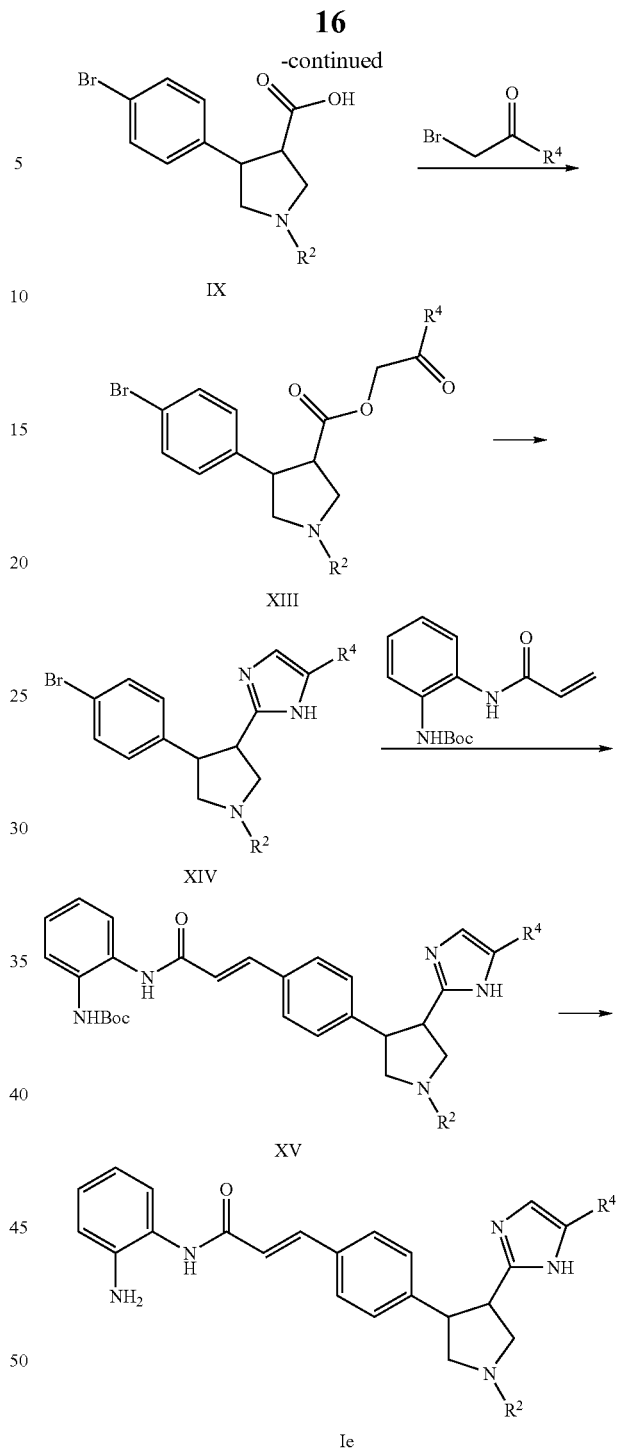

Compounds of interest Ie can be prepared according to Scheme 3. Starting with pyrrolidine VII, reductive amination with various aldehydes or ketones provides substituted pyrrolidines VIII. Hydrolysis of compounds VIII leads to acids IX, which are in turn alkylated with various alpha-bromoketones to give compounds XIII. Compounds XIII are then converted to imidazoles XIV via condensation with ammonium acetate. Heck reaction coupling of (2-acryloylamino-phenyl)-carbamic acid tert-butyl ester with XIV provides cinnamides XV. Acidic deprotection of the Boc protecting group in cinnamides XV generates compounds of interest Ie. 4-(4-Bromo-phenyl)-pyrrolidine-3-carboxylic acid ethyl ester (VII) can be prepared in racemic form according to the synthetic route described in Scheme 17 or in enantioselective fashion according to the synthetic route described in Scheme 18.

Substituted pyrrolidines VIII can be prepared from reductive amination of various aldehydes or ketones with compound VII. The reaction can be carried out with a suitable reducing agent such as sodium triacetoxyborohydride in an inert organic solvent such as dichloromethane, typically at room temperature for twelve to sixteen hours.

Acids IX can be prepared by hydrolysis of compounds VIII. The reaction is typically carried out with a suitable base such as sodium or lithium hydroxide in a suitable solvent mixture such as tetrahydrofuran and water or methanol and water at room temperature over several hours.

Compounds XIII can be prepared by alkylation of acids IX with various alpha-bromoketones. The reaction is typically performed by deprotonating the acids IX with a suitable inorganic base such as cesium carbonate, following by addition of the alpha-bromoketone in an organic solvent such as DMF, typically at room temperature for twelve to sixteen hours.

Imidazoles XIV can be prepared via reaction of compounds XIII with ammonium acetate. The reaction is typically performed by heating compounds XIII with ammonium acetate in toluene, usually at reflux temperature for several hours.

Cinnamides XV can be prepared by Heck coupling of imidazoles XIV with (2-acryloylamino-phenyl)-carbamic acid tert-butyl ester. The reaction is typically performed in deoxygenated dimethylformamide with triethylamine, tri-ortho-tolyl-phosphine, $Pd_2(dba)_3$, at 80-100 degrees Celsius for about four to ten hours under inert atmosphere.

Compounds of interest Ie are obtained by deprotection of compounds XV. The reaction is typically performed in methanolic hydrogen chloride at room temperature over several hours.

D. General Synthetic Route for Synthesis of $R^2$ Analogues (Scheme 4)

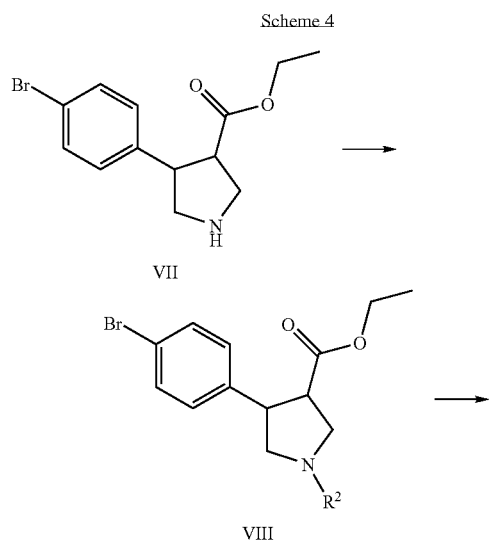

Scheme 4

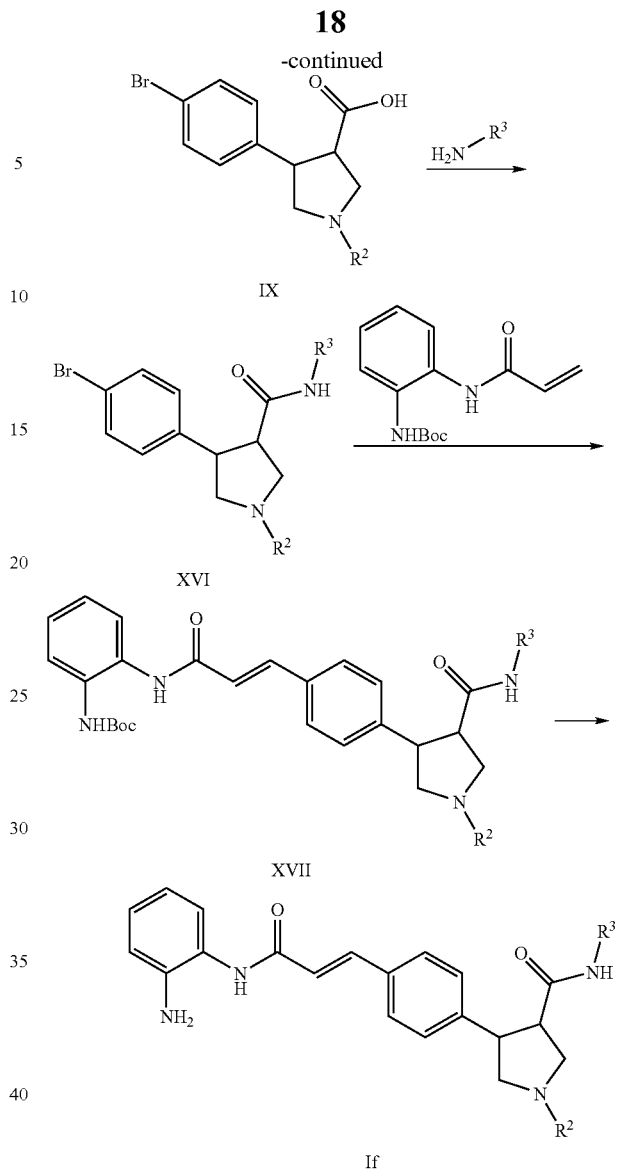

Compounds of interest If can be prepared according to Scheme 4. Starting with pyrrolidine VII, reductive amination with various aldehydes/ketones or alkylation with various halides provides substituted pyrrolidines VIII. Hydrolysis of compounds VIII leads to acids IX, which are in turn coupled with various amines to give amides XVI. Heck reaction coupling of (2-acryloylamino-phenyl)-carbamic acid tent-butyl ester with XVI provides cinnamides XVII. Acidic deprotection of the Boc protecting group in cinnamides XVII generates compounds of interest If.

4-(4-Bromo-phenyl)-pyrrolidine-3-carboxylic acid ethyl ester (VII) can be prepared in racemic form according to the synthetic route described in Scheme 17 or in enantioselective fashion according to the synthetic route described in Scheme 18.

Substituted pyrrolidines VIII can be prepared from reductive amination of various aldehydes or ketones with compound VII. The reaction can be carried out with a suitable reducing agent such as sodium triacetoxyborohydride in an inert organic solvent such as dichloromethane, typically at room temperature for twelve to sixteen hours.

Substituted pyrrolidines VIII can also be prepared from alkylation of compound VII with various halides. The reaction can be carried out with a suitable base such as potassium carbonate in an organic solvent such as dimethylforamide, typically at 100 degrees Celsius for twelve to sixteen hours.

Acids IX can be prepared by hydrolysis of compounds VIII. The reaction is typically carried out with a suitable base such as sodium or lithium hydroxide in a suitable solvent mixture such as tetrahydrofuran and water or methanol and water at room temperature over several hours.

Amides XVI can be prepared from coupling various amines with acids IX. The reaction is typically performed with standard peptide coupling reagents such as EDCI and HOBt, PyBrop and diisopropylethylamine, or HATU and triethylamine in a suitable inert solvent such as dichloromethane or dimethylformamide or mixtures thereof at room temperature for several hours.

Cinnamides XVII can be prepared by Heck coupling of amides XVI with (2-acryloylamino-phenyl)-carbamic acid tent-butyl ester. The reaction is typically performed in deoxygenated dimethylformamide with triethylamine, tri-ortho-tolyl-phosphine, Pd$_2$(dba)$_3$, at 80-100 degrees Celsius for about four to ten hours under inert atmosphere.

Compounds of interest If are obtained by deprotection of compounds XVII. The reaction is typically performed in methanolic hydrogen chloride at room temperature over several hours.

E. General Synthetic Route for Synthesis of R$^2$ 2-Hydroxy-1,1-Dimethyl Ethyl Analogues (Scheme 5)

Scheme 5

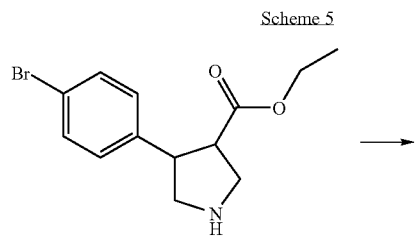

VII

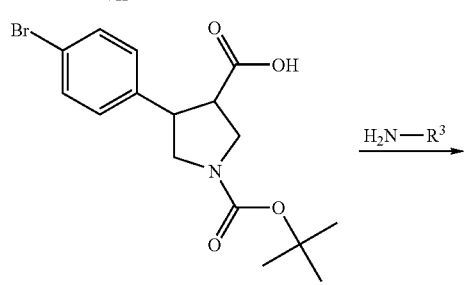

XVIII

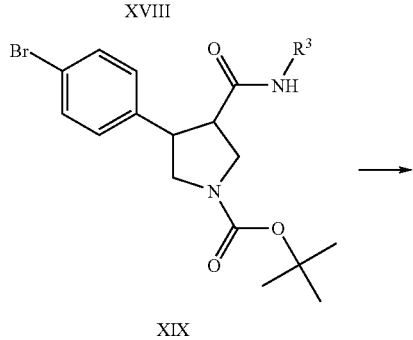

XIX

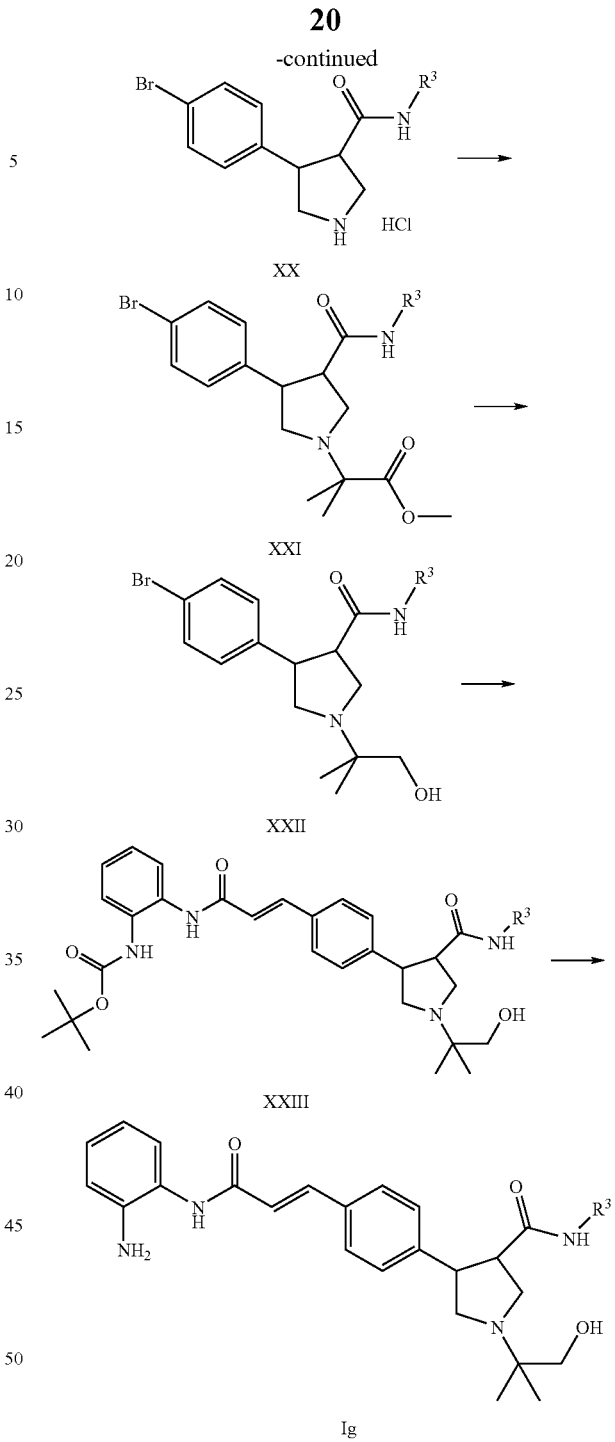

Compounds of interest Ig can be prepared according to Scheme 5. Starting with pyrrolidine VII, concomitant ester hydrolysis and pyrrolidine protection with Boc anhydride gives 4-(4-bromo-phenyl)-pyrrolidine-1,3-dicarboxylic acid 1-tent-butyl ester XVIII. Coupling of XVIII with various amines provides amides XIX. Subsequent Boc deprotection generates pyrrolidines XX, which are then alkylated with 2-bromo-2-methyl-propionic acid methyl ester to obtain compounds XXI. Reduction of the methyl ester in compounds XXI gives alcohols XXII, which in turn can undergo Heck reaction coupling with (2-acryloylamino-phenyl)-carbamic acid tent-butyl ester to provide cinnamides XXIII.

Acidic deprotection of the Boc protecting group in cinnamides XXIII generates compounds of interest Ig.

4-(4-Bromo-phenyl)-pyrrolidine-3-carboxylic acid ethyl ester (VII) can be prepared in racemic form according to the synthetic route described in Scheme 17 or in enantioselective fashion according to the synthetic route described in Scheme 18.

4-(4-Bromo-phenyl)-pyrrolidine-1,3-dicarboxylic acid 1-tent-butyl ester XVIII can be prepared from one-pot basic hydrolysis and Boc protection of compound VII. The reaction is carried out in two operations, beginning with use of a suitable inorganic base such as sodium hydroxide in a mixture of water and acetonitrile, at room temperature for several hours, followed by addition of Boc anhydride and further stirring at room temperature for several additional hours.

Amides XIX can be prepared from coupling various amines with 4-(4-bromo-phenyl)-pyrrolidine-1,3-dicarboxylic acid 1-tent-butyl ester XVIII. The reaction is typically performed with standard peptide coupling reagents such as EDCI and HOBt, PyBrop and diisopropylethylamine, or HATU and triethylamine in a suitable inert solvent such as dichloromethane or dimethylformamide or mixtures thereof at room temperature for several hours.

Pyrrolidines XX are obtained by standard Boc deprotection of amides XIX. The reaction is typically carried out in methanolic hydrogen chloride for several hours at room temperature.

Compounds XXI can be prepared by alkylation of pyrrolidines XX with 2-bromo-2-methyl-propionic acid methyl ester. The reaction is typically performed in dimethylformamide with a suitable inorganic base such as potassium carbonate, at 50 degrees Celsius for about five hours.

Alcohols XXII can be obtained by reduction of the methyl ester in compounds XXI. The reaction is carried out with a suitable reducing agent such as lithium or sodium borohydride in an inert organic solvent such as tetrahydrofuran, typically at room temperature for several hours to days (depending on the reducing agent reactivity).

Cinnamides XXIII can be prepared by Heck coupling of alcohols XXII with (2-acryloylamino-phenyl)-carbamic acid tent-butyl ester. The reaction is typically performed in deoxygenated dimethylformamide with triethylamine, tri-ortho-tolyl-phosphine, $Pd_2(dba)_3$, at 80-100 degrees Celsius for about four to ten hours under inert atmosphere.

Compounds of interest Ig are obtained by deprotection of cinnamides XXIII. The reaction is typically performed in methanolic hydrogen chloride at room temperature over several hours.

F. General Synthetic Route for Synthesis of $R^2$ 2-Hydroxy-2,2-Dimethyl Ethyl Analogues (Scheme 6)

Scheme 6

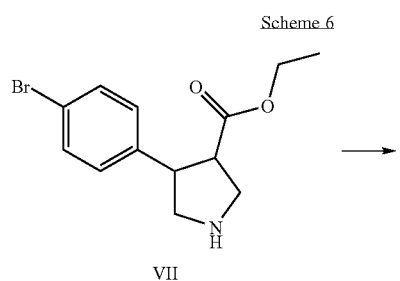

VII

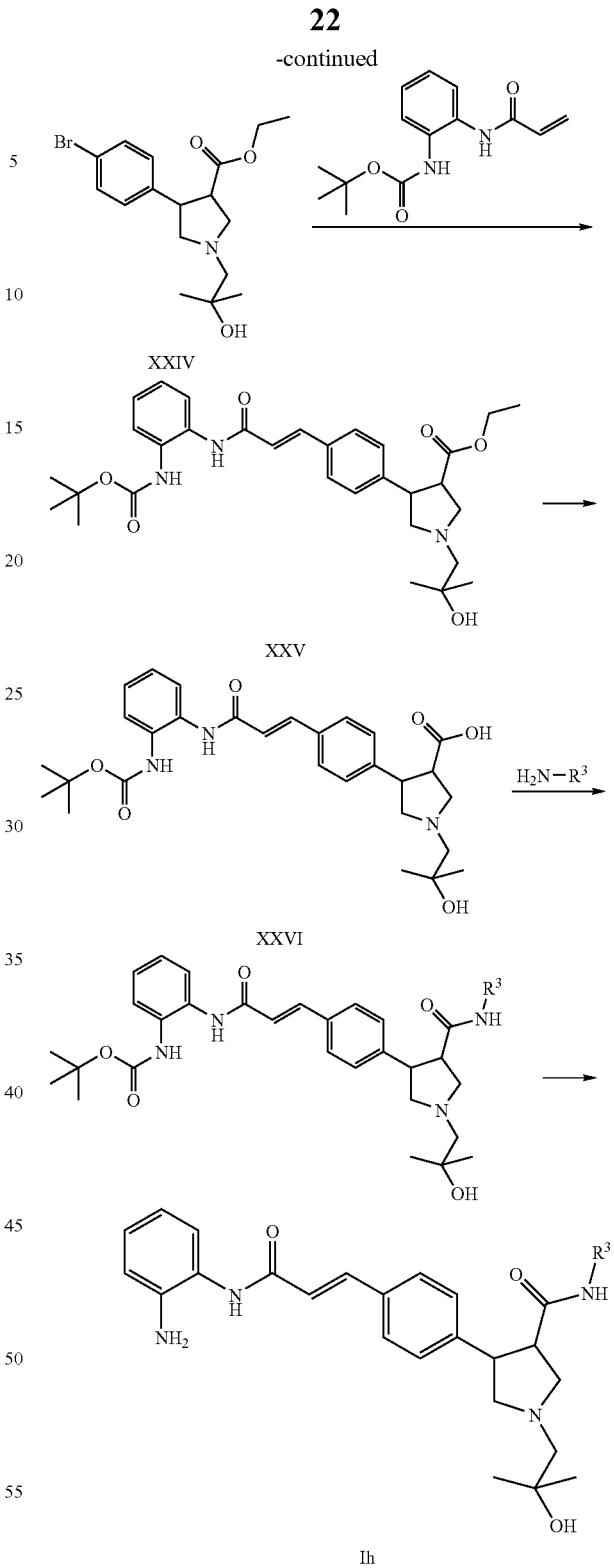

Compounds of interest Ih can be prepared according to Scheme 6. Starting with pyrrolidine VII, alkylation with 2,2-dimethyl-oxirane provides 4-(4-bromo-phenyl)-1-(2-hydroxy-2-methyl-propyl)-pyrrolidine-3-carboxylic acid ethyl ester (XXIV), which then undergoes Heck reaction coupling with (2-acryloylamino-phenyl)-carbamic acid tert-butyl ester to provide 4-{4-[2-(2-tert-butoxycarbonylamino-phenylcarbamoyl)-vinyl]-phenyl}-1-(2-hydroxy-2-methyl-propyl)- pyrrolidine-3-carboxylic acid ethyl ester (XXV). Hydrolysis of XXV under basic conditions gives 4-{4-[2-(2-tert-butoxy-carbonylamino-phenylcarbamoyl)-vinyl]-phenyl}-1-(2-hydroxy-2-methyl-propyl)-pyrrolidine-3-carboxylic acid (XXVI), which is then coupled with various amines to provide amides XXVII. Acidic deprotection of the Boc protecting group in amides XXVII generates compounds of interest Ih.

4-(4-Bromo-phenyl)-pyrrolidine-3-carboxylic acid ethyl ester (VII) can be prepared in racemic form according to the synthetic route described in Scheme 17 or in enantioselective fashion according to the synthetic route described in Scheme 18.

4-(4-Bromo-phenyl)-1-(2-hydroxy-2-methyl-propyl)-pyrrolidine-3-carboxylic acid ethyl ester (XXIV) can be prepared by reacting 4-(4-bromo-phenyl)-pyrrolidine-3-carboxylic acid ethyl ester (VII) with 2,2-dimethyl-oxirane. The reaction is typically performed in a sealed tube at 80 degrees Celsius for five hours.

4-{4-[2-(2-tert-Butoxycarbonylamino-phenylcarbamoyl)-vinyl]-phenyl}-1-(2-hydroxy-2-methyl-propyl)-pyrrolidine-3-carboxylic acid ethyl ester (XXV) can be prepared by Heck coupling of 4-(4-bromo-phenyl)-1-(2-hydroxy-2-methyl-propyl)-pyrrolidine-3-carboxylic acid ethyl ester (XXIV) with (2-acryloylamino-phenyl)-carbamic acid tert-butyl ester. The reaction is typically performed in deoxygenated dimethylformamide with triethylamine, tri-ortho-tolyl-phosphine, $Pd_2(dba)_3$, at 80-100 degrees Celsius for about four to ten hours under inert atmosphere.

4-{4-[2-(2-tert-Butoxycarbonylamino-phenylcarbamoyl)-vinyl]-phenyl}-1-(2-hydroxy-2-methyl-propyl)-pyrrolidine-3-carboxylic acid (XXVI) can be prepared by hydrolysis of 4-{4-[2-(2-tert-butoxycarbonylamino-phenylcarbamoyl)-vinyl]-phenyl}-1-(2-hydroxy-2-methyl-propyl)-pyrrolidine-3-carboxylic acid ethyl ester (XXV). The reaction is typically carried out with a suitable base such as sodium or lithium hydroxide in a suitable solvent mixture such as tetrahydrofuran and water or methanol and water at room temperature over several hours.

Amides XXVII can be prepared from coupling various amines with 4-{4-[2-(2-tert-butoxycarbonylamino-phenylcarbamoyl)-vinyl]-phenyl}-1-(2-hydroxy-2-methyl-propyl)-pyrrolidine-3-carboxylic acid (XXVI). The reaction is typically performed with standard peptide coupling reagents such as EDCI and HOBt, PyBrop and diisopropylethylamine, or HATU and triethylamine in a suitable inert solvent such as dichloromethane or dimethylformamide or mixtures thereof at room temperature for several hours.

Compounds of interest Ih are obtained by deprotection of cinnamides XXVII. The reaction is typically performed in methanolic hydrogen chloride at room temperature over several hours.

G. General Synthetic Route for Synthesis of $R^2$ Tert-Butyl Analogues (Scheme 7)

Scheme 7

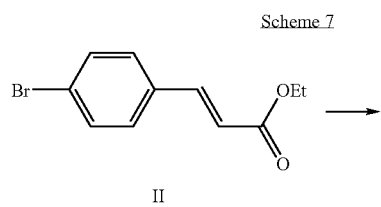

II

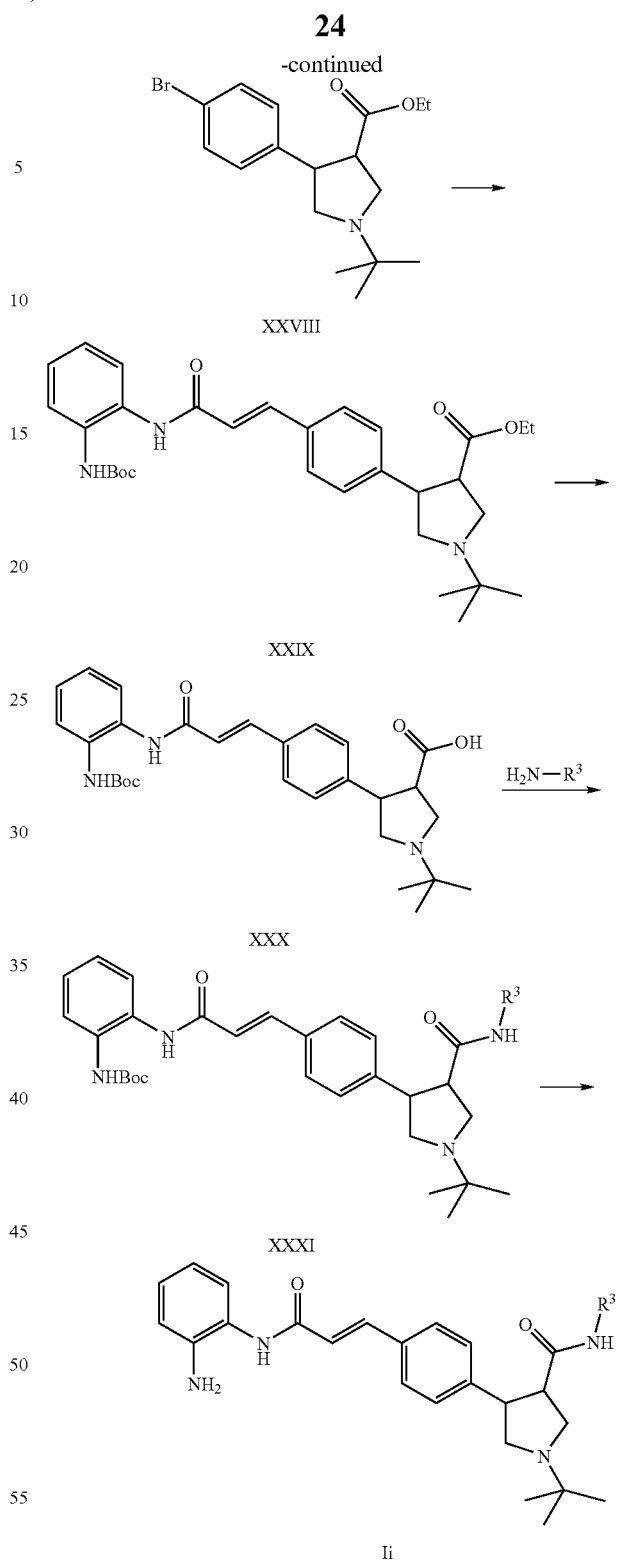

Compounds of interest Ii can be prepared according to Scheme 7. Starting with ester II, imminium ylide cycloaddition with N-t-butylglycine and paraformaldehyde gives pyrrolidine XXVIII. Heck reaction coupling of (2-acryloylamino-phenyl)-carbamic acid tent-butyl ester with XXVIII provides cinnamide XXIX. Basic hydrolysis of cinnamide XXIX to XXX followed by coupling of various amines to XXX furnishes amides XXXI. Acidic deprotection of the Boc protecting group generates compounds of interest Ii.

3-(4-Bromo-phenyl)-acrylic acid ethyl ester (II) can be prepared from condensation of 4-bromobenzaldehyde with malonic acid monoethyl ester. The reaction can be carried out in a suitable organic solvent such as dimethylformamide, typically at 100 degrees Celsius over several hours.

4-(4-Bromo-phenyl)-1-tent-butyl-pyrrolidine-3-carboxylic acid ethyl ester (XXVIII) can be prepared from imminium glide cycloaddition of N-tert-butylglycine and paraformaldehyde with II. The reaction can be carried out in a suitable organic solvent such as toluene, typically at refluxing conditions over several hours in the presence of 3 Angstrom molecular sieves.

4-{4-[2-(2-tert-Butoxycarbonylamino-phenylcarbamoyl)-vinyl]-phenyl}-1-t-butyl-pyrrolidine-3-carboxylic acid ethyl ester (XXIX) can be prepared by Heck coupling of XXVIII with (2-acryloylamino-phenyl)-carbamic acid tent-butyl ester. The reaction is typically performed in deoxygenated dimethylformamide with triethylamine, tri-ortho-tolyl-phosphine, $Pd_2(dba)_3$, at 80-100 degrees Celsius for about four to ten hours under inert atmosphere.

4-{4-[2-(2-tert-Butoxycarbonylamino-phenylcarbamoyl)-vinyl]-phenyl}-1-t-butyl-pyrrolidine-3-carboxylic acid (XXX) can be prepared by hydrolysis of XXIX. The reaction is typically carried out with a suitable base such as sodium or lithium hydroxide in a suitable solvent mixture such as tetrahydrofuran and water or methanol and water at room temperature over several hours.

Amide compounds XXXI can be prepared from coupling various amines with 4-{4-[2-(2-tert-butoxycarbonylamino-phenylcarbamoyl)-vinyl]-phenyl}-1-t-butyl-pyrrolidine-3-carboxylic acid (XXX). The reaction is typically performed with standard peptide coupling reagents such as EDCI and HOBt, PyBrop and diisopropylethylamine, or HATU and triethylamine in a suitable inert solvent such as dichloromethane or dimethylformamide or mixtures thereof at room temperature for several hours.

Compounds of interest Ii are obtained by deprotection of compounds XXXI. The reaction is typically performed in methanolic hydrogen chloride at room temperature over several hours.

H. General Synthetic Route for Synthesis of $R^2$ 2,2-Difluoro-Ethyl Analogues (Scheme 8)

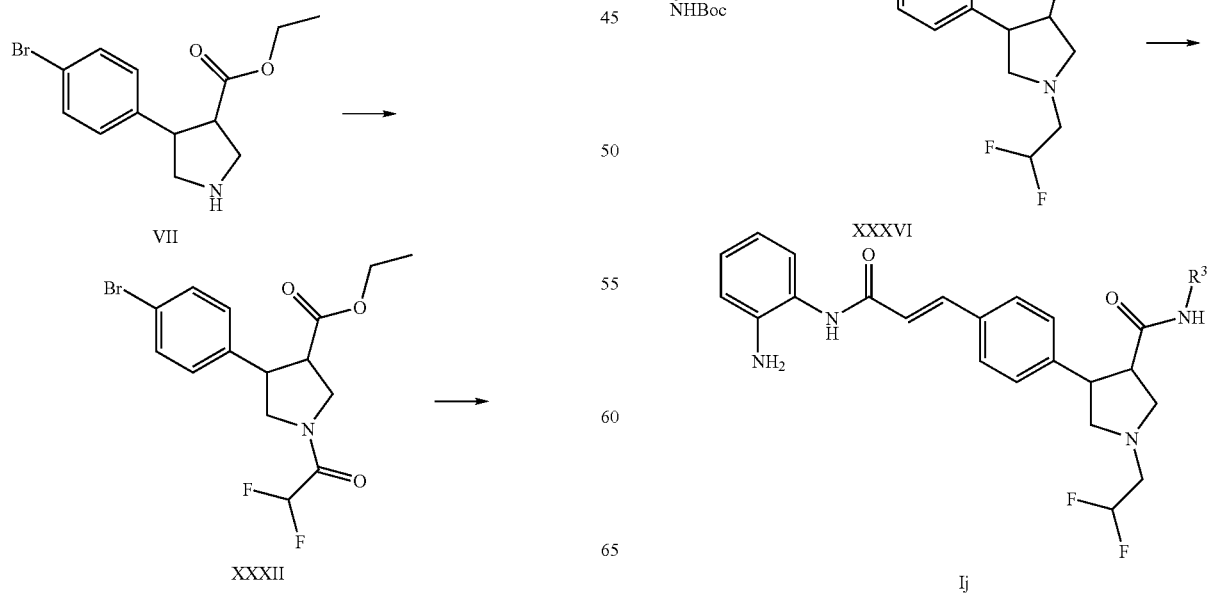

Compounds of interest Ij can be prepared according to Scheme 8. Starting with pyrrolidine VII, coupling of VII with difluoroacetyl chloride provides amide XXXII. Reduction of the amide in compound XXXII gives N-difluoroethyl-pyrrolidine XXXIII, which in turn can undergo Heck reaction coupling with (2-acryloylamino-phenyl)-carbamic acid tert-butyl ester to provide cinnamide XXXIV. Basic hydrolysis of cinnamide XXXIV to XXXV followed by coupling of various amines to XXXV furnishes amides XXXVI. Acidic deprotection of the Boc protecting group in cinnamides XXXVI generates compounds of interest Ij.

4-(4-Bromo-phenyl)-pyrrolidine-3-carboxylic acid ethyl ester (VII) can be prepared in racemic form according to the synthetic route described in Scheme 17 or in enantioselective fashion according to the synthetic route described in Scheme 18.

4-(4-Bromo-phenyl)-1-(2,2-difluoro-acetyl)-pyrrolidine-3-carboxylic acid ethyl ester XXXII can be prepared from coupling of compound VII with difluoroacetyl chloride. The reaction is typically performed under standard acetylation conditions such as diisopropylethylamine or triethylamine in a suitable inert solvent such as terahydrofuran, dichloromethane, dimethylformamide, or mixtures thereof at room temperature for several hours.

4-(4-Bromo-phenyl)-1-(2,2-difluoro-ethyl)-pyrrolidine-3-carboxylic acid ethyl ester XXXIII can be obtained by reduction of the amide in compound XXXII. The reaction is carried out with a suitable reducing agent such as borane in an inert organic solvent such as tetrahydrofuran, typically at room temperature for several hours.

4-{4-[2-(2-tert-Butoxycarbonylamino-phenylcarbamoyl)-vinyl]-phenyl}-1-(2,2-difluoro-ethyl)-pyrrolidine-3-carboxylic acid ethyl ester XXXIV can be prepared by Heck reaction coupling of XXXIII with (2-acryloylamino-phenyl)-carbamic acid tert-butyl ester. The reaction is typically performed in deoxygenated dimethylformamide with triethylamine, tri-ortho-tolyl-phosphine, $Pd_2(dba)_3$, at 80-100 degrees Celsius for about four to ten hours under inert atmosphere.

4-{4-[2-(2-tert-Butoxycarbonylamino-phenylcarbamoyl)-vinyl]-phenyl}-1-(2,2-difluoro-ethyl)-pyrrolidine-3-carboxylic acid XXXV can be prepared by hydrolysis of XXXIV. The reaction is typically carried out with a suitable base such as sodium or lithium hydroxide in a suitable solvent mixture such as tetrahydrofuran and water or methanol and water at room temperature over several hours.

Amides XXXVI can be prepared from coupling various amines with 4-{4-[2-(2-tert-butoxycarbonylamino-phenylcarbamoyl)-vinyl]-phenyl}-1-(2,2-difluoro-ethyl)-pyrrolidine-3-carboxylic acid (XXXV). The reaction is typically performed with standard peptide coupling reagents such as EDCI and HOBt, PyBrop and diisopropylethylamine, or HATU and triethylamine in a suitable inert solvent such as dichloromethane or dimethylformamide or mixtures thereof at room temperature for several hours.

Compounds of interest Ij are obtained by deprotection of cinnamides XXXVI. The reaction is typically performed in methanolic hydrogen chloride at room temperature over several hours.

I. General Synthetic Route for Synthesis of $R^2$ 2,2,2-Trifluoro-Ethyl Analogues (Scheme 9)

Scheme 9

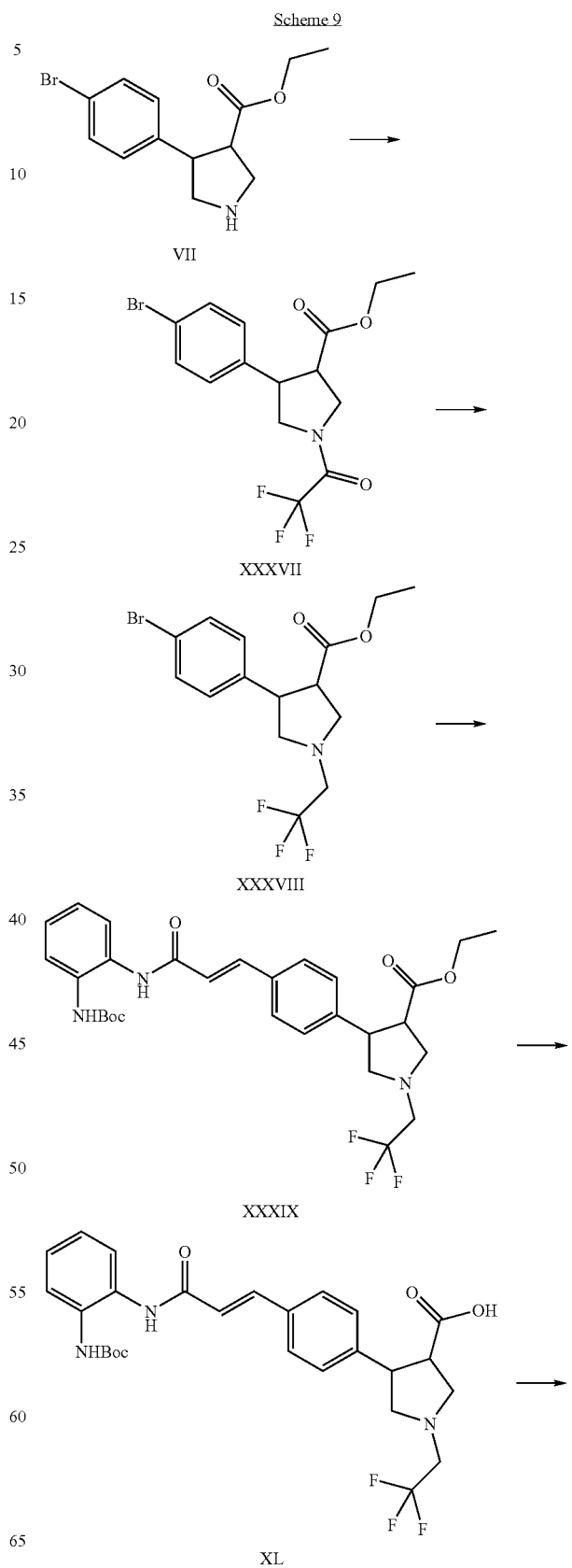

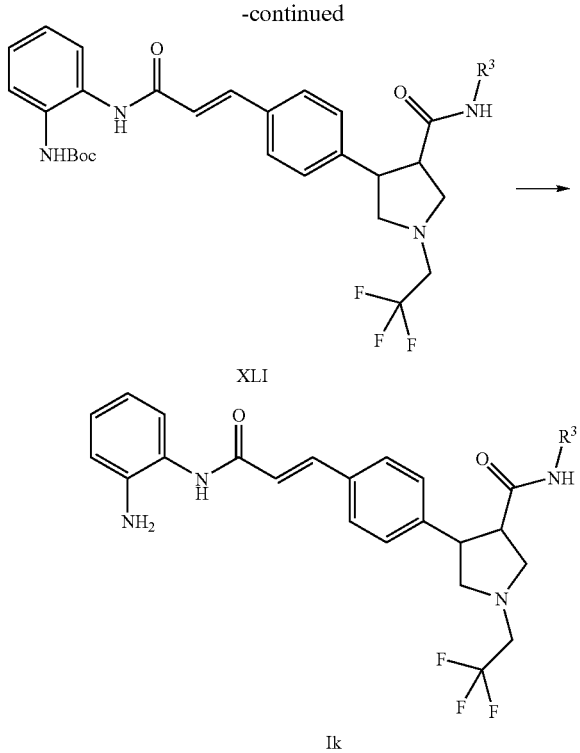

Compounds of interest Ik can be prepared according to Scheme 9. Starting with pyrrolidine VII, acylation of VII with trifluoroacetic anhydride provides amide XXXVII. Reduction of the amide in compound XXXVII gives N-trifluoroethyl-pyrrolidine XXXVIII, which in turn can undergo Heck reaction coupling with (2-acryloylamino-phenyl)-carbamic acid tert-butyl ester to provide cinnamide XXXIX. Basic hydrolysis of cinnamide XXXIX to XL followed by coupling of various amines to XL furnishes amides XLI. Acidic deprotection of the Boc protecting group in cinnamides XLI generates compounds of interest Ik.

4-(4-Bromo-phenyl)-pyrrolidine-3-carboxylic acid ethyl ester (VII) can be prepared in racemic form according to the synthetic route described in Scheme 17 or in enantioselective fashion according to the synthetic route described in Scheme 18.

4-(4-Bromo-phenyl)-1-(3,3,3-trifluoro-propionyl)-pyrrolidine-3-carboxylic acid ethyl ester XXXVII can be prepared from acylation of compound VII with trifluoroacetic anhydride. The reaction is typically performed under standard acylation conditions such as diisopropylethylamine or triethylamine in a suitable inert solvent such as terahydrofuran, dichloromethane, dimethylformamide, or mixtures thereof at room temperature for several hours.

4-(4-Bromo-phenyl)-1-(3,3,3-trifluoro-propyl)-pyrrolidine-3-carboxylic acid ethyl ester XXXVIII can be obtained by reduction of the amide in compound XXXVII. The reaction is carried out with a suitable reducing agent such as borane in an inert organic solvent such as tetrahydrofuran, typically at room temperature for several hours.

4-{4-[2-(2-tert-Butoxycarbonylamino-phenylcarbamoyl)-vinyl]-phenyl}-1-(3,3,3-trifluoro-propyl)-pyrrolidine-3-carboxylic acid ethyl ester XXXIX can be prepared by Heck coupling of 4-(4-Bromo-phenyl)-1-(3,3,3-trifluoro-propyl)-pyrrolidine-3-carboxylic acid ethyl ester XXXVII with (2-acryloylamino-phenyl)-carbamic acid tert-butyl ester. The reaction is typically performed in deoxygenated dimethylformamide with triethylamine, tri-ortho-tolyl-phosphine, $Pd_2(dba)_3$, at 80-100 degrees Celsius for about four to ten hours under inert atmosphere.

4-{4-[2-(2-tert-Butoxycarbonylamino-phenylcarbamoyl)-vinyl]-phenyl}-1-(3,3,3-trifluoro-propyl)-pyrrolidine-3-carboxylic acid XL can be prepared by hydrolysis of XXXIX. The reaction is typically carried out with a suitable base such as sodium or lithium hydroxide in a suitable solvent mixture such as tetrahydrofuran and water or methanol and water at room temperature over several hours.

Amides XLI can be prepared from coupling various amines with 4-{4-[2-(2-tert-butoxycarbonylamino-phenylcarbamoyl)-vinyl]-phenyl}-1-(3,3,3-trifluoro-propyl)-pyrrolidine-3-carboxylic acid (XL). The reaction is typically performed with standard peptide coupling reagents such as EDCI and HOBt, PyBrop and diisopropylethylamine, or HATU and triethylamine in a suitable inert solvent such as dichloromethane or dimethylformamide or mixtures thereof at room temperature for several hours.

Compounds of interest Ik are obtained by deprotection of cinnamides XLI. The reaction is typically performed in methanolic hydrogen chloride at room temperature over several hours.

J. General Synthetic Route for Synthesis of Benzothiophene R Analogues (Scheme 10)

Scheme 10

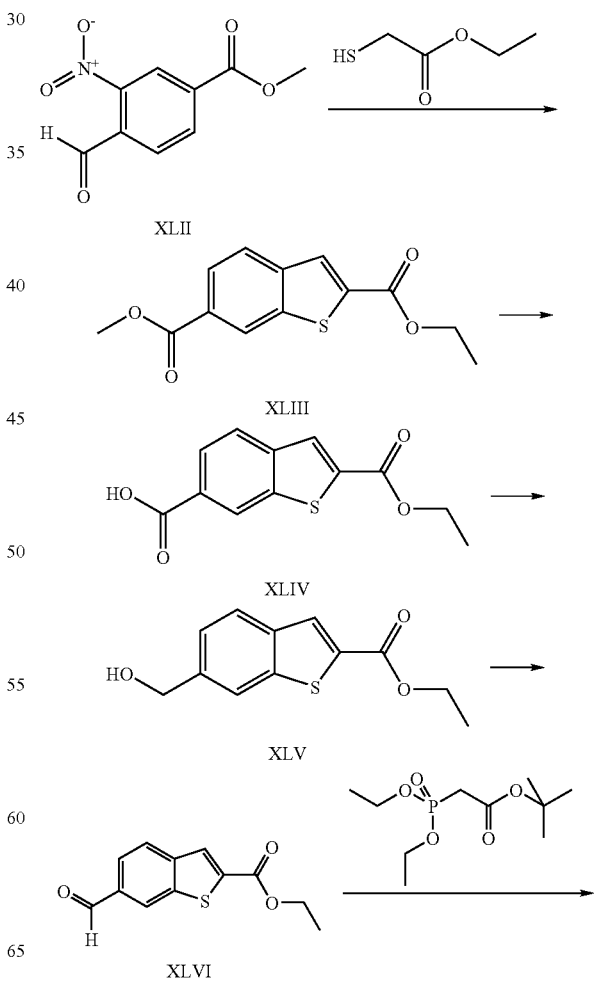

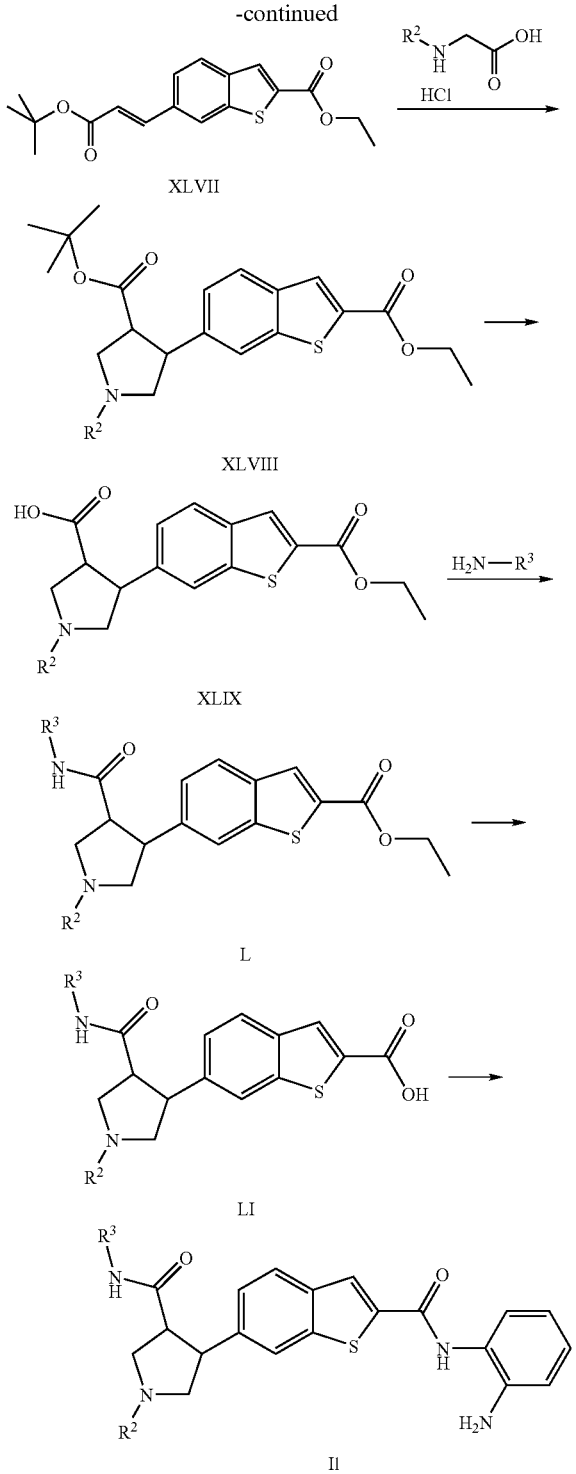

with substituted glycine and paraformaldehyde to give pyrrolidines XLVIII. Acidic hydrolysis of pyrrolidines XLVIII to XLIX followed by coupling of various amines to XLIX furnishes amides L. Basic hydrolysis of amides L to acids LI followed by coupling of ortho-1,2-phenylenediamine to LI generates compounds of interest II.

Benzo[b]thiophene-2,6-dicarboxylic acid 2-ethyl ester 6-methyl ester (XLIII) can be prepared from condensation of mercaptoacetic acid ethyl ester with XLII (commercially available). The reaction is typically carried out with a suitable base such as potassium or sodium carbonate in a suitable organic solvent such as dimethylformamide at 50-100 degrees Celsius for 6-12 hours.

Benzo[b]thiophene-2,6-dicarboxylic acid 2-ethyl ester (XLIV) can be prepared from regioselective hydrolysis of benzo[b]thiophene-2,6-dicarboxylic acid 2-ethyl ester 6-methyl ester XLIII with potassium iodide. The reaction can be carried out in a suitable solvent such as pyridine at reflux for 1-3 days.

6-Hydroxymethyl-benzo[b]thiophene-2-carboxylic acid ethyl ester (XLV) can be prepared from reduction of benzo[b]thiophene-2,6-dicarboxylic acid 2-ethyl ester (XLIV) with borane. The reaction is typically carried out in a suitable organic solvent such as tetrahydrofuran at room temperature for 6-12 hours.

6-Formyl-benzo[b]thiophene-2-carboxylic acid ethyl ester (XLVI) can be prepared from oxidation of 6-hydroxymethyl-benzo[b]thiophene-2-carboxylic acid ethyl ester (XLV) with $MnO_2$. The reaction can be carried out in a suitable solvent such as dichloromethane at room temperature for 0.5-3 hours.

6-(2-tent-Butoxycarbonyl-vinyl)-benzo[b]thiophene-2-carboxylic acid ethyl ester (XLVII) can be prepared from condensation of 6-formyl-benzo[b]thiophene-2-carboxylic acid ethyl ester (XLVI) with (diethoxyphosphoryl)-acetic acid tent-butyl ester. The reaction is typically carried out with a base such as n-Butyllithium in an inert solvent such as tetrahydrofuran or toluene at −78 degrees Celsius for 0.5-3 hours.

Pyrrolidines (XLVIII) can be prepared from imminium ylide cycloaddition of substituted glycine and paraformaldehyde with XLVII. The reaction can be carried out in a suitable organic solvent such as toluene, typically at refluxing conditions over several hours in the presence of 3 Angstrom molecular sieves.

Acids (XLIX) can be prepared by hydrolysis of pyrrolidines XLVIII. The reaction is typically carried out with a suitable acid such as trifluoroacetic acid in a suitable solvent such as dichloromethane or methanol at room temperature over several hours.

Amide compounds L can be prepared from coupling various amines with acids XLIX. The reaction is typically performed with standard peptide coupling reagents such as EDCI and HOBt, PyBrop and diisopropylethylamine, or HATU and triethylamine in a suitable inert solvent such as dichloromethane or dimethylformamide or mixtures thereof at room temperature for several hours.

Acids LI can be prepared by hydrolysis of amides L. The reaction is typically carried out with a suitable base such as sodium or lithium hydroxide in a suitable solvent mixture such as tetrahydrofuran and water or methanol and water at room temperature over several hours.

Compounds of interest II are obtained by coupling of acids LI with ortho-1,2-phenylenediamine. The reaction is typically carried out with standard peptide coupling reagents such as EDCI and HOBt, PyBrop and diisopropylethylamine, or HATU and triethylamine in a suitable inert solvent such as dichloromethane or dimethylformamide or mixtures thereof at room temperature for several hours.

Compounds of interest II can be prepared according to Scheme 10. Starting with 4-formyl-3-nitro-benzoic acid methyl ester XLII, reaction with mercapto-acetic acid ethyl ester gives benzo[b]thiophene-2,6-dicarboxylic acid 2-ethyl ester 6-methyl ester XLIII. Regioselective hydrolysis of diester XLIII gives monoacid XLIV. Reduction of mono-acid XLIV to alcohol XLV and subsequent oxidation of alcohol XLV provides aldehyde XLVI. Condensation of aldehyde with phosphonium ylide produces cinnamate t-butyl ester XLVII, which then undergoes imminium ylide cycloaddition K. General Synthetic Route for Synthesis of 5-Vinyl-Pyridin-2-yl R Analogues (Scheme 11)

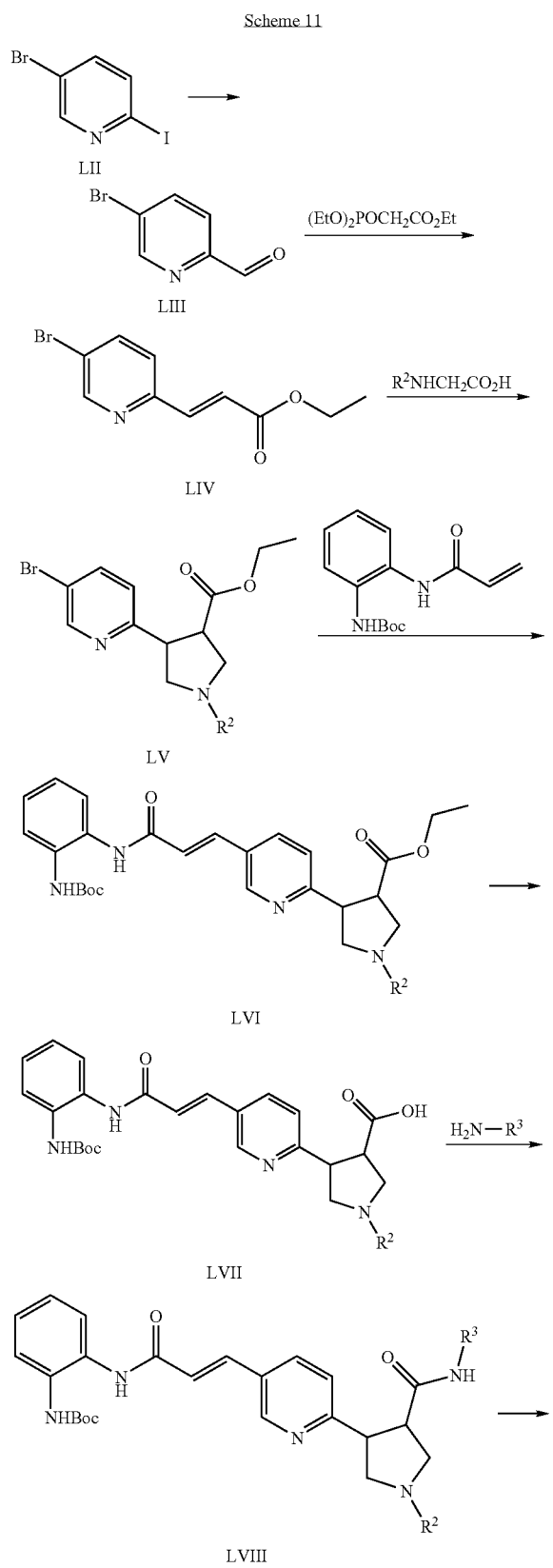

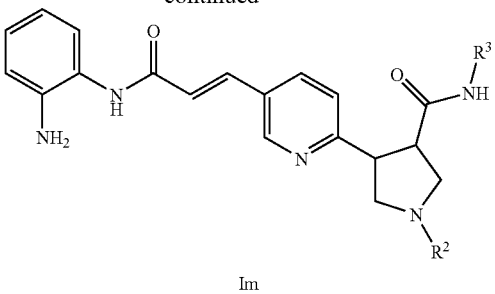

Compounds of interest Im can be prepared according to Scheme 11. Starting with 2-iodopyridine LII, formylation and subsequent condensation of 2-formylpyridine LIII with phosphonium ylide gives cinnamate LIV. Imminium ylide cycloaddition of cinnamate LIV with substituted glycine and paraformaldehyde gives pyrrolidines LV. Heck reaction coupling of (2-acryloylamino-phenyl)-carbamic acid tert-butyl ester with LV provides cinnamides LVI. Basic hydrolysis of cinnamides LVI to acids LVII followed by coupling of various amines to LVII furnishes amides LVIII. Acidic deprotection of the Boc protecting group generates compounds of interest Im.

5-Bromo-pyridine-2-carbaldehyde (LIII) can be prepared from formylation of 5-bromo-2-iodo-pyridine LII (commercially available). The reaction can be carried out with a suitable Grignard reagent such as isopropyl magnesium chloride in an inert solvent such as tetrahydrofuran at −20 degrees Celsius for 2 hours first, and then with dimethylformamide at room temperature for 1 hour.

3-(5-Bromo-pyridin-2-yl)-acrylic acid ethyl ester (LIV) can be prepared from condensation of 5-bromo-pyridine-2-carbaldehyde with triethyl phosphonoacetate. The reaction can be carried out with a suitable base such as triethylamine in a suitable organic solvent such as acetonitrile typically at room temperature over several hours.

Pyrrolidines LV can be prepared from imminium ylide cycloaddition of substituted glycine and paraformaldehyde with LIV. The reaction can be carried out in a suitable organic solvent such as toluene, typically at refluxing conditions over several hours in the presence of 3 Angstrom molecular sieves.

Cinnamides LVI can be prepared by Heck coupling of LV with (2-acryloylamino-phenyl)-carbamic acid tert-butyl ester. The reaction is typically performed in deoxygenated dimethylformamide with triethylamine, tri-ortho-tolyl-phosphine, $Pd_2(dba)_3$, at 80-100 degrees Celsius for about four to ten hours under inert atmosphere.

Acids LVII can be prepared by hydrolysis of cinnamides LVI. The reaction is typically carried out with a suitable base such as sodium or lithium hydroxide in a suitable solvent mixture such as tetrahydrofuran and water or methanol and water at room temperature over several hours.

Amide compounds LVIII can be prepared from coupling various amines with 4-{5-[2-(2-tert-butoxycarbonylamino-phenylcarbamoyl)-vinyl]-pyridin-2-yl}-1-methyl-pyrrolidine-3-carboxylic acid (LVII). The reaction is typically performed with standard peptide coupling reagents such as EDCI and HOBt, PyBrop and diisopropylethylamine, or HATU and triethylamine in a suitable inert solvent such as dichloromethane or dimethylformamide or mixtures thereof at room temperature for several hours.

Compounds of interest Im are obtained by deprotection of compounds LVIII. The reaction is typically performed in methanolic hydrogen chloride at room temperature over several hours.

L. General Synthetic Route for Synthesis of 6-Vinyl-Pyridin-3-yl R Analogues (Scheme 12)

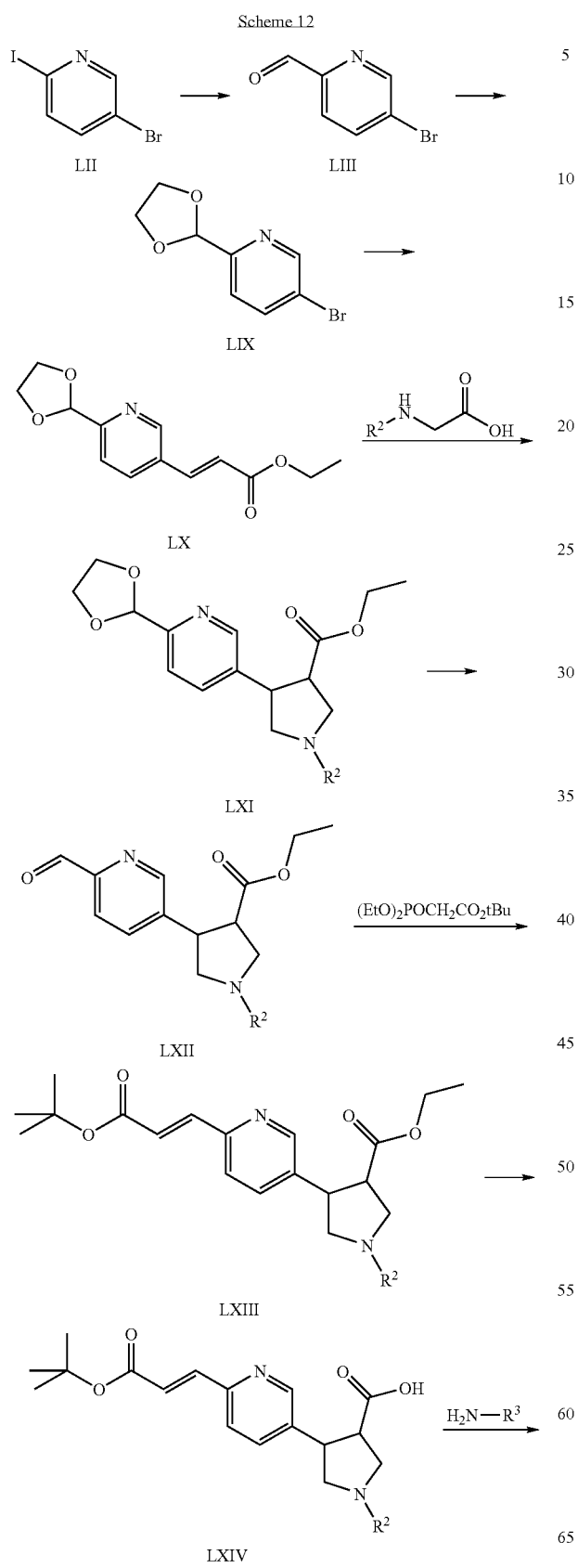

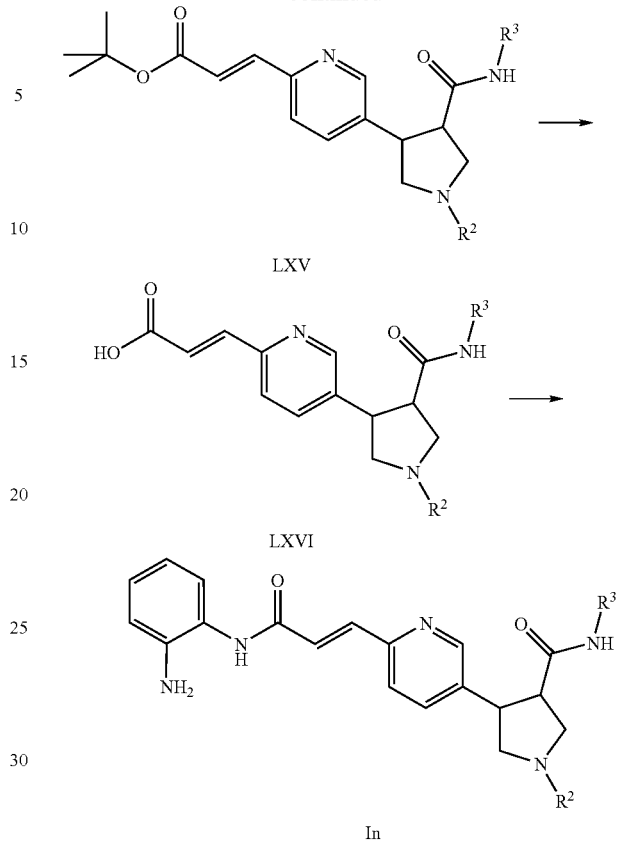

Compounds of interest In can be prepared according to Scheme 12. Starting with 2-iodopyridine LII, formylation and subsequent protection of aldehyde gives 5-bromo-pyridine LIX. Heck coupling of LIX with ethyl acrylate produces ethyl 3-(2-[1,3]-dioxolan-pyridinyl)-acrylate LX. Imminium ylide cycloaddition of cinnamate LX with substituted glycines and paraformaldehyde gives pyrrolidines LXI. Deprotection and subsequent condensation of 2-formylpyridine LXII with diethyl t-butyl phosphoacetate gives cinnamate t-butyl ester LXIII. Basic hydrolysis of LXIII to LXIV followed by coupling of various amines to LXIV furnishes amides LXV. Acidic hydrolysis of t-butyl ester LXV to cinnamic acids LXVI followed by coupling of ortho-1,2-phenylenediamine to LXVI generates compounds of interest In.

5-Bromo-pyridine-2-carbaldehyde (LIII) can be prepared from formylation of 5-bromo-2-iodo-pyridine LII (commercially available). The reaction can be carried out with a suitable Grignard reagent such as isopropylmagnesium chloride in an inert solvent such as tetrahydrofuran at −20 degrees Celsius for 2 hours first, and then with dimethylformamide at room temperature for 1 hour.

5-Bromo-2-[1,3]dioxolan-2-ylpyridine (LIX) can be prepared from protection of 5-bromo-pyridine-2-carbaldehyde (LIII) with ethane-1,2-diol. The reaction can be carried out with an acid such as para-toluenesulfonic acid in a suitable solvent such as toluene at reflux over several hours.

3-(6-[1,3]Dioxolan-2-yl-pyridin-3-yl)-acrylic acid ethyl ester (LX) can be prepared by Heck coupling of LIX with ethyl acrylate. The reaction is typically performed in deoxygenated dimethylformamide with triethylamine, tri-ortho-tolyl-phosphine, $Pd_2(dba)_3$, at 80-100 degrees Celsius for about four to ten hours under inert atmosphere.

Pyrrolidines (LXI) can be prepared from imminium ylide cycloaddition of substituted glycines and paraformaldehyde with LX. The reaction can be carried out in a suitable organic solvent such as toluene, typically at refluxing conditions over several hours in the presence of 3 Angstrom molecular sieves.

Aldehydes LXII can be prepared from deprotection of LXI with LiCl. The reaction can be carried out in a suitable solvent such as dimethylsulfoxide at 150 degrees Celsius under microwave irradiation.

Cinnamate tert-butyl ester LXIII can be prepared from condensation of LXII with diethyl tert-butyl phosphoacetate. The reaction can be carried out with a suitable base such as n-butyllithium in a suitable organic solvent such as tetrahydrofuran typically between −78 and zero degrees Celsius over several hours.

Acids LXIV can be prepared by hydrolysis of LXIII. The reaction is typically carried out with a suitable base such as lithium or sodium hydroxide in a suitable solvent mixture such as tetrahydrofuran and water or methanol and water at room temperature over several hours.

Amide compounds LXV can be prepared from coupling various amines with acids (LXIV). The reaction is typically performed with standard peptide coupling reagents such as EDCI and HOBt, PyBrop and diisopropylethylamine, or HATU and triethylamine in a suitable inert solvent such as dichloromethane or dimethylformamide or mixtures thereof at room temperature for several hours.

Cinnamic acids LXVI can be prepared by acidic hydrolysis of LXV. The reaction is typically carried out with a suitable acid such as trifluoroacetic acid in a suitable solvent such as tetrahydrofuran or dichloromethane at room temperature over several hours.

Compounds of interest In are obtained by coupling of acids LXVI with ortho-1,2-phenylenediamine. The reaction is typically performed with standard peptide coupling reagents such as EDCI and HOBt, PyBrop and diisopropylethylamine, or HATU and triethylamine in a suitable inert solvent such as dichloromethane or dimethylformamide or mixtures thereof at room temperature for several hours.

M. General Synthetic Route for Synthesis of 5-Vinyl-Pyrimidin2-yl R Analogues (Scheme 13)

Scheme 13

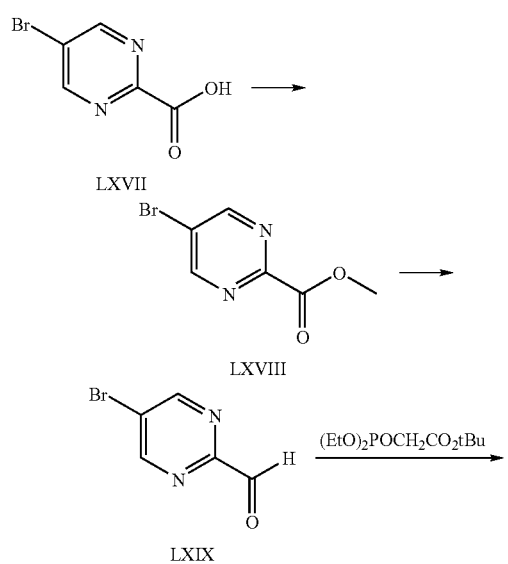

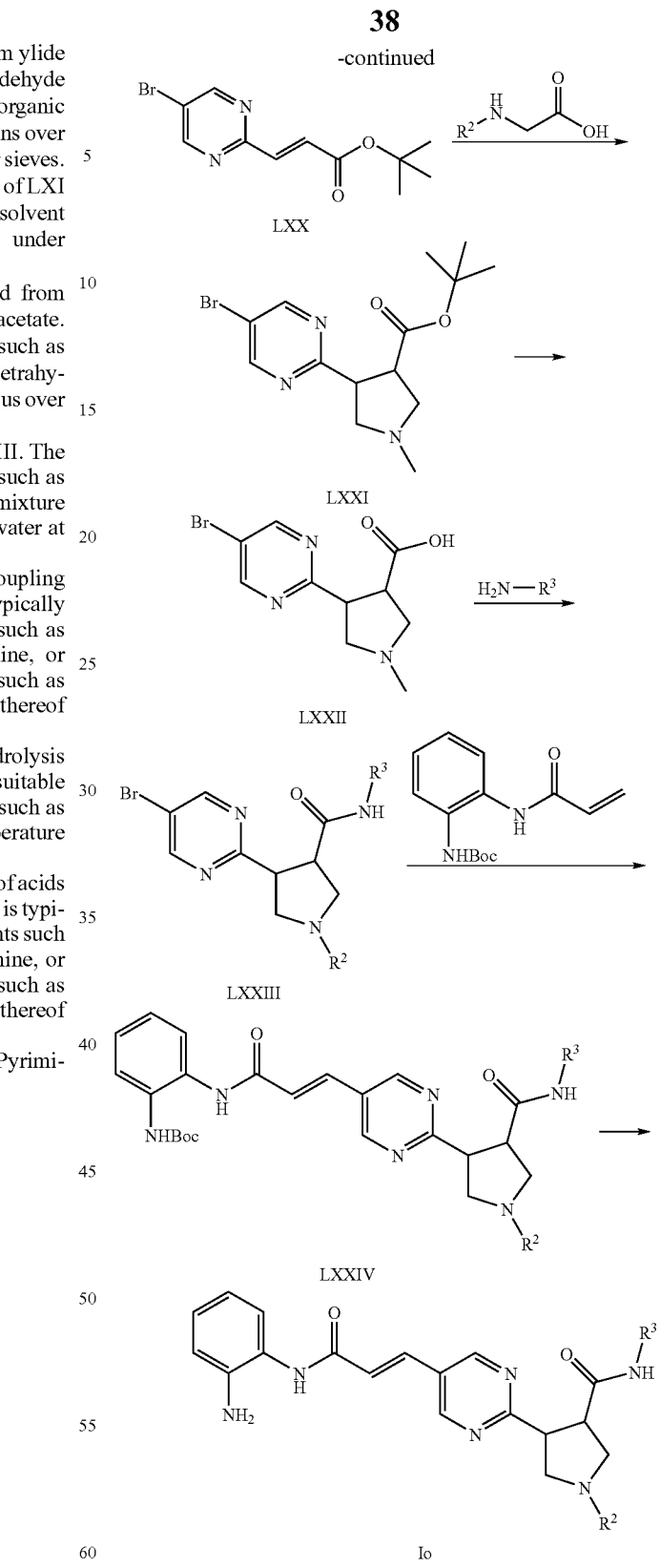

Compounds of interest Io can be prepared according to Scheme 13. 5-Bromo-2-pyrimidine carboxylic acid (LXVII) is esterified to methyl ester LXVIII, followed by reduction of LXVIII to aldehyde LXIX and subsequent condensation with phosphonium ylide to give t-butyl pyrimidine-2-acrylate (LXX). Imminium ylide cycloaddition of LXX with substituted glycines and paraformaldehyde gives pyrrolidines LXXI. Acidic hydrolysis of pyrrolidines LXXI to acids LXXII followed by coupling of various amines to LXXII furnishes amides LXXIII. Heck reaction coupling of (2-acryloylamino-phenyl)-carbamic acid tent-butyl ester with LXXIII provides cinnamides LXXIV. Acidic deprotection of the Boc protecting group generates compounds of interest Io.

5-Bromo-2-pyrimidine-carboxylic acid methyl ester (LXVIII) can be prepared from esterification of 5-bromo-2-pyrimidine-carboxylic acid (commercially available). The reaction is typically carried out with thionyl chloride in methanol at reflux over several hours to days.

5-Bromo-pyrimidine-2-carbaldehyde (LXIX) can be prepared from reduction of 5-bromo-2-pyrimidine-carboxylic acid methyl ester (LXVIII). The reaction can be carried out with a suitable reducing agent such as diisobutylaluminum hydride in an inert solvent such as tetrahydrofuran at −70 degrees Celsius for several hours.

3-(5-Bromo-pyrimidin-2-yl)-acrylic acid t-butyl ester (LXX) can be prepared from condensation of 5-bromo-pyrimidine-2-carbaldehyde with diethyl tent-butyl phosphonoacetate. The reaction can be carried out with a suitable base such as lithium n-butyl in a suitable organic solvent such as tetrahydrofuran typically at −78 degrees Celsius over several hours.

Pyrrolidines LXXI can be prepared from imminium glide cycloaddition of substituted glycines and paraformaldehyde with LXX. The reaction can be carried out in a suitable organic solvent such as toluene, typically at refluxing conditions over several hours in the presence of 3 Angstrom molecular sieves.

Acids LXXII can be prepared by acidic hydrolysis of LXXI. The reaction is typically carried out with a suitable acid such as trifluoroacetic acid in a suitable solvent such as tetrahydrofuran or dichloromethane at zero degrees Celsius over several hours.

Amide compounds LXXIII can be prepared from coupling various amines with acids LXXII. The reaction is typically performed with standard peptide coupling reagents such as EDCI and HOBt, PyBrop and diisopropylethylamine, or HATU and triethylamine in a suitable inert solvent such as dichloromethane or dimethylformamide or mixtures thereof at room temperature for several hours.

Pyrimidine-5-acrylamides LXXIV can be prepared by Heck coupling of LXXIII with (2-acryloylamino-phenyl)-carbamic acid tent-butyl ester. The reaction is typically performed in deoxygenated dimethylformamide with triethylamine, tri-ortho-tolyl-phosphine, Pd$_2$(dba)$_3$, at 80-100 degrees Celsius for about four to ten hours under inert atmosphere.

Compounds of interest Io are obtained by deprotection of compounds LXXIV. The reaction is typically performed in methanolic hydrogen chloride at room temperature over several hours.

N. General Synthetic Route for Synthesis of 2-Fluoro-4-Vinyl-Phenyl R Analogues (Scheme 14)

Scheme 14

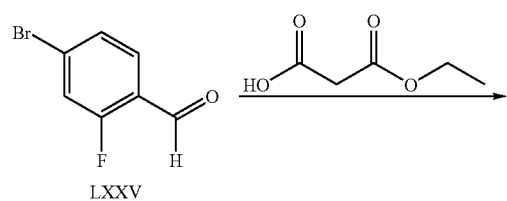

LXXV

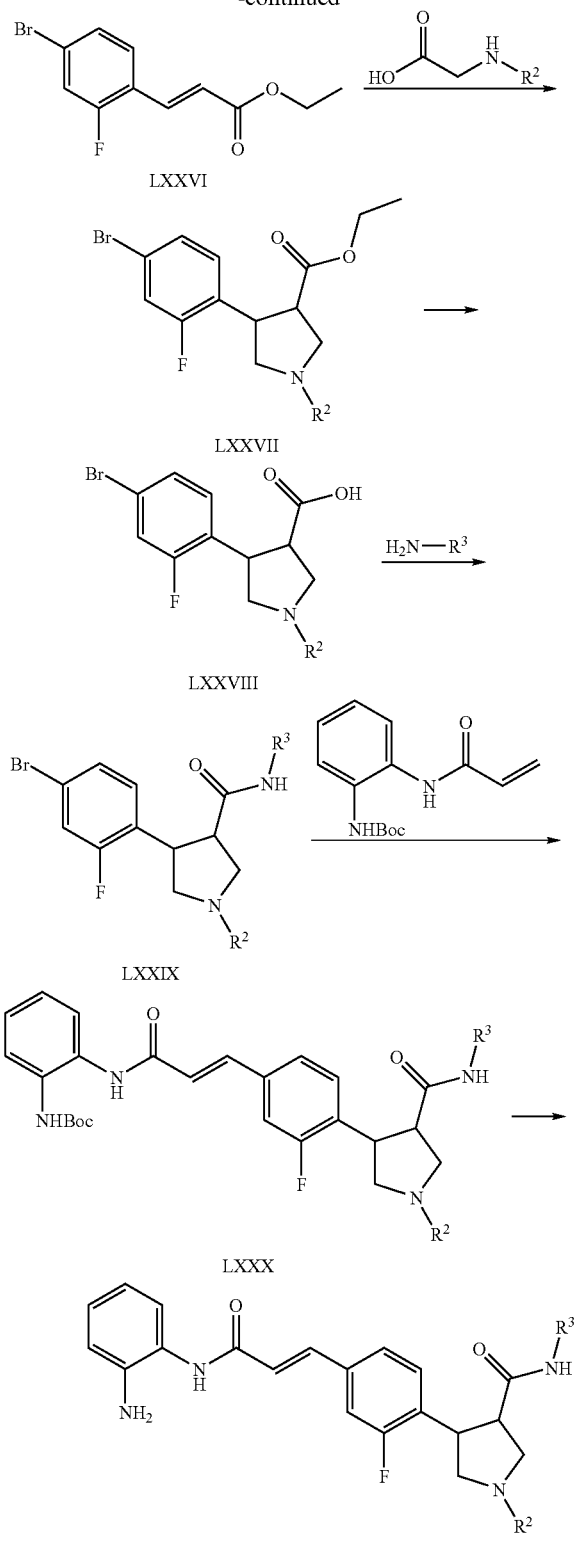

Compounds of interest Ip can be prepared according to Scheme 14. Starting with aldehyde LXXV, condensation of LXXV with malonic monoethyl ester gives ethyl ester LXXVI. Imminium glide cycloaddition of LXXVI with substituted glycines and paraformaldehyde gives pyrrolidines LXXVII. Basic hydrolysis of pyrrolidines LXXVII to acids LXXVIII followed by coupling of various amines to LXXVIII furnishes amides LXXIX. Heck reaction coupling of (2-acryloylamino-phenyl)-carbamic acid tert-butyl ester with LXXIX provides cinnamides LXXX. Acidic deprotection of the Boc protecting group generates compounds of interest Ip.

3-(4-Bromo-2-fluoro-phenyl)-acrylic acid ethyl ester (LXXVI) can be prepared from condensation of 4-bromo-2-fluorobenzaldehyde (commercially available) with malonic acid monoethyl ester. The reaction can be carried out in a suitable organic solvent such as dimethylformamide, typically at 100 degrees Celsius over several hours.

Pyrrolidines LXXVII can be prepared from imminium ylide cycloaddition of substituted glycines and paraformaldehyde with LXXVI. The reaction can be carried out in a suitable organic solvent such as toluene, typically at refluxing conditions over several hours in the presence of 3 Angstrom molecular sieves.

Pyrrolidine-3-carboxylic acids LXXVIII can be prepared by hydrolysis of pyrrolidines LXXVII. The reaction is typically carried out with a suitable base such as sodium or lithium hydroxide in a suitable solvent mixture such as tetrahydrofuran and water or methanol and water at room temperature over several hours.

Amide compounds LXXIX can be prepared from coupling various amines with pyrrolidine-3-carboxylic acids LXXVIII. The reaction is typically performed with standard peptide coupling reagents such as EDCI and HOBt, PyBrop and diisopropylethylamine, or HATU and triethylamine in a suitable inert solvent such as dichloromethane or dimethylformamide or mixtures thereof at room temperature for several hours.

Cinnamides LXXX can be prepared by Heck coupling of LXXIX with (2-acryloylamino-phenyl)-carbamic acid tert-butyl ester. The reaction is typically performed in deoxygenated dimethylformamide with triethylamine, tri-ortho-tolylphosphine, Pd$_2$(dba)$_3$, at 80-100 degrees Celsius for about four to ten hours under inert atmosphere.

Compounds of interest Ip are obtained by deprotection of compounds LXXX. The reaction is typically performed in methanolic hydrogen chloride at room temperature over several hours.

O. General Synthetic Route for Synthesis of 3-Fluoro-4-Vinyl-Phenyl R Analogues (Scheme 15)

Scheme 15

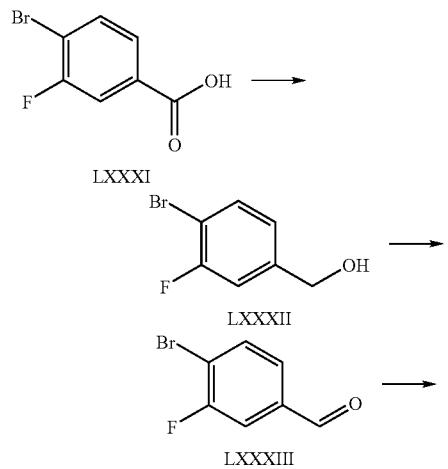

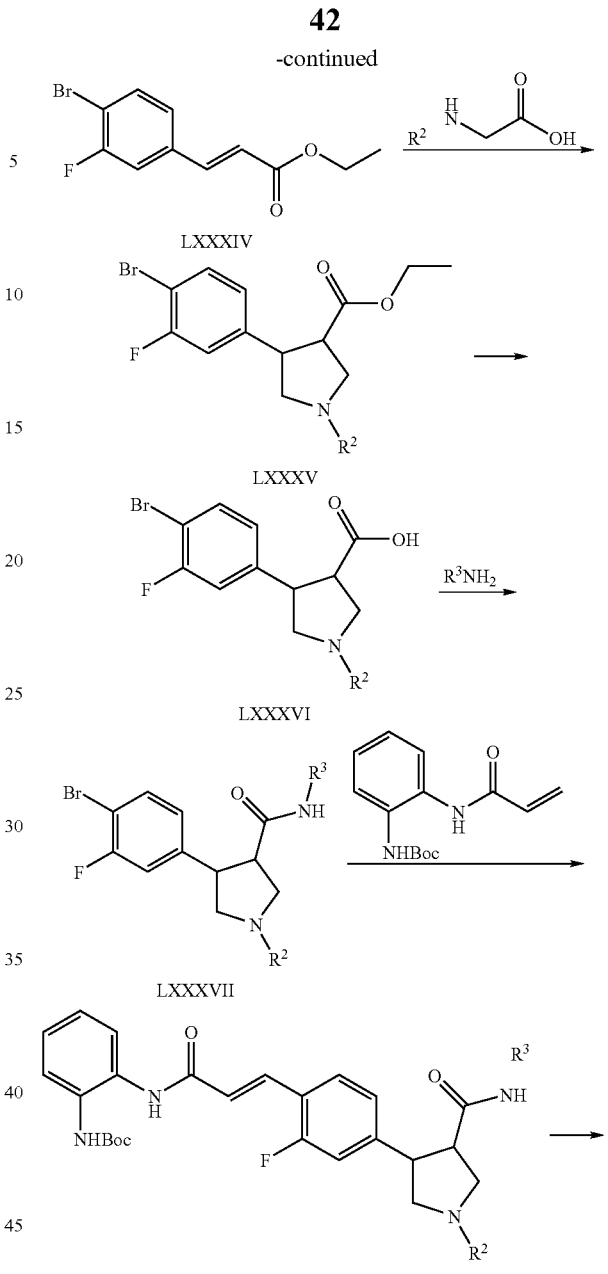

Compounds of interest Iq can be prepared according to Scheme 15. Starting with acid LXXXI, reduction of acid to alcohol LXXXII and subsequent oxidation of alcohol gives aldehyde LXXXIII Condensation of LXXXIII with malonic monoethyl ester gives cinnamate ethyl ester LXXXIV. Imminium ylide cycloaddition of LXXXIV with substituted glycines and paraformaldehyde gives pyrrolidines LXXXV.

Basic hydrolysis of pyrrolidines LXXXV to acids LXXXVI followed by coupling of various amines to LXXXVI furnishes amides LXXXVII. Heck reaction coupling of (2-acryloylamino-phenyl)-carbamic acid tent-butyl ester with LXXXVII provides cinnamides LXXXVIII. Acidic deprotection of the Boc protecting group generates compounds of interest Iq.

(4-Bromo-3-fluoro-phenyl)-methanol (LXXXII) can be prepared from reduction of 4-bromo-3-fluoro-benzoic acid LXXXI (commercially available) with borane. The reaction is typically carried out in a suitable organic solvent such as tetrahydrofuran at reflux for several hours.

4-Bromo-3-fluoro-benzaldehyde (LXXXIII) can be prepared from oxidation of (4-bromo-3-fluoro-phenyl)-methanol (LXXXII) with MnO$_2$. The reaction can be carried out in a suitable solvent such as dichloromethane at room temperature for 0.5-3 hours.

3-(4-Bromo-3-fluoro-phenyl)-acrylic acid ethyl ester (LXXXIV) can be prepared from condensation of 4-bromo-3-fluorobenzaldehyde (LXXXIII) with malonic acid monoethyl ester. The reaction can be carried out in a suitable organic solvent such as dimethylformamide, typically at 100 degrees Celsius over several hours.

Pyrrolidines LXXXV can be prepared from imminium ylide cycloaddition of substituted glycines and paraformaldehyde with LXXXIV. The reaction can be carried out in a suitable organic solvent such as toluene, typically at refluxing conditions over several hours in the presence of 3 Angstrom molecular sieves.

Pyrrolidine-3-carboxylic acids LXXXVI can be prepared by hydrolysis of pyrrolidines LXXXV. The reaction is typically carried out with a suitable base such as sodium or lithium hydroxide in a suitable solvent mixture such as tetrahydrofuran and water or methanol and water at room temperature over several hours.

Amide compounds LXXXVII can be prepared from coupling various amines with pyrrolidine-3-carboxylic acids LXXXVI. The reaction is typically performed with standard peptide coupling reagents such as EDCI and HOBt, PyBrop and diisopropylethylamine, or HATU and triethylamine in a suitable inert solvent such as dichloromethane or dimethylformamide or mixtures thereof at room temperature for several hours.

Cinnamides LXXXVIII can be prepared by Heck coupling of LXXXVII with (2-acryloylamino-phenyl)-carbamic acid tent-butyl ester. The reaction is typically performed in deoxygenated dimethylformamide with triethylamine, tri-ortho-tolyl-phosphine, Pd$_2$(dba)$_3$, at 80-100 degrees Celsius for about four to ten hours under inert atmosphere.

Compounds of interest Iq are obtained by deprotection of compounds LXXXVIII. The reaction is typically performed in methanolic hydrogen chloride at room temperature over several hours.

P. General Synthetic Route for Synthesis of 2,6-Difluoro-4-Vinyl-Phenyl R Analogues (Scheme 16)

Scheme 16

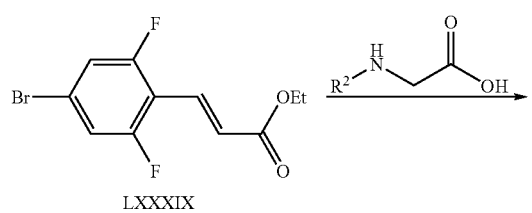

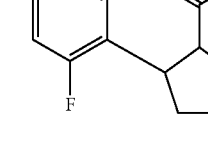

XC

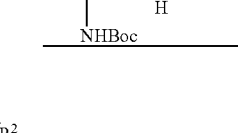

XCI

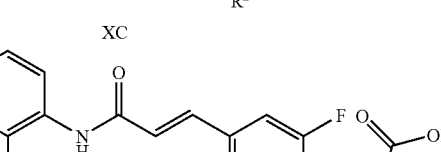

XCII

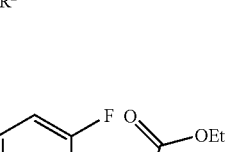

XCIII

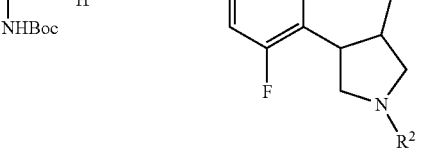

Ir

Compounds of interest Ir can be prepared according to Scheme 16. Starting with cinnamate ethyl ester LXXXIX, imminium ylide cycloaddition with substituted glycines and paraformaldehyde gives pyrrolidines XC. Heck reaction coupling of (2-acryloylamino-phenyl) -carbamic acid tent-butyl ester with XC provides cinnamides XCI. Basic hydrolysis of cinnamides XCI to acids XCII followed by coupling of various amines to XCII furnishes amides XCIII. Acidic deprotection of the Boc protecting group generates compounds of interest Ir.

3-(4-Bromo-2,6-difluoro-phenyl)-acrylic acid ethyl ester (LXXXIX) can be prepared from condensation of 4-bromo- 2,6-difluoro-benzaldehyde (commercially available) with malonic acid monoethyl ester. The reaction can be carried out in a suitable organic solvent such as dimethylformamide, typically at 100 degrees Celsius over several hours.

Pyrrolidines XC can be prepared from imminium ylide cycloaddition of substituted glycines and paraformaldehyde with LXXXIX. The reaction can be carried out in a suitable organic solvent such as toluene, typically at refluxing conditions over several hours in the presence of 3 Angstrom molecular sieves.

Cinnamides XCI can be prepared by Heck coupling of XC with (2-acryloylamino-phenyl) -carbamic acid tent-butyl ester. The reaction is typically performed in deoxygenated dimethylformamide with triethylamine, tri-ortho-tolyl-phosphine, Pd$_2$(dba)$_3$, at 80-100 degrees Celsius for about four to ten hours under inert atmosphere.

Pyrrolidine-3-carboxylic acids XCII can be prepared by hydrolysis of XCI. The reaction is typically carried out with a suitable base such as sodium or lithium hydroxide in a suitable solvent mixture such as tetrahydrofuran and water or methanol and water at room temperature over several hours.

Amide compounds XCIII can be prepared from coupling various amines with pyrrolidine-3-carboxylic acids XCII. The reaction is typically performed with standard peptide coupling reagents such as EDCI and HOBt, PyBrop and diisopropylethylamine, or HATU and triethylamine in a suitable inert solvent such as dichloromethane or dimethylformamide or mixtures thereof at room temperature for several hours.

Compounds of interest Ir are obtained by deprotection of compounds XCIII. The reaction is typically performed in methanolic hydrogen chloride at room temperature over several hours.

Q. General Synthetic Route for Racemic Synthesis of Key Intermediate VII (Scheme 17)

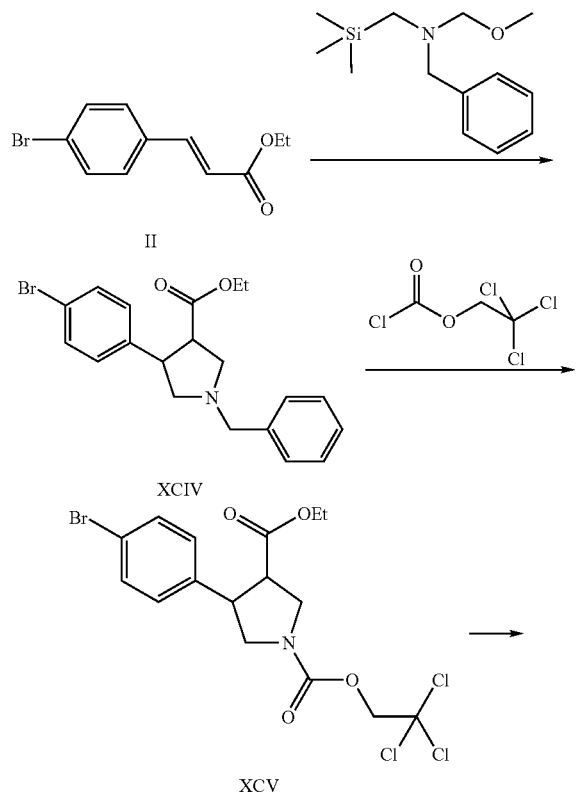

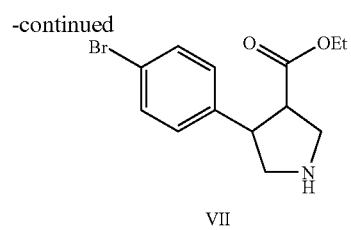

Compound of interest VII can be prepared according to Scheme 17. Starting with cinnamate ethyl ester II, imminium ylide cycloaddition with benzyl-methoxymethyl-trimethylsilanyl-methyl-amine gives pyrrolidine XCIV. De-benzylation of the benzyl protecting group in XCIV and subsequent reduction of XCV provides compound of interest VII.

3-(4-Bromo-phenyl)-acrylic acid ethyl ester (II) can be prepared from condensation of 4-bromobenzaldehyde with malonic acid monoethyl ester. The reaction can be carried out in a suitable organic solvent such as dimethylformamide, typically at 100 degrees Celsius over several hours.

Benzyl-4-(4-bromo-phenyl)-pyrrolidine-3-carboxylic acid ethyl ester (XCIV) can be prepared from imminium ylide cycloaddition of benzyl-methoxymethyl-trimethylsilanyl-methyl-amine (commercially available) with II. The reaction can be carried out in a suitable organic solvent such as toluene or dichloromethane, typically at room temperature over several hours to days in the presence of acid such as orthoboric acid.

4-(4-Bromo-phenyl)-pyrrolidine-1,3-dicarboxylic acid 3-ethyl ester 1-(2,2,2-trichloro-ethyl)ester (XCV) can be prepared from 1-benzyl-4-(4-bromo-phenyl)-pyrrolidine-3-carboxylic acid ethyl ester (XCIV) with 2,2,2-trichloroethyl chloroformate. The reaction can be carried out in a suitable solvent such as acetonitrile between room temperature and 60 degrees Celsius in the presence of a suitable base such as potassium carbonate over several hours.

4-(4-Bromo-phenyl)-pyrrolidine-3-carboxylic acid ethyl ester (VII) can be prepared from reduction of 4-(4-bromo-phenyl)-pyrrolidine-1,3-dicarboxylic acid 3-ethyl ester 1-(2,2,2-trichloro-ethyl)ester (XCV) with zinc. The reaction is typically carried out in a suitable solvent such as acetic acid at room temperature over several hours.

R. General Synthetic Route for Enantioselective Synthesis of Key Intermediate VII (Scheme 18)

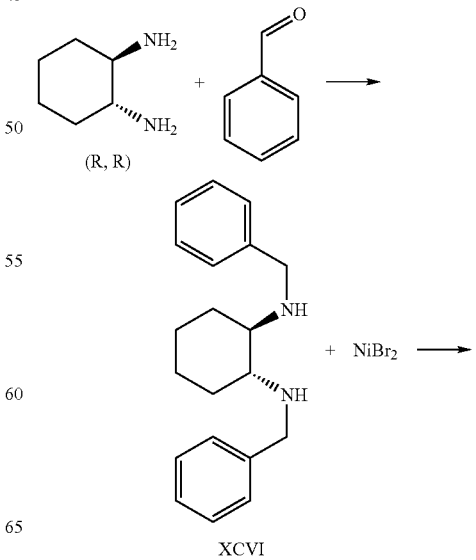

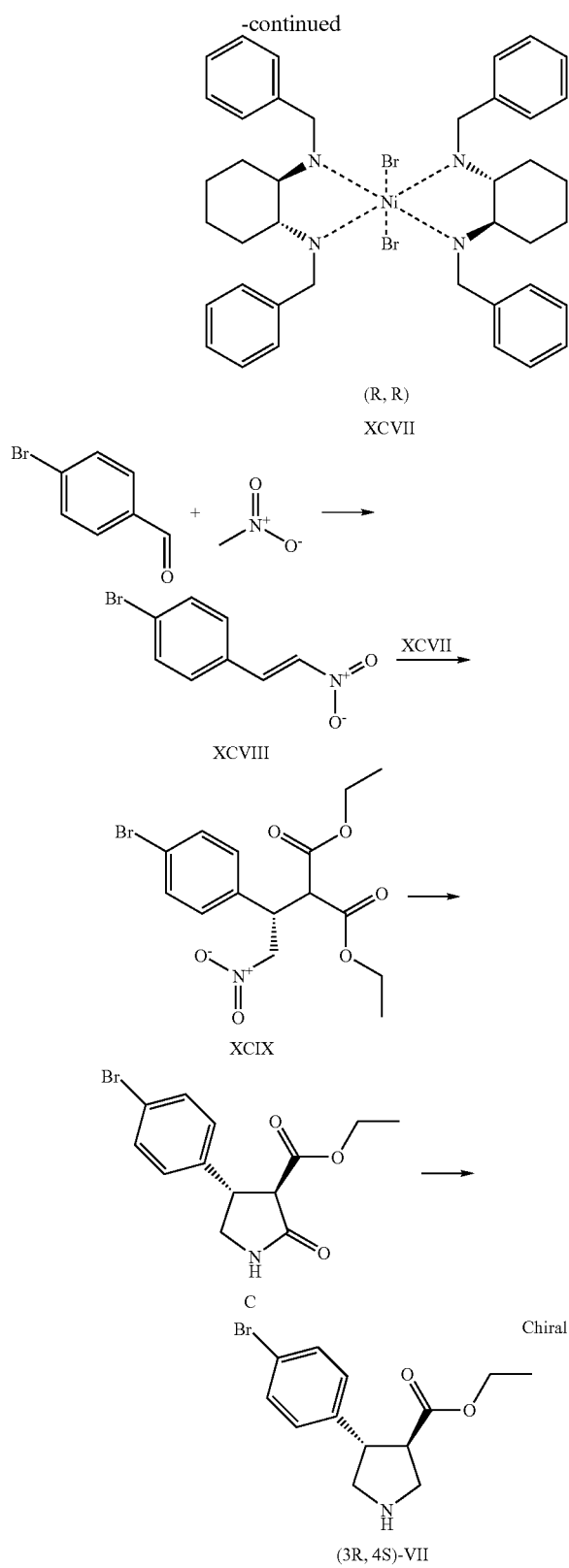

lidinone C to 2-methoxy-4,5-dihydro-3H-pyrrole and subsequent reduction of 2-methoxy-4,5-dihydro-3H-pyrrole provides compound of interest (3R,4S)-VII.

(R,R)-N,N'-Dibenzyl-cyclohexane-1,2-diamine (XCVI) can be prepared from reductive amination of benzaldehyde with (R,R)-cyclohexane-1,2-diamine. The reaction is typically carried out with a suitable reducing agent such as sodium cyanoborohydride in an organic solvent such as dichloromethane or methanol, typically at reflux for several hours.

(R,R)-Chiral catalyst XCVII can be prepared from (R,R)-N,N'-dibenzyl-cyclohexane-1,2-diamine XCVI with $NiBr_2$. The reaction can be carried out in a suitable solvent such as acetonitrile at reflux over several hours.

Bromo-4-(2-nitro-vinyl)-benzene XCVIII can be prepared from condensation of 4-bromo-benzaldehyde with nitromethane. The reaction is typically carried out in the presence of ammonium acetate in acetic acid at 100 degrees Celsius over several hours.

2-[1-(4-Bromo-phenyl)-2-nitro-ethyl]-malonic acid diethyl ester (XCIX) can be prepared from Michael addition of 1-Bromo-4-(2-nitro-vinyl)-benzene XCVIII with malonic acid diethyl ester (commercially available). The reaction can be carried out in a suitable solvent such as toluene in presence of (R,R)-Chiral catalyst XCVII at reflux for over several hours to days.

4-(4-Bromo-phenyl)-2-oxo-pyrrolidine-3-carboxylic acid ethyl ester (C) can be prepared from reduction of nitro group in XCIX with zinc and subsequent cyclization of the amine. The reaction can be carried out in a suitable solvent such as methanol in the presence of concentrated hydrogen chloride at room temperature for several hours.

(3R,4S)-4-(4-Bromo-phenyl)-pyrrolidine-3-carboxylic acid ethyl ester ((3R,4S)-VII) can be prepared from conversion of 4-(4-bromo-phenyl)-2-oxo-pyrrolidine-3-carboxylic acid ethyl ester (C) to 4-(4-bromo-phenyl)-2-methoxy-4,5-dihydro-3H-pyrrole-3-carboxylic acid ethyl ester with trimethyloxonium tetrafluoroborate and subsequent reduction of 2-methoxy-4,5-dihydro-3H-pyrrole. Conversion of 4-(4-bromo-phenyl)-2-oxo-pyrrolidine-3-carboxylic acid ethyl ester (C) to 4-(4-bromo-phenyl)-2-methoxy-4,5-dihydro-3H-pyrrole-3-carboxylic acid ethyl ester can be carried out in an inert solvent such as tetrahydrofuran at room temperature for several hours to days. The reduction can be carried out with a suitable reducing reagent such as sodium cyanoborohydride in an organic solvent such as methanol in presence of dichloromethane at room temperature for over several hours.

EXAMPLES

The following examples were prepared by the general methods outlined in the schemes above. They are intended to illustrate the meaning of the present invention but should by no means represent a limitation within the meaning of the present invention:

Example 1

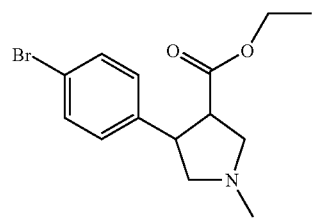

rac-(trans-3,4)-4-(4-Bromo-phenyl)-1-methyl-pyrrolidine-3-carboxylic acid ethyl ester A mixture of sarcosine (44.5 g, 0.5 mol, 2.5 equiv), paraformaldehyde (60 g, 2 mol, 10 equiv), and the ethyl (3R,4S)-Enantiomer of compound VII can be prepared according to Scheme 18. Starting with 1-bromo-4-(2-nitro-vinyl)-benzene XCVIII, steroselective Michael addition of malonic acid diethyl ester with XCVIII gives XCIX. Reduction of the nitro group in compound XCIX and subsequent cyclization furnishes pyrrolidinone C. Conversion of pyrrocinnamate (50 g, 196 mmol, 1 equiv) was heated under reflux in toluene (500 mL). The H₂O formed was removed with the aid of a Dean-Stark trap. After 4 hours, the cooled mixture was filtered. The filtrate was concentrated. The residue was purified by chromatography on silica gel eluted with hexane-EtOAc to give 28 g of product (yield was 46%) and 26 g of starting material ethyl cinnamate (52%). MS: calc'd (MH+) 312, exp (MH+) 312. ¹H NMR (CDCl₃, 400 MHz), 7.48 (d, 1H, J=8.4 Hz), 7.29 (d, 2H, J=8.4 Hz), 4.15 (q, 2H, 6.8 Hz), 3.51 (m, 1H), 3.30 (m, 2H), 3.20 (m, 2H), 2.72 (s, 3H), 1.21 (t, 3H, 6.8 Hz).

Example 2

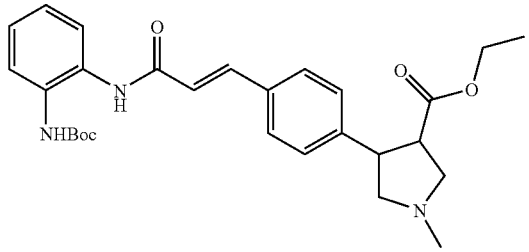

rac-(trans-3,4)-4-{4-[2-(2-tert-Butoxycarbonylamino-phenylcarbamoyl)-vinyl]-phenyl}-1-methyl-pyrrolidine-3-carboxylic acid ethyl ester The mixture of compound rac-(trans-3,4)-4-(4-bromophenyl)-1-methyl-pyrrolidine-3-carboxylic acid ethyl ester (10.3 g, 33 mmol), (2-acryloylamino-phenyl)-carbamic acid tert-butyl ester (9.51 g, 36.3 mmol), Pd₂(dba)₃ (300 mg, 0.33 mmol), P(o-tolyl)₃ (1.0 g, 3.3 mmol) in DMF (50 mL) and TEA (9 mL, 66 mmol) was stirred at 110 degrees Celsius under N₂ in a sealed tube overnight. LC-MS indicated that the reaction was completed. The cooled mixture was partitioned between water and ethyl acetate. The organic phase was dried and concentrated. The residue was purified by chromatography on silica gel eluted by dichloromethane to give 14.22 g of desired product (yield was 87%). MS: calc'd (MH+) 494, exp (MH+) 494.

Example 3

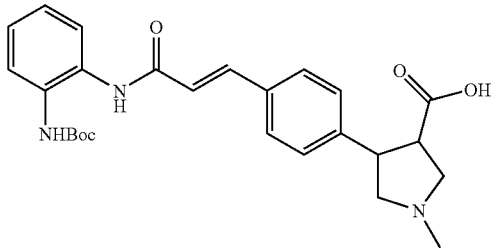

rac-(trans-3,4)-4-{4-[2-(2-tert-Butoxycarbonylamino-phenylcarbamoyl)-vinyl]-phenyl}-1-methyl-pyrrolidine-3-carboxylic acid Lithium hydroxide monohydrate (2.42 g, 57.6 mmol) in water (20 mL) was added to a solution of compound rac-(trans-3,4)-4-{4-[2-(2-tert-butoxycarbonylamino-phenylcarbamoyl)-vinyl]-phenyl}-1-methyl-pyrrolidine-3-carboxylic acid ethyl ester (14.22 g, 28.8 mmol) in methanol (80 mL). Then the mixture was stirred at room temperature overnight. LC-MS indicated that the start material was consumed. The mixture was adjusted to pH=6-8 with 6 N HCl. The solvent was removed to give crude product which was used in the next step without further purification. ¹H NMR (CD₃OD, 400 MHz), 7.81 (d, 1H, J=15.6 Hz), 7.76 (d, 2H, J=7.6 Hz), 7.70 (d, 1H, J=7.6 Hz), 7.62 (d, 1H, J=7.6 Hz), 7.58 (d, 2H, J=8.0 Hz), 7.36 (t, 1H, J=7.2 Hz), 7.29 (t, 1H, J=7.2 Hz), 6.97 (d, 1H, J=15.6 Hz), 4.02-3.84 (m, 2H), 3.82-3.64 (m, 2H), 3.33-3.26 (m, 2H), 3.12 (s, 3H), 1.63 (s, 9H).

Example 4

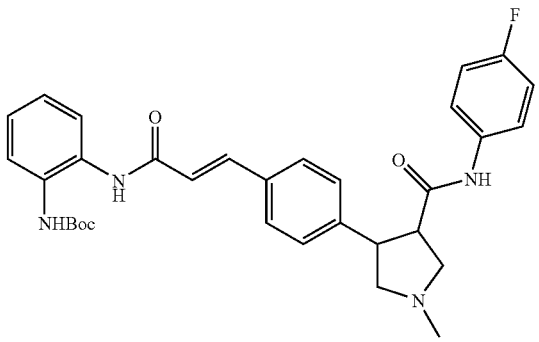

rac-[2-(3-{4-[(trans-3,4)-4-(4-Fluoro-phenylcarbamoyl)-1-methyl-pyrrolidin-3-yl]-phenyl}-acryloylamino)-phenyl]-carbamic acid tert-butyl ester HATU (13.3 g, 35 mmol) was added to a solution of compound rac-(trans-3,4)-4-{4-[2-(2-amino-phenylcarbamoyl)-vinyl]-phenyl}-1-methyl-pyrrolidine-3-carboxylic acid (crude material, 28.8 mmol) and 4-fluoro-phenylamine (3.55 g, 32 mmol) in TEA (10 mL, 72 mmol), DMF (30 mL) and dichloromethane (300 mL) at rt. Then the mixture was stirred at rt for 3 hours. LC-MS indicated that the reaction was completed. The mixture was partitioned between water and dichloromethane. The organic phase was dried and concentrated. The residue was purified by chromatography on silica gel to give 14.1 g of product (yield was 88% for 2 steps). MS: calc'd (MH+) 559, exp (MH+) 559.

Example 5

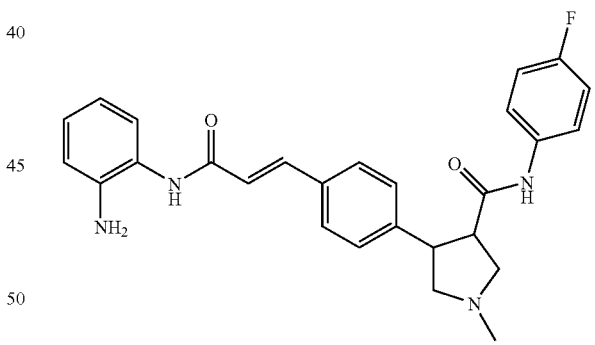

rac-(trans-3,4)-4-{4-[2-(2-Amino-phenylcarbamoyl)-vinyl]-phenyl}-1-methyl-pyrrolidine-3-carboxylic acid (4-fluoro-phenyl)-amide The compound rac-[2-(3-{4-[(trans-3,4)-4-(4-fluoro-phenylcarbamoyl)-1-methyl-pyrrolidin-3-yl]-phenyl}-acryloylamino)-phenyl]-carbamic acid tert-butyl ester (14.5 g, 25.3 mmol) was dissolved in 150 mL of MeOH (with 1N HCl) and stirred for 4 hours. LC-MS indicated that the reaction was completed. The solvent was removed and the residue was basified with TEA and purified by prep-HPLC to give 5 g of product. MS: calc'd (MH+) 459, exp (MH+) 459. ¹H NMR (CD₃OD, 400 MHz), 7.63-7.58 (m, 3H), 7.53-7.50 (m, 2H), 7.40 (d, 2H, J=8.0 Hz), 7.21 (d, 1H, J=7.6 Hz), 7.08-7.00 (m, 3H), 6.90-6.74 (m, 3H), 3.85 (m, 1H), 3.21-3.11 (m, 3H), 2.97-2.93 (m, 2H), 2.50 (s, 3H).

Compounds 5-2 through 5-47 described in the following tables were prepared by methods analogous to the preparation of Example 5 described above, by combining Example 3 with the appropriate starting materials indicated in Table 1. Compounds that are specifically indicated as chiral were obtained via chiral separation.

TABLE 1

Starting materials and MS data of examples 5-2 to 5-47

| Example # | Structure | Starting Material |
|---|---|---|
| 5-2 | 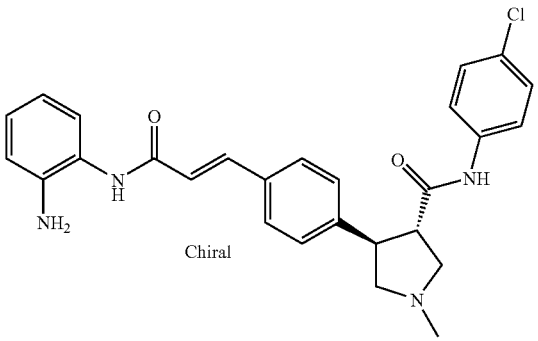 MW 474.99; MH+ calc. 475; MH+ expt. 475 | 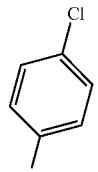 commercially available |
| 5-3 | 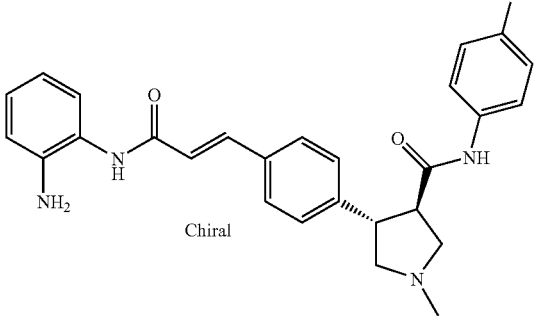 MW 474.99; MH+ calc. 475; MH+ expt. 475 | 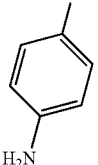 commercially available |
| 5-4 | 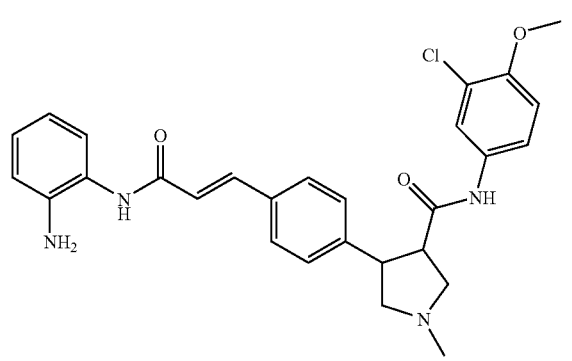 MW 505.02; MH+ calc. 505; MH+ expt. 505 | 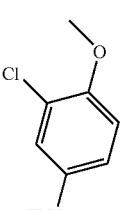 commercially available |

TABLE 1-continued

Starting materials and MS data of examples 5-2 to 5-47

| Example # | Structure | Starting Material |
|---|---|---|
| 5-5 | MW 533.47; MH$^+$ calc. 533; MH$^+$ expt. 533 | commercially available |
| 5-6 | MW 472.57; MH$^+$ calc. 473; MH$^+$ expt. 473 | commercially available |
| 5-7 | MW 488.57; MH$^+$ calc. 489; MH$^+$ expt. 489 | commercially available |
| 5-8 | MW 458.54; MH$^+$ calc. 459; MH$^+$ expt. 459 | commercially available |

TABLE 1-continued
Starting materials and MS data of examples 5-2 to 5-47
| Example # | Structure | Starting Material |
|---|---|---|
| 5-9 | 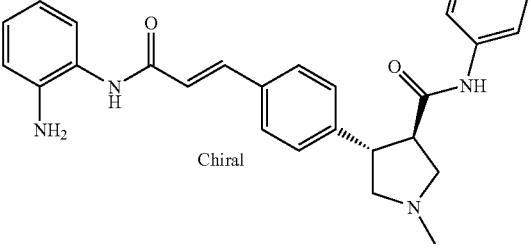<br>Chiral<br>MW 458.54; MH+ calc. 459; MH+ expt. 459 | 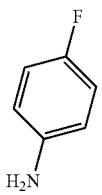<br>commercially available |
| 5-10 | 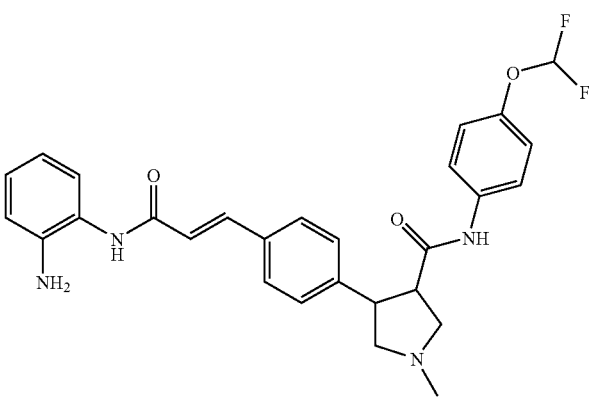<br>MW 506.56; MH+ calc. 507; MH+ expt. 507 | 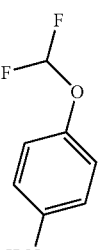<br>commercially available |
| 5-11 | 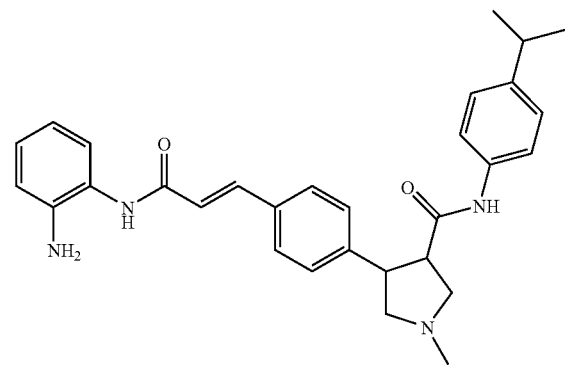<br>MW 482.63; MH+ calc. 483; MH+ expt. 483 | 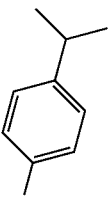<br>commercially available |

TABLE 1-continued
Starting materials and MS data of examples 5-2 to 5-47
| Example # | Structure | Starting Material |
|---|---|---|
| 5-12 | 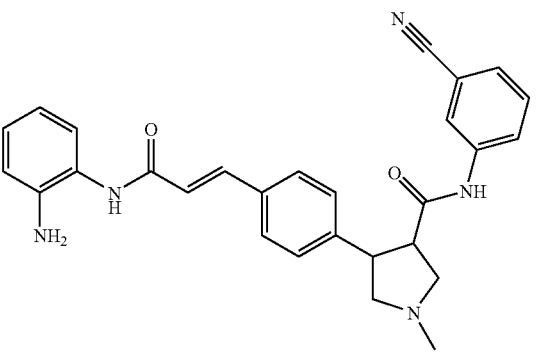<br>MW 465.56; MH+ calc. 466; MH+ expt. 466 | 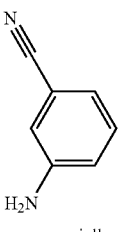<br>commercially available |
| 5-13 | 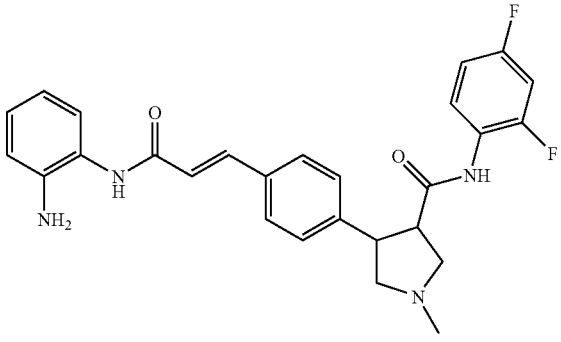<br>MW 476.53; MH+ calc. 477; MH+ expt. 477 | 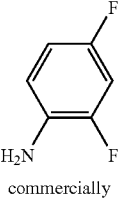<br>commercially available |
| 5-14 | 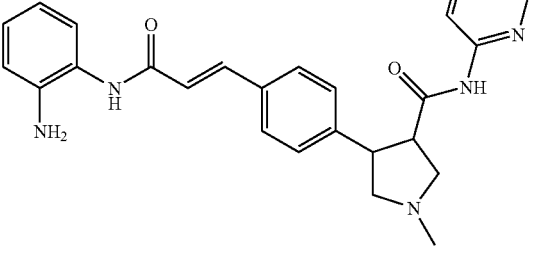<br>MW 475.98; MH+ calc. 476; MH+ expt. 476 | 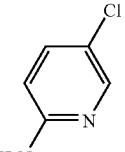<br>commercially available |
| 5-15 | 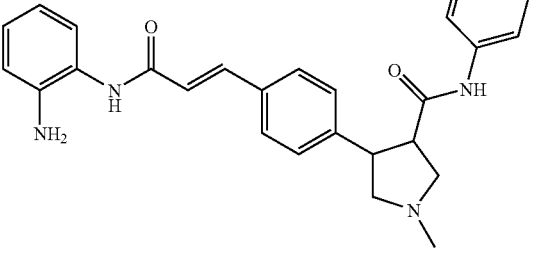<br>MW 505.01; MH+ calc. 505; MH+ expt. 505 | 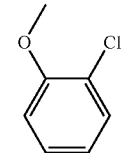<br>commercially available |

TABLE 1-continued
Starting materials and MS data of examples 5-2 to 5-47
| Example # | Structure | Starting Material |
|---|---|---|
| 5-16 | 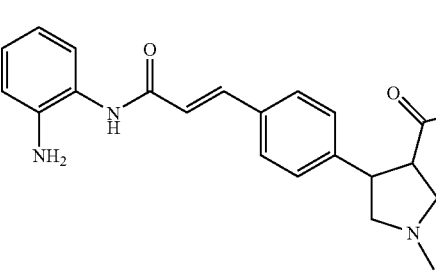 MW 458.54; MH+ calc. 459; MH+ expt. 459 | 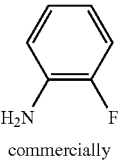 commercially available |
| 5-17 | 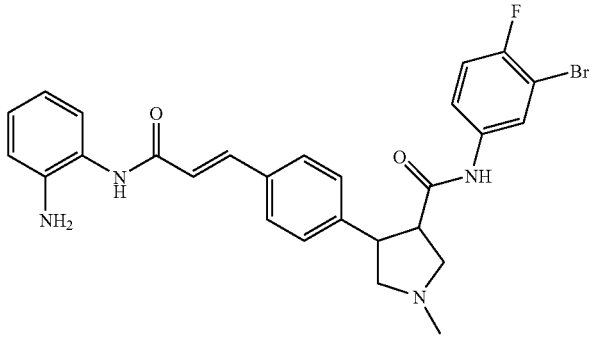 MW 537.44; MH+ calc. 537; MH+ expt. 537 | 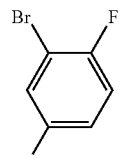 commercially available |
| 5-18 | 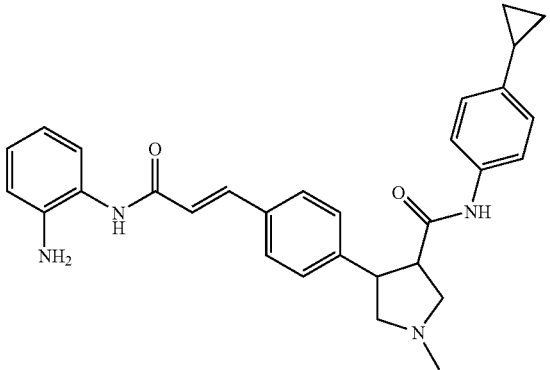 MW 480.62; MH+ calc. 481; MH+ expt. 481 | 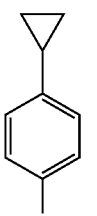 commercially available |
| 5-19 | 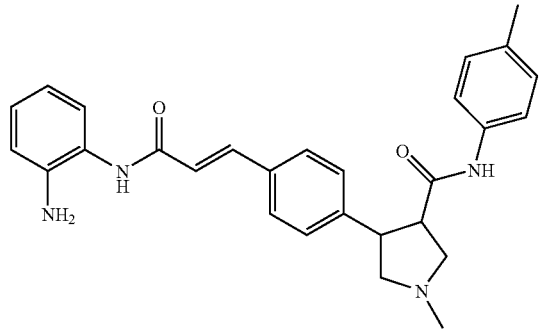 MW 454.58; MH+ calc. 455; MH+ expt. 455 | 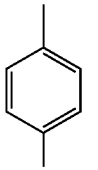 commercially available |

TABLE 1-continued
Starting materials and MS data of examples 5-2 to 5-47
| Example # | Structure | Starting Material |
|---|---|---|
| 5-20 | 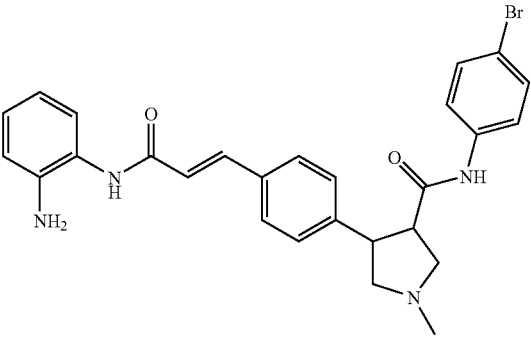 MW 519.45; MH+ calc. 519; MH+ expt. 519 | 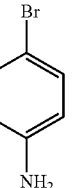 commercially available |
| 5-21 | 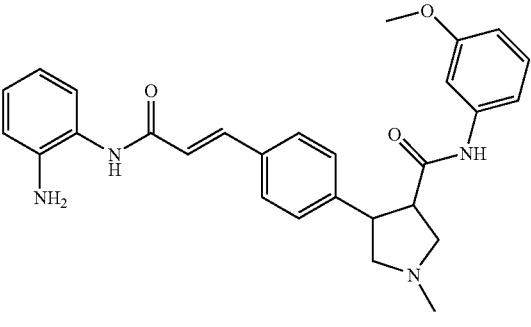 MW 470.58; MH+ calc. 471; MH+ expt. 471 | 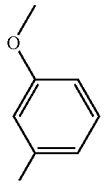 commercially available |
| 5-22 | 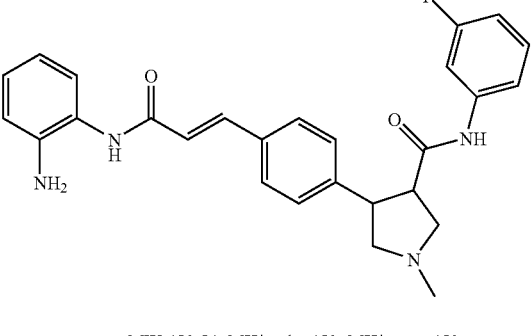 MW 458.54; MH+ calc. 459; MH+ expt. 459 | 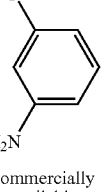 commercially available |
| 5-23 | 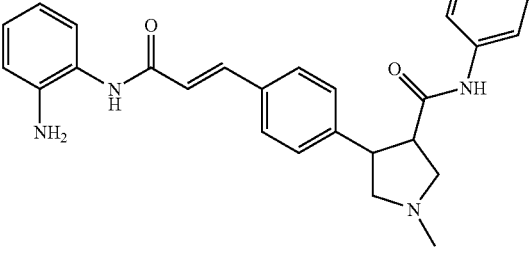 MW 441.52; MH+ calc. 442; MH+ expt. 442 | 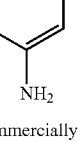 commercially available |

TABLE 1-continued

Starting materials and MS data of examples 5-2 to 5-47

| Example # | Structure | Starting Material |
|---|---|---|
| 5-24 | MW 441.52; MH+ calc. 442; MH+ expt. 442 | commercially available |
| 5-25 | MW 474.99; MH+ calc. 475; MH+ expt. 475 | commercially available |
| 5-26 | MW 442.52; MH+ calc. 443; MH+ expt. 443 | *HCl commercially available |
| 5-27 | MW 472.57; MH+ calc. 473; MH+ expt. 473 | commercially available |

TABLE 1-continued

Starting materials and MS data of examples 5-2 to 5-47

| Example # | Structure | Starting Material |
|---|---|---|
| 5-28 | MW 454.58; MH⁺ calc. 455; MH⁺ expt. 455 | 3-methylaniline; commercially available |
| 5-29 | MW 489.02; MH⁺ calc. 489; MH⁺ expt. 489 | 4-chloro-3-methylaniline; commercially available |
| 5-30 | MW 492.99; MH⁺ calc. 493; MH⁺ expt. 493 | 3-chloro-4-fluoroaniline; commercially available |
| 5-31 | MW 519.45; MH⁺ calc. 519; MH⁺ expt. 519 | 3-bromoaniline; commercially available |

TABLE 1-continued
Starting materials and MS data of examples 5-2 to 5-47
| Example # | Structure | Starting Material |
|---|---|---|
| 5-32 | 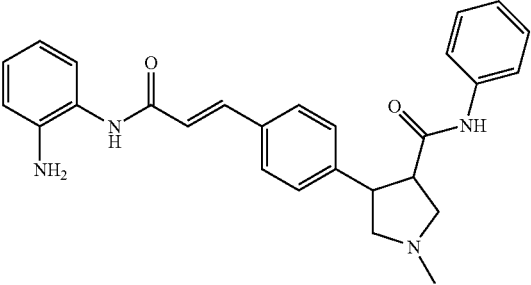<br>MW 440.55; MH⁺ calc. 441; MH⁺ expt. 441 | commercially available |
| 5-33 | 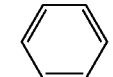<br>MW 470.58; MH⁺ calc. 471; MH⁺ expt. 471 | commercially available |
| 5-34 | 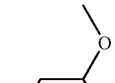<br>MW 508.55; MH⁺ calc. 509; MH⁺ expt. 509 | commercially available |
| 5-35 | 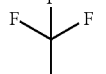<br>MW 509.54; MH⁺ calc. 510; MH⁺ expt. 510 | commercially available |

TABLE 1-continued
Starting materials and MS data of examples 5-2 to 5-47
| Example # | Structure | Starting Material |
|---|---|---|
| 5-36 | 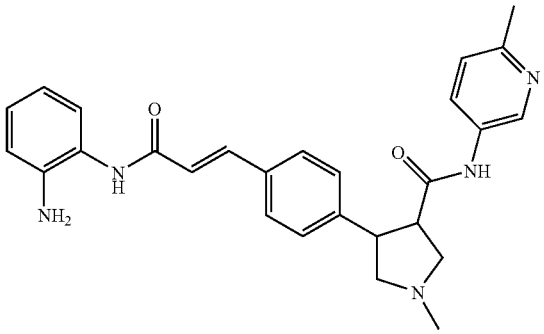<br>MW 455.56; MH⁺ calc. 456; MH⁺ expt. 456 | 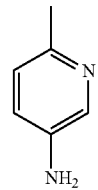<br>commercially available |
| 5-37 | 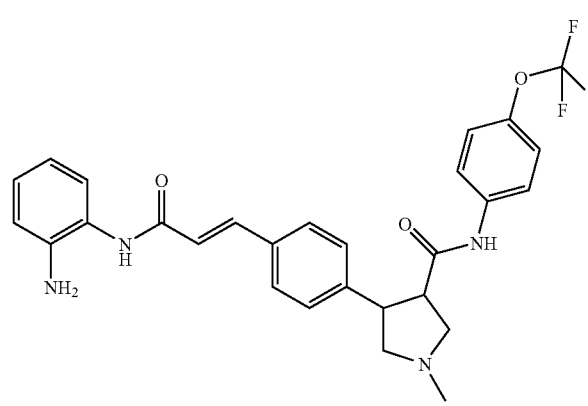<br>MW 524.55; MH⁺ calc. 525; MH⁺ expt. 525 | 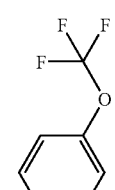<br>commercially available |
| 5-38 | 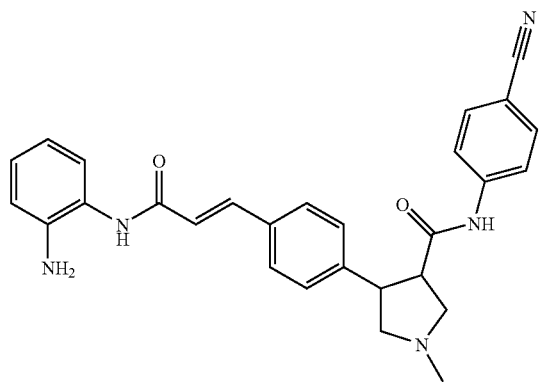<br>MW 465.56; MH⁺ calc. 466; MH⁺ expt. 466 | 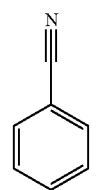<br>commercially available |

TABLE 1-continued

Starting materials and MS data of examples 5-2 to 5-47

| Example # | Structure | Starting Material |
|---|---|---|
| 5-39 | MW 509.44; MH+ calc. 509; MH+ expt. 509 | commercially available |
| 5-40 | MW 459.53; MH+ calc. 460; MH+ expt. 460 | commercially available |
| 5-41 | MW 476.53; MH+ calc. 477; MH+ expt. 477 | commercially available |
| 5-42 | MW 508.55; MH+ calc. 509; MH+ expt. 509 | commercially available |

TABLE 1-continued

Starting materials and MS data of examples 5-2 to 5-47

| Example # | Structure | Starting Material |
|---|---|---|
| 5-43 | MW 474.99; MH⁺ calc. 475; MH⁺ expt. 475 | 3-chloroaniline, commercially available |
| 5-44 | MW 488.55; MH⁺ calc. 489; MH⁺ expt. 489 | 4-fluoro-3-methoxyaniline, commercially available |
| 5-45 | MW 489.02; MH⁺ calc. 489; MH⁺ expt. 489 | 4-chloro-N-methylaniline, commercially available |
| 5-46 | MW 492.97; MH⁺ calc. 493; MH⁺ expt. 493 | 4-chloro-2-fluoroaniline, commercially available |

TABLE 1-continued

Starting materials and MS data of examples 5-2 to 5-47

| Example # | Structure | Starting Material |
|---|---|---|
| 5-47 | 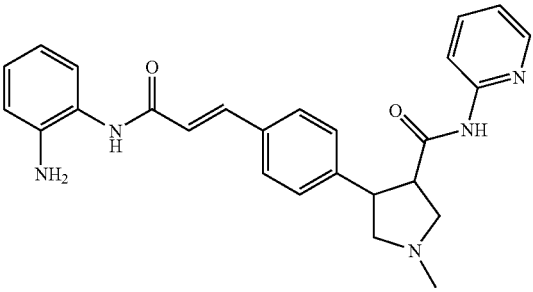<br>MW 441.54; MH⁺ calc. 442; MH⁺ expt. 442 | <br>commercially available |

TABLE 2

NMR data for examples 5-2 to 5-47

| Example # | NMR data |
|---|---|
| 5-2 | ¹H NMR (CD₃OD, 400 MHz), 7.64 (d, 1H, J = 15.6 Hz), 7.58 (d, 2H, J = 8.0 Hz), 7.51 (d, 2H, J = 8.8 Hz), 7.39 (d, 2H, J = 8.4 Hz), 7.27 (d, 2H, J = 8.8 Hz), 7.19 (d, 1H, J = 8.0 Hz), 7.04 (t, 1H, J = 7.2 Hz), 6.87 (d, 1H, J = 8.0 Hz), 6.82 (d, 1H, J = 15.6 Hz), 6.74 (t, 1H, J = 7.6 Hz), 3.84 (m, 1H), 3.18-3.07 (m, 3H), 2.91 (m, 2H), 2.46 (s, 3H). |
| 5-3 | ¹H NMR (CD₃OD, 400 MHz), 7.64 (d, 1H, J = 15.6 Hz), 7.58 (d, 2H, J = 8.0 Hz), 7.51 (d, 2H, J = 8.8 Hz), 7.39 (d, 2H, J = 8.4 Hz), 7.27 (d, 2H, J = 8.8 Hz), 7.19 (d, 1H, J = 8.0 Hz), 7.04 (t, 1H, J = 7.2 Hz), 6.87 (d, 1H, J = 8.0 Hz), 6.82 (d, 1H, J = 15.6 Hz), 6.74 (t, 1H, J = 7.6 Hz), 3.84 (m, 1H), 3.18-3.07 (m, 3H), 2.91 (m, 2H), 2.46 (s, 3H). |
| 5-4 | ¹H NMR (CD₃OD, 400 MHz), 7.68-7.62 (m, 4H), 7.42 (d, 2H, J = 8.0 Hz), 7.34 (d, 1H, J = 8.8 Hz), 7.21 (d, 1H, J = 8.0 Hz), 7.06 (t, 1H, J = 7.6 Hz), 7.00 (d, 1H, J = 8.8 Hz), 6.89 (d, 1H, J = 8.0 Hz), 6.85 (d, 1H, J = 16.0 Hz), 6.76 (t, 1H, J = 7.6 Hz), 3.88 (s, 3H), 6.30-3.20 (m, 4H), 3.14-3.06 (m, 2H), 2.61 (s, 3H). |
| 5-5 | ¹H NMR (CD₃OD, 400 MHz), 7.89 (s, 1H), 7.67 (d, 1H, J = 15.6 Hz), 7.61 (d, 2H, J = 7.6 Hz), 7.41 (d, 2H, J = 8.0 Hz), 7.34 (d, 1H, J = 8.4 Hz), 7.21 (m, 2H), 7.07 (t, 1H, J = 7.6 Hz), 6.91-6.83 (m, 2H), 6.77 (t, 1H, J = 7.6 Hz), 3.85 (m, 1H), 3.20-3.10 (m, 3H), 2.98-2.92 (m, 2H), 2.49 (s, 3H), 2.35 (s, 3H). |
| 5-6 | ¹H NMR (CD₃OD, 400 MHz), 7.66 (d, 1H, J = 16.0 Hz), 7.60 (d, 2H, J = 8.0 Hz), 7.45-7.39 (m, 3H), 7.21 (d, 1H, J = 8.0 Hz), 7.15-7.04 (m, 3H), 6.89 (d, 1H, J = 8.0 Hz), 6.84 (d, 1H, J = 16.0 Hz), 6.76 (t, 1H, J = 7.6 Hz), 3.86 (m, 1H), 3.22-3.11 (m, 3H), 2.98-2.92 (m, 2H), 2.50 (s, 3H), 2.21 (s, 3H). |
| 5-7 | ¹H NMR (d₆-DMSO, 400 MHz), 9.93 (s, 1H), 9.38 (s, 1H), 7.61-7.55 (m, 4H), 7.38-7.33 (m, 3H), 7.21 (d, 1H, J = 8.8 Hz), 7.09 (t, 1H, J = 9.2 Hz), 6.94-6.85 (m, 2H), 6.75 (d, 1H, J = 8.0 Hz), 6.58 (t, 1H, J = 7.6 Hz), 4.94 (s, 2H), 3.79 (s, 3H), 3.71 (m, 1H), 3.08 (m, 2H), 2.87 (m, 1H), 2.75 (m, 1H), 2.62 (m, 1H), 2.33 (s, 3H). |
| 5-8 | ¹H NMR (CD₃OD, 400 MHz), 7.63-7.58 (m, 3H), 7.53-7.50 (m, 2H), 7.40 (d, 2H, J = 8.0 Hz), 7.21 (d, 1H, J = 7.6 Hz), 7.08-7.00 (m, 3H), 6.90-6.74 (m, 3H), 3.85 (m, 1H), 3.21-3.11 (m, 3H), 2.97-2.93 (m, 2H), 2.50 (s, 3H). |
| 5-9 | ¹H NMR (CD₃OD, 400 MHz), 7.63-7.58 (m, 3H), 7.53-7.50 (m, 2H), 7.40 (d, 2H, J = 8.0 Hz), 7.21 (d, 1H, J = 7.6 Hz), 7.08-7.00 (m, 3H), 6.90-6.74 (m, 3H), 3.85 (m, 1H), 3.21-3.11 (m, 3H), 2.97-2.93 (m, 2H), 2.50 (s, 3H). |
| 5-10 | ¹H NMR (d₆-DMSO, 400 MHz), 10.00 (s, 1H), 9.40 (s, 1H), 7.61-7.50 (m, 5H), 7.37-7.30 (m, 3H), 7.12 (d, 2H, J = 8.0 Hz), 6.93-6.84 (m, 2H), 6.75 (d, 1H, J = 8.0 Hz), 6.58 (t, 1H, J = 7.6 Hz), 4.93 (s, 2H), 3.73 (m, 2H), 3.10 (m, 2H), 2.88 (t, 1H, J = 6.6 Hz), 2.75 (m, 1H), 2.73 (m, 1H), 2.32 (s, 3H). |
| 5-11 | ¹H NMR (CD₃OD, 400 MHz), 7.66 (d, 1H, J = 15.6 Hz), 7.61 (d, 2H, J = 8.0 Hz), 7.41 (d, 4H, J = 8.0 Hz), 7.21 (d, 1H, J = 8.0 Hz), 7.17 (d, 2H, J = 8.0 Hz), 7.06 (t, 1H, J = 7.6 Hz), 6.89 (d, 1H, J = 8.0 Hz), 6.24 (d, 1H, J = 15.6 Hz), 6.76 (t, 1H, J = 7.6 Hz), 3.87 (m, 1H), 3.22-3.14 (m, 3H), 3.03-2.97 (m, 2H), 2.89-2.85 (m, 1H), 2.53 (s, 3H), 1.23 (d, 6H, J = 6.8 Hz). |

TABLE 2-continued

NMR data for examples 5-2 to 5-47

| Example # | NMR data |
|---|---|
| 5-12 | $^1$H NMR (CD$_3$OD, 400 MHz), 8.06 (s, 1H), 7.73-7.60 (m, 4H), 7.49-7.41 (m, 4H), 7.20 (d, 1H, J = 7.6 Hz), 7.06 (t, 1H, J = 7.6 Hz), 6.90-6.82 (m, 2H), 6.75 (t, 1H, J = 7.6 Hz), 3.88 (m, 1H), 3.28-3.22 (m, 3H), 3.12 (m, 1H), 3.06 (m, 1H), 2.58 (s, 3H). |
| 5-13 | $^1$H NMR (CD$_3$OD, 400 MHz), 7.75 (m, 1H), 7.67 (d, 1H, J = 15.6 Hz), 7.61 (d, 2H, J = 8.0 Hz), 7.43 (d, 2H, J = 8.0 Hz), 7.22 (d, 1H, J = 7.6 Hz), 7.08-6.84 (m, 5H), 6.77 (t, 1H, J = 7.6 Hz), 3.85 (m, 1H), 3.28 (m, 1H), 3.17-3.12 (m, 2H), 2.99 (m, 1H), 2.90 (m, 1H), 2.49 (s, 3H). |
| 5-14 | $^1$H NMR (CD$_3$OD, 400 MHz), 8.23 (s, 1H), 8.16 (d, 1H, J = 8.8 Hz), 7.77 (d, 1H, J = 8.8 Hz), 7.65 (d, 1H, J = 15.6 Hz), 7.59 (d, 2H, J = 7.6 Hz), 7.40 (d, 2H, J = 7.6 Hz), 7.20 (d, 1H, J = 7.6 Hz), 7.05 (t, 1H, J = 7.6 Hz), 6.89-6.81 (m, 2H), 6.75 (t, 1H, J = 7.6 Hz), 3.88 (m, 1H), 3.21-3.14 (m, 3H), 3.02-2.97 (m, 1H), 2.87-2.82 (m, 1H), 2.49 (s, 3H). |
| 5-15 | $^1$H NMR (CD$_3$OD, 400 MHz), 7.67 (d, 1H, J = 15.6 Hz), 7.63 (d, 2H, J = 8.0 Hz), 7.48-7.42 (m, 3H), 7.26-7.21 (m, 2H), 7.08-7.00 (m, 2H), 6.91-6.84 (m, 2H), 6.76 (t, 1H, J = 7.6 Hz), 4.04 (m, 1H), 3.28-3.24 (m, 5H), 3.19-3.07 (m, 3H), 2.62 (s, 3H). |
| 5-16 | $^1$H NMR (CD$_3$OD, 400 MHz), 7.82 (t, 1H, J = 8.0 Hz), 7.69-7.63 (m, 3H), 7.45 (d, 2H, J = 8.0 Hz), 7.21 (d, 1H, J = 8.0 Hz), 7.19-7.13 (m, 3H), 7.07 (t, 1H, J = 7.2 Hz), 6.91-6.85 (m, 2H), 6.77 (t, 1H, J = 7.6 Hz), 3.89 (m, 1H), 3.46-3.38 (m, 3H), 3.23-3.16 (m, 1H), 2.71 (s, 3H). |
| 5-17 | $^1$H NMR (CD$_3$OD, 400 MHz), 7.96-7.94 (m, 1H), 7.66-7.58 (m, 3H), 7.42-7.38 (m, 3H), 7.19 (d, 1H, J = 7.6 Hz), 7.13 (t, 1H, J = 8.4 Hz), 7.04 (t, 1H, J = 8.0 Hz), 6.88 (d, 1H, J = 8.0 Hz), 6.83 (d, 1H, J = 15.6 Hz), 6.75 (t, 1H, J = 7.6 Hz), 3.82 (m, 1H), 3.15-3.08 (m, 3H), 2.93-2.91 (m, 2H), 2.46 (s, 3H). |
| 5-18 | $^1$H NMR (CD$_3$OD, 400 MHz), 7.68-7.62 (m, 3H), 7.43 (d, 2H, J = 8.0 Hz), 7.37 (d, 2H, J = 8.0 Hz), 7.21 (d, 1H, J = 8.0 Hz), 7.07 (t, 1H, J = 8.0 Hz), 7.01 (d, 2H, J = 8.8 Hz), 6.90-6.84 (m, 2H), 6.76 (t, 1H, J = 7.6 Hz), 3.88 (m, 1H), 3.41-3.37 (m, 2H), 3.30-3.16 (m, 3H), 2.70 (s, 3H), 1.87 (m, 1H), 0.96-0.91 (m, 2H), 0.65-0.63 (m, 2H). |
| 5-19 | $^1$H NMR (CD$_3$OD, 400 MHz), 7.66 (d, 1H, J = 16.0 Hz), 7.60 (d, 2H, J = 8.0 Hz), 7.42-7.37 (m, 4H), 7.21 (d, 1H, J = 8.0 Hz), 7.12-7.04 (m, 3H), 6.89 (d, 1H, J = 8.0 Hz), 6.84 (d, 1H, J = 16.0 Hz), 6.76 (t, 1H, J = 8.0 Hz), 3.86 (m, 1H), 3.22-3.14 (m, 3H), 3.01-2.97 (m, 2H), 2.52 (s, 3H), 2.30 (s, 3H). |
| 5-20 | $^1$H NMR (CD$_3$OD, 400 MHz), 7.66 (d, 1H, J = 16.0 Hz), 7.61 (d, 2H, J = 8.0 Hz), 7.50-7.40 (m, 6H), 7.21 (d, 1H, J = 8.0 Hz), 7.06 (t, 1H, J = 7.6 Hz), 6.89 (d, 1H, J = 7.6 Hz), 6.84 (d, 1H, J = 15.6 Hz), 6.76 (t, 1H, J = 7.6 Hz), 3.86 (m, 1H), 3.25-3.20 (m, 3H), 3.08-3.00 (m, 2H), 2.56 (s, 3H). |
| 5-21 | $^1$H NMR (CD$_3$OD, 400 MHz), 7.66 (d, 1H, J = 16.0 Hz), 7.62 (d, 2H, J = 8.4 Hz), 7.42 (d, 2H, J = 8.0 Hz), 7.26-7.17 (m, 3H), 7.08-7.01 (m, 2H), 6.90-6.83 (m, 2H), 6.76 (t, 1H, J = 7.2 Hz), 6.74-6.66 (m, 1H), 3.88 (m, 1H), 3.78 (s, 3H), 3.77-3.74 (m, 1H), 3.32-3.10 (m, 4H), 2.65 (s, 3H). |
| 5-22 | $^1$H NMR (CD$_3$OD, 400 MHz), 7.65 (d, 1H, J = 16 Hz), 7.59 (d, 2H, J = 8.0 Hz), 7.52 (d, 1H, J = 11.2 Hz), 7.40 (d, 2H, J = 8.0 Hz), 7.27 (q, 1H, J = 8.0 Hz), 7.20 (t, 2H, J = 7.2 Hz), 7.04 (t, 1H, J = 7.2 Hz), 6.87 (t, 1H, J = 8.0 Hz), 6.81 (m, 2H), 6.75 (t, 1H, J = 8.0 Hz), 3.86 (m, 1H), 3.17 (m, 3H), 2.98 (m, 2H), 2.52 (s, 3H). |
| 5-23 | $^1$H NMR (CD$_3$OD, 400 MHz), 8.39 (d, 2H, J = 6 Hz), 7.64 (m, 5H), 7.42 (d, 2H, J = 7.6 Hz), 7.22 (d, 1H, J = 8 Hz), 7.07 (t, 1H, J = 7.6 Hz), 6.91-6.66 (m, 3H), 3.90 (m, 1H), 3.28-3.13 (m, 3H), 2.89-3.0 (m, 2H), 2.49 (s, 3H). |
| 5-24 | $^1$H NMR (CD$_3$OD, 400 MHz), 9.10 (s, 1H), 8.43 (d, 1H, J = 5.2 Hz), 8.29 (d, 1H, J = 8.4 Hz), 7.75 (m, 3H), 7.65 (d, 2H, J = 8.0 Hz), 7.48 (d, 2H, J = 8.0 Hz), 7.33 (s, 4H), 6.87 (d, 1H, J = 15.6 Hz), 3.95 (m, 4H), 3.63 (m, 2H), 3.09 (s, 3H). |
| 5-25 | $^1$H NMR (CD$_3$OD, 400 MHz), 7.74 (m, 4H), 7.53 (d, 2H, J = 8 Hz), 7.46 (d, 1H, J = 8 Hz), 7.33 (t, 1H, J = 8.0 Hz), 7.24 (m, 2H,), 7.09 (t, 1H, J = 8.0 Hz), 6.93 (m, 2H), 6.80 (t, 1H, J = 7.6 Hz), 3.91 (m, 1H), 3.66-3.55 (m, 4H), 3.28 (m, 1H), 2.90 (s, 3H). |
| 5-26 | $^1$H NMR (CD$_3$OD, 400 MHz), 8.93 (d, 1H, J = 4.4 Hz), 7.53 (d, 1H, J = 8.8 Hz), 7..70 (m, 4H), 7.46 (d, 2H, J = 8.0 Hz), 7.24 (d, 1H, J = 8 Hz), 7.09 (t, 1H, J = 7.6 Hz), 6.90 (m, 2H,), 6.79 (t, 1H, J = 8 Hz), 4.99 (m, 1H), 3.56-3.45 (m, 3H), 3.24 (m, 1H), 3.06 (m, 1H), 2.72 (s, 3H). |
| 5-27 | $^1$H NMR (d-DMSO, 400 MHz), 7.68-7.59 (m, 3H), 7.39 (m, 3H), 7.31 (m, 1H), 7.21 (d, 1H, J = 7.6 Hz), 7.05 (t, 1H, J = 7.2 Hz), 6.95 (t, 1H, J = 9.2 Hz), 6.90-6.82 (m, 2H), 6.76 (t, 1H, J = 7.2 Hz), 3.85 (m, 1H), 3.19-3.10 (m, 3H), 2.95 (m, 2H), 2.49 (s, 3H), 2.23 (s, 3H). |
| 5-28 | $^1$H NMR (CD$_3$OD, 400 MHz), 7.71-7.64 (m, 3H), 7.45 (d, 2H, J = 8.0 Hz), 7.37-7.31 (m, 2H), 7.25-7.17 (m, 2H), 6.95 (t, 1H, J = 6.8 Hz), 6.93-6.79 (m, 4H), 3.91 (m, 1H), 3.43-3.39 (m, 2H), 3.33-3.20 (m, 3H), 2.71 (s, 3H), 2.33 (s, 3H). |

TABLE 2-continued

NMR data for examples 5-2 to 5-47

| Example # | NMR data |
|---|---|
| 5-29 | $^1$H NMR (CD$_3$OD, 400 MHz), 7.68-7.59 (m, 3H), 7.48 (d, 1H, J = 2 Hz), 7.41-7.35 (m, 3H), 7.26-7.20 (m, 2H), 7.06 (t, 1H, J = 7.2 Hz), 6.90-6.82 (m, 2H), 6.75 (t, 1H, J = 8.0 Hz), 3.85 (m, 1H), 3.31-3.08 (m, 3H), 2.95-2.91 (m, 2H), 2.33 (s, 3H), 2.22 (s, 3H). |
| 5-30 | $^1$H NMR (d$_6$-DMSO, 400 MHz), 7.81 (m, 1H), 7.66-7.57 (m, 3H), 7.40-7.34 (m, 3H), 7.20-7.12 (m, 2H), 7.04 (t, 1H, J = 7.2 Hz), 6.88-6.80 (m, 2H), 6.74 (t, 1H, J = 7.2 Hz), 3.84 (m, 1H), 3.18-3.12 (m, 3H), 2.98-2.93 (m, 2H), 2.50 (s, 3H). |
| 5-31 | $^1$H NMR (CD$_3$OD, 400 MHz), 7.89 (s, 1H), 7.68-7.60 (m, 3H), 7.41 (m, 3H), 7.25-7.18 (m, 3H), 7.06 (t, 1H, J = 7.6 Hz), 6.90-6.82 (m, 2H), 6.76 (t, 1H, J = 7.6 Hz), 3.86 (m, 1H), 3.20-3.10 (m, 3H), 2.96-2.92 (m, 2H), 2.25 (s, 3H). |
| 5-32 | $^1$H NMR (CD$_3$OD, 400 MHz), 7.66 (d, 1H, J = 15.6 Hz), 7.60 (d, 2H, J = 8.4 Hz), 7.49 (d, 2H, J = 8.0 Hz), 7.41 (d, 2H, J = 8.0 Hz), 7.28 (t, 2H, J = 8.0 Hz), 7.21 (d, 1H, J = 7.6 Hz), 7.10-7.03 (m, 2H), 6.88 (d, 1H, J = 7.2 Hz), 6.82 (d, 1H, J = 15.6 Hz), 6.75 (t, 1H, J = 7.2 Hz), 3.85 (m, 1H), 3.27-3.21 (m, 3H), 3.08-2.02 (m, 2H), 2.57 (s, 3H). |
| 5-33 | $^1$H NMR (CD$_3$OD, 400 MHz), 7.69-7.64 (m, 3H), 7.47-7.39 (m, 4H), 7.21 (d, 1H, J = 7.6 Hz), 7.05 (t, 1H, J = 8.0 Hz), 6.90-6.84 (m, 4H), 6.77 (t, 1H, J = 8.0 Hz), 3.90 (m, 1H), 3.78 (s, 3H,), 3.50-3.43 (m, 2H), 3.19-3.15 (m, 3H), 2.76 (s, 3H). |
| 5-34 | $^1$H NMR (CD$_3$OD, 400 MHz), 7.75 (d, 2H, J = 8.8 Hz), 7.66 (d, 1H, J = 15.6 Hz), 7.60 (m, 4H), 7.42 (d, 2H, J = 8.4 Hz), 7.21 (d, 1H, J = 8.0 Hz), 7.07 (d, 1H, J = 8.0 Hz), 6.89 (d, 1H, J = 8.0 Hz), 6.84 (d, 1H, J = 15.6 Hz), 6.75 (t, 1H, J = 7.2 Hz), 3.89 (m, 1H), 3.27-3.16 (m, 3H), 2.99 (m, 2H), 2.53 (s, 3H). |
| 5-35 | $^1$H NMR (CD$_3$OD, 400 MHz), 8.57 (s, 1H), 8.36 (d, 1H, J = 8.8 Hz), 8.06 (t, 1H, J = 6.8 Hz), 7.66 (d, 1H, J = 15.6 Hz), 7.61 (d, 2H, J = 8.0 Hz), 7.42 (d, 2H, J = 8.0 Hz), 7.21 (d, 1H, J = 7.6 Hz), 7.06 (t, 1H, J = 7.6 Hz), 6.89 (d, 1H, J = 8.0 Hz), 6.84 (d, 1H, J = 15.6 Hz), 6.76 (t, 1H, J = 7.6 Hz), 3.93 (m, 1H), 3.12-3.41 (m, 4H), 2.94 (m, 1H), 2.56 (s, 3H). |
| 5-36 | $^1$H NMR (CD$_3$OD, 400 MHz), 8.57 (s, 1H), 7.94 (t, 1H, J = 2.4 Hz), 7.66 (d, 1H, J = 15.6 Hz), 7.60 (d, 2H, J = 8.0 Hz), 7.41 (d, 2H, J = 8.0 Hz), 7.25 (d, 1H, J = 8.4 Hz), 7.21 (d, 1H, J = 7.6 Hz), 7.06 (t, 1H, J = 7.6 Hz), 6.89 (d, 1H, J = 8.0 Hz), 6.84 (d, 1H, J = 15.6 Hz), 6.76 (t, 1H, J = 8.0 Hz), 3.87 (m, 1H), 3.24-3.14 (m, 3H), 2.99-2.92 (m, 2H), 2.50 (s, 3H), 2.48 (s, 3H). |
| 5-37 | $^1$H NMR (CD$_3$OD, 400 MHz), 7.68-7.61 (m, 5H), 7.42 (d, 2H, J = 8.0 Hz), 7.21 (d, 3H, J = 8.4 Hz), 7.05 (t, 1H, J = 7.6 Hz), 6.89 (d, 1H, J = 8.0 Hz), 6.85 (d, 1H, J = 15.6 Hz), 6.77 (t, 1H, J = 7.6 Hz), 3.89 (m, 1H), 3.37-3.12 (m, 5H), 2.65 (s, 3H). |
| 5-38 | $^1$H NMR (CD$_3$OD, 400 MHz), 7.71 (d, 2H, J = 8.4 Hz), 7.65-7.61 (m, 5H), 7.42 (d, 2H, J = 7.6 Hz), 7.17 (d, 1H, J = 7.6 Hz), 7.03 (t, 1H, J = 7.6 Hz), 6.86 (d, 1H, J = 7.2 Hz), 6.81 (d, 1H, J = 15.6 Hz), 6.71 (t, 1H, J = 8.0 Hz), 3.93 (s, 1H), 3.77-3.67 (m, 3H), 3.46 (m, 2H), 2.95 (s, 3H). |
| 5-39 | $^1$H NMR (CD$_3$OD, 400 MHz), 7.96 (m, 1H), 7.70 (d, 1H, J = 15.6 Hz), 7.65 (d, 2H, J = 9.6 Hz), 7.48-7.42 (m, 4H), 7.26 (d, 1H, J = 7.6 Hz), 7.11 (t, 1H, J = 7.6 Hz), 6.91 (t, 1H, J = 8.0 Hz), 6.89 (d, 1H, J = 15.6 Hz), 6.80 (d, 1H, J = 8.0 Hz) 3.91 (m, 1H), 3.25-3.17 (m, 3H), 3.03-2.97 (m, 2H), 2.55 (s, 3H). |
| 5-40 | $^1$H NMR (CD$_3$OD, 400 MHz), 7.66 (d, 1H, J = 15.6 Hz), 7.61-7.55 (m, 3H), 7.41 (d, 2H, J = 8.0 Hz), 7.21 (d, 1H, J = 8.0 Hz), 7.06 (t, 1H, J = 7.6 Hz), 6.89 (d, 1H, J = 8.0 Hz), 6.84 (d, 1H, J = 15.6 Hz), 6.76 (t, 1H, J = 7.6 Hz), 3.89 (m, 1H), 3.29-3.01 (m, 2H), 3.11-2.97 (m, 1H), 3.01-2.77 (m, 2H), 2.46 (s, 3H). |
| 5-41 | $^1$H NMR (CD$_3$OD, 400 MHz), 7.76-7.72 (m, 1H), 7.69 (d, 1H, J = 15.6 Hz), 7.64 (d, 2H, J = 8.0 Hz), 7.44 (d, 2H, J = 8.0 Hz), 7.25-7.19 (m, 3H), 7.07-7.11 (t, 1H, J = 7.6 Hz), 6.92 (d, 1H, J = 8.0 Hz), 6.87 (d, 1H, J = 15.6 Hz), 6.78 (t, 1H, J = 8.0 Hz), 3.89 (m, 1H), 3.35-3.22 (m, 3H), 3.14-3.04 (m, 2H), 2.61 (s, 1H). |
| 5-42 | $^1$H NMR (CD$_3$OD, 400 MHz), 8.03 (s, 1H), 7.71-7.62 (m, 4H), 7.52-7.37 (m, 4H), 7.21 (d, 1H, J = 8.0 Hz), 7.06 (t, 1H, J = 7.6 Hz), 6.89 (d, 1H, J = 8.0 Hz), 6.85 (d, 1H, J = 15.6 Hz), 6.76 (t, 1H, J = 8 Hz), 3.90 (m, 1H), 3.31-3.06 (m, 5H), 2.62 (s, 3H). |
| 5-43 | $^1$H NMR (CD$_3$OD, 400 MHz), 7.73 (s, 1H), 7.68-7.59 (m, 3H), 7.42-7.34 (m, 3H), 7.26 (t, 1H, J = 8.0 Hz), 7.20 (d, 1H, J = 7.6 Hz), 7.10-7.03 (m, 2H), 6.88 (d, 1H, J = 7.6 Hz), 6.83 (d, 1H, J = 15.6 Hz), 6.75 (t, 1H, J = 7.6 Hz), 3.86 (m, 1H), 3.33-3.15 (m, 3H), 3.05-2.95 (m, 2H), 2.52 (s, 3H). |
| 5-44 | $^1$H NMR (CD$_3$OD, 400 MHz), 7.65-7.55 (m, 3H), 7.42-7.32 (m, 3H), 7.17 (d, 1H, J = 8.0 Hz), 7.03-6.86 (m, 3H), 6.87-6.72 (m, 3H), 3.82 (m, 4H), 3.15-3.04 (m, 3H), 2.92-2.87 (m, 2H), 2.44 (s, 3H). |

TABLE 2-continued

NMR data for examples 5-2 to 5-47

| Example # | NMR data |
|---|---|
| 5-45 | $^1$H NMR (d$_6$-DMSO, 400 MHz), 9.38 (s, 1H), 7.56-7.49 (m, 3H), 7.37-7.32 (m, 3H), 7.15-7.02 (m, 4H), 6.93 (d, 1H, J = 7.6 Hz), 6.88 (d, 1H, J = 16 Hz), 6.76 (d, 1H, J = 7.6 Hz), 6.59 (t, 1H, J = 7.6 Hz), 4.95 (s, 2H), 3.67 (s, 1H), 3.10 (s, 3H), 2.99-2.67 (m, 5H), 2.35 (s, 3H). |
| 5-46 | $^1$H NMR (CD$_3$OD, 400 MHz), 8.0-7.68 (m, 4H), 7.62-7.55 (m, 1H), 7.53-7.46 (d, 2H, J = 7.6 Hz), 7.33-7.18 (m, 3H), 7.13 (d, 1H, J = 8.0 Hz), 7.06 (t, 1H, J = 7.1 Hz), 6.90 (d, 1H, J = 15.6 Hz), 4.30-3.40 (m, 6H), 3.12 (s, 3H). |
| 5-47 | $^1$H NMR (CD$_3$OD, 400 MHz), 8.24 (d, 1H, J = 4.0 Hz), 8.08 (m, 1H), 7.75 (m, 1H), 7.66-7.58 (m, 3H), 7.40 (d, 2H, J = 8.0 Hz), 7.19 (d, 1H, J = 8.0 Hz), 7.11-7.02 (m, 2H), 6.87 (d, 1H, J = 7.6 Hz), 6.82 (d, 1H, J = 15.6 Hz), 6.75 (d, 1H, J = 7.2 Hz), 3.88 (m, 1H), 3.40-3.15 (m, 3H), 3.14-3.05 (m, 1H), 3.00-2.85 (m, 1H), 2.55 (s, 3H). |

Example 6

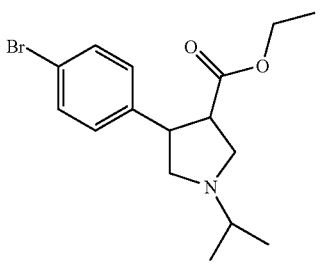

rac-(trans-3,4)-4-(4-Bromo-phenyl)-1-isopropyl-pyrrolidine-3-carboxylic acid ethyl ester To a solution of rac-(trans-3,4)-4-(4-bromo-phenyl)-pyrrolidine-3-carboxylic acid ethyl ester (2.5 g, 8.39 mmol) in methanol is added acetone (9.73 g, 16.78 mmol), NaBH(OAc)$_3$ (3.56 g, 16.78 mmol) and catalytic acetic acid. This mixture was stirred at rt overnight until the starting material had been consumed. Water was added, and the organic phase washed by brine, dried over Na$_2$SO$_4$, and concentrated to give 1.8 g of product (yield 64%). MS: calc'd 340 (MH+), exp 340 (MH+).

Example 7

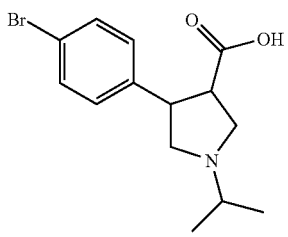

rac-(trans-3,4)-4-(4-Bromo-phenyl)-1-isopropyl-pyrrolidine-3-carboxylic acid

To a solution of rac-(trans-3,4)-4-(4-bromo-phenyl)-1-isopropyl-pyrrolidine-3-carboxylic acid ethyl ester (1.8 g, 5.3 mmol) in MeOH (10 mL) was added 2M LiOH (5.3 mL). This mixture was stirred at room temperature overnight and then evaporated to remove most of the MeOH. The mixture was acidified to pH=5 and extracted with ethyl acetate (3×60 mL). The combined organic layer was washed with brine, dried with Na$_2$SO$_4$, filtered, and evaporated to give 1.1 g product. MS: calc'd 312 (MH+), exp 312 (MH+).

Example 8

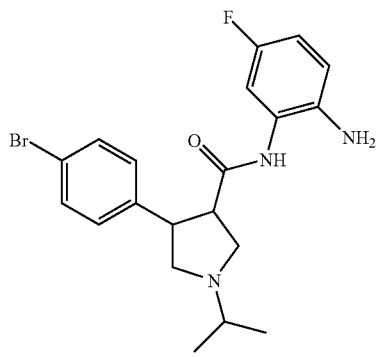

rac-(trans-3,4)-4-(4-Bromo-phenyl)-1-isopropyl-pyrrolidine-3-carboxylic acid (2-amino-5-fluoro-phenyl)-amide To a solution of rac-(trans-3,4)-4-(4-bromo-phenyl)-1-isopropyl-pyrrolidine-3-carboxylic acid (1.1 g, 3.52 mmol) in DCM (10 mL) was added dropwise oxalyl chloride (491 mg, 3.87 mmol) at 0 degrees Celsius. The solution was stirred at rt for 1 hours, then it was added to a mixture of 4-fluoro-benzene-1,2-diamine (488 mg, 3.87 mmol) and Et$_3$N (533 mg, 5.28 mmol) in DCM (10 mL) This mixture was stirred at rt overnight, and then water (20 mL) was added. The organic layer was washed with brine, dried with Na$_2$SO$_4$, filtered, and evaporated to give 1.2 g of the crude product. It was used in the next step without further purification. MS: calc'd 420 (MH+), exp 420 (MH+).

Example 9

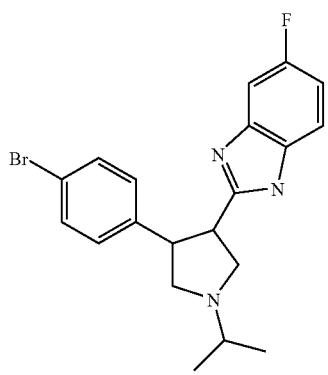

rac-2-[(trans-3,4)-4-(4-Bromo-phenyl)-1-isopropyl-pyrrolidin-3-yl]-5-fluoro-1H-benzoimidazole To a solution of rac-(trans-3,4)-4-(4-bromo-phenyl)-1-isopropyl-pyrrolidine-3-carboxylic acid (2-amino-5-fluoro-phenyl)-amide (1.2 g, 2.86 mmol) in acetic acid (10 mL) was added sodium acetate (0.78 g, 5.72 mmol). The mixture was heated at reflux overnight and then evaporated to remove most of the acetic acid. The mixture was diluted with $CH_2Cl_2$ (20 mL) and washed with water (10 mL) and brine (10 mL), dried with $Na_2SO_4$, filtered, and evaporated in vacuo to obtain 0.85 g of product which was used without further purification. MS: calc'd 402 (MH+), exp 402 (MH+).

Example 10

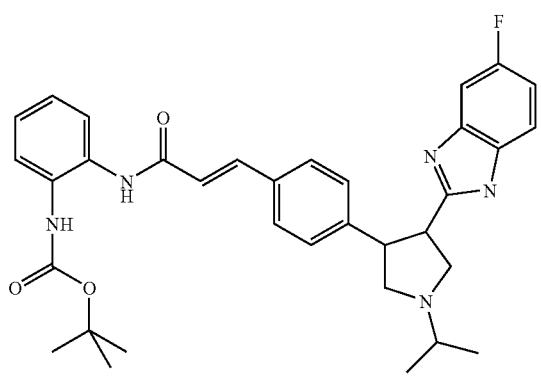

rac-[2-(3-{4-[(trans-3,4)-4-(5-Fluoro-1H-benzoimidazol-2-yl)-1-isopropyl-pyrrolidin-3-yl]-phenyl}-acryloylamino)-phenyl]-carbamic acid tert-butyl ester To a solution of rac-2-[(trans-3,4)-4-(4-bromo-phenyl)-1-isopropyl-pyrrolidin-3-yl]-5-fluoro-1H-benzoimidazole (200 mg, 0.5 mmol), $Pd_2(dba)_3$ (45.7 mg, 0.05 mmol), tri-(o-tolyl) phosphine (15.2 mg, 0.05 mmol) and $Et_3N$ (2 g, 2 mmol) in DMF (3 mL) was added (2-acryloylamino-phenyl)-carbamic acid tert-butyl ester (157 mg, 0.6 mmol). This mixture was stirred at 100 degrees Celsius for about 3 hours until the starting material had been consumed. The solution was then cooled, filtered, poured into water (15 mL), and extracted with ethyl acetate (3×15 mL). The combined organic layer was washed with brine, dried with $Na_2SO_4$, filtered, and evaporated. The crude product was used without further purification. MS: calc'd 552 (MH+), exp 552 (MH+).

Example 11

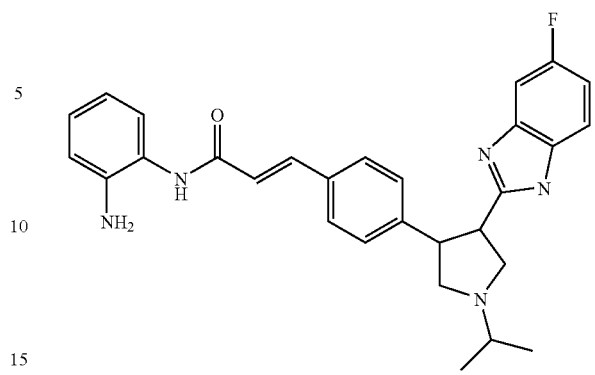

rac-N-(2-Amino-phenyl)-3-{4-[(trans-3,4)-4-(5-fluoro-1H-benzoimidazol-2-yl)-1-isopropyl-pyrrolidin-3-yl]-phenyl}-acrylamide Hydrochloric acid in methanol (1.25 M, 5 mL) was added to rac-[2-(3-{4-[(trans-3,4)-4-(5-fluoro-1H-benzoimidazol-2-yl)-1-isopropyl-pyrrolidin-3-yl]-phenyl}-acryloylamino)-phenyl]-carbamic acid tent-butyl ester (100 mg), the mixture was stirred for 3 h, and then $NaHCO_3$ was added to the reaction system. After filtration of solids, the crude mixture was purified by preparative HPLC to obtain 30 mg of light yellow solid. MS: calc'd 483 (MH+), exp 483 (MH+). $^1$H NMR ($d_6$-DMSO, 400 MHz), 9.37 (s, 1H), 7.55-7.49 (m, 4H), 7.40-7.38 (d, 2H, J=8.0 Hz), 7.34-7.32 (d, 1H, J=8.0 Hz), 7.17-7.16 (m, 1H), 6.88-6.84 (m, 2H), 6.76-6.74 (d, 2H, J=8.0 Hz), 6.59-6.55 (m, 1H), 4.93 (d, 2H), 3.87-3.85 (m, 1H), 3.62-3.60 (m, 1H), 3.30-3.28 (m, 1H), 3.16-3.14 (m, 1H), 2.94-2.88 (m, 2H), 2.60 (m, 1H), 1.12-1.08 (m, 6H).

Example 11-2a

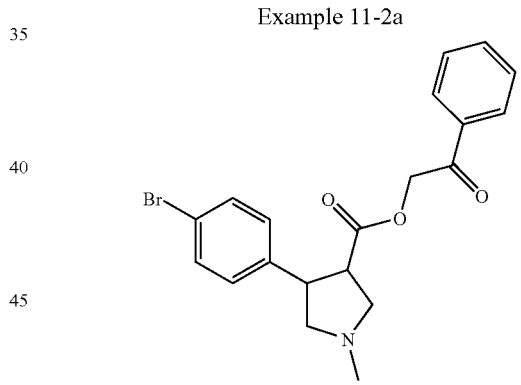

rac-(trans-3,4)-4-(4-Bromo-phenyl)-1-methyl-pyrrolidine-3-carboxylic acid 2-oxo-2-phenyl-ethyl ester rac-(trans-3,4)-4-(4-Bromo-phenyl)-1-methyl-pyrrolidine-3-carboxylic acid ethyl ester (1.04 g, 3.3 mol) was dissolved in 6 mL THF, to which was added 6.7 mL 1M LiOH, and the resultant mixture stirred at room temperature. After two hours, the reaction mixture was acidified to pH 2.5, and then solvent was removed by vacuum to give a white solid. This solid was then dissolved in 7 mL DMF containing $Cs_2CO_3$ (1.2 g, 3.7 mmol) and 2-bromo-1-phenyl-ethanone (0.6 g, 3 mmol) and the resultant mixture stirred at room temperature overnight. After the reaction had gone to completion, the reaction mixture was diluted with water and extracted with ethyl acetate. The combined organic layer was washed with brine, dried over sodium sulfate, and then concentrated in vacuo. The crude product was purified by column chromatography to obtain 700 mg pure product (58% yield). MS: calc'd 402 (MH+), exp 402 (MH+).

Example 11-2b

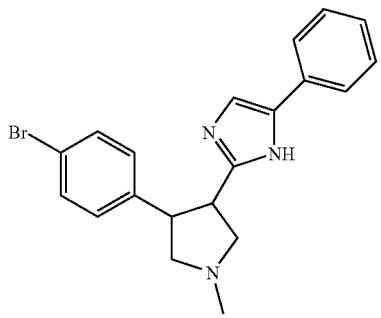

rac-2-[(trans-3,4)-4-(4-Bromo-phenyl)-1-methyl-pyrrolidin-3-yl]-5-phenyl-1H-imidazole rac-(trans-3,4)-4-(4-Bromo-phenyl)-1-methyl-pyrrolidine-3-carboxylic acid 2-oxo-2-phenyl-ethyl ester (0.7 g, 1.75 mmol) and NH$_4$OAc (2.7 g, 35 mmol) were suspended in 10 mL toluene in a reaction flask equipped with Dean-Stark trap and refluxed. After two hours, the reaction mixture was diluted with water and adjusted to pH 10, then extracted with ethyl acetate. The combined organic layers were washed with brine, dried over sodium sulfate, then concentrated in vacuo. The crude product was purified by column chromatography to obtain 80 mg pure product (12%). MS: calc'd 382 (MH+), exp 382 (MH+).

Compounds II-2 through 11-6 described in the following tables were prepared by methods analogous to the synthetic methods used for the preparation of Example 11 described above, by combining (2-acryloylamino-phenyl)-carbamic acid tert-butyl ester with the appropriate starting materials as indicated in Table 3

TABLE 3

Starting material(s) and MS data of examples 11-2 to 11-6

| Example # | Structure | Starting Material(s) |
|---|---|---|
| 11-2 | MW 463.59; MH+ calc. 464; MH+ expt. 464 | Example 11-2b |
| 11-3 | MW 437.55; MH+ calc. 438; MH+ expt. 438 | Example 1, commercially available |
| 11-4 | MW 471.99; MH+ calc. 472; MH+ expt. 472 | Example 1, commercially available |

TABLE 3-continued

Starting material(s) and MS data of examples 11-2 to 11-6

| Example # | Structure | Starting Material(s) |
|---|---|---|
| 11-5 | MW 500.05; MH+ calc. 500; MH+ expt. 500 | Example 6, commercially available |
| 11-6 | MW 455.54; MH+ calc. 456; MH+ expt. 456 | Example 1, commercially available |

TABLE 4

NMR data for examples 11-2 to 11-6

| Example # | NMR data |
|---|---|
| 11-2 | $^1$H NMR (d$_6$-DMSO, 400 MHz), 9.38 (s, 1H), 7.73 (d, 2H), 7.59-7.61 (d, 2H, J = 8.0 Hz), 7.41-7.43 (d, 2H, J = 8.0 Hz), 7.43-7.51 (m, 2H), 7.33-7.37 (m, 3H), 7.18-7.22 (m, 1H), 6.90-6.94 (m, 2H), 6.74-6.76 (d, 1H, J = 8.0 Hz), 6.56-6.6 (m, 1H), 4.94 (d, 2H), 3.9-4.01 (m, 1H), 3.75-3.83 (m, 1H), 3.21 (s, 1H), 3.22-3.32 (m, 2H), 3.01-3.09 (m, 2H), 2.4 (s, 3H). |
| 11-3 | $^1$H NMR (d$_6$-DMSO, 400 MHz), 9.37 (s, 1H), 7.57 (d, 2H), 7.53-7.54 (d, 2H, J = 4.0 Hz), 7.39-7.41 (d, 2H, J = 8.0 Hz), 7.32-7.34 (d, 2H, J = 8.0 Hz), 7.11-7.15 (m, 2H), 6.84-6.93 (m, 2H), 6.74-6.76 (d, 1H, J = 8.0 Hz), 6.55-6.59 (m, 1H), 4.94 (d, 2H), 3.91-3.94 (m, 1H), 3.67-3.69 (m, 1H), 3.25 (s, 1H), 3.19-3.22 (m, 1H), 2.94-3 (m, 2H), 2.43 (s, 3H). |
| 11-4 | $^1$H NMR (d$_6$-DMSO, 400 MHz), 9.37 (s, 1H), 7.48-7.56 (m, 4H), 7.38-7.4 (d, 2H, J = 8.0 Hz), 7.33-7.35 (d, 1H, J = 8.0 Hz), 7.16-7.17 (m, 1H), 6.84-6.93 (m, 2H), 6.74-6.76 (d, 2H, J = 8.0 Hz), 6.55-6.59 (m, 1H), 4.94 (d, 2H), 3.87-3.89 (m, 1H), 3.64-3.66 (m, 1H), 3.33 (s, 1H), 3.24-3.26 (m, 1H), 3.09-3.11 (m, 1H), 2.85-2.92 (m, 2H), 2.43 (s, 3H). |
| 11-5 | $^1$H NMR (d$_6$-DMSO, 400 MHz), 9.38 (s, 1H), 7.49-7.55 (m, 5H), 7.37-7.39 (d, 2H, J = 8.0 Hz), 7.32-7.34 (d, 1H, J = 8.0 Hz), 7.13-7.16 (m, 1H), 6.84-6.93 (m, 2H), 6.83-6.93 (m, 2H), 6.74-6.76 (d, 1H, J = 8.0 Hz), 6.55-6.59 (m, 1H), 4.93 (d, 2H), 3.85-3.86 (m, 1H), 3.61-3.63 (m, 1H), 3.26-3.33 (m, 2H), 3.13-3.17 (m, 1H), 2.84-2.93 (m, 2H), 1.07-1.11 (m, 6H). |
| 11-6 | $^1$H NMR (d$_6$-DMSO, 400 MHz), 9.37 (s, 1H), 7.48-7.56 (m, 4H), 7.38-7.4 (d, 2H, J = 8.0 Hz), 7.33-7.35 (d, 1H, J = 8.0 Hz), 7.16-7.17 (m, 1H), 6.84-6.88 (m, 2H), 6.74-6.76 (d, 2H, J = 8.0 Hz), 6.55-6.59 (m, 1H), 4.94 (d, 2H), 3.87-3.89 (m, 1H), 3.60-3.62 (m, 1H), 3.17-3.21 (m, 1H), 3.03-3.07 (m, 1H), 2.77-2.86 (m, 2H), 2.38 (s, 3H). |

Example 12

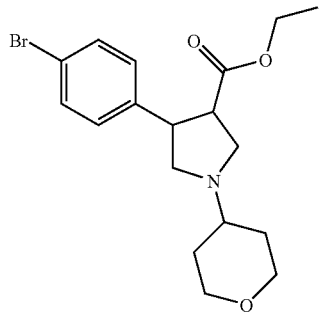

rac-(trans-3,4)-4-(4-Bromo-phenyl)-1-(tetrahydro-pyran-4-yl)-pyrrolidine-3-carboxylic acid ethyl ester To a solution of rac-(trans-3,4)-4-(4-bromo-phenyl)-pyrrolidine-3-carboxylic acid ethyl ester (150 mg, 0.5 mmol) and tetrahydropyran-4-one (100 mg, 1 mmol) in $CH_2Cl_2$ (5 mL) was added $NaBH(OAc)_3$ (320 mg, 1.5 mmol), and this mixture was stirred for about 1 h at room temperature, diluted with $H_2O$ and extracted with $CH_2Cl_2$ (3×10 mL). The combined organic layer was washed with brine, dried over $Na_2SO_4$, filtered, and evaporated to obtain 153 mg (yield 80%) of product as yellow oil. MS: calc'd 382 (MH+), exp 382 (MH+).

Example 13

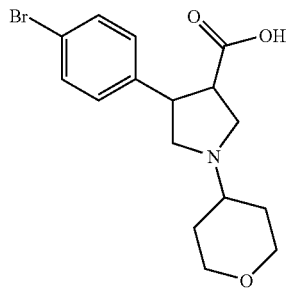

rac-(trans-3,4)-4-(4-Bromo-phenyl)-1-(tetrahydro-pyran-4-yl)-pyrrolidine-3-carboxylic acid To a solution of rac-(trans-3,4)-4-(4-bromo-phenyl)-1-(tetrahydro-pyran-4-yl)-pyrrolidine-3-carboxylic acid ethyl ester (153 mg, 0.4 mmol) in $EtOH/H_2O$ (10 mL/4 mL) was added NaOH (80 mg, 2 mmol). This mixture was stirred for about 5 h at room temperature, and then was evaporated to remove most of the EtOH. The aqueous layer was acidified with concentrated HCl to pH 6-7. The acidified aqueous layer was extracted with ethyl acetate (3×10 mL). The combined organic layer was washed with brine, dried over $Na_2SO_4$, filtered, and evaporated to obtain 133 mg (yield 95%) of product as white solid. MS: calc'd 312 (MH+), exp 312 (MH+).

Example 14

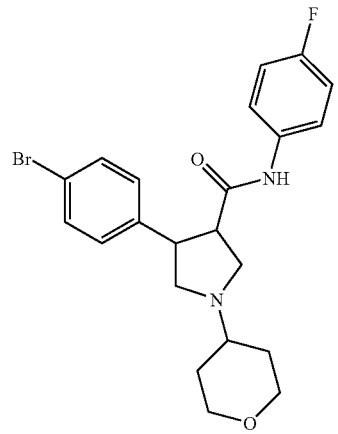

rac-(trans-3,4)-4-(4-Bromo-phenyl)-1-(tetrahydro-pyran-4-yl)-pyrrolidine-3-carboxylic acid (4-fluoro-phenyl)-amide To a solution of rac-(trans-3,4)-4-(4-bromo-phenyl)-1-(tetrahydro-pyran-4-yl)-pyrrolidine-3-carboxylic acid (141 mg, 0.4 mmol), HATU (304 mg, 0.8 mmol) in $CH_2Cl_2$ (5 mL) was added 4-fluoroaniline (89 mg, 0.8 mmol). This mixture was stirred overnight at room temperature and then diluted with $CH_2Cl_2$ (20 mL), washed with water and brine, dried over $Na_2SO_4$, filtered, and evaporated. The crude product was purified by column chromatography (PE:EtOAc=3:1-1:1) to get 98 mg (55%) of a yellow solid. MS: calc'd 447 (MH+), exp 447 (MH+).

Example 15

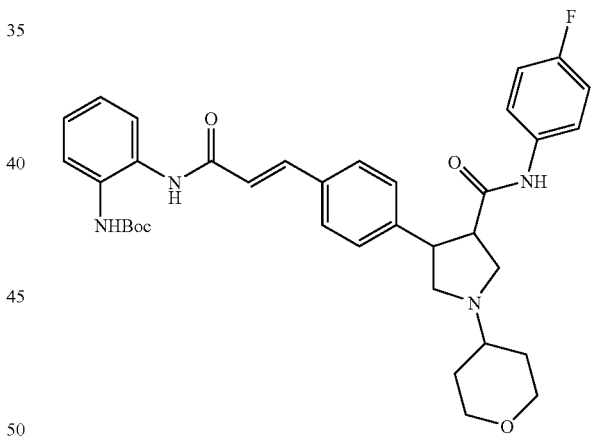

rac-[2-(3-{4-[(trans-3,4)-4-(4-Fluoro-phenylcarbamoyl)-1-(tetrahydro-pyran-4-yl)pyrrolidin-3-yl]-phenyl}-acryloylamino)-phenyl]-carbamic acid tert-butyl ester The mixture of rac-(trans-3,4)-4-(4-bromo-phenyl)-1-(tetrahydro-pyran-4-yl)-pyrrolidine-3-carboxylic acid-(4-fluoro-phenyl)-amide (229 mg, 0.51 mmol), (2-acryloylamino-phenyl)-carbamic acid tert-butyl ester (135 mg, 0.51 mmol), $Pd_2(dba)_3$ (47 mg, 0.05 mmol), tri-o-tolylphosphine (47 mg, 0.15 mmol) in DMF (5 mL) and TEA (0.142 mL, 1.02 mmol) was heated at 110 degrees Celsius under Ar in a sealed tube for 4 h. The cooled mixture was concentrated in vacuo to remove DMF. The residue was purified by column chromatography ($CH_2Cl_2$:methanol=40:1-20:1 and with $Et_3N$ (1/1000) to get the product (226 mg, 70%). MS: calc'd 629 (MH+), exp 629 (MH+).

Example 16

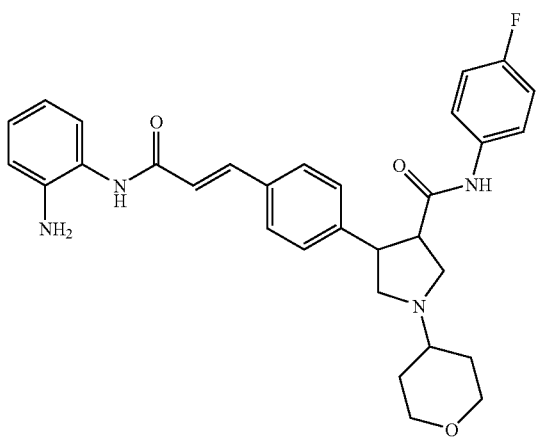

rac-(trans-3,4)-4-{4-[2-(2-Amino-phenylcarbamoyl)-vinyl]-1-phenyl}-1-(tetrahydro-pyran-4-yl)-pyrrolidine-3-carboxylic acid (4-fluoro-phenyl)-amide Hydrochloric acid in methanol (1.25 M, 5 mL) was added to [2-(3-{4-[4-(4-fluoro-phenylcarbamoyl)-1-(tetrahydro-pyran-4-yl)pyrrolidin-3-yl]-phenyl}-acryloylamino)-phenyl]-carbamic acid tert-butyl ester (226 mg, 0.36 mmol), the mixture was stirred for about 4 h, and then NaHCO$_3$ was added to the reaction system. After filtration of solids, the crude mixture was purified by preparative HPLC to obtain light yellow solid. MS: calc'd 529 (MH+), exp 529 (MH+). $^1$H NMR (CD$_3$OD, 400 MHz), 7.652 (d, 1H, J=15.6 Hz), 7.593 (d, 2H, J=8 Hz), 7.523-7.489 (m, 2H), 7.416 (d, 2H, J=8 Hz), 7.206 (d, 1H, J=7.6 Hz), 7.073-7.003 (m, 3H), 6.885 (d, 1H, J=8 Hz), 6.834 (d, 1H, J=16 Hz), 6.754 (t, 1H, J=7.6 Hz), 3.999-3.972 (broad d, 2H), 3.791-3.770 (m, 1H), 3.460 (t, 2H, J=12 Hz, J=10.4 Hz), 3.277-3.141 (m, 3H), 2.995-2.944 (m, 2H), 2.487-2.478 (m, 1H), 1.925-1.893 (m, 2H), 1.635-1.577 (m, 2H).

Compounds 16-2 through 16-20 described in the following tables were prepared by methods analogous to the synthetic methods described above for Example 16, by combining (2-acryloylamino-phenyl)-carbamic acid tert-butyl ester with the appropriate starting materials as indicated in Table 5.

TABLE 5

Starting material(s) and MS data of examples 16-2 to 16-20

| Example # | Structure | Starting Materials |
|---|---|---|
| 16-2 | (structure shown) MW 545.09; MH+ calc. 545; MH+ expt. 545 | Example 12, 4-Cl-aniline commercially available |
| 16-3 | (structure shown) MW 558.64; MH+ calc. 559; MH+ expt. 559 | Example 12, 3-methoxy-4-fluoroaniline commercially available |

TABLE 5-continued
Starting material(s) and MS data of examples 16-2 to 16-20
| Example # | Structure | Starting Materials |
|---|---|---|
| 16-4 | 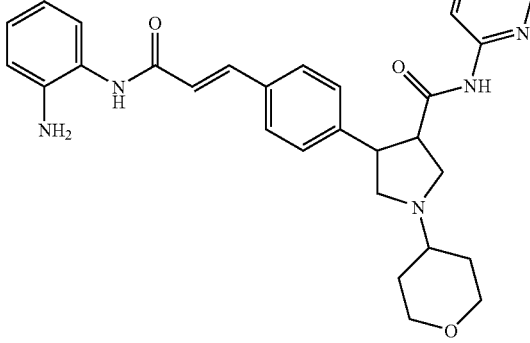<br>MW 546.06; MH+ calc. 546; MH+ expt. 546 | Example 12,<br>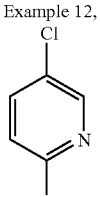<br>commercially available |
| 16-5 | 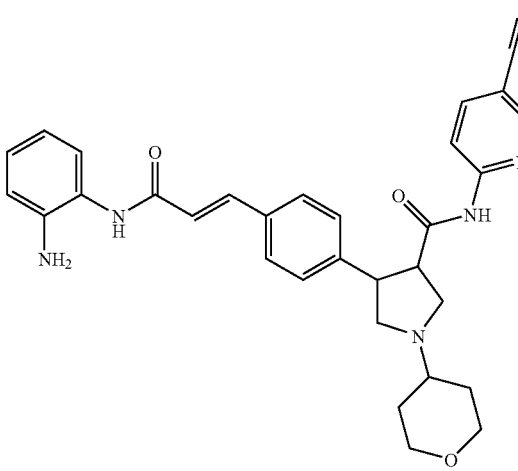<br>MW 535.64; MH+ calc. 536; MH+ expt. 536 | Example 12,<br>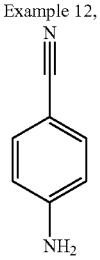<br>commercially available |
| 16-6 | 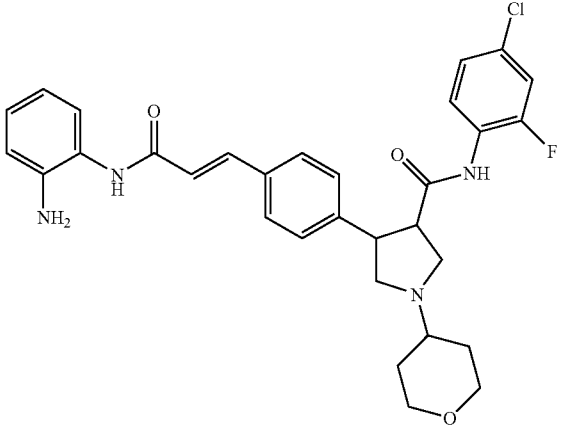<br>MW 563.06; MH+ calc. 563; MH+ expt. 563 | Example 12,<br>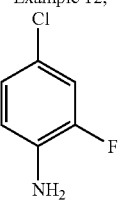<br>commercially available |

TABLE 5-continued
Starting material(s) and MS data of examples 16-2 to 16-20
| Example # | Structure | Starting Materials |
|---|---|---|
| 16-7 | 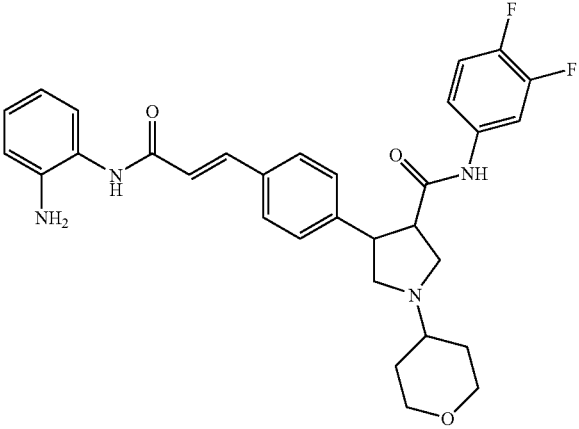<br>MW 546.62; MH+ calc. 547; MH+ expt. 547 | Example 12,<br>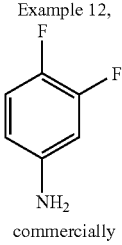<br>commercially available |
| 16-8 | 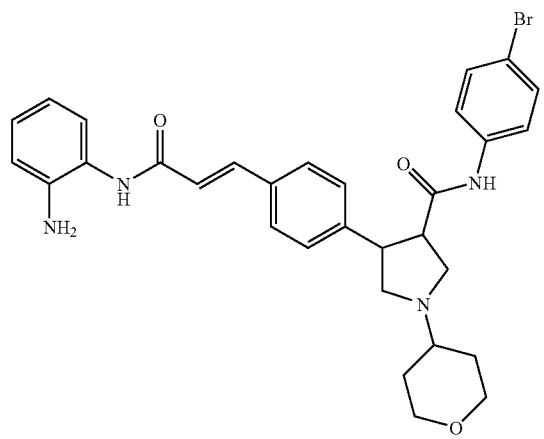<br>MW 589.54; MH+ calc. 589; MH+ expt. 589 | Example 12,<br>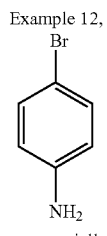<br>commercially available |
| 16-9 | 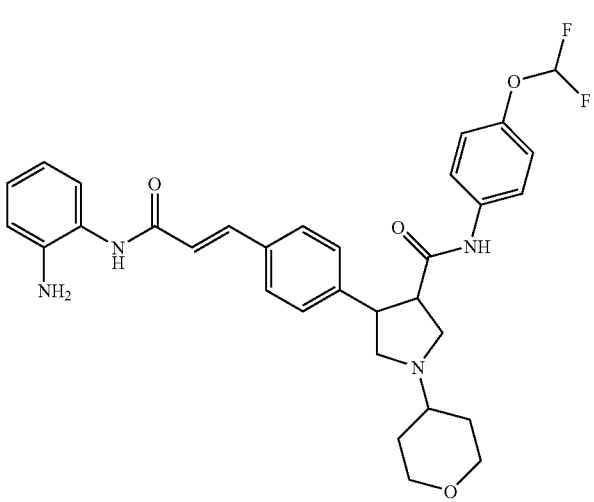<br>MW 576.65; MH+ calc. 577; MH+ expt. 577 | Example 12,<br>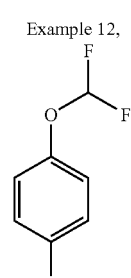<br>commercially available |

TABLE 5-continued

Starting material(s) and MS data of examples 16-2 to 16-20

| Example # | Structure | Starting Materials |
|---|---|---|
| 16-10 | MW 529.62; MH⁺ calc. 530; MH⁺ expt. 530 | Example 12, 5-fluoro-2-aminopyridine, commercially available |
| 16-11 | MW 563.08; MH⁺ calc. 563; MH⁺ expt. 563 | Example 12, 3-chloro-4-fluoroaniline, commercially available |
| 16-12 | MW 576.65; MH⁺ calc. 577; MH⁺ expt. 577 | Example 12, 3-(difluoromethoxy)aniline, commercially available |

TABLE 5-continued

Starting material(s) and MS data of examples 16-2 to 16-20

| Example # | Structure | Starting Materials |
|---|---|---|
| 16-13 | MW 546.62; MH+ calc. 547; MH+ expt. 547 | Example 12, 2,4-difluoroaniline commercially available |
| 16-14 | MW 504.58; MH+ calc. 505; MH+ expt. 505 | Example 6, 2,4-difluoroaniline commercially available |
| 16-15 | MW 486.59; MH+ calc. 487; MH+ expt. 487 | Example 6, 4-fluoroaniline commercially available |

TABLE 5-continued

Starting material(s) and MS data of examples 16-2 to 16-20

| Example # | Structure | Starting Materials |
|---|---|---|
| 16-16 | MW 547.50; MH+ calc. 547; MH+ expt. 547 | Example 6, 4-bromoaniline commercially available |
| 16-17 | MW 503.05; MH+ calc. 503; MH+ expt. 503 | Example 6, 4-chloroaniline commercially available |
| 16-18 | MW 493.61; MH+ calc. 494; MH+ expt. 494 | Example 6, 4-cyanoaniline commercially available |

TABLE 5-continued

Starting material(s) and MS data of examples 16-2 to 16-20

| Example # | Structure | Starting Materials |
|---|---|---|
| 16-19 | 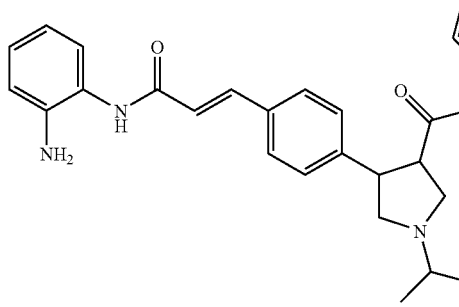<br>MW 504.58; MH+ calc. 505; MH+ expt. 505 | Example 6,<br>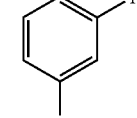<br>commercially available |
| 16-20 | 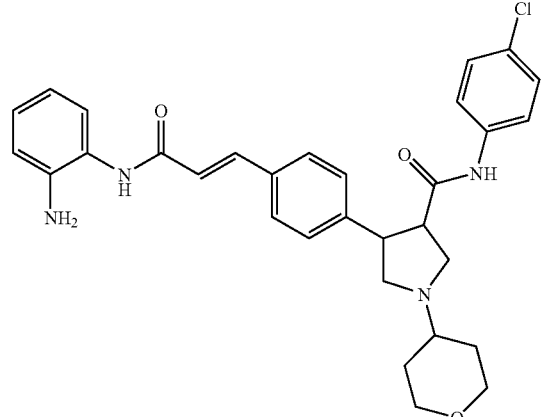<br>MW 547.50; MH+ calc. 547; MH+ expt. 547 | Example 6,<br>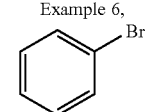<br>commercially available |

TABLE 6

NMR data of examples 16-2 to 16-20

| Example # | NMR data |
|---|---|
| 16-2 | $^1$H NMR (CD$_3$OD, 400 MHz), 7.660 (d, 1H, J = 15.6 Hz), 7.602 (d, 2H, J = 8 Hz), 7.529 (d, 2H, J = 8.4 Hz), 7.423 (d, 2H, J = 7.6 Hz), 7.290 (d, 2H, J = 8.4 Hz), 7.215 (d, 1H, J = 7.6 Hz), 7.064 (t, 1H, J = 7.6 Hz), 6.895 (d, 1H, J = 8 Hz), 6.841 (d, 1H, J = 15.6 Hz), 6.764 (t, 1H, J = 7.2 Hz), 4.007-3.982 (broad d, 2H), 3.803-3.783 (m, 1H), 3.471 (t, 2H, J = 11.6 Hz), 3.284-3.157 (m, 3H), 2.995-2.944 (m, 2H), 2.487-2.478 (m, 1H), 1.932-1.909 (m, 2H), 1.645-1.595 (m, 2H) |
| 16-3 | $^1$H NMR (CD$_3$OD, 400 MHz), 7.653 (d, 1H, J = 15.6 Hz), 7.590 (d, 2H, J = 8 Hz), 7.448-7.407 (m, 3H), 7.213 (d, 1H, J = 8 Hz), 7.076-6.971 (m, 3H), 6.898-6.731 (m, 3H), 4.000-3.974 (broad d, 2H), 3.818-3.776 (m, 4H), 3.490-3.432 (m, 2H), 3.328-3.142 (m, 3H), 2.995-2.937 (m, 2H), 2.482 (broad s, 1H), 1.921-1.891 (m, 2H), 1.635-1.585 (m, 2H) |
| 16-4 | $^1$H NMR (CD$_3$OD, 400 MHz), 8.253 (d, 1H, J = 2.4 Hz), 8.167 (d, 1H, J = 8.8 Hz), 7.805-7.776 (m, 1H), 7.670 (d, 1H, J = 15.6 Hz), 7.609 (d, 2H, J = 8 Hz), 7.433 (d, 2H, J = 8 Hz), 7.223 (d, 1H, J = 8 Hz), 7.090-7.052 (m, 1H), 6.912-6.752 (m, 3H), 4.022-3.994 (broad d, 2H), 3.838-3.818 (m, 1H), 3.480 (t, 2H, J = 11.6 Hz, J = 11.2 Hz), 3.306-3.238 (m, 3H), 3.091-3.075 (m, 1H), 2.900 (t, 1H, J = 8.8 Hz), 2.526 (broad s, 1H), 1.946-1.917 (m, 2H), 1.663-1.604 (m, 2H) |

TABLE 6-continued

NMR data of examples 16-2 to 16-20

| Example # | NMR data |
|---|---|
| 16-5 | $^1$H NMR (d$_6$-DMSO, 400 MHz), 10.388 (s, 1H), 9.388 (s, 1H), 7.748 (s, 4H), 7.581-7.504 (m, 3H), 7.388-7.306 (m, 3H), 6.940-6.838 (m, 2H), 6.754 (d, 1H, J = 8 Hz), 6.581 (t, 1H, J = 7.6 Hz), 4.932 (s, 2H), 3.861 (broad s, 2H), 3.722-3.685 (m, 1H), 3.326-3.042 (m, 3H), ), 2.856 (broad s, 1H), 2.730 (broad s, 1H), ), 2.110 (broad s, 1H), 1.838-1.777 (m, 2H), 1.464-1.365 (m, 2H), |
| 16-6 | $^1$H NMR (CD$_3$OD, 400 MHz), 7.912 (t, 1H, J = 8.4 Hz), 7.688-7.601 (m, 3H), 7.431 (d, 2H, J = 8 Hz), 7.266-7.168 (m, 3H), 7.084-7.046 (m, 1H), 6.906-6.831 (m, 2H), 6.784-6.746 (m, 1H), 4.012-3.984 (broad d, 2H), 3.786-3.767 (m, 1H), 3.472 (t, 2H, J = 11.2 Hz), 3.299-3.201 (m, 3H), 3.097-3.063 (m, 1H), 2.908-2.865 (m, 1H), 2.509-2.481 (m, 1H), 1.943-1.914 (broad d, 2H), 1.654-1.596 (m, 2H) |
| 16-7 | $^1$H NMR (CD$_3$OD, 400 MHz), 7.718-7.596 (m, 4H), 7.423 (d, 2H, J = 8 Hz), 7.220-7.161 (m, 3H), 7.081-7.044 (m, 1H), 6.902-6.822 (m, 2H), 6.780-6.743 (m, 1H), 4.014-3.986 (broad d, 2H), 3.805-3.785 (m, 1H), 3.470 (t, 2H, J = 11.2 Hz), 3.290-3.151 (m, 3H), 3.047-2.982 (m, 2H), 2.550 (broad s, 1H), 1.945-1.889 (m, 2H), 1.651-1.602 (m, 2H) |
| 16-8 | $^1$H NMR (CD$_3$OD, 400 MHz), 7.674-7.585 (m, 3H), 7.486-7.406 (m, 6H), 7.209 (d, 1H, J = 7.6 Hz), 7.077-7.039 (m, 1H), 6.899-6.815 (m, 2H), 6.777-6.739 (m, 1H), 4.004-3.977 (broad d, 2H), 3.796-3.776 (m, 1H), 3.464 (t, 2H, J = 11.2 Hz, J = 11.6 Hz), 3.279-3.150 (m, 3H), 2.999-2.945 (m, 2H), 2.494 (broad s, 1H), 1.928-1.898 (m, 2H), 1.638-1.588 (m, 2H) |
| 16-9 | $^1$H NMR (CD$_3$OD, 400 MHz), 7.662-7.526 (m, 5H), 7.405 (d, 2H, J = 8 Hz), 7.205 (d, 1H, J = 7.6 Hz), 7.083-7.031 (m, 3H), 6.926-6.730 (m, 4H), 3.992-3.964 (broad d, 2H), 3.787-3.746 (m, 1H), 3.451 (t, 2H, J = 11.2 Hz), 3.288-3.122 (m, 3H), 2.992-2.931 (m, 2H), 2.475-2.448 (m, 1H), 1.912-1.883 (m, 2H), 1.634-1.595 (m, 2H) |
| 16-10 | $^1$H NMR (CD$_3$OD, 400 MHz), 8.188-8.161 (m, 2H), 7.685-7.558 (m, 4H), 7.427 (d, 2H, J = 8 Hz), 7.224 (d, 1H, J = 8 Hz), 7.088-7.050 (m, 1H), 6.909-6.827 (m, 2H), 6.787-6.749 (m, 1H), 4.015-3.989 (broad d, 2H), 3.831-3.811 (m, 1H), 3.475 (t, 2H, J = 11.6 Hz, J = 11.2 Hz), 3.309-3.225 (m, 3H), 3.075-3.040 (m, 1H), 2.909-2.866 (m, 1H), 2.531-2.477 (m, 1H), 1.937-1.908 (m, 2H), 1.665-1.597 (m, 2H) |
| 16-11 | $^1$H NMR (CD$_3$OD, 400 MHz), 7.809 (broad s, 1H), 7.667-7.577 (m, 3H), 7.418-7.351 (m, 3H), 7.224-7.132 (m, 2H), 7.076-7.040 (m, 1H), 6.899-6.816 (m, 2H), 6.774-6.738 (m, 1H), 4.000-3.973 (broad d, 2H), 3.793-3.773 (m, 1H), 3.456 (t, 2H, J = 11.6 Hz, J = 11.2 Hz), 3.298-3.136 (m, 3H), 3.010-2.942 (m, 2H), 2.495 (broad s, 1H), 1.920-1.890 (m, 2H), 1.633-1.583 (m, 2H) |
| 16-12 | $^1$H NMR (CD$_3$OD, 400 MHz), 7.664-7.527 (m, 4H), 7.408 (d, 2H, J = 8 Hz), 7.291 (d, 2H, J = 5.2 Hz), 7.208 (d, 1H, J = 7.6 Hz), 7.071-7.033 (m, 1H), 6.893-6.849 (m, 2H), 6.810-6.731 (m, 3H), 3.996-3.968 (broad d, 2H), 3.798-3.757 (m, 1H), 3.452 (t, 2H, J = 11.6 Hz, J = 11.2 Hz), 3.301-3.136 (m, 3H), 3.010-2.939 (m, 2H), 2.520-2.466 (m, 1H), 1.918-1.887 (m, 2H), 1.639-1.571 (m, 2H) |
| 16-13 | $^1$H NMR (CD$_3$OD, 400 MHz), 7.788-7.751 (m, 1H), 7.692-7.607 (m, 3H), 7.441 (d, 2H, J = 8 Hz), 7.220 (d, 1H, J = 7.6 Hz), 7.085-6.997 (m, 2H), 6.968-6.835 (m, 3H), 6.786-6.748 (m, 1H), 4.015-3.988 (broad d, 2H), 3.788-3.769 (m, 1H), 3.474 (t, 2H, J = 11.4 Hz), 3.287-3.246 (m, 3H), 3.075 (broad s, 1H), 2.942-2.899 (m, 1H), 2.519 (broad s, 1H), 1.947-1.918 (m, 2H), 1.657-1.601 (m, 2H) |
| 16-14 | $^1$H NMR (CD$_3$OD, 400 MHz), 7.80-7.76 (m, 1H), 7.67 (d, 1H, J = 16.4 Hz), 7.62 (d, 2H, J = 8.0 Hz), 7.43 (d, 2H, J = 8.0 Hz), 7.22 (d, 1H, J = 7.6 Hz), 7.08-6.99 (m, 2H), 6.96-6.84 (m, 3H), 6.79-6.75 (m, 1H), 3.81-3.76 (m, 1H), 3.28-3.20 (m, 3H), 3.13-3.10 (m, 1H), 2.94-2.89 (m, 1H), 2.68-2.65 (m, 1H), 1.22-1.19 (m, 6H). |
| 16-15 | $^1$H NMR (CD$_3$OD, 400 MHz), 7.65 (d, 1H, J = 15.6 Hz), 7.59 (d, 2H, J = 8.0 Hz), 7.52-7.49 (m, 2H), 7.41 (d, 2H, J = 8.0 Hz), 7.21 (d, 1H, J = 7.6 Hz), 7.08-7.00 (m, 3H), 6.90-6.82 (m, 2H), 6.78-6.74 (m, 1H), 3.82-3.78 (m, 1H), 3.25-3.15 (m, 3H), 3.03-2.93 (m, 2H), 2.63-2.60 (m, 1H), 1.21-1.17 (m, 6H). |
| 16-16 | $^1$H NMR (d$_6$-DMSO, 400 MHz), 10.09 (s, 1H), 9.44 (s, 1H), 7.57-7.49 (m, 5H), 7.46 (d, 2H, J = 8.8 Hz), 7.36 (d, 2H, J = 8.0 Hz), 7.30 (d, 1H, J = 7.6 Hz), 6.95-6.91 (m, 1H), 6.85 (d, 1H, J = 16.0 Hz), 6.76 (d, 1H, J = 8.0 Hz), 6.61-6.56 (m, 1H), 4.91 (s, 2H), 3.72-3.66 (m, 2H), 3.20-3.15 (m, 1H), 3.13-3.09 (m, 1H), 3.04-2.99 (m, 1H), 2.87-2.77 (m, 1H), 2.71-2.67 (m, 1H), 2.49-2.46 (m, 1H), 1.08-1.05 (m, 6H). |
| 16-17 | $^1$H NMR (CD$_3$OD, 400 MHz), 7.76 (d, 1H, J = 15.6 Hz), 7.69 (d, 2H, J = 8.0 Hz), 7.53-7.48 (m, 4H), 7.34-7.25 (m, 6H), 6.89 (d, 1H, J = 15.6 Hz), 3.83 (broad s, 2H), 3.63 (broad s, 2H), 3.57-2.84 (m, 3H), 1.41-1.37 (m, 6H). |
| 16-18 | $^1$H NMR (CD$_3$OD, 400 MHz), 7.68-7.56 (m, 4H), 7.45-7.38 (m, 4H), 7.18-7.12 (m, 2H), 7.04-7.00 (m, 1H), 6.86-6.82 (m, 2H), 6.74-6.70 (m, 1H), 3.82-3.78 (m, 1H), 3.44-3.36 (m, 2H), 3.24-3.12 (m, 3H), 2.89-2.87 (m, 1H), 1.25-1.22 (m, 6H). |

TABLE 6-continued

NMR data of examples 16-2 to 16-20

| Example # | NMR data |
|---|---|
| 16-19 | $^1$H NMR (CD$_3$OD, 400 MHz), 7.69-7.64 (m, 2H), 7.60 (d, 2H, J = 8.0 Hz), 7.42 (d, 2H, J = 8.0 Hz), 7.22-7.16 (m, 3H), 7.07-7.05 (m, 1H), 6.91-6.83 (m, 2H), 6.79-6.76 (m, 1H), 3.82-3.78 (m, 1H), 3.25-3.14 (m, 3H), 3.03-2.95 (m, 2H), 2.64-2.62 (m, 1H), 1.22-1.18 (m, 6H). |
| 16-20 | $^1$H NMR (CD$_3$OD, 400 MHz), 7.88 (s, 1H), 7.66 (d, 1H, J = 15.6 Hz), 7.60 (d, 2H, J = 8.0 Hz), 7.43-7.41 (m, 3H), 7.25-7.17 (m, 3H), 7.08-7.04 (m, 1H), 6.90-6.82 (m, 2H), 6.78-6.74 (m, 1H), 3.82-3.79 (m, 1H), 3.28-3.16 (m, 3H), 3.04-2.86 (m, 2H), 2.64-2.60 (m, 1H), 1.21-1.18 (m, 6H). |

Example 17

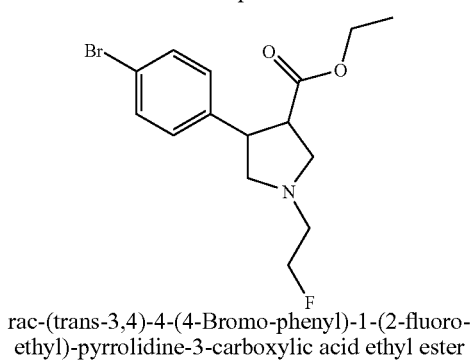

rac-(trans-3,4)-4-(4-Bromo-phenyl)-1-(2-fluoro-ethyl)-pyrrolidine-3-carboxylic acid ethyl ester A 20 mL microwave process vial was charged with rac-(trans-3,4)-4-(4-bromo-phenyl)-pyrrolidine-3-carboxylic acid ethyl ester (1.49 g, 5 mmol), K$_2$CO$_3$ (1.38 g, 10 mmol), KI (41.5 mg, 0.25 mmol) and 1-bromo-2-fluoro-ethane (0.76 g, 6 mmol) in DMF (15 mL). The vial was sealed and heated at 130 degrees Celsius for 20 min under microwave irradiation. After cooling, the solution was poured into water (30 ml), and the aqueous layer was extracted with ethyl acetate (3×50 mL). The combined organic layer was washed with brine, dried with Na$_2$SO$_4$, filtered, and evaporated. The crude product was purified by column chromatography (PE: EtOAc=1:1) to give product as a yellow solid. MS: calc'd 344 (MH+), exp 344 (MH+).

Example 18

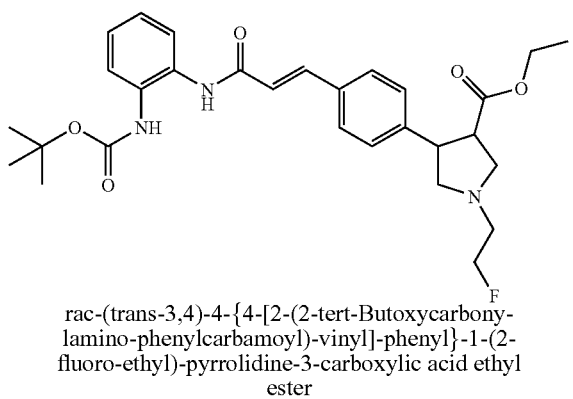

rac-(trans-3,4)-4-{4-[2-(2-tert-Butoxycarbony-lamino-phenylcarbamoyl)-vinyl]-phenyl}-1-(2-fluoro-ethyl)-pyrrolidine-3-carboxylic acid ethyl ester To a solution of rac-(trans-3,4)-4-(4-bromo-phenyl)-1-(2-fluoro-ethyl)-pyrrolidine-3-carboxylic acid ethyl ester (2.0 g, 5.81 mmol), Pd$_2$(dba)$_3$ (265.8 mg, 0.29 mmol), tri-(o-tolyl)-phosphine (88 mg, 0.29 mmol) and Et$_3$N (17.5 g, 17.4 mmol) in DMF (20 mL) was added (2-acryloylamino-phenyl)-carbamic acid tert-butyl ester (1.82 g, 6.97 mmol). This mixture was stirred at 100 degrees Celsius for about 3 h until the starting material had been consumed, then the reaction was cooled and filtered. The solution was poured into water (40 mL), extracted with ethyl acetate (3×60 mL). The combined organic layer was washed with brine, dried with Na$_2$SO$_4$, filtered, and evaporated. The crude product was purified by column chromatography (PE:EtOAc=1:1) to give yellow solid product. MS: calc'd 526 (MH+), exp 526 (MH+).

Example 19

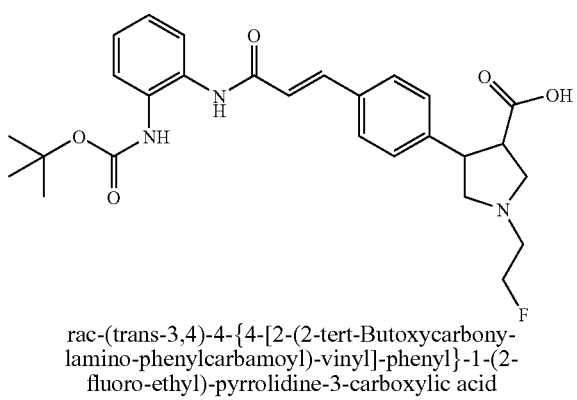

rac-(trans-3,4)-4-{4-[2-(2-tert-Butoxycarbony-lamino-phenylcarbamoyl)-vinyl]-phenyl}-1-(2-fluoro-ethyl)-pyrrolidine-3-carboxylic acid To a solution of rac-(trans-3,4)-4-{4-[2-(2-tert-butoxycar-bonylamino-phenylcarbamoyl)-vinyl]-phenyl}-1-(2-fluoro-ethyl)-pyrrolidine-3-carboxylic acid ethyl ester (1.05 g, 2.0 mmol) in MeOH/H$_2$O (20 mL/6 mL) was added LiOH.H$_2$O (252 mg, 6.0 mmol). This mixture was stirred at room temperature overnight and then evaporated to remove most of the MeOH. The mixture was extracted with ethyl acetate (3×50 mL). The combined organic layer was washed with brine, dried with Na$_2$SO$_4$, filtered, and evaporated to get yellow solid product. MS: calc'd 498 (MH+), exp 498 (MH+).

Example 20

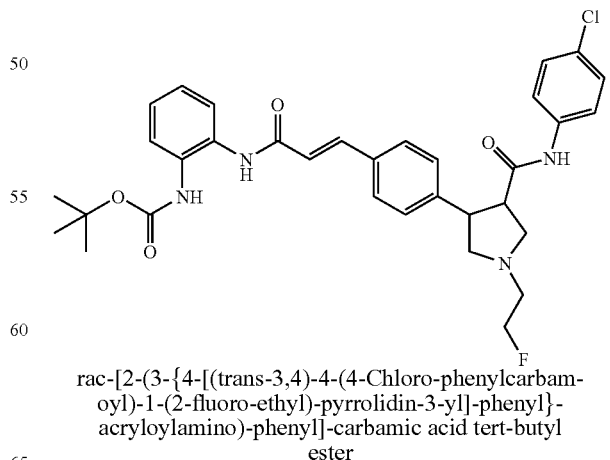

rac-[2-(3-{4-[(trans-3,4)-4-(4-Chloro-phenylcarbam-oyl)-1-(2-fluoro-ethyl)-pyrrolidin-3-yl]-phenyl}-acryloylamino)-phenyl]-carbamic acid tert-butyl ester To a solution of rac-(trans-3,4)-4-{4-[2-(2-tert-butoxycar-bonylamino-phenylcarbamoyl)-vinyl]-phenyl}-1-(2-fluoroethyl)-pyrrolidine-3-carboxylic acid (300 mg, 0.6 mmol), HATU (342 mg, 0.9 mmol) and Et$_3$N (181.8 mg, 1.8 mmol) in CH$_2$Cl$_2$ (15 mL) was added 4-chloroaniline (114.3 mg, 0.9 mmol). The reaction was stirred at room temperature overnight. The mixture was diluted with CH$_2$Cl$_2$ (15 mL) and washed with water (15 mL) and brine (15 mL), dried with Na$_2$SO$_4$, filtered, and evaporated in vacuo to obtain light yellow residue which was used without further purification. MS: calc'd 607 (MH+), exp 607 (MH+).

Example 21

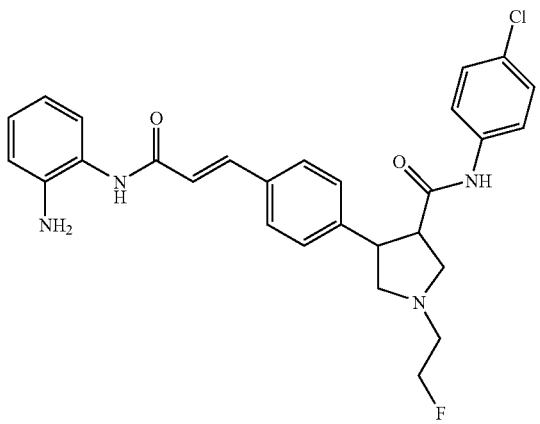

rac-(trans-3,4)-4-{4-[2-(2-Amino-phenylcarbamoyl)-vinyl]-phenyl}-1-(2-fluoro-ethyl)-pyrrolidine-3-carboxylic acid (4-chloro-phenyl)-amide Hydrochloric acid in methanol (1.25 M, 5 mL) was added to the rac-[2-(3-{4-[(trans-3,4)-4-(4-chloro-phenylcarbamoyl)-1-(2-fluoro-ethyl)-pyrrolidin-3-yl]-phenyl}-acryloylamino)-phenyl]-carbamic acid tert-butyl ester residue, the mixture was stirred for about 3 h, and then NaHCO$_3$ was added to the reaction system. After filtration of solids, the crude mixture was purified by preparative HPLC to obtain light yellow solid. MS: calc'd 507 (MH+), exp 507 (MH+). $^1$H NMR (CD$_3$OD, 400 MHz), 7.66 (d, 1H, J=15.6 Hz), 7.60 (d, 2H, J=8.0 Hz), 7.53 (d, 2H, J=8.8 Hz), 7.42 (d, 2H, J=8.0 Hz), 7.21 (d, 1H, J=8.0 Hz), 7.08-7.04 (m, 3H), 6.90-6.82 (m, 2H), 6.78-6.74 (m, 1H), 4.69 (t, 1H, J=4.8 Hz), 4.57 (t, 1H, J=4.8 Hz), 3.84-3.78 (m, 1H), 3.30-3.16 (m, 3H), 3.03-2.87 (m, 4H).

Compounds 21-2 through 21-17 described in the following tables were prepared by methods analogous to the synthetic methods described for previous examples (with further details provided under the "methods notes" column in Table 7) by combining (2-acryloylamino-phenyl)-carbamic acid tert-butyl ester with the appropriate starting materials as indicated in Table 7.

TABLE 7

Structure, staffing materials, and method notes for Examples 21-2 to 21-17

| Example # | Structure | Starting Materials |
|---|---|---|
| 21-2 | 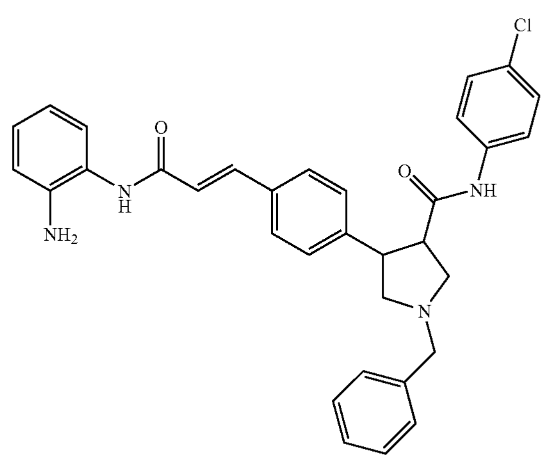 | Example 101, <br> <br> commercially available |

Method Notes: Start from N-benzyl-pyrrolidine Example 101. No alkylation step required.

TABLE 7-continued

Structure, staffing materials, and method notes for Examples 21-2 to 21-17

| Example # | Structure | Starting Materials |
|---|---|---|
| 21-3 | 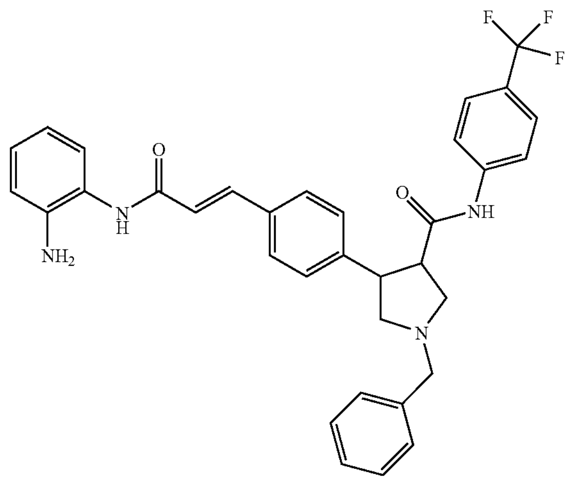 | Example 101, 4-CF₃-aniline commercially available |
| 21-4 | 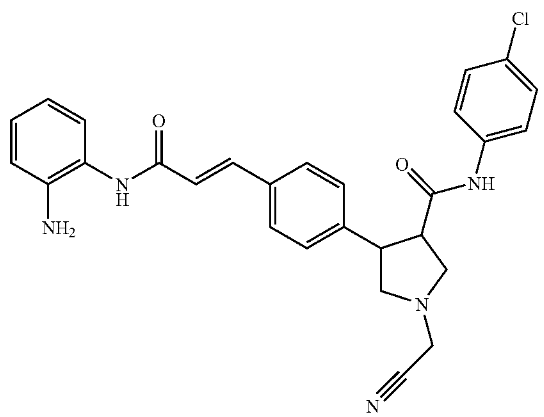 | Example 24, bromoacetonitrile commercially available |
| 21-5 | 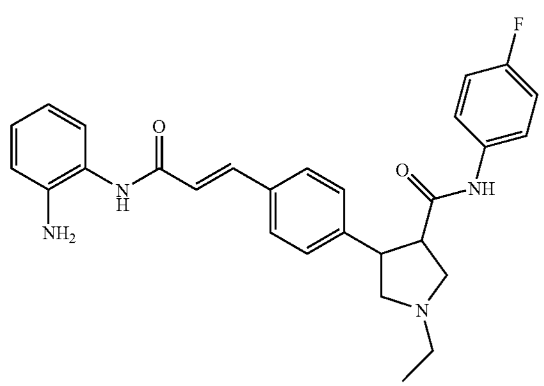 | Example 103, 4-F-aniline, acetaldehyde commercially available |

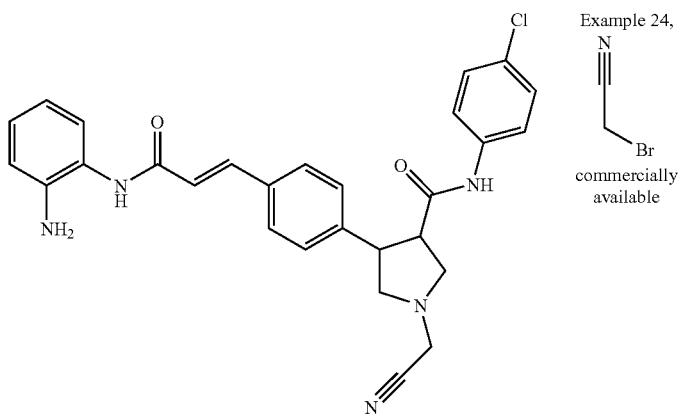

Method Notes: Start from N-benzyl pyrrolidine Example 101. No alkylation step required.

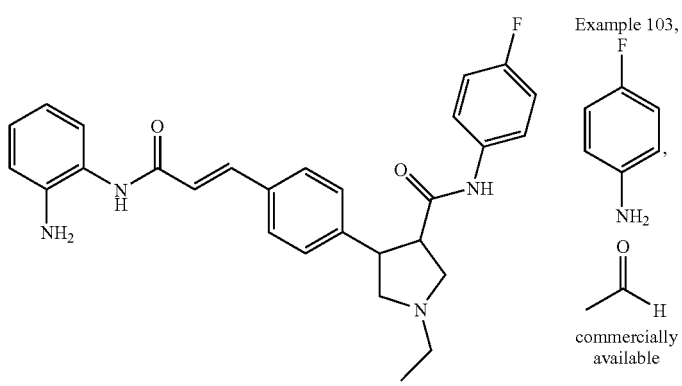

Method Notes: Alkylation of pyrrolidine Example 24 with bromo-acetonitrile, DIPEA, in MeOH/THF, 0 degrees Centigrade, 30 min.

Method Notes: Ethylation of pyrrolidine Example 103 via reductive amination using acetaldehyde, sodium triacetoxyborohydride and catalytic acetic acid (analogous to synthetic method for Example 16)

TABLE 7-continued

Structure, staffing materials, and method notes for Examples 21-2 to 21-17

| Example # | Structure | Starting Materials |
|---|---|---|
| 21-6 | 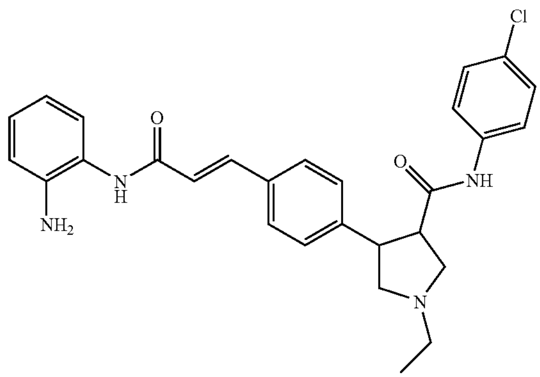 | Example 103, 4-chloroaniline, acetaldehyde, commercially available |

Method Notes: Ethylation of pyrrolidine Example 103 via reductive amination using acetaldehyde, sodium triacetoxyborohydride and catalytic acetic acid (analogous to synthetic method for Example 16)

| 21-7 | | Example 17, 4-bromoaniline, commercially available |

Method Notes: Analogous to synthetic method for Example 21

| 21-8 | | Example 17, 3-methoxy-4-chloroaniline, commercially available |

Method Notes: Analogous to synthetic method for Example 21

TABLE 7-continued

Structure, staffing materials, and method notes for Examples 21-2 to 21-17

| Example # | Structure | Starting Materials |
|---|---|---|
| 21-9 | 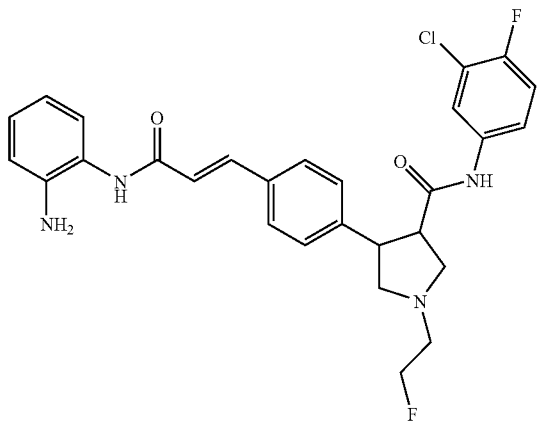 | Example 17, <br> commercially available |
| | Method Notes: Analogous to synthetic method for Example 21 | |
| 21-10 | 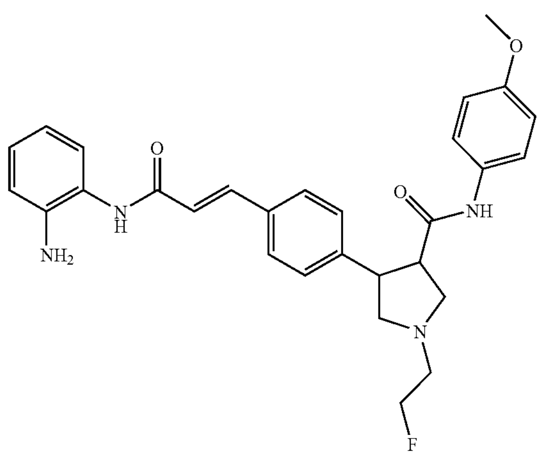 | Example 17, <br> commercially available |
| | Method Notes: Analogous to synthetic method for Example 21 | |
| 21-11 | 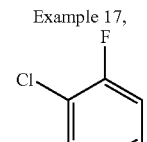 | Example 17, <br> commercially available |
| | Method Notes: Analogous to synthetic method for Example 21 | |

TABLE 7-continued

Structure, staffing materials, and method notes for Examples 21-2 to 21-17

| Example # | Structure | Starting Materials |
|---|---|---|
| 21-12 | 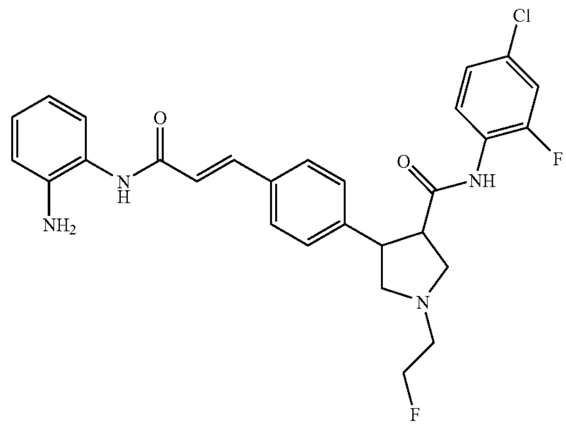 | Example 17, 4-chloro-2-fluoroaniline, commercially available |
| | Method Notes: Analogous to synthetic method for Example 21 | |
| 21-13 | 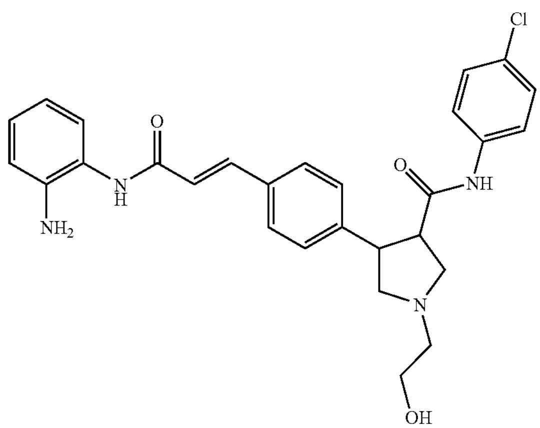 | Example 24, ethylene oxide, commercially available |
| | Method Notes: Alkylation of pyrrolidine Example 24 with neat ethylene oxide at r.t. overnight | |
| 21-14 | 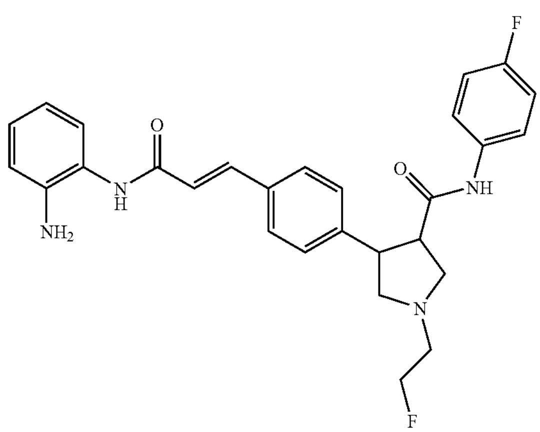 | Example 17, 4-fluoroaniline, commercially available |
| | Method Notes: Analogous to synthetic method for Example 21 | |

TABLE 7-continued

Structure, staffing materials, and method notes for Examples 21-2 to 21-17

| Example # | Structure | Starting Materials |
|---|---|---|
| 21-15 | [Structure: 2-aminophenyl cinnamide linked to phenyl-pyrrolidine-carboxamide (4-chlorophenyl), N-(2-methoxyethyl) pyrrolidine] | Example 103, 4-chloroaniline, 1-bromo-2-methoxyethane (commercially available) |

Method Notes: Alkylation of pyrrolidine Example 103 with 1-bromo-2-methoxy-ethane in a mixture of $K_2CO_3$ in DMF at room temp

| 21-16 | [Structure: 2-aminophenyl cinnamide linked to phenyl-pyrrolidine-carboxamide (4-chlorophenyl), N-(oxetan-3-yl) pyrrolidine] | Example 103, 4-chloroaniline, 3 equiv oxetan-3-yl tosylate (commercially available) |

Method Notes: Alkylation of pyrrolidine Example 103 with oxetane derivative in DMSO containing DBU at 120 degrees Centigrade (microwave conditions) for 40 min.

| 21-17 | [Structure: 2-aminophenyl cinnamide linked to phenyl-pyrrolidine-carboxamide (4-chlorophenyl), N-(pyrimidin-2-yl) pyrrolidine] | Example 103, 4-chloroaniline, 2-chloropyrimidine (commercially available) |

Method Notes: Arylation of pyrrolidine Example 103 with 2-chloropyrimidine in isopropyl alcohol containing DIPEA at 130 degrees centigrade (microwave conditions) for 10 min.

TABLE 8

MS and NMR data of examples 21-2 to 21-17

| Examples | MS and NMR data |
|---|---|
| 21-2 | $^1$H NMR (CD$_3$OD, 400 MHz), 7.63 (d, 1H, J = 15.6 Hz), 7.56 (d, 2H, J = 8.0 Hz), 7.52 (d, 2H, J = 8.8 Hz), 7.44-7.29 (m, 6H), 7.27-7.23 (m, 3H), 7.18 (dd, 1H, J = 8.4, 1.2 Hz), 7.05-7.01 (m, 1H), 6.86 (dd, 1H, J = 8.0, 1.2 Hz), 6.81 (d, 1H, J = 15.6 Hz), 6.76-6.71 (m, 1H), 3.81-3.68 (m, 3H), 3.20-3.06 (m, 3H), 2.91-2.84 (m, 2H). MS: calc'd 551 (MH+), exp 551 (MH+) |
| 21-3 | $^1$H NMR (d$_6$-DMSO, 400 MHz), 10.26 (s, 1H), 9.38 (s, 1H), 7.76 (d, 2H, J = 8.8 Hz), 7.64 (d, 2H, J = 8.4 Hz), 7.57-7.49 (m, 3H), 7.39-7.32 (m, 7H), 7.27-7.23 (m, 1H), 6.92-6.88 (m, 1H), 6.85 (d, 1H, J = 15.6 Hz), 6.74 (dd, 1H, J = 8.0, 1.2 Hz), 7.59-7.54 (m, 1H), 4.95 (s, 2H), 3.78-3.76 (m, 1H), 3.69 (s, 2H), 3.18-3.16 (m, 2H), 2.99-2.94 (m, 1H), 2.83-2.79 (m, 1H), 2.70-2.60 (m, 1H). MS: calc'd 585 (MH+), exp 585 (MH+) |
| 21-4 | $^1$H NMR (d$_6$-DMSO, 400 MHz), 10.12 (s, 1H), 9.39 (s, 1H), 7.61-7.57 (m, 4H), 7.53 (d, 1H, J = 16.0 Hz), 7.38-7.32 (m, 5H), 6.94-6.90 (m, 1H), 6.87 (d, 1H, J = 16.0 Hz), 6.75 (d, 1H, J = 7.6 Hz), 6.60-6.56 (m, 1H), 4.94 (s, 2H), 3.93 (s, 2H), 3.79-3.76 (m, 1H), 3.24-3.09 (m, 3H), 2.87-2.84 (m, 2H). MS: calc'd 500 (MH+), exp 500 (MH+) |
| 21-5 | $^1$H NMR (CD$_3$OD, 400 MHz), 7.72 (d, 1H, J = 15.6 Hz), 7.66 (d, 2H, J = 8.0 Hz), 7.59-7.56 (m, 2H), 7.48 (d, 2H, J = 8.0 Hz), 7.27 (d, 1H, J = 7.6 Hz), 7.14-7.07 (m, 3H), 6.95 (d, 1H, J = 8.0 Hz), 6.90 (d, 1H, J = 15.6 Hz), 6.84-6.80 (m, 1H), 3.90-3.87 (m, 1H), 3.25-3.18 (m, 3H), 3.03-2.98 (m, 2H), 2.78-2.75 (m, 2H), 1.28 (t, 3H, J = 7.2 Hz). MS: calc'd 473 (MH+), exp 473 (MH+) |
| 21-6 | $^1$H NMR (CD$_3$OD, 400 MHz), 7.64 (d, 1H, J = 15.6 Hz), 7.60 (d, 2H, J = 8.0 Hz), 7.51 (d, 2H, J = 8.8 Hz), 7.41 (d, 2H, J = 8.0 Hz), 7.27 (d, 2H, J = 8.8 Hz), 7.19 (d, 1H, J = 7.6 Hz), 7.06-7.02 (m, 1H), 6.87 (d, 1H, J = 8.0 Hz), 6.83 (d, 1H, J = 15.6 Hz), 6.76-6.72 (m, 1H), 3.86-3.80 (m, 1H), 3.28-3.19 (m, 5H), 2.86-2.72 (m, 2H), 1.22 (t, 3H, J = 7.2 Hz). MS: calc'd 489 (MH+), exp 489 (MH+) |
| 21-7 | $^1$H NMR (CD$_3$OD, 400 MHz), 7.63 (d, 1H, J = 15.6 Hz), 7.58 (d, 2H, J = 8.0 Hz), 7.46 (d, 2H, J = 8.8 Hz), 7.42-7.39 (m, 4H), 7.18 (d, 1H, J = 8.0 Hz), 7.04-7.01 (m, 1H), 6.88-6.83 (m, 2H), 6.76-6.73 (m, 1H), 4.66 (t, 1H, J = 4.8 Hz), 4.54 (t, 1H, J = 4.8 Hz), 3.80-3.77 (m, 1H), 3.24-3.20 (m, 3H), 3.00-2.91 (m, 4H). MS: calc'd 551 (MH+), exp 551 (MH+) |
| 21-8 | $^1$H NMR (CD$_3$OD, 400 MHz), 7.65 (d, 1H, J = 15.6 Hz), 7.59 (d, 2H, J = 8.0 Hz), 7.48-7.41 (m, 3H), 7.25-7.19 (m, 2H), 7.07-6.99 (m, 2H), 6.88 (d, 1H, J = 8.0 Hz), 6.79 (d, 1H, J = 15.6 Hz), 6.77-6.73 (m, 1H), 4.68 (t, 1H, J = 4.8 Hz), 4.56 (t, 1H, J = 4.8 Hz), 3.85 (m, 3H), 3.82-3.80 (m, 1H), 3.27-3.14 (m, 3H), 3.03-2.87 (m, 4H). MS: calc'd 537 (MH+), exp 537 (MH+) |
| 21-9 | $^1$H NMR (CD$_3$OD, 400 MHz), 7.78 (dd, 1H, J = 6.8, 2.8 Hz), 7.62 (d, 1H, J = 15.6 Hz), 7.57 (d, 2H, J = 8.0 Hz), 7.39 (d, 2H, J = 8.0 Hz), 7.36-7.32 (m, 1H), 7.18-7.11 (m, 1H), 7.04-7.00 (m, 2H), 6.86-6.78 (m, 2H), 6.74-6.70 (m, 1H), 4.65 (t, 1H, J = 4.8 Hz), 4.53 (t, 1H, J = 4.8 Hz), 3.78-3.76 (m, 1H), 3.25-3.08 (m, 3H), 2.97-2.84 (m, 4H). MS: calc'd 525 (MH+), exp 525 (MH+) |
| 21-10 | $^1$H NMR (CD$_3$OD, 400 MHz), 7.64 (d, 1H, J = 15.6 Hz), 7.58 (d, 2H, J = 8.0 Hz), 7.42-7.37 (m, 4H), 7.20-7.18 (m, 1H), 7.04-7.02 (m, 1H), 6.88-6.83 (m, 4H), 6.76-6.74 (m, 1H), 4.66 (t, 1H, J = 4.8 Hz), 4.54 (t, 1H, J = 4.8 Hz), 3.79-3.75 (m, 1H), 3.25-3.12 (m, 3H), 3.02-2.92 (m, 4H). MS: calc'd 503 (MH+), exp 503 (MH+) |
| 21-11 | $^1$H NMR (CD$_3$OD, 400 MHz), 7.67-7.60 (m, 3H), 7.53 (d, 2H, J = 8.8 Hz), 7.43 (d, 2H, J = 8.0 Hz), 7.19 (d, 1H, J = 7.6 Hz), 7.09-7.02 (m, 3H), 6.93-6.57 (m, 4H), 4.75 (t, 1H, J = 4.8 Hz), 4.63 (t, 1H, J = 4.8 Hz), 3.86-3.83 (m, 1H), 3.46-3.44 (m, 2H), 3.29-3.13 (m, 5H). MS: calc'd 539 (MH+), exp 539 (MH+) |
| 21-12 | $^1$H NMR (CD$_3$OD, 400 MHz), 7.90-7.86 (m, 1H), 7.65 (d, 1H, J = 15.6 Hz), 7.60 (d, 2H, J = 8.0 Hz), 7.42 (d, 2H, J = 8.0 Hz), 7.25-7.16 (m, 3H), 7.07-7.03 (m, 1H), 6.89-6.82 (m, 2H), 6.77-6.73 (m, 1H), 4.68 (t, 1H, J = 4.8 Hz), 4.56 (t, 1H, J = 4.8 Hz), 3.81-3.78 (m, 1H), 3.25-3.22 (m, 3H), 3.10-2.87 (m, 4H). MS: calc'd 525 (MH+), exp 525 (MH+) |
| 21-13 | $^1$H NMR (CD$_3$OD, 400 MHz), 7.69-7.63 (m, 3H), 7.53 (d, 2H, J = 8.8 Hz), 7.443 (d, 2H, J = 7.6 Hz), 7.30 (d, 2H, J = 8.8 Hz), 7.21 (d, 1H, J = 7.6 Hz), 7.09-7.05 (m, 1H), 6.91-6.84 (m, 2H), 6.78-6.75 (m, 1H), 3.90-3.81 (m, 3H), 3.57-3.39 (m, 4H), 3.29-3.04 (m, 3H). MS: calc'd 505 (MH+), exp 505 (MH+) |
| 21-14 | $^1$H NMR (CD$_3$OD, 400 MHz), 7.66 (d, 1H, J = 16.0 Hz), 7.60 (d, 2H, J = 8.0 Hz), 7.54-7.50 (m, 2H), 7.43 (d, 2H, J = 8.0 Hz), 7.22 (d, 1H, J = 8.0 Hz), 7.06-7.01 (m, 3H), 6.90-6.80 (m, 2H), 6.78-6.75 (m, 1H), 4.69 (t, 1H, J = 4.8 Hz), 4.57 (t, 1H, J = 4.8 Hz), 3.84-3.78 (m, 1H), 3.28-3.25 (m, 1H), 3.20-3.16 (m, 2H), 3.03-2.94 (m, 4H). MS: calc'd 491 (MH+), exp 491 (MH+) |

TABLE 8-continued

MS and NMR data of examples 21-2 to 21-17

| Examples | MS and NMR data |
|---|---|
| 21-15 | $^1$H NMR (CD$_3$OD, 400 MHz), 7.76 (d, 1H, J = 15.6 Hz), 7.69 (d, 2H, J = 8.0 Hz), 7.53-7.48 (m, 4H), 7.35-7.26 (m, 6H), 6.90 (d, 1H, J = 15.6 Hz), 4.0 (broad m, 4H), 3.78 (t, 2H, J = 4.8 Hz), 3.62-3.51 (m, 4H), 3.47 (s, 3H). MS: calc'd 519 (MH+), exp 519 (MH+) |
| 21-16 | $^1$H NMR (d$_6$-DMSO, 400 MHz), 10.34 (s, 1H), 9.60 (s, 1H), 7.54-7.65 (m, 5H), 7.47 (d, 2H, J = 8.0 Hz), 7.27-7.38 (m, 3H), 6.86-7.14 (m, 5H), 6.72 (t, 1H, J = 7.6 Hz), 4.82 (m, 2H), 4.69-4.80 (m, 2H), 4.67 (broad s, 2H), 3.90 (broad s, 2H), 3.48-3.53 (m, 3H) MS: calc'd 517 (MH+), exp 517 (MH+) |
| 21-17 | $^1$H NMR (CD$_3$OD, 400 MHz), 8.38 (d, 2H, J = 4.8 Hz), 7.69-7.62 (m, 3H), 7.53-7.46 (m, 4H), 7.29 (d, 2H, J = 8.8 Hz), 7.21 (d, 1H, J = 7.6 Hz), 7.08-7.04 (m, 1H), 6.90-6.83 (m, 2H), 6.78-6.74 (m, 1H), 6.70-6.67 (m, 1H), 4.26-4.16 (m, 2H), 3.95-3.90 (m, 1H), 3.83-3.70 (m, 2H), 3.47-3.40 (m, 1H). MS: calc'd 539 (MH+), exp 539 (MH+) |

Example 22

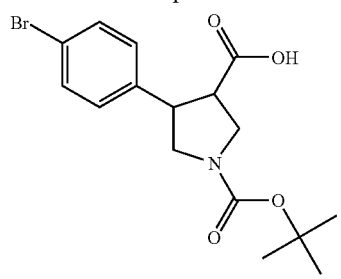

rac-(trans-3,4)-4-(4-Bromo-phenyl)-pyrrolidine-1,3-dicarboxylic acid 1-tert-butyl ester To a solution of rac-(trans-3,4)-4-(4-bromo-phenyl)-pyrrolidine-3-carboxylic acid ethyl ester (5.0 g, 16.8 mmol) in 20 mL acetonitrile was added 20 mL 2.5M NaOH and the resulted mixture was stirred at room temperature for two hours. Then Na$_2$CO$_3$ (3.56 g 33.6 mmol) and Boc$_2$O (11 g, 50.4 mmol) were added and the mixture was stirred at rt overnight. After removal of acetonitrile by vacuum, the residue was adjusted to pH=3. The solid was collected and triturated in hexane twice, dried by vacuum. Yield was 50%. MS: calc'd 370 (MH+), exp 370 (MH+).

Example 23

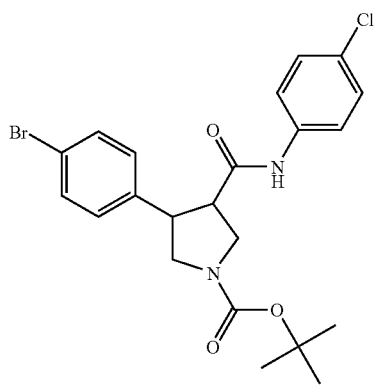

rac-(trans-3,4)-3-(4-Bromo-phenyl)-4-(4-chloro-phenylcarbamoyl)-pyrrolidine-1-carboxylic acid tert-butyl ester A suspension of rac-(trans-3,4)-4-(4-bromo-phenyl)-pyrrolidine-1,3-dicarboxylic acid 1-tert-butyl ester (3.1 g, 8.4 mmol), 4-chloroaniline (1.6 g, 12.6 mmol), HOBt (1.7 g, 12.6 mmol) and EDCI (2.4 g, 12.6 mmol) in 50 mL of dichloromethane was stirred at rt overnight, and the reaction mixture was washed with 1M NaOH, water and brine. The organic layer was dried over Na$_2$SO$_4$, and concentrated to give yellow oil, which was used directly in next step without purification. MS: calc'd 479 (MH+), exp 479 (MH+).

Example 24

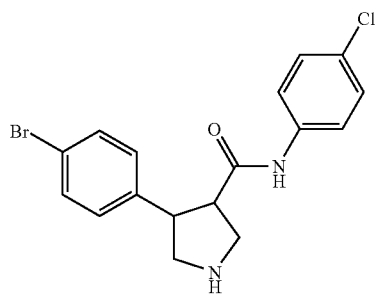

rac-(trans-3,4)-4-(4-Bromo-phenyl)-pyrrolidine-3-carboxylic acid (4-chloro-phenyl)-amide rac-(trans-3,4)-3-(4-Bromo-phenyl)-4-(4-chloro-phenylcarbamoyl)-pyrrolidine-1-carboxylic acid tert-butyl ester from the previous step was dissolved in 15 mL HCl/MeOH (1.25M) and stirred at r.t. for 3 hours. The reaction mixture was treated with saturated Na$_2$CO$_3$ solution and was extracted with dichloromethane. The organic layer was concentrated to give yellow oil which was used without further purification. MS: calc'd 379 (MH+), exp 379 (MH+).

Example 25

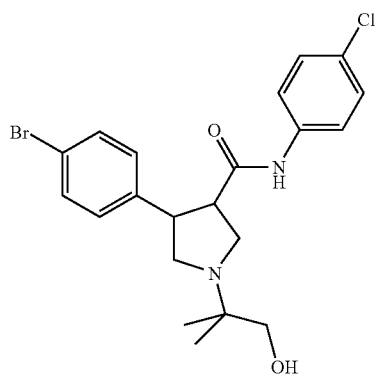

rac-(trans-3,4)-4-(4-Bromo-phenyl)-1-(2-hydroxy-1,1-dimethyl-ethyl)-pyrrolidine-3-carboxylic acid (4-chloro-phenyl)-amide To a solution of rac-(trans-3,4)-4-(4-bromo-phenyl)-pyrrolidine-3-carboxylic acid (4-chloro-phenyl)-amide (1.12 g, 2.98 mmol) in 5 mL DMF was added $K_2CO_3$ (1.24 g, 8.9 mmol) and 2-bromo-2-methyl-propionic acid methyl ester (0.81 g, 4.47 mmol), and the mixture was heated at 50 degrees Celsius for five hours. The reaction mixture was diluted with water and extracted with EtOAc, and the organic layer was washed with water and brine. After removal of solvent, the residue was dissolved in 30 mL dry THF under $N_2$ atmosphere, and then $LiBH_4$ (2M in THF, 2.9 mL, 5.8 mmol) was added dropwise at room temperature over 5 min. The resulting mixture was kept at this temperature for two hours and then quenched by adding water carefully. The mixture was extracted with EtOAc, and the crude product was purified by column chromatography. 0.23 g of product was obtained with a yield of 17%. MS: calc'd 451 (MH+), exp 451 (MH+).

Example 26

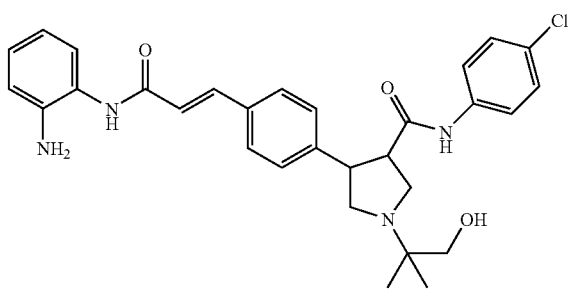

rac-(trans-3,4)-4-{4-[2-(2-Amino-phenylcarbamoyl)-vinyl]-phenyl}-1-(2-hydroxy-1,1-dimethyl-ethyl)-pyrrolidine-3-carboxylic acid (4-chloro-phenyl)-amide The mixture of rac-(trans-3,4)-4-(4-bromo-phenyl)-1-(2-hydroxy-1,1-dimethyl-ethyl)-pyrrolidine-3-carboxylic acid (4-chloro-phenyl)-amide (0.23 g, 0.5 mmol), (2-acryloylamino-phenyl)-carbamic acid tert-butyl ester (0.14 g, 0.53 mmol), $Pd_2(dba)_3$ (37 mg, 0.04 mmol), tri-(o-tolyl)-phosphine (27 mg, 0.08 mmol) in DMF (3 mL) and TEA (0.35 mL, 2.5 mmol) was stirred at 100 degrees Celsius under $N_2$ in a sealed tube for three hours. The cooled mixture was partitioned between water and ethyl acetate. The organic phase was washed with water and brine, dried over $Na_2SO_4$, and concentrated to give crude yellow oil. The crude oil was dissolved in 3 mL HCl/MeOH (1.25M) and stirred at room temperature for three hours. The resultant mixture was neutralized with $NH_3$/EtOH solution and purified by prep-HPLC to obtain 66 mg yellow solid as product. Yield was 24% over two steps. MS: calc'd 533 (MH+), exp 533 (MH+). $^1$H NMR ($d_6$-DMSO, 400 MHz), 10.09 (s, 1H), 9.36 (s, 1H), 7.50-7.61 (m, 5H), 7.33-7.39 (m, 5H), 6.84-6.94 (m, 2H), 6.75 (d, 1H, J=8.0 Hz), 6.58 (t, 1H, J=7.2 Hz), 4.93 (s, 2H), 4.46 (s, 1H), 3.62 (q, 1H, J=7.6 Hz), 3.30 (m, 2H), 3.21-3.29 (m, 2H), 3.04 (q, 1H, J=7.6 Hz), 2.78-2.88 (m, 2H), 1.03 (s, 3H), 1.01 (s, 3H)

Compounds 26-2 through 26-7 described in the following tables were prepared by methods analogous to the synthetic methods described above for Example 26, by combining Example 22, 2-bromo-2-methyl-propionic acid methyl ester, and (2-acryloylamino-phenyl)-carbamic acid tert-butyl ester with the appropriate starting material indicated in Table 9. Compounds that are specifically indicated as chiral were obtained via chiral separation.

TABLE 9

| Starting material and MS data of examples 26-2 to 26-7 | | |
|---|---|---|
| Example # | Structure | Starting Material |
| 26-2 | ![structure] MW 516.62; MH+ calc. 517; MH+ expt. 517 | 4-fluoroaniline commercially available |
| 26-3 | ![structure] Chiral MW 533.08; MH+ calc. 533; MH+ expt. 533 | 4-chloroaniline commercially available |

TABLE 9-continued
Starting material and MS data of examples 26-2 to 26-7
| Example # | Structure | Starting Material |
|---|---|---|
| 26-4 | 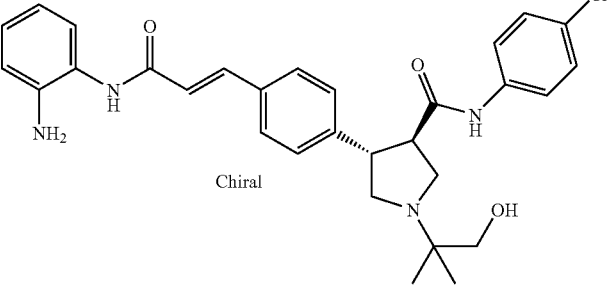 <br> Chiral <br> MW 533.08; MH⁺ calc. 533; MH⁺ expt. 533 | 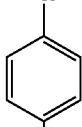 <br> commercially available |
| 26-5 | 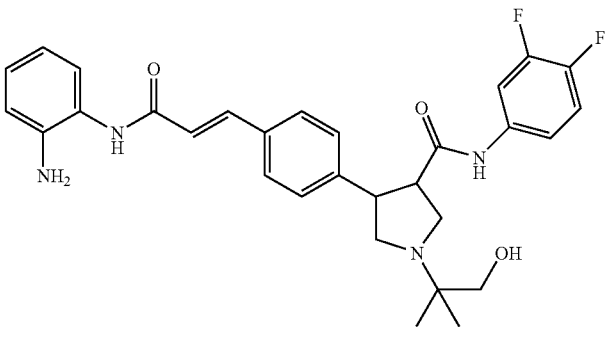 <br> MW 534.61; MH⁺ calc. 535; MH⁺ expt. 535 | 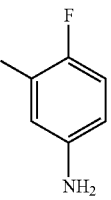 <br> commercially available |
| 26-6 | 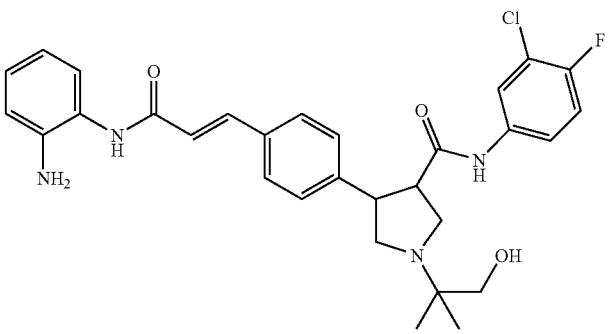 <br> MW 551.05; MH⁺ calc. 551; MH⁺ expt. 551 | 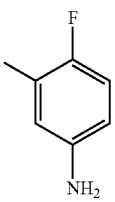 <br> commercially available |
| 26-7 | 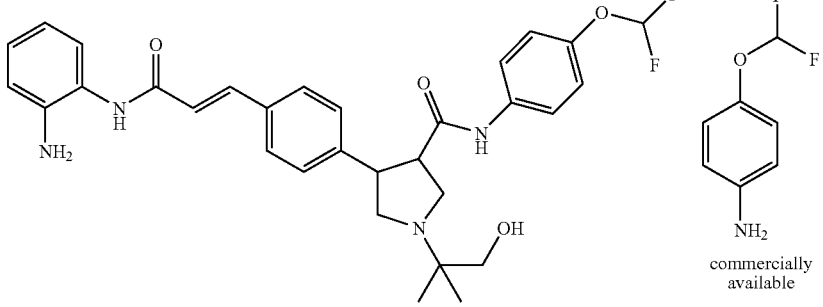 <br> MW 564.64; MH⁺ calc. 565; MH⁺ expt. 565 | 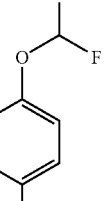 <br> commercially available |

TABLE 10

NMR data of examples 26-2 to 26-7

| Example # | NMR data |
|---|---|
| 26-2 | $^1$H NMR (d$_6$-DMSO, 400 MHz), 10.11 (s, 1H), 9.37 (s, 1H), 7.50-7.61 (m, 5H), 7.33-7.39 (m, 2H), 6.74-6.94 (m, 2H), 6.75 (d, 1H, J = 8.0 Hz), 6.58 (t, 1H, J = 7.2 Hz), 4.94 (s, 2H), 4.50 (broad s, 1H), 3.63 (broad s, 1H), 3.07-3.31 (broad m, 5H), 2.88 (broad s, 2H), 1.02 (s, 6H) |
| 26-3 | $^1$H NMR (d$_6$-DMSO, 400 MHz), 10.09 (s, 1H), 9.36 (s, 1H), 7.50-7.61 (m, 5H), 7.33-7.39 (m, 5H), 6.84-6.94 (m, 2H), 6.75 (d, 1H, J = 8.0 Hz), 6.58 (t, 1H, J = 7.6 Hz), 4.93 (s, 2H), 4.47 (s, 1H), 3.61 (q, 1H, J = 7.6 Hz), 3.30 (m, 2H), 3.21-3.29 (m, 2H), 3.04 (q, 1H, J = 8.0 Hz), 2.79-2.88 (m, 2H), 1.04 (s, 3H), 1.01 (s, 3H) |
| 26-4 | $^1$H NMR (d$_6$-DMSO, 400 MHz), 10.09 (s, 1H), 9.36 (s, 1H), 7.50-7.61 (m, 5H), 7.33-7.39 (m, 5H), 6.84-6.94 (m, 2H), 6.75 (d, 1H, J = 8.0 Hz), 6.58 (t, 1H, J = 7.6 Hz), 4.93 (s, 2H), 4.47 (s, 1H), 3.61 (q, 1H, J = 7.6 Hz), 3.30 (m, 2H), 3.21-3.29 (m, 2H), 3.04 (q, 1H, J = 8.0 Hz), 2.79-2.88 (m, 2H), 1.04 (s, 3H), 1.01 (s, 3H) |
| 26-5 | $^1$H NMR (CD$_3$OD, 400 MHz), 7.58-7.71 (m, 4H), 7.4 (d, 1H, J = 7.6 Hz), 7.16-7.23 (m, 4H), 7.06 (t, 1H, J = 7.2 Hz), 6.74-6.90 (m, 3H), 3.69 (q, 1H, J = 8.0 Hz), 3.50 (s, 2H), 3.40 (m, 2H), 3.11 (m, 2H), 2.94 (t, 1H, J = 8.8 Hz), 1.17 (s, 3H), 1.15 (s, 3H) |
| 26-6 | $^1$H NMR (CD$_3$OD, 400 MHz), 7.83 (d, 1H, J = 4.8 Hz), 7.59-7.68 (m, 3H), 7.41-7.43 (m, 3H), 7.15-7.23 (m, 2H), 7.07 (t, 1H, J = 7.6 Hz), 6.75-6.91 (m, 3H), 3.68-3.70 (m, 1H), 3.51 (s, 2H), 3.37-3.42 (m, 2H), 3.10-3.16 (m, 2H), 2.95 (t, 1H, J = 8.8 Hz), 1.18 (s, 3H), 1.16 (s, 3H) |
| 26-7 | $^1$H NMR (CD$_3$OD, 400 MHz), 7.66 (d, 1H, J = 16 Hz), 7.55-7.60 (m, 4H), 7.42 (d, 2H, J = 8.0 Hz), 7.21 (d, 1H, J = 7.6 Hz), 7.07 (t, 2H, J = 8.8 Hz), 6.57-6.94 (m, 4H), 3.68 (q, 1H, J = 8.0 Hz), 3.50 (s, 2H), 3.29-3.40 (m, 3H), 3.10-3.15 (m, 2H), 2.94 (t, 1H, J = 8.8 Hz), 1.17 (s, 3H), 1.15 (s, 3H) |

Example 27

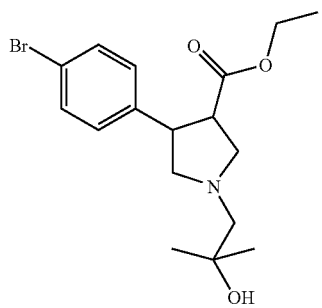

rac-(trans-3,4)-4-(4-Bromo-phenyl)-1-(2-hydroxy-2-methyl-propyl)-pyrrolidine-3-carboxylic acid ethyl ester To a solution of rac-(trans-3,4)-4-(4-bromo-phenyl)-pyrrolidine-3-carboxylic acid ethyl ester (5.0 g, 16.78 mmol) in ethanol (60 mL) was added 2,2-dimethyl-oxirane (8 mL), This mixture was heated for about 5 h at 80 degrees Celsius in a sealed tube until the starting material had been consumed, and then evaporated in vacuo to give 6.0 g (96%) of crude product as a yellow oil. MS: calc'd 370 (MH+), exp 370 (MH+).

Example 28

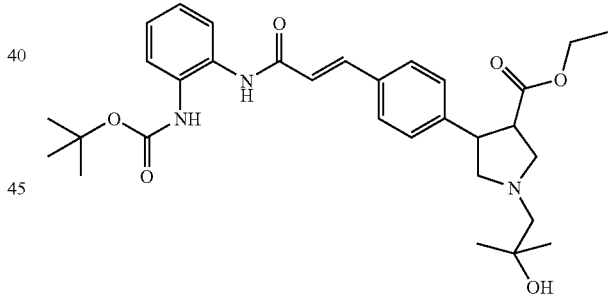

rac-(trans-3,4)-4-{4-[2-(2-tert-Butoxycarbonylamino-phenylcarbamoyl)-vinyl]-phenyl}-1-(2-hydroxy-2-methyl-propyl)-pyrrolidine-3-carboxylic acid ethyl ester To a solution of rac-(trans-3,4)-4-(4-bromo-phenyl)-1-(2-hydroxy-2-methyl-propyl)-pyrrolidine-3-carboxylic acid ethyl ester (3.69 g, 10 mmol), Pd$_2$(dba)$_3$ (457.5 mg, 0.5 mmol), tri-(o-tolyl)-phosphine (152 mg, 0.5 mmol) and Et$_3$N (3.0 g, 30 mmol) in DMF (30 mL) was added (2-acryloylamino-phenyl)-carbamic acid tert-butyl ester (3.14 mg, 12 mmol). This mixture was stirred at 100 degrees Celsius for about 3 hours until the starting material had been consumed, then the reaction was cooled and filtered. The solution was poured into water (60 mL), extracted with ethyl acetate (3×100 mL), and the combined organic layer was washed with brine, dried with Na₂SO₄, filtered, and evaporated. The crude product was purified by column chromatography (PE:EtOAc=1:1) to get yellow solid product. MS: calc'd 552 (MH+), exp 552 (MH+).

Example 29

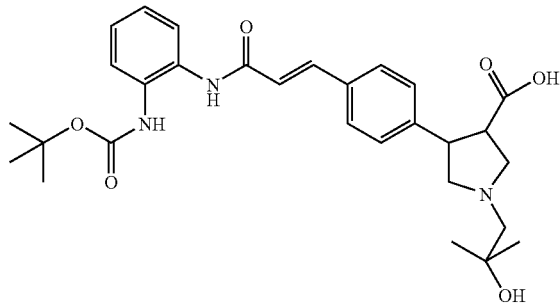

rac-(trans-3,4)-4-{4-[2-(2-tert-Butoxycarbonylamino-phenylcarbamoyl)-vinyl]-phenyl}-1-(2-hydroxy-2-methyl-propyl)-pyrrolidine-3-carboxylic acid To a solution of rac-(trans-3,4)-4-{4-[2-(2-tert-butoxycarbonylamino-phenylcarbamoyl)-vinyl]-phenyl}-1-(2-hydroxy-2-methyl-propyl)-pyrrolidine-3-carboxylic acid ethyl ester (2.2 g, 4.0 mmol) in MeOH/H₂O (40 mL/12 mL) was added lithium hydroxide monohydrate (504 mg, 12.0 mmol). This mixture was stirred at room temperature overnight and then evaporated to remove most of the MeOH. The mixture was extracted with ethyl acetate (3×60 mL). The combined organic layer was washed with brine, dried with Na₂SO₄, filtered, and evaporated to get product as yellow solid. MS: calc'd 524 (MH+), exp 524 (MH+).

Example 30

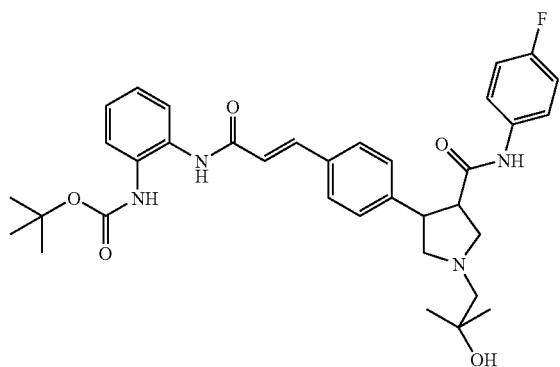

rac-[2-(3-{4-[(trans-3,4)-4-(4-Fluoro-phenylcarbamoyl)-1-(2-hydroxy-2-methyl-propyl)-pyrrolidin-3-yl]-phenyl}-acryloylamino)-phenyl]-carbamic acid tert-butyl ester To a solution of rac-(trans-3,4)-4-{4-[2-(2-tert-butoxycarbonylamino-phenylcarbamoyl)-vinyl]-phenyl}-1-(2-hydroxy-2-methyl-propyl)-pyrrolidine-3-carboxylic acid (200 mg, 0.381 mmol), HATU (217.7 mg, 0.572 mmol) and Et₃N (115.4 mg, 1.143 mmol) in CH₂Cl₂ (10 mL) was added 4-fluoro-phenylamine (63.4 mg, 0.572 mmol). The reaction mixture was stirred at room temperature overnight. The mixture was diluted with CH₂Cl₂ (10 mL) and washed with water (10 mL) and brine (10 mL), dried with Na₂SO₄, filtered, and evaporated in vacuo to obtain light yellow residue which was used without further purification. MS: calc'd 617 (MH+), exp 617 (MH+).

Example 31

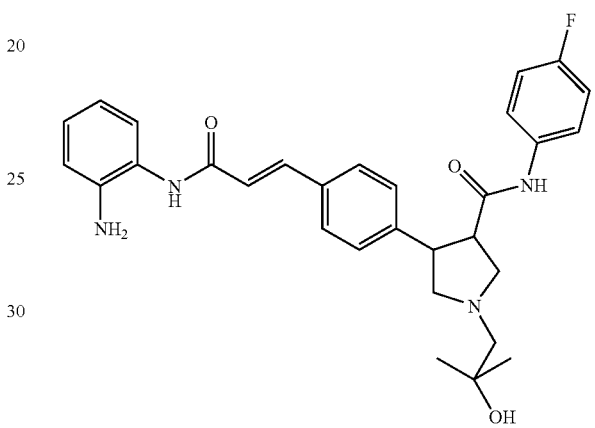

rac-(trans-3,4)-4-{4-[2-(2-Amino-phenylcarbamoyl)-vinyl]-phenyl}-1-(2-hydroxy-2-methyl-propyl)-pyrrolidine-3-carboxylic acid (4-fluoro-phenyl)-amide Hydrochloric acid in methanol (1.25 M, 5 mL) was added to the rac-[2-(3-{4-[(trans-3,4)-4-(4-fluoro-phenylcarbamoyl)-1-(2-hydroxy-2-methyl-propyl) -pyrrolidin-3-yl]-phenyl}-acryloylamino)-phenyl]-carbamic acid tert-butyl ester residue, the mixture was stirred for about 3 h, and then NaHCO₃ was added to the reaction mixture. After filtration of solids, the crude mixture was purified by preparative HPLC to obtain light yellow solid. MS: calc'd 517 (MH+), exp 517 (MH+). ¹H NMR (CD₃OD, 400 MHz), 7.51-7.55 (m, 5H), 7.42-7.44 (d, 2H, J=8.0 Hz), 7.20-7.22 (d, 1H, J=8.0 Hz), 7.01-7.08 (m, 3H), 6.82-6.90 (m, 2H), 6.74-6.78 (t, 1H, J=16.0 Hz), 3.72-3.77 (m, 1H), 3.31 (m, 1H), 3.23 (m, 1H), 3.13 (m, 1H), 3.06 (m, 2H), 2.63 (d, 1H, J=13.2 Hz), 2.58 (d, 1H, J=13.2 Hz), 1.27 (s, 6H).

Compounds 31-2 through 31-13 described in the following tables were prepared by methods analogous to the synthetic methods described above for Example 31, by combining Example 29 with the appropriate starting material as indicated in Table 11. Compounds that are specifically indicated as chiral were obtained via chiral separation.

TABLE 11
Starting material and MS data of examples 31-2 to 31-13
| Example # | Structure | Starting Material |
|---|---|---|
| 31-2 | 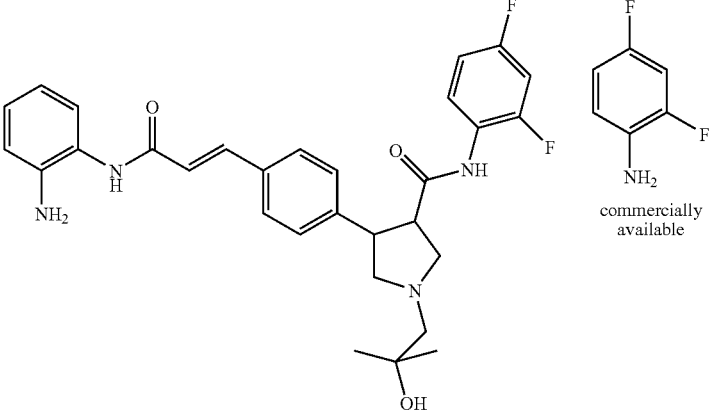<br>MW 534.61; MH+ 535; MH+ 535 | 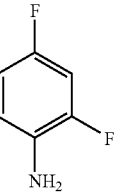<br>commercially available |
| 31-3 | 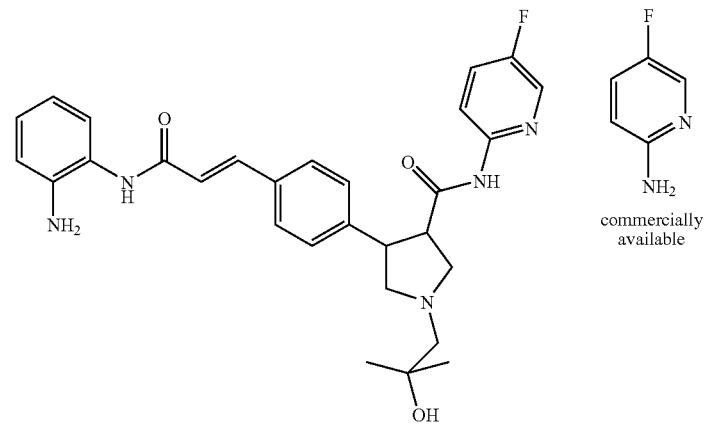<br>MW 517.61; MH+ 518; MH+ 518 | 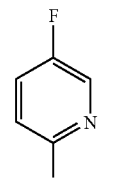<br>commercially available |
| 31-4 | 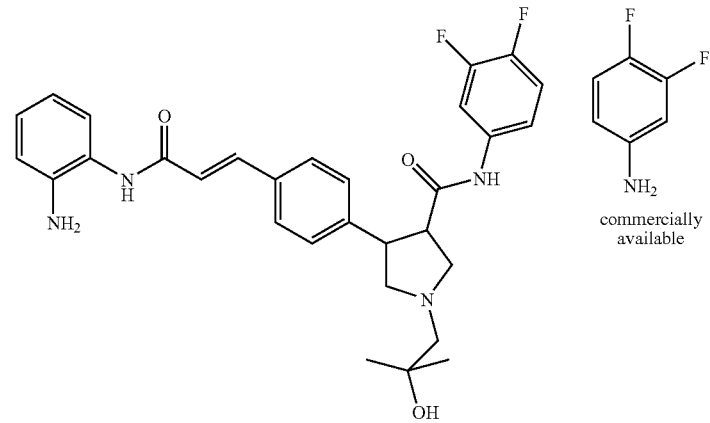<br>MW 534.61; MH+ 535; MH+ 535 | 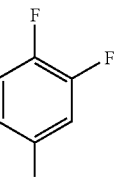<br>commercially available |

TABLE 11-continued

Starting material and MS data of examples 31-2 to 31-13

| Example # | Structure | Starting Material |
|---|---|---|
| 31-5 | MW 523.63; MH+ 524; MH+ 524 | commercially available |
| 31-6 | MW 534.06; MH+ 534; MH+ 534 | commercially available |
| 31-7 | MW 551.07; MH+ 551; MH+ 551 | commercially available |

TABLE 11-continued
Starting material and MS data of examples 31-2 to 31-13
| Example # | Structure | Starting Material |
|---|---|---|
| 31-8 | 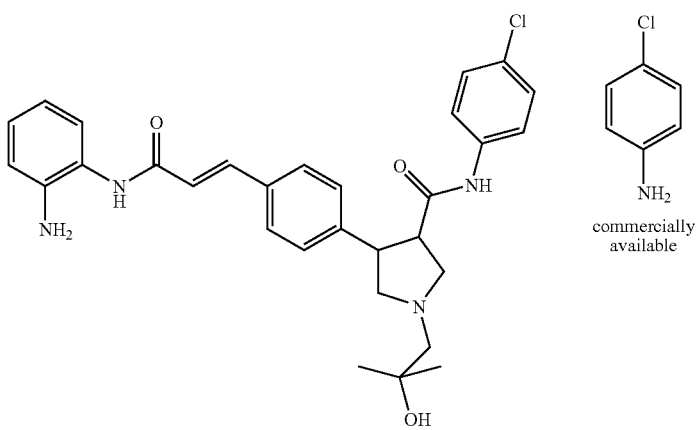<br>MW 533.08; MH+ 533; MH+ 533 | 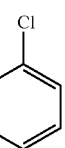<br>commercially available |
| 31-9 | 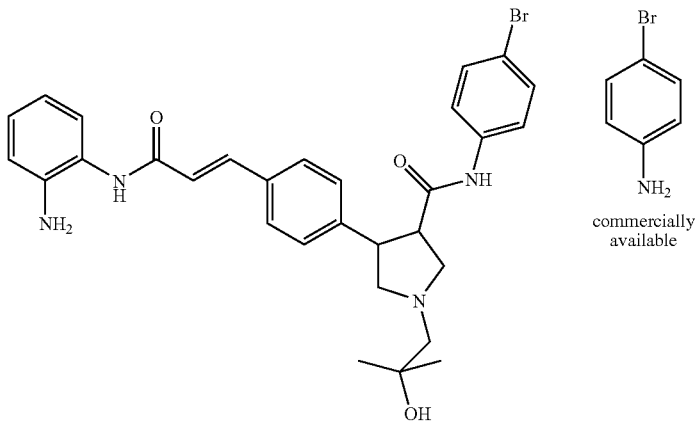<br>MW 577.53; MH+ 577; MH+ 577 | 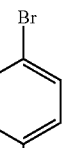<br>commercially available |
| 31-10 | 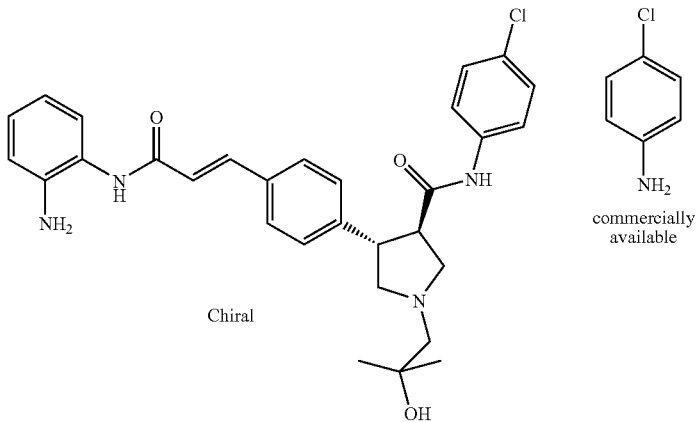<br>Chiral<br>MW 533.08; MH+ 533; MH+ 533 | 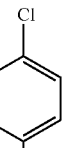<br>commercially available |

TABLE 11-continued

Starting material and MS data of examples 31-2 to 31-13

| Example # | Structure | Starting Material |
|---|---|---|
| 31-11 | MW 564.64; MH+ 565; MH+ 565 | commercially available |
| 31-12 | MW 533.08; MH+ 533; MH+ 533 (Chiral) | commercially available |
| 31-13 | MW 551.07; MH+ 551; MH+ 551 | commercially available |

TABLE 12

| NMR data of examples 31-2 to 31-13 |  |
|---|---|
| Examples | NMR data |
| 31-2 | $^1$H NMR (CD$_3$OD, 400 MHz), 7.60-7.76 (m, 4H), 7.44-7.46 (d, 2H, J = 8.0 Hz), 7.21-7.23 (d, 1H, J = 8.0 Hz), 6.83-7.07 (m, 5H), 6.75-6.79 (t, 1H, J = 16.0 Hz), 3.72-3.77 (m, 1H), 3.23-3.35 (m, 2H), 3.14 (m, 1H), 3.03 (m, 1H), 2.63 (d, 1H, J = 13.2 Hz), 2.58 (d, 1H, J = 13.2 Hz), 1.27 (s, 6H). |
| 31-3 | $^1$H NMR (CD$_3$OD, 400 MHz), 8.15-8.18 (q, 2H), 7.57-7.69 (m, 4H), 7.43-7.45 (d, 2H, J = 8.0 Hz), 7.21-7.23 (d, 1H, J = 8.0 Hz), 7.05-7.09 (t, 1H), 6.83-6.91 (m, 2H), 6.75-6.79 (t, 1H, J = 16.0 Hz), 3.77-3.79 (m, 1H), 3.23-3.31 (m, 3H), 3.10-3.14 (m, 1H), 2.94-2.98 (t, 1H, J = 16.0 Hz), 2.63 (d, 1H, J = 13.2 Hz), 2.58 (d, 1H, J = 13.2 Hz), 1.28 (s, 6H). |
| 31-4 | $^1$H NMR (CD$_3$OD, 400 MHz), 7.59-7.68 (m, 4H), 7.42-7.44 (d, 2H, J = 8.0 Hz), 7.19-7.23 (m, 3H), 7.06 (t, 1H), 6.82-6.90 (m, 2H), 6.75-6.79 (t, 1H, J = 16.0 Hz), 3.72-3.77 (m, 1H), 3.12-3.33 (m, 3H), 3.03-3.07 (m, 2H), 2.63 (d, 1H, J = 13.2 Hz), 2.58 (d, 1H, J = 13.2 Hz), 1.28 (s, 6H). |
| 31-5 | $^1$H NMR (CD$_3$OD, 400 MHz), 7.63-7.77 (m, 5H), 7.57-7.59 (d, 2H, J = 8.0 Hz), 7.40-7.42 (d, 2H, J = 8.0 Hz), 7.20-7.22 (d, 1H, J = 8.0 Hz), 7.03-7.07 (t, 1H), 6.81-6.89 (m, 2H), 6.73-6.77 (t, 1H, J = 16.0 Hz), 3.72-3.77 (m, 1H), 3.32-3.34 (m, 1H), 3.22-3.26 (m, 1H), 3.10-3.15 (m, 1H), 3.00-3.08 (m, 2H), 2.63 (d, 1H, J = 13.2 Hz), 2.58 (d, 1H, J = 13.2 Hz), 1.27 (s, 6H). |
| 31-6 | $^1$H NMR (CD$_3$OD, 400 MHz), 8.25 (s, 1H), 8.14-8.16 (d, 1H, J = 8.0 Hz), 7.59-7.80 (m, 4H), 7.43-7.45 (d, 2H, J = 8.0 Hz), 7.21-7.23 (d, 1H, J = 8.0 Hz), 7.04-7.06 (t, 1H), 6.83-6.91 (m, 2H), 6.74-6.78 (t, 1H, J = 16.0 Hz), 3.77-3.83 (m, 1H), 3.20-3.40 (m, 4H), 3.01-3.04 (t, 1H), 2.73 (d, 1H, J = 13.2 Hz), 2.68 (d, 1H, J = 13.2 Hz), 1.29 (s, 6H). |
| 31-7 | $^1$H NMR (CD$_3$OD, 400 MHz), 7.61-7.65 (t, 1H), 7.56-7.58 (m, 3H) 7.39-7.41 (d, 2H, J = 8.0 Hz), 7.13-7.22 (m, 3H), 7.01-7.05 (t, 1H), 6.80-6.88 (m, 2H), 6.71-6.75 (t, 1H, J = 16.0 Hz), 3.71-3.73 (m, 1H), 3.23-3.30 (m, 1H), 3.10-3.14 (t, 1H), 2.95-2.99 (m, 3H), 2.63 (d, 1H, J = 13.2 Hz), 2.58 (d, 1H, J = 13.2 Hz), 1.25 (s, 6H). |
| 31-8 | $^1$H NMR (CD$_3$OD, 400 MHz), 7.53-7.59 (m, 5H), 7.41-7.43 (d, 2H, J = 8.0 Hz), 7.27-7.29 (d, 2H, J = 8.0 Hz), 7.21-7.23 (d, 1H, J = 8.0 Hz), 7.04-7.08 (t, 1H), 6.82-6.90 (m, 2H), 6.74-6.78 (t, 1H, J = 16.0 Hz), 3.71-3.77 (m, 1H), 3.20-3.33 (m, 1H), 3.11-3.17 (m, 1H), 3.07 (m, 1H), 3.00-3.05 (m, 2H), 2.63 (d, 1H, J = 13.2 Hz), 2.58 (d, 1H, J = 13.2 Hz), 1.27 (s, 6H). |
| 31-9 | $^1$H NMR (CD$_3$OD, 400 MHz), 7.48-7.67 (m, 7H), 7.41-7.43 (d, 2H, J = 8.0 Hz), 7.20-7.22 (d, 1H, J = 8.0 Hz), 7.04-7.08 (t, 1H), 6.82-6.90 (m, 2H), 6.74-6.78 (t, 1H, J = 16.0 Hz), 3.72-3.77 (m, 1H), 3.25-3.34 (m, 2H), 3.04-3.17 (m, 3H), 2.68 (d, 1H, J = 13.2 Hz), 2.63 (d, 1H, J = 13.2 Hz), 1.27 (s, 6H). |
| 31-10 | $^1$H NMR (CD$_3$OD, 400 MHz), 7.53-7.57 (m, 5H), 7.41-7.43 (d, 2H, J = 8.0 Hz), 7.28-7.30 (d, 2H, J = 8.0 Hz), 7.21-7.23 (d, 1H, J = 8.0 Hz), 7.04-7.08 (t, 1H), 6.82-6.90 (m, 2H), 6.74-6.78 (t, 1H, J = 16.0 Hz), 3.72-3.77 (m, 1H), 3.29-3.33 (m, 1H), 3.20-3.25 (m, 1H), 3.11-3.17 (m, 1H), 3.00-3.07 (m, 2H), 2.63 (d, 1H, J = 13.2 Hz), 2.58 (d, 1H, J = 13.2 Hz), 1.27 (s, 6H). |
| 31-11 | $^1$H NMR (CD$_3$OD, 400 MHz), 7.56-7.64 (m, 5H), 7.42-7.44 (d, 2H, J = 8.0 Hz), 7.20-7.22 (d, 1H, J = 8.0 Hz), 7.04-7.10 (m, 3H), 6.82-6.90 (m, 2H), 6.74-6.78 (t, 1H, J = 16.0 Hz), 6.57 (s, 1H), 3.72-3.76 (m, 1H), 3.29-3.33 (m, 1H), 3.21-3.25 (m, 1H), 3.11-3.17 (m, 1H), 3.01-3.08 (m, 2H), 2.63 (d, 1H, J = 13.2 Hz), 2.58 (d, 1H, J = 13.2 Hz), 1.27 (s, 6H). |
| 31-12 | $^1$H NMR (CD$_3$OD, 400 MHz), 7.53-7.67 (m, 5H), 7.41-7.43 (d, 2H, J = 8.0 Hz), 7.27-7.29 (d, 2H, J = 8.0 Hz), 7.21-7.23 (d, 1H, J = 8.0 Hz), 7.04-7.08 (t, 1H), 6.81-6.90 (m, 2H), 6.74-6.78 (t, 1H, J = 16.0 Hz), 3.71-3.77 (m, 1H), 3.20-3.33 (m, 2H), 3.11-3.17 (m, 1H), 3.00-3.07 (m, 2H), 2.63 (d, 1H, J = 13.2 Hz), 2.58 (d, 1H, J = 13.2 Hz), 1.27 (s, 6H). |
| 31-13 | $^1$H NMR (CD$_3$OD, 400 MHz), 7.64-7.80 (m, 2H), 7.60-7.62 (d, 2H J = 8.0 Hz), 7.56-7.58 (m, 4H), 7.37-7.44 (m, 4H), 7.15-7.22 (m, 2H), 7.07-7.10 (t, 1H), 6.84-6.92 (m, 2H), 6.78-6.81 (t, 1H, J = 16.0 Hz), 3.74-3.76 (q, 1H), 3.24-3.33 (m, 2H), 3.16-3.18 (m, 1H), 3.06-3.10 (m, 1H), 3.00-3.03 (m, 1H), 2.57-2.69 (q, 2H), 1.27 (s, 6H). |

Example 32

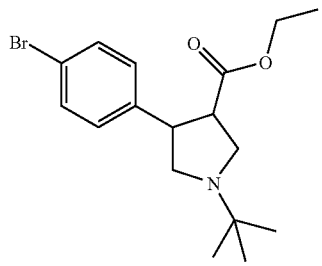

rac-(trans-3,4)-4-(4-Bromo-phenyl)-1-tert-butyl-
pyrrolidine-3-carboxylic acid ethyl ester A mixture of N-tert-butylglycine hydrochloride salt (0.9 g, 6.8 mmol), paraformaldehyde (1.5 g, 50 mmol), and ethyl cinnamate (0.9 g, 35 mmol) was heated under reflux in toluene (30 mL). The $H_2O$ formed was removed with the aid of a Dean-Stark trap. After 4 hours, the cooled mixture was filtered. The filtrate was concentrated. The residue was purified by chromatography on silica gel eluted with hexane-EtOAc to give 300 mg of product (yield was 12%). MS: calc'd 354 (MH+), exp 354 (MH+).

Example 33

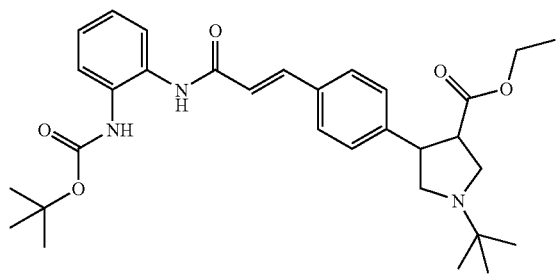

rac-(trans-3,4)-4-{4-[2-(2-tert-Butoxycarbony-
lamino-phenylcarbamoyl)-vinyl]-phenyl}-1-tert-
butyl-pyrrolidine-3-carboxylic acid ethyl ester A mixture of the product from Example 32 (0.5 g, 1.4 mmol), (2-acryloylamino-phenyl)-carbamic acid tert-butyl ester (0.5 g, 1.9 mmol), $Pd_2(dba)_3$ (100 mg, 0.01 mmol), P(o-tolyl)$_3$ (100 mg, 0.33 mmol) in DMF (5 mL) and TEA (1 mL) was stirred at 110 degrees Celsius under $N_2$ in a sealed tube overnight. LC-MS indicated that the reaction was completed. The cooled mixture was partitioned between water and ethyl acetate. The organic phase was dried and concentrated. The residue was purified by chromatography on silica gel eluted by dichloromethane to give 0.4 g of product (yield was 53%). MS: calc'd 536 (MH+), exp 536 (MH+).

Example 34

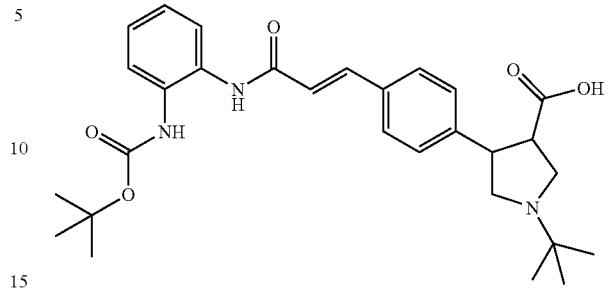

rac-(trans-3,4)-4-{4-[2-(2-tert-Butoxycarbony-
lamino-phenylcarbamoyl)-vinyl]-phenyl}-1-tert-
butyl-pyrrolidine-3-carboxylic acid A solution of lithium hydroxide monohydrate (2.1 g, 50 mmol) in water (50 mL) was added to a solution of the product from Example 33 (0.4 g, 0.74 mmol) in THF (50 mL), and the mixture was stirred at room temperature overnight. LC-MS indicated that the starting material was consumed. The mixture was adjusted to pH=6-8 with 6 N HCl. The solvent was removed to give crude product which was used in the next step without further purification. MS: calc'd 508 (MH+), exp 508 (MH+).

Example 35

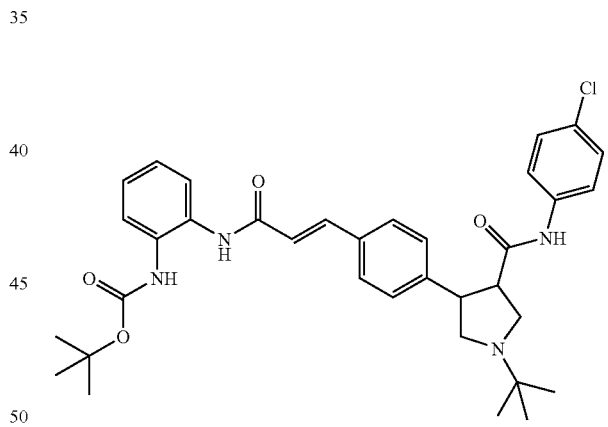

rac-[2-(3-{4-[(trans-3,4)-1-tert-Butyl-4-(4-chloro-
phenylcarbamoyl)-pyrrolidin-3-yl]-phenyl}-acryloy-
lamino)-phenyl]-carbamic acid tert-butyl ester HATU (0.2 g, 0.52 mmol) was added to a solution of product from Example 34 (crude material, 0.2 mmol) and 4-chloro-phenylamine (0.1 g, 0.78 mmol) in TEA (0.1 mL), and dichloromethane (7 mL) at rt, and the mixture was stirred at rt overnight. LC-MS indicated that the reaction was completed. The mixture was partitioned between water and dichloromethane. The organic phase was dried and concentrated. The residue was purified by chromatography on silica gel to give 80 mg of product (yield was 66%). MS: calc'd 617 (MH+), exp 617 (MH+).

Example 36

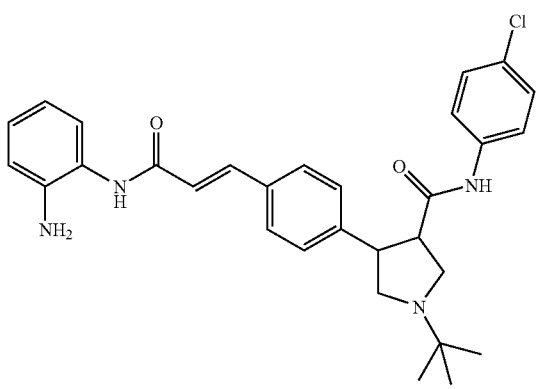

rac-(trans-3,4)-4-{4-[2-(2-Amino-phenylcarbamoyl)-vinyl]-phenyl}-1-tert-butyl-pyrrolidine-3-carboxylic acid (4-chloro-phenyl)-amide The product from Example 35 (80 mg, 0.13 mmol) was dissolved in MeOH (1.25 M HCl, 10 mL) and stirred for 4 hours. LC-MS indicated that the reaction was completed. The solvent was removed and the residue was basified with TEA and purified by prep-HPLC to give 18 mg of product. MS: calc'd (MH+) 517, exp (MH+) 517. $^1$H NMR (CD$_3$OD, 400 MHz), 7.64 (d, 1H, J=15.4 Hz), 7.55 (d, 2H, J=8.0 Hz), 7.48 (d, 2H, J=8.8 Hz), 7.39 (d, 2H, J=8.0 Hz), 7.25 (d, 2H, J=8.8 Hz), 7.19 (d, 1H, J=8.0 Hz), 7.04 (t, 1H, J=7.2 Hz), 6.87 (d, 1H, J=8.0 Hz), 6.82 (d, 1H, J=15.6 Hz), 6.74 (t, 1H, J=7.6 Hz), 3.72 (m, 1H), 3.18-3.07 (m, 3H), 2.91 (m, 2H), 1.16 (s, 9H).

Compounds 36-2 through 36-11 described in the following tables were prepared by methods analogous to the synthetic methods described above for Example 36, by combining Example 34 with the appropriate starting material as indicated in Table 13.

TABLE 13

Starting material and MS data of examples 36-2 to 36-11

| Example # | Structure | Starting Material |
|---|---|---|
| 36-2 | (structure shown) MW 535.07; MH+ calc. 535; MH+ expt. 535 | (4-chloro-2-fluoroaniline) commercially available |
| 36-3 | (structure shown) MW 561.53; MH+ calc. 561; MH+ expt. 561 | (4-bromoaniline) commercially available |

TABLE 13-continued
Starting material and MS data of examples 36-2 to 36-11
| Example # | Structure | Starting Material |
|---|---|---|
| 36-4 | 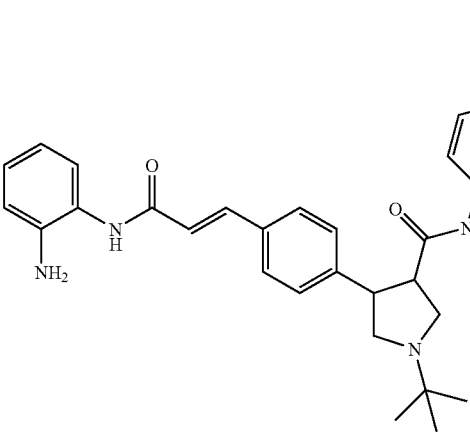<br>MW 548.64; MH⁺ calc. 549; MH⁺ expt. 549 | 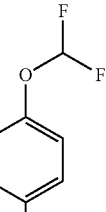<br>commercially available |
| 36-5 | 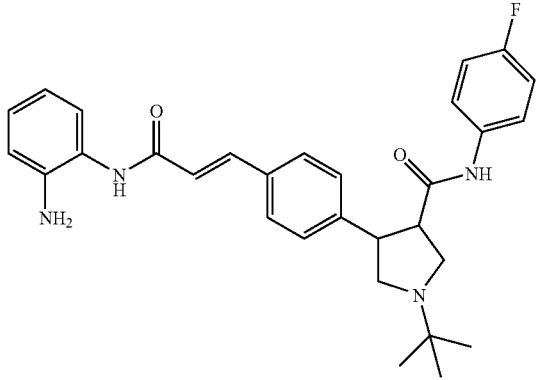<br>MW 500.62; MH⁺ calc. 501; MH⁺ expt. 501 | 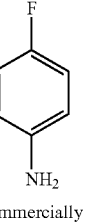<br>commercially available |
| 36-6 | 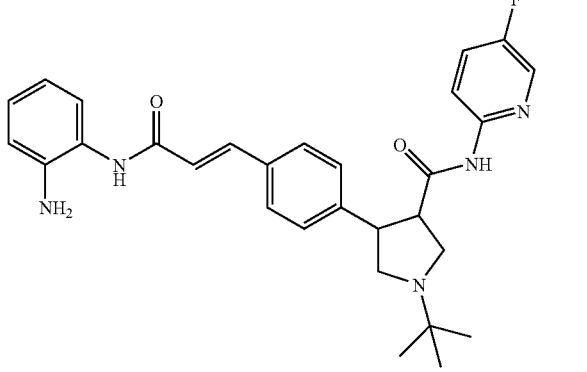<br>MW 501.61; MH⁺ calc. 502; MH⁺ expt. 502 | 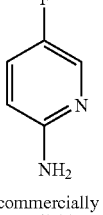<br>commercially available |

TABLE 13-continued
Starting material and MS data of examples 36-2 to 36-11
| Example # | Structure | Starting Material |
|---|---|---|
| 36-7 | 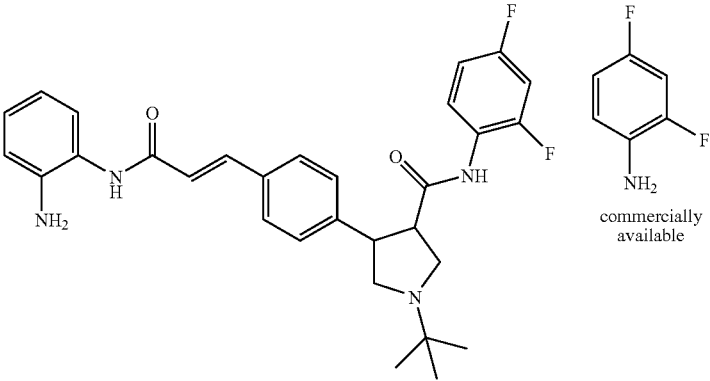<br>MW 518.61; MH⁺ calc. 519; MH⁺ expt. 519 | 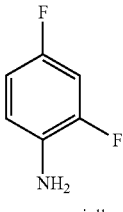<br>commercially available |
| 36-8 | 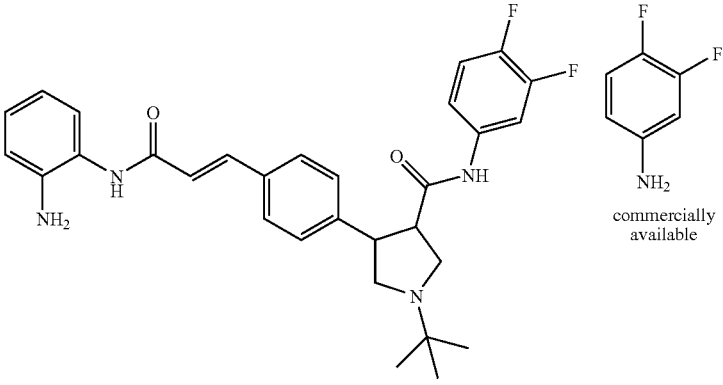<br>MW 518.61; MH⁺ calc. 519; MH⁺ expt. 519 | 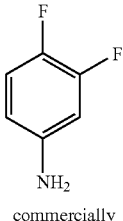<br>commercially available |
| 36-9 | 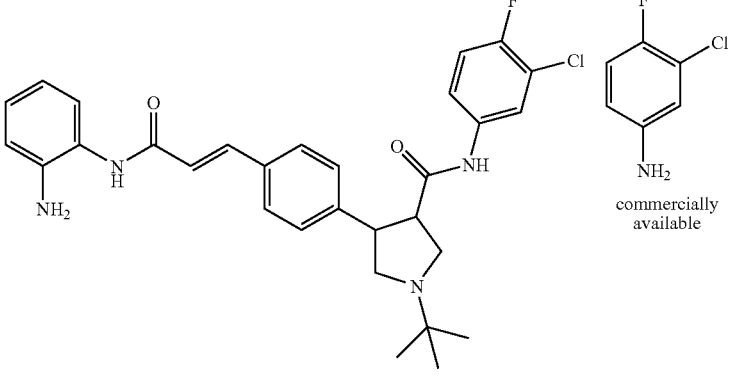<br>MW 535.07; MH⁺ calc. 535; MH⁺ expt. 535 | 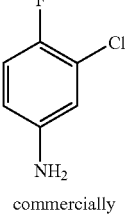<br>commercially available |

TABLE 13-continued

Starting material and MS data of examples 36-2 to 36-11

| Example # | Structure | Starting Material |
|---|---|---|
| 36-10 | 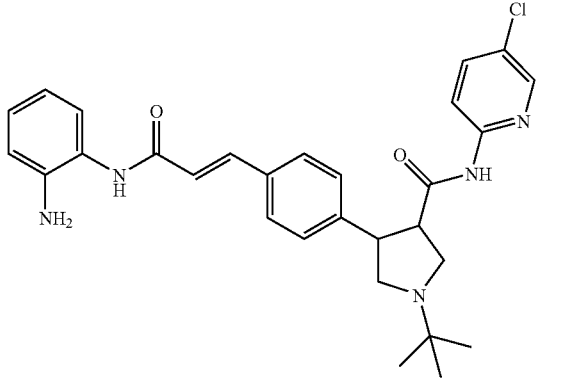<br>MW 518.06; MH⁺ calc. 518; MH⁺ expt. 518 | 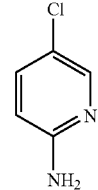<br>commercially available |
| 36-11 | 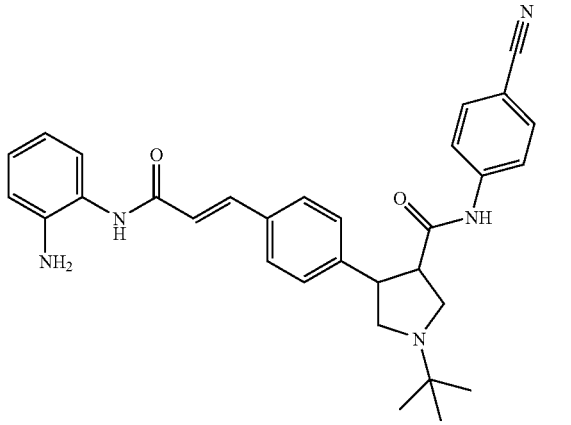<br>MW 507.64; MH⁺ calc. 508; MH⁺ expt. 508 | 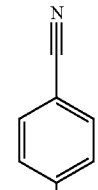<br>commercially available |

TABLE 14

NMR data of examples 36-2 to 36-11

| Examples | NMR data |
|---|---|
| 36-2 | ¹H NMR (CD$_3$OD, 400 MHz), 7.95 (t, 1H, J = 8.4 Hz), 7.69 (d, 1H, J = 15.6 Hz), 7.62 (d, 2H, 8.0 Hz), 7.44 (d, 2H, J = 8.0 Hz), 7.26 (m, 3H), 7.09 (t, 1H. 7.6 Hz), 6.8 (m, 3H), 3.72 (m, 1H), 3.3-3.0 (m, 3H), 2.91 (m, 2H), 1.18 (s, 9H). |
| 36-3 | ¹H NMR (CD$_3$OD, 400 MHz), 7.66 (d, 1H, J = 15.6 Hz), 7.59 (d, 2H, 8.0 Hz), 7.44 (m, 6H), 7.20 (d, 1H, 8.0 Hz), 7.04 (t, 1H), 6.8 (m, 3H), 3.72 (m, 1H), 3.3-3.0 (m, 3H), 2.91 (m, 2H), 1.18 (s, 9H). |
| 36-4 | ¹H NMR (CD$_3$OD, 400 MHz), 7.66 (d, 1H, J = 15.6 Hz), 7.58 (d, 2H, 8.0 Hz), 7.52 (d, 2H, 8.8 Hz), 7.41 (d, 1H, 8.0 Hz), 7.20 (d, 1H, 7.6 Hz), 7.07 (m, 3H), 6.8 (m, 3H), 3.72 (m, 1H), 3.3-3.0 (m, 3H), 2.91 (m, 2H), 1.18 (s, 9H). |
| 36-5 | ¹H NMR (CD$_3$OD, 400 MHz), 7.65 (d, 1H, J = 15.6 Hz), 7.57 (d, 2H, J = 8.0 Hz), 7.48 (m, 2H), 7.39 (d, 2H, J = 8.0 Hz), 7.20 (d, 1H, J = 8.0 Hz), 7.0 (m, 3H), 6.88 (d, 1H, J = 8.0 Hz), 6.83 (d, 1H, J = 15.6 Hz), 6.74 (t, 1H, J = 7.6 Hz), 3.72 (m, 1H), 3.3-3.0 (m, 3H), 2.91 (m, 2H), 1.18 (s, 9H). |
| 36-6 | ¹H NMR (CD$_3$OD, 400 MHz), 8.15 (m, 2H), 7.66 (d, 1H, J = 15.6 Hz), 7.58 (m, 3H), 7.43 (d, 2H, 8.0 Hz), 7.21 (d, 1H, 8.0 Hz), 7.07 (t, 1H, 7.6 Hz), 6.8 (m, 3H), 3.72 (m, 1H), 3.3-3.0 (m, 3H), 2.91 (m, 2H), 1.18 (s, 9H). |
| 36-7 | ¹H NMR (CD$_3$OD, 400 MHz), 7.79 (m, 1H), 7.69 (d, 1H, J = 15.6 Hz), 7.62 (d, 2H, J = 8.0 Hz), 7.44 (d, 2H, J = 8.0 Hz), 7.22 (d, 1H, J = 8.0 Hz), 7.07 (m, 2H), 6.8 (m, 4H), 3.72 (m, 1H), 3.3-3.0 (m, 3H), 2.91 (m, 2H), 1.18 (s, 9H). |
| 36-8 | ¹H NMR (CD$_3$OD, 400 MHz), 7.69 (m, 4H), 7.43 (d, 2H, J = 8.0 Hz), 7.21 (m, 4H), 6.88 (m, 3H), 3.72 (m, 1H), 3.3-3.0 (m, 3H), 2.91 (m, 2H), 1.18 (s, 9H). |

TABLE 14-continued

NMR data of examples 36-2 to 36-11

| Examples | NMR data |
|---|---|
| 36-9 | $^1$H NMR (CD$_3$OD, 400 MHz), 7.81 (m, 1H), 7.67 (m, 3H), 7.44 (d, 2H, J = 8.4 Hz), 7.36 (m, 1H), 7.20 (m, 2H), 7.07 (m, 1H), 6.80 (m, 3H), 3.76 (m, 1H), 3.3-3.0 (m, 3H), 2.91 (m, 2H), 1.18 (s, 9H). |
| 36-10 | $^1$H NMR (CD$_3$OD, 400 MHz), 8.27 (d, 1H, J = 2.4 Hz), 8.17 (d, 1H, J = 9.2 Hz), 7.81 (m, 1H), 7.70 (m, 3H), 7.46 (d, 2H, J = 8.0 Hz), 7.25 (d, 1H, J = 7.6 Hz), 7.10 (t, 1H, J = 7.6 Hz), 6.88 (m, 3H), 3.80 (m, 1H), 3.3-3.0 (m, 3H), 2.91 (m, 2H), 1.18 (s, 9H). |
| 36-11 | $^1$H NMR (CD$_3$OD, 400 MHz), 7.73 (m, 7H), 7.47 (d, 2H, J = 8.0 Hz), 7.21 (d, 1H, J = 7.6 Hz), 7.06 (m, 1H), 6.87 (m, 3H), 3.83 (m, 1H), 3.18-3.07 (m, 3H), 2.91 (m, 2H), 1.16 (s, 9H). |

Example 37

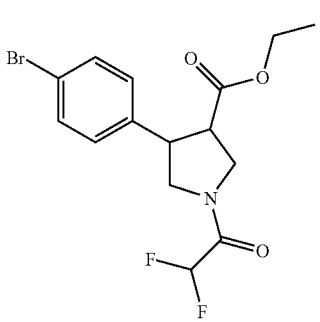

rac-(trans-3,4)-4-(4-Bromo-phenyl)-1-(2,2-difluoro-acetyl)-pyrrolidine-3-carboxylic acid ethyl ester To a solution of rac-(trans-3,4)-4-(4-bromo-phenyl)-pyrrolidine-3-carboxylic acid ethyl ester (1.485 g, 5 mmol) in CH$_2$Cl$_2$ (20 mL) was added difluoro-acetyl chloride (2 mL). The resulting mixture was stirred for 1 hour at room temperature until the starting material had been consumed, and then was evaporated in vacuo to give 1.82 g (97%) of a yellow residue. MS: calc'd (MH+) 376, exp (MH+) 376.

Example 38

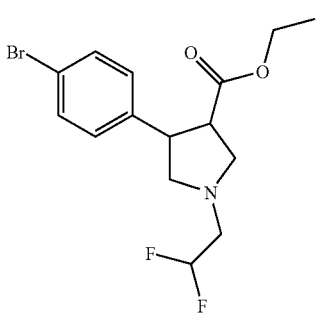

rac-(trans-3,4)-4-(4-Bromo-phenyl)-1-(2,2-difluoro-ethyl)-pyrrolidine-3-carboxylic acid ethyl ester To a solution of rac-(trans-3,4)-4-(4-bromo-phenyl)-1-(2,2-difluoro-acetyl)-pyrrolidine-3-carboxylic acid ethyl ester (1.82 g, 4.85 mmol) in THF (20 mL) was added BH$_3$-THF (8 mL), the mixture was heated for 5 h at 60 degrees Celsius until the starting material had been consumed, and then evaporated in vacuo. The crude product was purified by column chromatography (PE:EtOAc=1:1) to give product as a white solid (1.10 g, 63%). MS: calc'd (MH+) 362, exp (MH+) 362.

Example 39

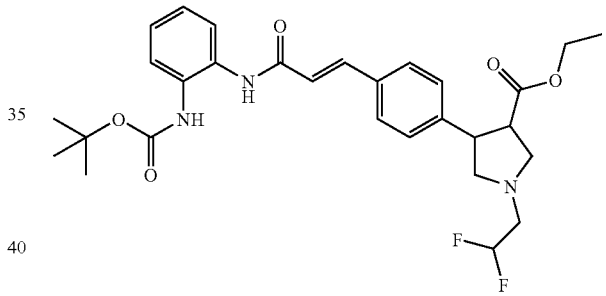

rac-(trans-3,4)-4-{4-[2-(2-tert-Butoxycarbony-lamino-phenylcarbamoyl)-vinyl]-phenyl}-1-(2,2-difluoro-ethyl)-pyrrolidine-3-carboxylic acid ethyl ester To a solution of rac-(trans-3,4)-4-(4-bromo-phenyl)-1-(2, 2-difluoro-acethyl)-pyrrolidine-3-carboxylic acid ethyl ester (1.1 g, 3 mmol), Pd$_2$(dba)$_3$ (91.5 mg, 0.1 mmol), tri-(o-tolyl)-phosphine (30.4 mg, 0.5 mmol) and Et$_3$N (1.0 g, 10 mmol) in DMF (10 mL) was added (2-acryloylamino-phenyl)-carbamic acid tert-butyl ester (917 mg, 3.5 mmol). This mixture was stirred at 100 degrees Celsius for 4 h until the starting material had been consumed, and then the mixture was cooled and filtered. The solution was poured into water (30 mL) and extracted with ethyl acetate (3×30 mL). The combined organic layer was washed with brine, dried with Na$_2$SO$_4$, filtered, and evaporated. The crude product was purified by column chromatography (PE:EtOAc=1:1) to get light yellow solid product (1.33 g, 81.6%). MS: calc'd (MH+) 544, exp (MH+) 544.

Example 40

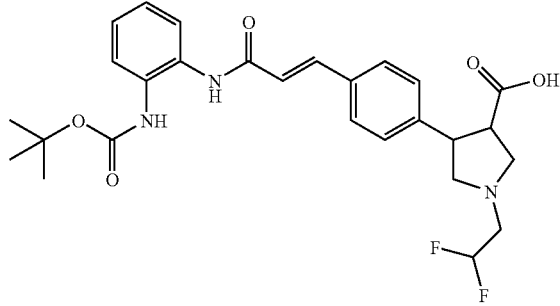

rac-(trans-3,4)-4-{4-[2-(2-tert-Butoxycarbonylamino-phenylcarbamoyl)-vinyl]-phenyl}-1-(2,2-difluoro-ethyl)-pyrrolidine-3-carboxylic acid To a solution of rac-(trans-3,4)-4-{4-[2-(2-tert-butoxycarbonylamino-phenylcarbamoyl)-vinyl]-phenyl}-1-(2,2-difluoro-ethyl)-pyrrolidine-3-carboxylic acid ethyl ester (1.33 g, 2.4 mmol) in MeOH/H$_2$O (15 mL/15 mL) was added lithium hydroxide monohydrate (504 mg, 12.0 mmol). This mixture was stirred at room temperature overnight and then evaporated to remove most of the MeOH. The mixture was extracted with ethyl acetate (3×20 mL). The combined organic layer was washed with brine, dried with Na$_2$SO$_4$, filtered, and evaporated to get white solid product (1.17 g, 94.6%). MS: calc'd (MH+) 516, exp (MH+) 516.

Example 41

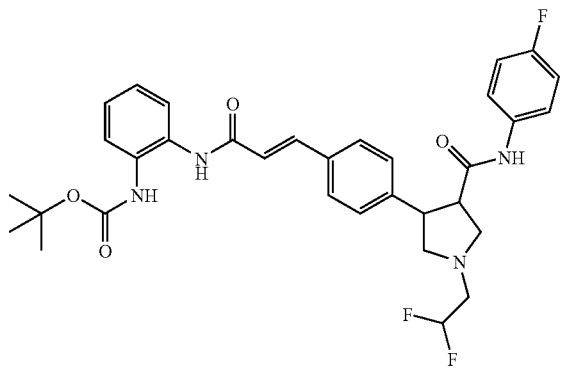

rac-[2-(3-{4-[(trans-3,4)-4-(4-Fluoro-phenylcarbamoyl)-1-(2,2-difluoro-ethyl)-pyrrolidin-3-yl]-phenyl}-acryloylamino)-phenyl]-carbamic acid tert-butyl ester To a solution of rac-(trans-3,4)-4-{4-[2-(2-tert-butoxycarbonylamino-phenylcarbamoyl)-vinyl]-phenyl}-1-(2,2-difluoro-ethyl)-pyrrolidine-3-carboxylic acid (200 mg, 0.388 mmol), HATU (217.7 mg, 0.572 mmol) and Et$_3$N (115.4 mg, 1.143 mmol) in DMF (10 mL) was added 4-fluorophenylamine (63.4 mg, 0.572 mmol). The reaction was stirred for 1 h at room temperature. The mixture was diluted with H$_2$O (10 mL) and washed with water (10 mL) and brine (10 mL), dried with Na$_2$SO$_4$, filtered, and evaporated in vacuo to obtain light yellow residue which was used without further purification. MS: calc'd (MH+) 609, exp (MH+) 609.

Example 42

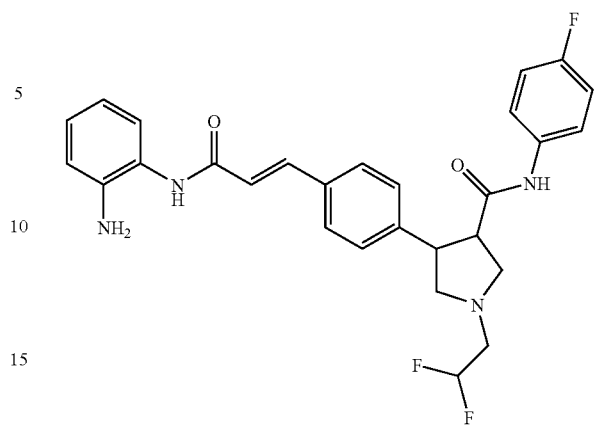

rac-(trans-3,4)-4-{4-[2-(2-Amino-phenylcarbamoyl)-vinyl]-phenyl}-1-(2,2-difluoro-ethyl)-pyrrolidine-3-carboxylic acid (4-fluoro-phenyl)-amide Hydrochloric acid in methanol (1.25 M, 5 mL) was added to rac-[2-(3-{4-[(trans-3,4)-4-(4-fluoro-phenylcarbamoyl)-1-(2,2-difluoro-ethyl)-pyrrolidin-3-yl]-phenyl}-acryloylamino)-phenyl]-carbamic acid tert-butyl ester residue, the mixture was stirred for 3 h and treated with NaHCO$_3$. After filtration of solids, the crude mixture was purified by preparative HPLC to obtain light yellow solid. MS: calc'd (MH+) 509, exp (MH+) 509. $^1$H NMR (CD$_3$OD, 400 MHz), 7.68 (d, 1H, J=15.6 Hz), 7.61 (d, 2H, J=8.0 Hz), 7.53-7.50 (m, 2H), 7.41 (m, 2H), 7.22 (d, 1H, J=8.0 Hz), 7.08-7.01 (m, 3H), 6.90-6.82 (m, 2H), 6.76 (t, 1H, J=7.6 Hz), 3.81-3.76 (m, 1H), 3.37-3.11 (m, 2H), 3.06-2.91 (m, 4H), 0.92 (m, 2H).

Example 42-2 described below was prepared by a method analogous to the synthetic method described above for Example 42, by combining Example 40 with 4-chloro-aniline (commercially available).

Example 42-2

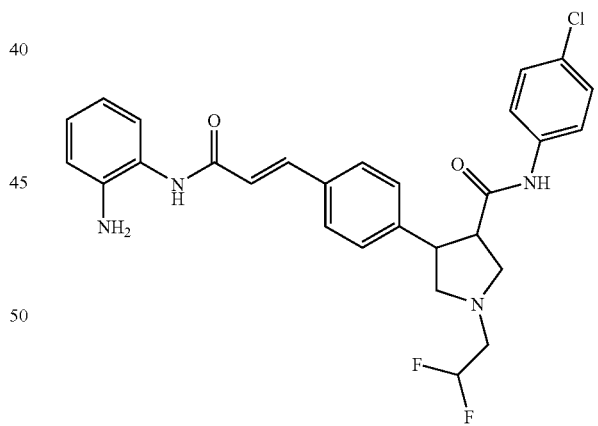

| Example # | MS and NMR data |
|---|---|
| 42-2 | $^1$H NMR (CD$_3$OD, 400 MHz), 7.66 (d, 1H, J = 15.6 Hz), 7.60 (d, 2H, J = 8.0 Hz), 7.53 (d, 2H, J = 8.8 Hz), 7.42 (d, 2H, J = 8.0 Hz), 7.29 (d, 2H, J = 8.8 Hz), 7.22 (d, 1H, J = 7.6 Hz), 7.06 (t, 1H, J = 7.6 Hz), 6.90-6.82 (m, 2H), 6.76 (t, 1H, J = 7.6 Hz), 3.81-3.76 (m, 1H), 3.29-3.11 (m, 2H), 3.07-2.91 (m, 4H), 0.92 (m, 2H). MS: calc'd (MH+) 525, exp (MH+) 525. |

Example 43

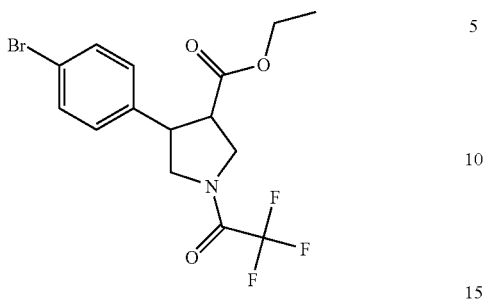

rac-(trans-3,4)-4-(4-Bromo-phenyl)-1-(2,2,2-trifluoro-acetyl)-pyrrolidine-3-carboxylic acid ethyl ester To a suspension of rac-(trans-3,4)-(4-(4-bromo-phenyl)-pyrrolidine-3-carboxylic acid ethyl ester hydrochloride (1.10 g, 3.28 mmol) in DCM (10 mL) was added Et₃N (1.4 mL, 9.86 mmol). This mixture was stirred for about 5 min at room temperature, and then cooled to 0 degrees Celsius. To the resulting mixture was added trifluoroacetate anhydride (0.9 g, 4.28 mmol). The mixture was stirred for 30 min at 0 degrees Celsius, warmed to room temperature and stirred for one hour. The resulting mixture was washed with water and brine, dried over Na₂SO₄, filtered, and concentrated in vacuo. The crude product was purified by flash chromatography (Pet:EtOAc=10:1) to get colorless oil product (0.88 g, 68.1%).

Example 44

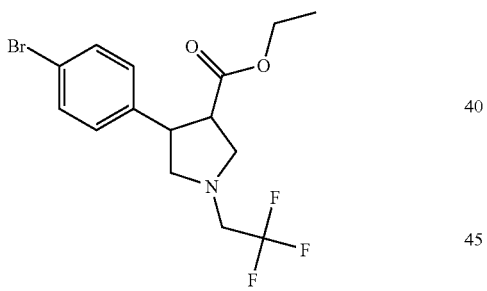

rac-(trans-3,4)-4-(4-Bromo-phenyl)-1-(2,2,2-trifluoro-ethyl)-pyrrolidine-3-carboxylic acid ethyl ester To a solution of rac-(trans-3,4)-4-(4-bromo-phenyl)-1-(2,2,2-trifluoro-acetyl)-pyrrolidine-3-carboxylic acid ethyl ester (0.82 g, 2.08 mmol) was added a solution of borane in THF (3.3 mL, 3.3 mmol) at 0 degrees Celsius. Then the mixture was refluxed for 2 hours. The resulting mixture was cooled and quenched by aqueous HCl (6 N). The mixture was concentrated in vacuo to remove THF. The residue was basified by solid Na₂CO₃, then extracted with EtOAc. The organic layer was washed with brine, dried with Na₂SO₄, and concentrated in vacuo. The crude product was purified by flash chromatography (Pet:EtOAc=20:1) to get colorless oil product (230 mg); 188 mg of starting material was recovered. MS: calc'd 380 (MH+), exp 380 (MH+). $^1$H NMR (CDCl₃, 400 MHz), 7.45 (d, 2H, J=8.4 Hz), 7.23 (d, 2H, J=8.4 Hz), 4.13-4.19 (m, 2H), 3.61-3.66 (m, 1H), 3.34-3.37 (m, 1H), 3.04-3.24 (m, 6H), 1.24 (t, 3H, J=6.8 Hz).

Example 45

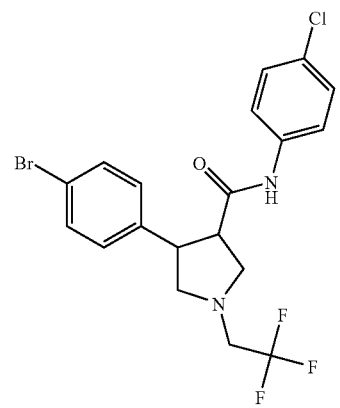

rac-(trans-3,4)-4-(4-Bromo-phenyl)-1-(2,2,2-trifluoro-ethyl)-pyrrolidine-3-carboxylic acid (4-chlorophenyl)-amide To a solution of rac-(trans-3,4)-4-(4-bromo-phenyl)-1-(2,2,2-trifluoro-ethyl)-pyrrolidine-3-carboxylic acid ethyl ester (440 mg, 1.16 mmol) in methanol (3 mL) was added aqueous NaOH (2.9 mL, 2 M). The mixture was stirred at rt for 4 hours. Then the mixture was concentrated in vacuo to remove methanol and the residue was acidified by aqueous HCl and lyophilized to offer a colorless solid. MS: calc'd 352 (MH+), exp 352 (MH+), calc'd 350 (M−H), exp 350 (M−H).

To a suspension of the crude acid in DCM (10 mL) was added PyBrop (811 mg, 1.74 mmol), 4-chlorophenylamine (177 mg, 1.39 mmol) and DIPEA (0.5 mL, 2.84 mmol). The reaction was stirred at room temperature overnight and diluted with CH₂Cl₂ (10 mL). The mixture was washed with water (10 mL) and brine (10 mL), dried with Na₂SO₄, filtered, and concentrated in vacuo. The crude product was purified by flash chromatography on silica gel (Pet:EtOAc=5:1-2:1) to get the product (483 mg, 90%). MS: calc'd 461 (MH+), exp 461 (MH+).

Example 46

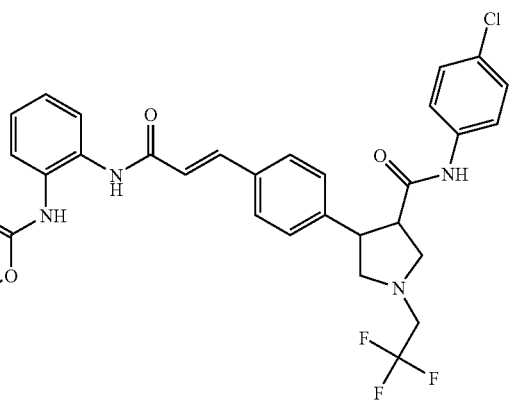

rac-[2-(3-{4-[(trans-3,4)-4-(4-Chloro-phenylcarbamoyl)-1-(2,2,2-trifluoro-ethyl)-pyrrolidin-3-yl]-phenyl}-acryloylamino)-phenyl]-carbamic acid tert-butyl ester The mixture of rac-(trans-3,4)-4-(4-bromo-phenyl)-1-(2,2,2-trifluoro-ethyl)-pyrrolidine-3-carboxylic acid (4-chlorophenyl)-amide (483 mg, 1.05 mmol), (2-acryloylamino-phenyl)-carbamic acid tert-butyl ester (302 mg, 1.15 mmol), Pd$_2$(dba)$_3$ (28.8 mg, 0.03 mmol), P(o-tolyl)$_3$ (38.4 mg, 0.12 mmol) in DMF (50 mL) and TEA (0.42 mL, 3 mmol) was heated at 110 degrees Celsius under Ar in a sealed tube for 4 h. The cooled mixture was concentrated in vacuo to remove DMF. The residue was purified by chromatography on silica gel (DCM:methanol=40:1-20:1) to give the product (580 mg, 86%). MS: calc'd 643 (MH+), exp 643 (MH+).

Example 47

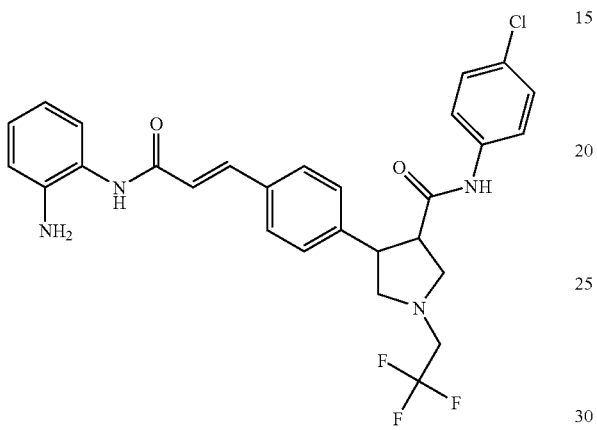

rac-(trans-3,4)-4-{4-[2-(2-Amino-phenylcarbamoyl)-vinyl]-phenyl}-1-(2,2,2-trifluoro-ethyl)-pyrrolidine-3-carboxylic acid (4-chloro-phenyl)-amide To a solution of the rac-[2-(3-{4-[(trans-3,4)-4-(4-chloro-phenylcarbamoyl)-1-(2,2,2-trifluoro-ethyl)-pyrrolidin-3-yl]-phenyl}-acryloylamino)-phenyl]-carbamic acid tert-butyl ester (580 mg, 0.9 mmol) in DCM (6 mL) was added trifluoroacetic acid (2 mL) and stirred for 2 hour. The solvent was removed and the residue was basified with TEA and purified by prep-HPLC. MS: calc'd 543 (MH+), exp 543 (MH+). $^1$H NMR (CD$_3$OD, 400 MHz), 7.66 (d, 1H, J=15.6 Hz), 7.60 (d, 2H, J=8.0 Hz), 7.53 (d, 2H, J=8.4 Hz), 7.42 (d, 2H, J=8.0 Hz), 7.29 (d, 2H, J=8.4 Hz), 7.21 (d, 1H, J=7.6 Hz), 7.08-7.04 (m, 1H), 6.90-6.82 (m, 2H), 6.78-6.74 (m, 1H), 3.92-3.60 (m, 1H), 3.44-3.38 (m, 2H), 3.29-3.24 (m, 4H), 3.10-3.06 (m, 1H).

Example 48

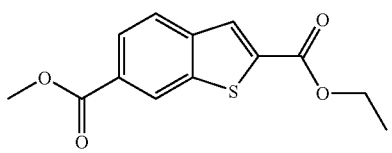

Benzo[b]thiophene-2,6-dicarboxylic acid 2-ethyl ester 6-methyl ester

A mixture of 4-formyl-3-nitro-benzoic acid methyl ester (14.1 g, 67.5 mmol), mercapto-acetic acid ethyl ester (8.17 mL, 74.2 mmol) and potassium carbonate (12.2 g, 87.7 mmol) in 100 mL of anhydrous DMF was heated at 50 degrees Celsius for about 6 hours. After cooling to rt, the mixture was poured into ice-water and the mixture was stirred for around 40 mins. The solid formed was collected, washed with water and dried to give benzo[b]thiophene-2,6-dicarboxylic acid 2-ethyl ester-6-methyl ester as a pale solid (16.1 g, 90.4%). MS: calc'd 265 (MH+), exp 265 (MH+). $^1$H NMR (CDCl$_3$, 400 MHz), 8.60 (s, 1H), 8.09 (s, 1H), 8.06 (d, 1H, J=8.8 Hz), 7.93 (d, 1H, J=8.8 Hz), 4.45 (q, 2H, J=6.8 Hz), 4.0 (s, 3H), 1.50 (t, 3H, J=7.2 Hz).

Example 49

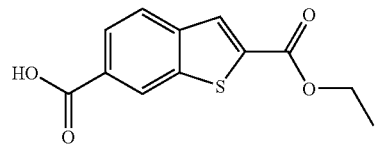

Benzo[b]thiophene-2,6-dicarboxylic acid 2-ethyl ester

A mixture of benzo[b]-thiophene-2,6-dicarboxylic acid 2-ethyl ester 6-methyl ester (16.19 g, 61.26 mmol) and LiI (34.68 g, 259.11 mmol) in 500 ml anhydrous pyridine was refluxed for 3 days. After cooling to rt, the mixture was poured into ice-cold 2N HCl (1000 mL). The solid was collected, washed with water and dried. The solid was crystallized from methanol to give benzo[b]thiophene-2,6-dicarboxylic acid 2-ethyl ester as a pale solid (11.65 g, 76%). MS: calc'd 251 (MH+), exp 251 (MH+). $^1$H NMR (d$_6$-DMSO, 400 MHz), 8.69 (s, 1H), 8.26 (s, 1H), 8.11 (d, 1H, J=8.4 Hz), 7.98 (d, 1H, J=8.4 Hz), 4.37 (q, 2H, J=6.8 Hz), 1.35 (t, 3H, J=7.2 Hz).

Example 50

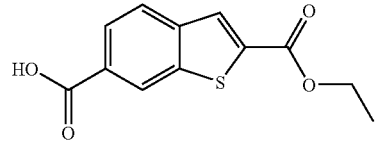

6-Hydroxymethyl-benzo[b]thiophene-2-carboxylic acid ethyl ester

To a solution of benzo[b]thiophene-2,6-dicarboxylic acid 2-ethyl ester (332 mg, 1.32 mmol) in 5 mL of anhydrous THF at 0 degrees Celsius was slowly added BH$_3$. The resulting mixture was allowed to stir at 0 degrees Celsius for 30 mins and at rt overnight. After cooling to 0 degrees Celsius, the reaction mixture was quenched with 1N HCl. Additional 120 mL of water was added and THF was removed in vacuo. The solid was filtered and washed with water. After drying, 6-hydroxymethyl-benzo[b]thiophene-2-carboxylic acid ethyl ester was obtained as pale solid (229 mg, 73.2%). MS: calc'd 237 (MH+), exp 237 (MH+). $^1$H NMR (CDCl$_3$, 400 MHz), 8.04 (s, 1H), 7.88 (s, 1H), 7.85 (d, 1H, J=8.4 Hz), 7.40 (d, 1H, J=8.0 Hz), 4.42 (q, 2H, J=7.2 Hz), 1.43 (t, 3H, J=7.2 Hz).

Example 51

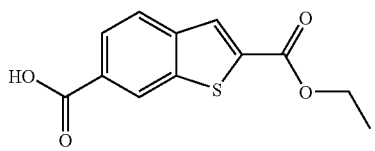

6-Formyl-benzo[b]thiophene-2-carboxylic acid ethyl ester

To a solution of 6-hydroxymethyl-benzo[b]thiophene-2-dicarboxylic acid ethyl ester (213 mg, 0.91 mmol) in 5 mL of dichloromethane at 0 degrees Celsius was added $MnO_2$. The mixture was allowed to stir at rt for 30 min and then filtered through a pad of Celite. The filtrate was concentrated and dried to give 6-formyl-benzo[b]thiophene-2-carboxylic acid ethyl ester as a pale solid (191 mg, 90.5%). MS: calc'd 235 (MH+), exp 235 (MH+). $^1$H NMR ($d_6$-DMSO, 400 MHz), 10.12 (s, 1H), 8.70 (s, 1H), 8.31 (s, 1H), 8.20 (d, 1H, J=8.4 Hz), 7.94 (d, 1H, J=8.4 Hz), 4.39 (q, 2H, J=7.2 Hz), 1.36 (t, 3H, J=7.2 Hz).

Example 52

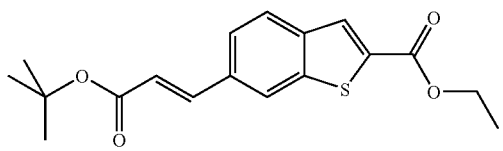

6-(2-tert-Butoxycarbonyl-vinyl)-benzo[b]thiophene-2-carboxylic acid ethyl ester

To a stirred solution of tert-butyl phosphonoacetate (1.7 g, 7.27 mmol) in THF (20 mL) was slowly added n-butyllithium (1.6 M, 5 mL) with cooling to −78 degrees Celsius. After stirring for 30 minutes at −78 degrees Celsius, this solution was added into a solution of 6-formyl-benzo[b]thiophene-2-carboxylic acid ethyl ester (1.83 g, 7.27 mmol). The resulting solution was stirred at −78 degrees Celsius for 30 minutes before being allowed to warm to room temperature. The solution was subsequently cooled back to −78 degrees Celsius and quenched with sat. aq $NH_4Cl$. The mixture was extracted with ethyl acetate, and the combined organic extracts were dried over anhydrous sodium sulfate. After being filtrated and concentrated, the residue was purified by flash column chromatography to give 1.7 g (71%) of 6-(2-tert-butoxycarbonyl-vinyl)-benzo[b]thiophene-2-carboxylic acid ethyl ester. MS: calc'd 333 (MH+), exp 333 (MH+). $^1$H NMR ($d_6$-DMSO, 400 MHz), 8.38 (s, 1H), 8.18 (s, 1H), 8.02 (d, 1H, J=8.4 Hz), 7.82 (d, 1H, J=8.4 Hz), 7.66 (d, 1H, J=16.0 Hz), 6.66 (d, 1H, J=16.0 Hz), 4.36 (q, 2H, J=7.2 Hz), 1.49 (s, 9H), 1.34 (t, 3H, J=7.2 Hz).

Example 53

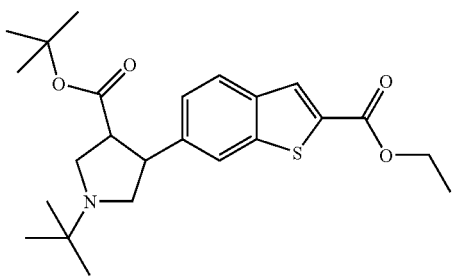

rac-(trans-3,4)-1-tert-Butyl-4-(2-ethoxycarbonyl-benzo[b]thiophen-6-yl)-pyrrolidine-3-carboxylic acid tert-butyl ester A mixture of 6-(2-tert-butoxycarbonyl-vinyl)-benzo[b]thiophene-2-carboxylic acid ethyl ester (740 mg, 2.3 mmol), paraformaldehyde (1 g) and N-tert-butyl-glycine hydrochloride (600 mg, 4.6 mmol) in dry toluene was refluxed for 4 hours under the aid of a Dean-Stark trap to remove water formed. After removal of solvent, a solution of the residue in ethyl acetate was washed with water, brine, dried, evaporated to dryness. The residue was purified with flash column chromatography to give 210 mg (24%) of desired product. MS: calc'd 432 (MH+), exp 432 (MH+). $^1$H NMR ($d_6$-DMSO, 400 MHz), 8.15 (s, 1H), 7.99 (s, 1H), 7.96 (d, 1H, J=8.4 Hz), 7.45 (d, 1H, J=8.0 Hz), 4.35 (q, 2H, J=7.2 Hz), 3.51 (q, 2H, J=7.6 Hz), 3.15-3.05 (m, 2H), 3.02-2.89 (m, 2H), 2.71 (t, 1H, J=8.4 Hz), 1.36 (t, 3H, J=7.2 Hz), 1.35 (s, 9H), 1.05 (s, 9H).

Example 54

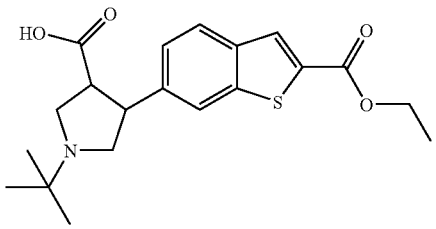

rac-(trans-3,4)-1-tert-Butyl-4-(2-ethoxycarbonyl-benzo[b]thiophen-6-yl)-pyrrolidine-3-carboxylic acid To a solution of rac-(trans-3,4)-1-tert-butyl-4-(2-ethoxycarbonyl-benzo[b]thiophen-6-yl)-pyrrolidine-3-carboxylic acid tert-butyl ester (1.29 g, 3 mmol) in dichloromethane was added trifluoroacetic acid (6 ml, 26.9 mmol), and the solution was stirred at room temperature for 3 hours. After the solvent was removed, the residue was obtained as an oil. MS: calc'd 376 (MH+), exp 376 (MH+).

Example 55

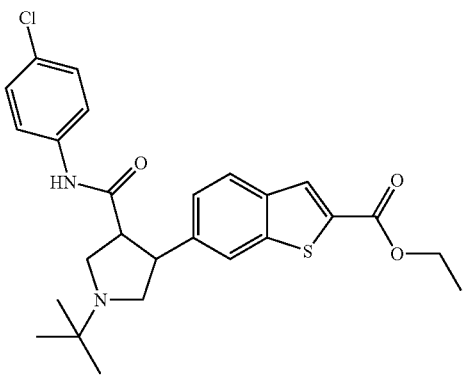

rac-6-[(trans-3,4)-1-tert-Butyl-4-(4-chloro-phenyl-carbamoyl)-pyrrolidin-3-yl]-benzo[b]thiophene-2-carboxylic acid ethyl ester To a suspension of 1-tert-butyl-4-(2-ethoxycarbonyl-benzo[b]thiophen-6-yl)-pyrrolidine-3-carboxylic acid (1.13 g, 3 mmol) in dichloromethane was added 4-chloroamine (419 mg, 3.3 mmol), EDCI (632 mg, 3.3 mmol) and HOBt (446 mg, 3.3 mmol). The reaction mixture was stirred at room temperature overnight. Then this solution was washed with water, brine, and dried over anhydrous sodium sulfate. After being filtered and concentrated, the obtained residue was purified by flash column chromatography to give rac-6-[(trans-3,4)-1-tert-butyl-4-(4-chloro-phenylcarbamoyl)-pyrrolidin-3-yl]-benzo[b]thiophene-2-carboxylic acid ethyl ester (1.31 g, 90%). MS: calc'd 485 (MH+), exp 485 (MH+).

Example 56

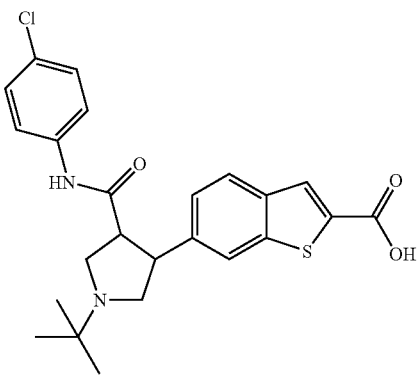

rac-6-[(trans-3,4)-1-tert-Butyl-4-(4-chloro-phenyl-carbamoyl)-pyrrolidin-3-yl]-benzo[b]thiophene-2-carboxylic acid To a mixture of rac-6-[(trans-3,4)-1-tert-butyl-4-(4-chloro-phenylcarbamoyl)-pyrrolidin-3-yl]-benzo[b]thiophene-2-carboxylic acid ethyl ester (1.31 g, 2.7 mmol) in a mixed solvent (ethanol:water=3:1) was added potassium hydroxide (226.8 mg, 4.05 mmol). Then this solution was stirred at room temperature for 3 hours. 1N HCl was added to adjust the pH of this solution to about 7. The solvent was removed under vacuum, and the residue was dried. Without further purification, the residue was used directly in next step. MS: calc'd 457 (MH+), exp 457 (MH+).

Example 57

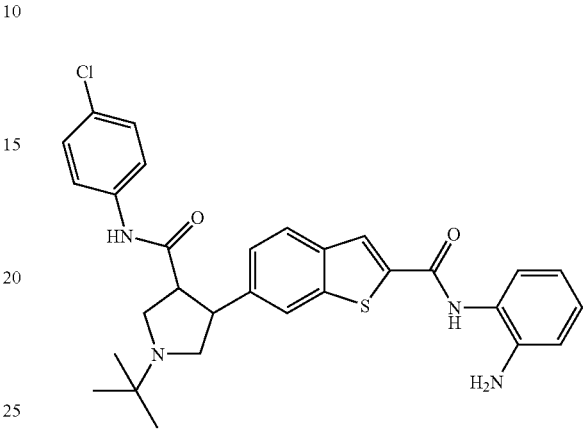

rac-(trans-3,4)-4-[2-(2-Amino-phenylcarbamoyl)-benzo[b]thiophen-6-yl]-1-tert-butyl-pyrrolidine-3-carboxylic acid (4-chloro-phenyl)-amide To a suspension of rac-6-[(trans-3,4)-1-tert-butyl-4-(4-chloro-phenylcarbamoyl)-pyrrolidin-3-yl]-benzo[b]thiophene-2-carboxylic acid (91.2 mg, 0.2 mmol) in dichloromethane was added successively with 1,2-phenylenediamine, EDCI and HOBt. Then this mixture was stirred at room temperature overnight, and the crude mixture was purified by preparative HPLC to obtain the desired product (55 mg, 50%). MS: calc'd 547 (MH+), exp 547 (MH+). $^1$H NMR ($d_6$-DMSO, 400 MHz), 10.35 (s, 1H), 8.30 (s, 1H), 10.30 (s, 1H), 10.05 (s, 1H), 8.21 (s, 1H), 7.97 (t, 1H, J=8.0 Hz), 7.56-7.52 (broad m, 2H), 7.43 (t, 1H, J=9.6 Hz), 7.37-7.34 (broad m, 2H), 7.21 (t, 1H, J=8.0 Hz), 7.05 (t, 1H, J=7.6 Hz), 6.87 (d, 1H, J=7.6 Hz), 6.71 (m, 1H), 4.13-3.78 (broad m, 3H), 3.62-3.44 (broad m, 3H), 1.41 (s, 9H).

Example 58

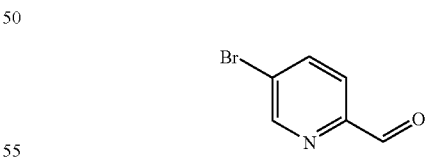

5-Bromo-pyridine-2-carbaldehyde

To a solution of 5-bromo-2-iodopyridine (14.2 g, 50 mmol) in dry THF (160 mL) was added dropwise isopropylmagnesium (30 mL, 60 mmol) at −20 degrees Celsius under $N_2$. After addition, the reaction mixture was stirred for about 2 h at the same temperature, and then DMF (5.11 g, 70 mmol) was added while keeping the temperature under 0 degrees Celsius. The reaction temperature was allowed to rise to rt and stirred for 1 hour, quenched with saturated ammonium chloride (10 ml), and then the solution pH was adjusted to 7-8 with 2.0 M HCl. The solvent was removed and extracted with ethyl acetate (2×200 mL). The combined organic layer was washed with brine, dried with Na$_2$SO$_4$, filtered, and evaporated to obtain 8.5 g (90%) of a yellow solid product which was used directly in the next step without further purification. MS: calc'd 186 (MH+), exp 186 (MH+).

Example 59

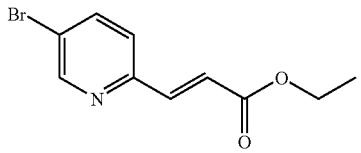

3-(5-Bromo-pyridin-2-yl)-acrylic acid ethyl ester

To a solution of triethyl phosphonoacetate (10.2 g, 45.7 mmol), Et$_3$N (7 mL, 50.3 mmol) and lithium bromide (4.3 g, 50.3 mol) in MeCN (120 mL) was added 5-bromo-pyridine-2-carbaldehyde (8.5 g, 45.7 mmol). This mixture was stirred overnight at room temperature. LC-MS indicated the reaction was complete, quenched with water (10 mL). Excess MeCN was removed in vacuo and then the remaining mixture extracted with EtOAc (2×100 mL). The combined organic layer was washed with brine, dried with Na$_2$SO$_4$, filtered, and evaporated. The crude product was purified by column chromatography (PE:EtOAc=5:1) to give 7.8 g (67%) of a yellow solid product. MS: calc'd 256 (MH+), exp 256 (MH+).

Example 60

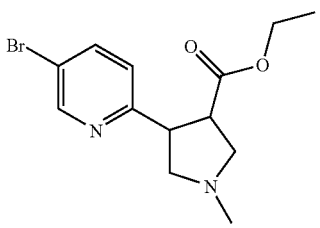

rac-(trans-3,4)-4-(5-Bromo-pyridin-2-yl)-1-methyl-pyrrolidine-3-carboxylic acid ethyl ester To a solution of 3-(5-bromo-pyridin-2-yl)-acrylic acid ethyl ester (3 g, 11.7 mmol) and paraformaldehyde (4.22 g, 140.4 mol) in toluene (200 mL) was added sarcosine (2.1 g, 23.4 mmol). This mixture was heated to reflux for 4 h, using Dean-stark trap to remove the water formed in the reaction. LC-MS indicated the reaction was complete. After cooling, the solution was filtered, and the solid was washed with EtOAc (2×50 mL). The combined organic layer was washed with water and brine, dried with Na$_2$SO$_4$, filtered, and evaporated. The crude product was purified by column chromatography (PE:EtOAc=3:1) to give 2.8 g (77%) of a white solid product. MS: calc'd 313 (MH+), exp 313 (MH+).

Example 61

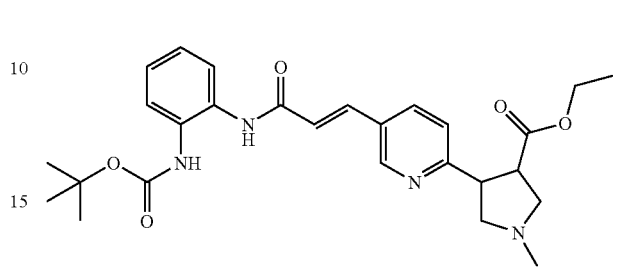

rac-(trans-3,4)-4-{5-[2-(2-tert-Butoxycarbonylamino-phenylcarbamoyl)-vinyl]-pyridin-2-yl}-1-methyl-pyrrolidine-3-carboxylic acid ethyl ester To a solution of rac-(trans-3,4)-4-(5-bromo-pyridin-2-yl)-1-methyl-pyrrolidine-3-carboxylic acid ethyl ester (2.1 g, 6.7 mmol) in dried DMF (50 ml) was added 2-acryloylamino-phenyl)-carbamic acid tert-butyl ester (2.1 g, 8.05 mmol), tris-o-tolylphosphine (0.41 g, 1.34 mmol), Pd$_2$(dba)$_3$ (0.62 g, 0.67 mmol) and Et$_3$N (2.7 g, 26.8 mmol). The resulting mixture was stirred for 3 h at 100 degrees Celsius under argon. After cooling, the mixture was filtered, the solvent was removed, diluted with EtOAc (100 ml), washed with water and brine, dried with Na$_2$SO$_4$, filtered, and evaporated to give an oil. The crude product was purified by column chromatography (PE:EtOAc=1:1) to give 2.5 g (75%) of a white solid product. MS: calc'd 495 (MH+), exp 495 (MH+).

Example 62

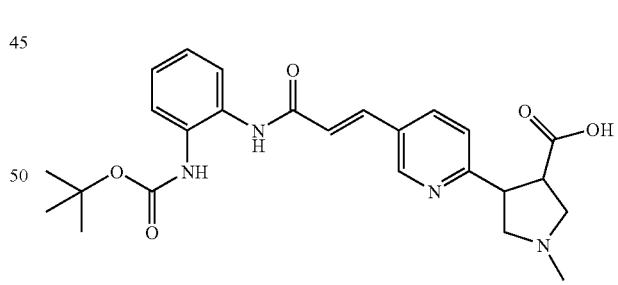

rac-(trans-3,4)-4-{5-[2-(2-tert-Butoxycarbonylamino-phenylcarbamoyl)-vinyl]-pyridin-2-yl}-1-methyl-pyrrolidine-3-carboxylic acid To a solution of rac-(trans-3,4)-4-{5-[2-(2-tert-butoxycarbonylamino-phenylcarbamoyl)-vinyl]-pyridin-2-yl}-1-methyl-pyrrolidine-3-carboxylic acid ethyl ester (2.5 g, 5 mmol) in THF/H$_2$O (45 mL/15 mL) was added LiOH monohydrate (1.05 g, 25 mmol). This mixture was stirred for about 5 h at room temperature, and then evaporated to remove most of the THF. The aqueous solution was acidified with 2 N HCl to pH 6-7, and then extracted with ethyl acetate (3×70 mL). The combined organic layer was washed with brine, dried with Na$_2$SO$_4$, filtered, and evaporated to obtain 2.0 g (85.6%) of a yellow solid product. MS: calc'd 467 (MH+), exp 467 (MH+).

Example 63

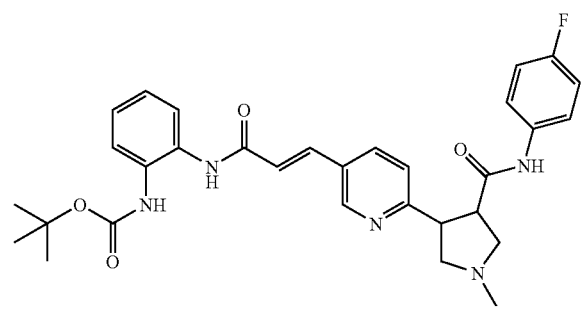

rac-2-(3-{6-[(trans-3,4)-4-(4-Fluoro-phenylcarbamoyl)-1-methyl-pyrrolidin-3-yl]-pyridin-3-yl}-acryloylamino)-phenyl]-carbamic acid tert-butyl ester To a solution of rac-(trans-3,4)-4-{5-[2-(2-tert-butoxycarbonylamino-phenylcarbamoyl)-vinyl]-pyridin-2-yl}-1-methyl-pyrrolidine-3-carboxylic acid (350 mg, 0.75 mmol), 4-fluorophenylamine (100 mg, 0.9 mmol) and Et$_3$N (227 mg, 2.25 mol) in CH$_2$Cl$_2$ (50 mL) was added HATU (430 mg, 1.125 mmol). This mixture was stirred overnight at room temperature and then diluted with CH$_2$Cl$_2$ (50 mL), washed with saturated aqueous NaHCO$_3$ solution, water and brine, dried with Na$_2$SO$_4$, and evaporated to obtain 0.23 g (54%) of a yellow solid. MS: calc'd 560 (MH+), exp 560 (MH+).

Example 64

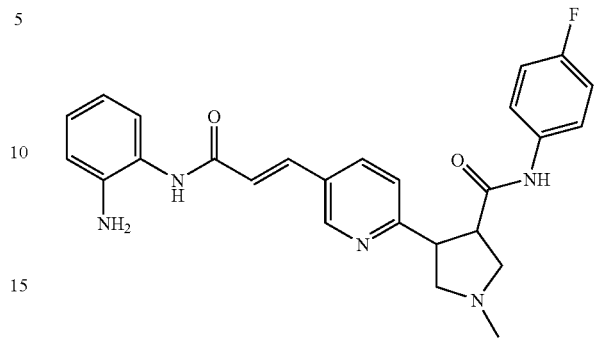

rac-(trans-3,4)-4-{5-[2-(2-Amino-phenylcarbamoyl)-vinyl]-pyridin-2-yl}-1-methyl-pyrrolidine-3-carboxylic acid (4-fluoro-phenyl)-amide The solution of rac-2-(3-{6-[(trans-3,4)-4-(4-fluoro-phenylcarbamoyl)-1-methyl-pyrrolidin-3-yl]-pyridin-3-yl}-acryloylamino)-phenyl]-carbamic acid tert-butyl ester (168 mg, 0.3 mmol) in 2 N HCl in MeOH (10 mL) was stirred for 4 h at room temperature, and then the pH of the solution was adjusted to 8-9 with NaHCO$_3$ solution. Then the mixture was diluted with water (50 mL), and extracted with EtOAc (2×50 mL). The combined organic layer was washed with brine, dried with Na$_2$SO$_4$, filtered, and evaporated. The crude product was purified by preparative HPLC to give a yellow solid product. MS: calc'd 460 (MH+), exp 460 (MH+). $^1$H NMR (CD$_3$OD, 400 MHz), 8.78 (s, 1H), 8.05 (dd, 1H, J=8.0 Hz, J=2.0 Hz), 7.70 (d, 1H, J=16.0 Hz), 7.57-7.54 (m, 2H), 7.45 (d, 1H, J=8.0 Hz), 7.22 (d, 1H, J=7.6 Hz), 7.08-7.02 (m, 3H), 6.96 (d, 1H, J=7.6 Hz), 6.89 (d, 1H, J=8.0 Hz), 6.76 (t, 1H, J=7.6 Hz), 4.04 (m, 1H), 3.51 (m, 1H), 3.28 (m, 1H), 3.20-3.18 (broad m, 2H), 3.13 (m, 1H), 2.56 (s, 3H).

Example 64-2 through 64-3 described in the following tables were prepared by methods analogous to the synthetic methods described for Example 36 and Example 64, respectively, using the appropriate starting materials as indicated in Table 15.

TABLE 15

Structure and starting materials for examples 64-2 to 64-3

| Example # | Structure |
|---|---|
| 64-2 | 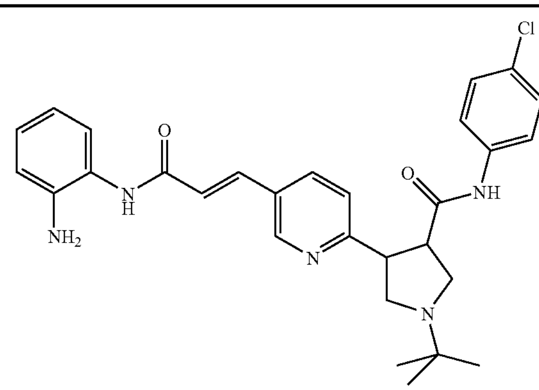 |

Starting Materials: Example 59, N-tert-butyl-glycine hydrochloride salt (commercially available), (2-acryloylamino-phenyl)-carbamic acid tert-butyl ester, TABLE 15-continued Structure and starting materials for examples 64-2 to 64-3

| Example # | Structure |
|---|---|

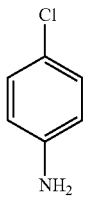

commercially
available 64-3

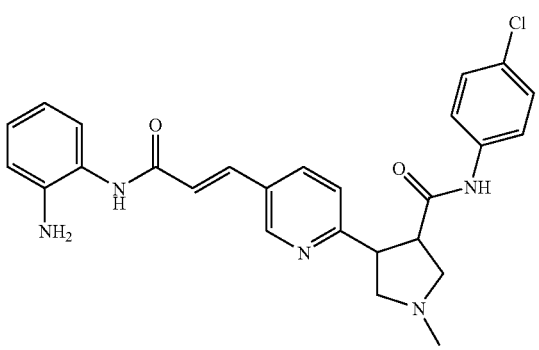

Starting Materials: Example 62,

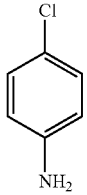

commercially
available

TABLE 16

MS and NMR data for examples 64-2 to 64-3

Example # MS and NMR data 64-2  $^1$H NMR (CD$_3$OD, 400 MHz), 8.76 (s, 1H), 8.01 (d, 1H, J = 8.0 Hz),
7.69 (d, 1H J = 16.0 Hz), 7.54 (d, 2H, J = 8.4 Hz), 7.45 (d, 1H, J = 8.4 Hz),
7.28 (d, 2H, J = 8.8 Hz), 7.22 (d, 1H, J = 7.6 Hz), 7.06 (t, 1H, J = 8.0 Hz),
6.94 (d, 1H, J = 16.0 Hz), 6.89 (d, 1H, J = 8.0 Hz), 6.76 (t, 1H, J = 7.6 Hz),
3.91 (m, 1H), 3.45-3.36 (broad m, 3H), 3.18-3.07 (broad m, 2H),
1.21 (s, 9H)
MS: calc'd 518 (MH+), exp 518 (MH+)

64-3  $^1$H NMR (d$_6$-DMSO, 400 MHz), 10.16 (s, 1H), 9.44 (s, 1H), 8.76 (s, 1H),
7.97 (d, 1H J = 8.0 Hz,), 7.63-7.56 (broad m, 3H), 7.41 (d, 1H, J = 8.4 Hz),
7.36-7.30 (broad m, 3H), 6.98-6.91 (broad m, 2H), 6.76 (d, 1H, J = 7.2 Hz),
6.58 (t, 1H, J = 7.2 Hz), 4.95 (broad s, 2H), 3.95 (m, 1H),
3.48 (m, 1H), 3.03 (broad m, 2H), 2.79 (m, 2H), 2.33 (s, 3H)
MS: calc'd 476 (MH+), exp 476 (MH+)

Example 65

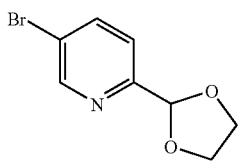

5-bromo-2-[1,3]dioxolan-2-ylpyridine

To a solution of 5-bromopyridine-2-aldehyde (3.72 g, 20 mmol) in toluene (60 mL) was added TsOH monohydrate (190 mg, 1 mmol) and ethane-1,2-diol (2.48 g, 40 mmol). The mixture was heated to reflux for 6 hours. The solvent was removed, and the residue was dissolved in ethyl acetate and washed with sodium bicarbonate and brine. The organic layer was dried with sodium sulfate and concentrated to give the crude product. MS: calc'd 230 (MH+), exp 230 (MH+).

Example 66

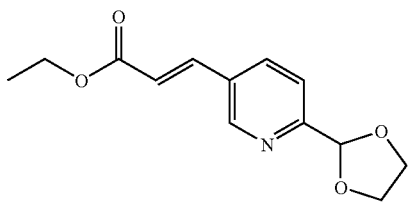

Ethyl 3-(2-[1,3]-dioxolan-pyridinyl)-acrylate

To a solution of 5-bromo-2-[1,3]dioxolan-2-ylpyridine (460 mg, 2.0 mmol) in DMF (10 mL) was added ethyl acrylate (240 mg, 2.4 mmol), Pd$_2$(dba)$_3$ (183 mg, 0.2 mmol), tris-o-tolylphosphine (122 mg, 0.4 mmol) and Et$_3$N (606 mg, 6 mmol). The mixture was heated to 110 degrees Celsius for 3 hours under protection of nitrogen. The mixture was diluted with ethyl acetate and washed with brine. The organic layer was dried with sodium sulfate and concentrated. The residue was purified by chromatography to give the pure product. MS: calc'd 250 (MH+), exp 250 (MH+).

Example 67

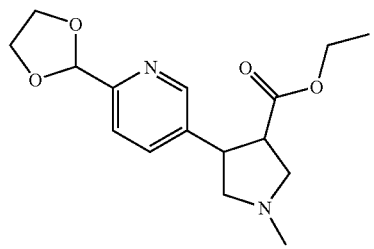

rac-(trans-3,4)-4-(6-[1,3]Dioxolan-2-yl-pyridin-3-yl)-1-methyl-pyrrolidine-3-carboxylic acid ethyl ester To a solution of ethyl 3-{2-[1,3]-dioxolan-pyridinyl}-acrylate (6 g, 24 mmol) in toluene (600 mL) was added N-methylglycine (10.7 g, 120 mmol) and paraformaldehyde (14.4 g, 480 mmol). The mixture was heated to reflux for 6 hours. After cooling down, the solvent was removed and the residue was purified by chromatography to give the pure product. MS: calc'd 307 (MH+), exp 307 (MH+).

Example 68

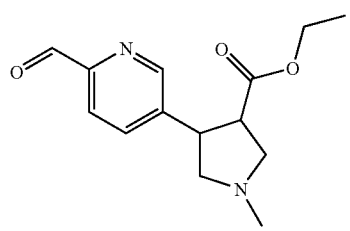

rac-(trans-3,4)-4-(6-Formyl-pyridin-3-yl)-1-methyl-pyrrolidine-3-carboxylic acid ethyl ester To a solution of rac-(trans-3,4)-4-(6-[1,3]dioxolan-2-yl-pyridin-3-yl)-1-methyl-pyrrolidine-3-carboxylic acid ethyl ester (612 mg, 2 mmol) in DMSO/H$_2$O (12 mL/4 mL) was added LiCl (509 mg, 12 mmol). The mixture was sealed in a microwave tube and heated to 150 degrees Celsius for 10 minutes under microwave conditions. The mixture was diluted with ethyl acetate and washed with brine. The organic layer was dried with sodium sulfate and concentrated. The residue was purified by chromatography to give the pure product. MS: calc'd 263 (MH+), exp 263 (MH+).

Example 69

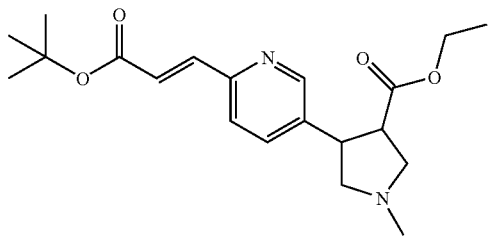

rac-(trans-3,4)-4-[6-(2-tert-Butoxycarbonyl-vinyl)-pyridin-3-yl]-1-methyl-pyrrolidine-3-carboxylic acid ethyl ester To the solution of rac-(trans-3,4)-4-(6-formyl-pyridin-3-yl)-1-methyl-pyrrolidine-3-carboxylic acid ethyl ester (1.31 g, 5 mmol) in THF (35 mL) was added diethyl tert-butyl phosphoacetate (1.78 g, 7 mmol) at rt. n-Butyllithium (4 mL, 8 mmol) was added dropwise to the above solution at −78 degrees Celsius. The solution was allowed to rise to 0 degrees Celsius slowly and stirred at 0 degrees Celsius for 2 hours. The reaction was quenched with saturated ammonium chloride. The solvent was removed and the residue was dissolved in ethyl acetate. The organic layer was washed with brine and dried with sodium sulfate. The solvent was concentrated and the residue was purified by chromatography to give the pure product. MS: calc'd 361 (MH+), exp 361 (MH+).

Example 70

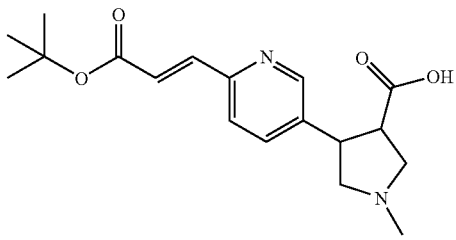

rac-(trans-3,4)-4-[6-(2-tert-Butoxycarbonyl-vinyl)-pyridin-3-yl]-1-methyl-pyrrolidine-3-carboxylic acid To a solution of rac-(trans-3,4)-4-[6-(2-tert-butoxycarbonyl-vinyl) -pyridin-3-yl]-1-methyl-pyrrolidine-3-carboxylic acid ethyl ester (500 mg, 1.39 mmol) in THF (9 mL) was added lithium hydroxide monohydrate (234 mg, 5.56 mmol) and water (3 mL). The mixture was stirred at rt for 3 hours. The solution was neutralized to pH=6-7. The solvent was removed and the residue was used directly in the next step. MS: calc'd 333 (MH+), exp 333 (MH+).

Example 71

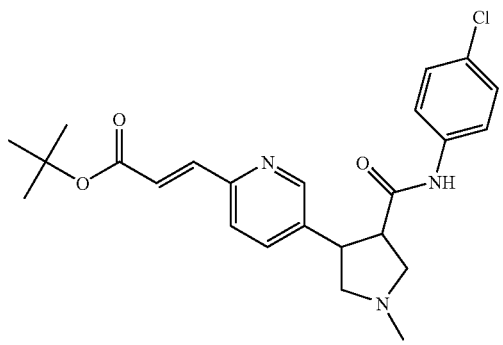

rac-3-{5-[(trans-3,4)-4-(4-Chloro-phenylcarbamoyl)-1-methyl-pyrrolidin-3-yl]-pyridin-2-yl}-acrylic acid tert-butyl ester To a solution of rac-(trans-3,4)-4-[6-(2-tert-butoxycarbonyl-vinyl) -pyridin-3-yl]-1-methyl-pyrrolidine-3-carboxylic acid (430 mg, 1.3 mmol) in dichloromethane (10 mL) was added HATU (990 mg, 2.6 mmol), Et₃N (525 mg, 5.2 mmol), 4-chloroaniline (249 mg, 1.95 mmol). The mixture was stirred at rt for 24 hours. The solvent was removed and the residue was dissolved in ethyl acetate. The organic layer was washed with brine and dried with sodium sulfate. The solvent was removed and the residue was purified by chromatography to give the pure product. MS: calc'd 442 (MH+), exp 442 (MH+).

Example 72

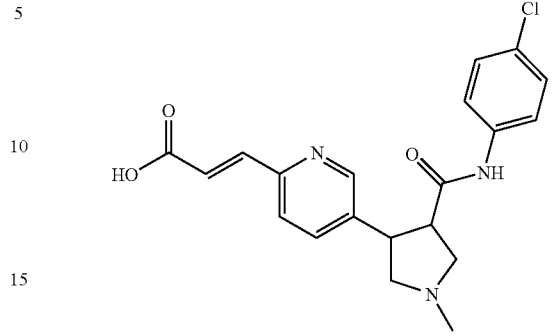

rac-3-{5-[(trans-3,4)-4-(4-Chloro-phenylcarbamoyl)-1-methyl-pyrrolidin-3-yl]-pyridin-2-yl}-acrylic acid To a solution of rac-3-{5-[(trans-3,4)-4-(4-chloro-phenylcarbamoyl)-1-methyl-pyrrolidin-3-yl]-pyridin-2-yl}-acrylic acid tert-butyl ester (172 mg, 0.5 mmol) in dichloromethane (5 mL) was added trifluoroacetic acid (570 mg, 5 mmol) at 0 degrees Celsius. The solution was allowed to rise to rt and stirred for 2 hours. The solvent was removed under reduced pressure to give the crude product which was used directly in next step. MS: calc'd 386 (MH+), exp 386 (MH+).

Example 73

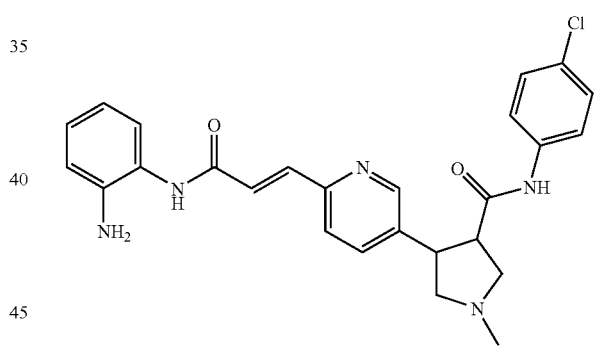

rac-(trans-3,4)-4-{6-[2-(2-Amino-phenylcarbamoyl)-vinyl]-pyridin-3-yl}-1-methyl-pyrrolidine-3-carboxylic acid (4-chloro-phenyl)-amide To a solution of rac-3-{5-[(trans-3,4)-4-(4-chloro-phenylcarbamoyl)-1-methyl-pyrrolidin-3-yl]-pyridin-2-yl}-acrylic acid (54 mg, 0.14 mmol) in dichloromethane (3 mL) was added 1,2-diaminobenzene (46 mg, 0.42 mmol), HATU (80 mg, 0.21 mmol), Et₃N (85 mg, 0.84 mmol). The mixture was stirred at rt for 12 hours. The solvent was removed and the residue was dissolved in ethyl acetate. The solution was washed with brine and dried with sodium sulfate. The solvent was concentrated to give the residue which was purified by preparative HPLC to give pure product. MS: calc'd 476 (MH+), exp 476 (MH+). ¹H NMR (CD₃OD, 400 MHz), 8.57 (s, 1H), 7.88 (d, 1H, J=8.4 Hz), 7.68-7.62 (m, 2H), 7.53 (d, 2H, J=8.8 Hz), 7.28 (d, 2H, J=8.8 Hz), 7.22-7.18 (m, 2H), 7.05 (t, 1H, J=7.6 Hz), 6.87 (d, 1H, J=8.0 Hz), 6.76 (t, 1H, J=7.6 Hz), 3.90 (q, 1H, J=8.0 Hz), 3.32-3.18 (broad m, 3H), 3.01 (t, 2H, J=8.4 Hz), 2.54 (s, 3H).

The following example was prepared by methods analogous to the synthetic methods described above for Example 73, by starting from Example 70 and 4-fluoro-aniline (commercially available).

Example 73-2

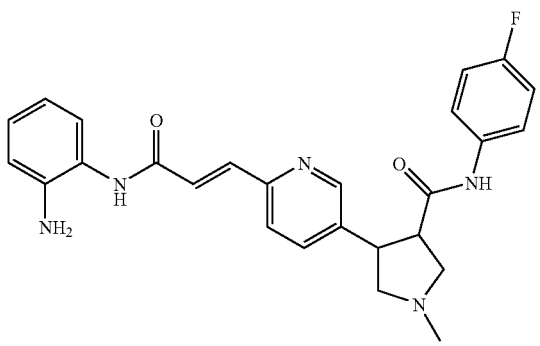

| Example # | MS and NMR data |
|---|---|
| 73-2 | ¹H NMR (CD₃OD, 400 MHz), 8.59 (s, 1H), 7.89 (dd, 1H, J = 8.0 and J = 2.0 Hz), 7.70-7.64 (m, 2H), 7.55-7.51 (m, 2H), 7.24-7.20 (m, 2H), 7.09-7.02 (m, 3H), 6.69 (d, 1H, J = 7.6 Hz), 6.77 (t, 1H, J = 7.6 Hz, 3.91 (q, 1H, J = 8.0 Hz), 3.32-3.15 (broad m, 3H), 2.99 (m, 2H), 2.53 (s, 3H). MS: calc'd 460 (MH+), exp 460 (MH+) |

Example 74

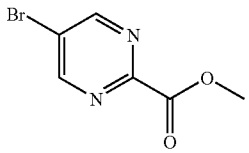

5-bromo-2-pyrimidine-carboxylic acid methyl ester

To a solution of 5-bromo-2-pyrimidine carboxylic acid (6 g, 29.6 mmol) in MeOH (300 mL) was added Et₃N (5.98 g, 59.2 mmol). The mixture was cooled to 0 degrees Celsius, and sulfonyl chloride (5.3 g, 44.4 mmol) was added dropwise to the solution. After addition, the mixture was stirred at rt for 12 hours. The solvent was removed and the residue was dissolved in ethyl acetate. The organic layer was washed with sodium bicarbonate, brine, and dried with sodium sulfate. The solvent was removed to give the pure product. MS: calc'd 217 (MH+), exp 217 (MH+).

Example 75

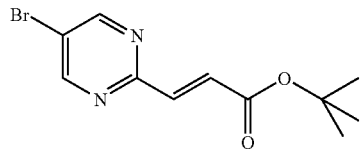

3-(5-Bromo-pyrimidin-2-yl)-acrylic acid tert-butyl ester

To a solution of 5-bromo-2-pyrimidine-carboxylic acid methyl ester (8 g, 36.9 mmol) in dichloromethane (100 mL) was added dropwise 1M DIBAL-H solution in toluene (40.6 ml, 40.6 mmol) at −78 degrees Celsius. The mixture was stirred at the same temperature for 3 hours.

To the solution of diethyl tert-butyl phosphonoacetate (11.2 g, 44.3 mmol) in THF (60 mL) was added dropwise 2.5 M n-butyllithium solution (17.8 ml, 44.3 mmol) at −78 degrees Celsius. After addition, the mixture was stirred at the same temperature for an hour, and added into the above aldehyde solution at −78 degrees Celsius, and the resulting mixture was stirred for an additional 3 hours. Saturated ammonium chloride solution was added to the above solution to quench the reaction. The solvent was removed and the residue was dissolved in ethyl acetate. The organic layer was washed with brine, and dried with sodium sulfate. The solvent was concentrated and the residue was purified by chromatography to give the pure product. MS: calc'd 285 (MH+), exp 285 (MH+).

Example 76

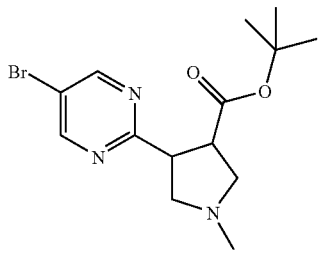

rac-(trans-3,4)-4-(5-Bromo-pyrimidin-2-yl)-1-methyl-pyrrolidine-3-carboxylic acid tert-butyl ester To a solution of 3-(5-bromo-pyrimidin-2-yl)-acrylic acid tert-butyl ester (3.5 g, 12.3 mmol) in toluene was added N-methylglycine (5.5 g, 61.5 mmol), paraformaldehyde (7.4 g, 246 mmol). The mixture was heated to reflux for 6 hours. The solvent was removed and the residue was purified by chromatography to afford the pure product. MS: calc'd 342 (MH+), exp 342 (MH+).

Example 77

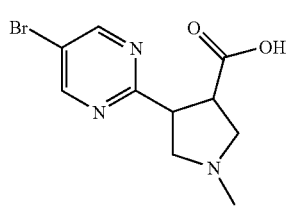

rac-(trans-3,4)-4-(5-Bromo-pyrimidin-2-yl)-1-methyl-pyrrolidine-3-carboxylic acid To a solution of rac-(trans-3,4)-4-(5-bromo-pyrimidin-2-yl)-1-methyl-pyrrolidine-3-carboxylic acid tert-butyl ester (172 mg, 0.5 mmol) in dry dichloromethane (5 mL) was added trifluoroacetic acid (570 mg, 5 mmol) at 0 degrees Celsius. The mixture was stirred at rt for 3 hours. The solvent was removed to give the crude product. MS: calc'd 286 (MH+), exp 286 (MH+).

Example 78

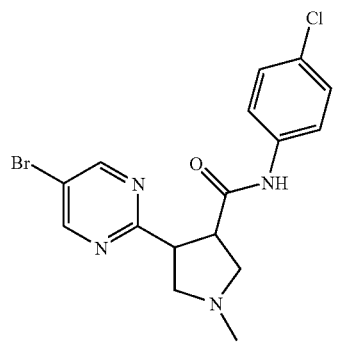

rac-(trans-3,4)-4-(5-Bromo-pyrimidin-2-yl)-1-methyl-pyrrolidine-3-carboxylic acid (4-chloro-phenyl)-amide To the solution of rac-(trans-3,4)-4-(5-bromo-pyrimidin-2-yl)-1-methyl-pyrrolidine-3-carboxylic acid (0.5 mmol) in dry dichloromethane (5 mL) was added Et₃N (303 mg, 3 mmol), 4-chloroaniline (96 mg, 0.75 mmol), HATU (285 mg, 0.75 mmol). The mixture was stirred at rt for 12 hours. After removal of solvent, the residue was dissolved in ethyl acetate and washed with brine. The organic layer was dried with sodium sulfate and concentrated to give the crude product which was purified by chromatography to give the pure product. MS: calc'd 395 (MH+), exp 395 (MH+).

Example 79

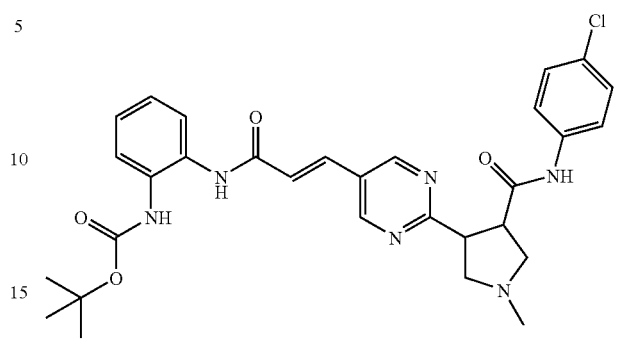

rac-[2-(3-{2-[(trans-3,4)-4-(4-Chloro-phenylcarbamoyl)-1-methyl-pyrrolidin-3-yl]-pyrimidin-5-yl}-acryloylamino)-phenyl]-carbamic acid tert-butyl ester To the solution of rac-(trans-3,4)-4-(5-bromo-pyrimidin-2-yl)-1-methyl-pyrrolidine-3-carboxylic acid (4-chloro-phenyl)-amide (220 mg, 0.56 mmol) in DMF (10 mL) was added arylamide (160 mg, 0.61 mmol), Et₃N (170 mg, 1.68 mmol), Pd₂(dba)₃ (52 mg, 0.056 mmol), tris-o-tolylphosphine (34 mg, 0.112 mmol). The mixture was heated to 110 degrees Celsius for 3 hours. The solvent was removed and the residue was dissolved in ethyl acetate. The organic layer was washed with brine and dried with sodium sulfate. The solvent was removed and the residue was purified by chromatography to give the pure product. MS: calc'd 577 (MH+), exp 577 (MH+).

Example 80

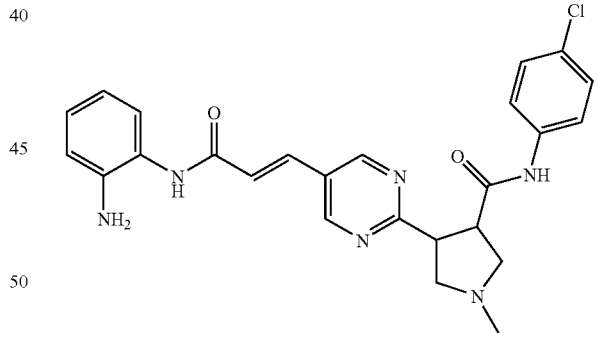

rac-(trans-3,4)-4-{5-[2-(2-Amino-phenylcarbamoyl)-vinyl]-pyrimidin-2-yl}-1-methyl-pyrrolidine-3-carboxylic acid (4-chloro-phenyl)-amide To the solution of rac-[2-(3-{2-[(trans-3,4)-4-(4-chloro-phenylcarbamoyl)-1-methyl-pyrrolidin-3-yl]-pyrimidin-5-yl}-acryloylamino)-phenyl]-carbamic acid tert-butyl ester (270 mg, 0.47 mmol) in dry dichloromethane (20 mL) was added trifluoroacetic acid (2 mL) at 0 degrees Celsius. The mixture was stirred at rt for 3 hours. The solvent was removed and the residue was dissolved in ethyl acetate. The organic layer was washed with sodium bicarbonate, brine and dried with sodium sulfate. The solvent was removed and the residue was purified by preparative HPLC to give the pure product. MS: calc'd 477 (MH+), exp 477 (MH+). $^1$H NMR (CD$_3$OD, 400 MHz), 8.97 (s, 2H), 7.66-7.57 (m, 3H), 7.29 (d, 2H, J=8.8 Hz), 7.21 (d, 1H, J=7.6 Hz), 7.07-7.00 (m, 2H), 6.87 (d, 1H, J=8.0 Hz), 6.74 (t, 1H, J=7.6 Hz), 4.14 (q, 1H, J=7.0 Hz), 3.67 (q, 1H, J=7.0 Hz), 3.27-3.24 (m, 1H), 3.18-3.07 (m, 2H), 3.00-2.96 (m, 1H), 2.43 (s, 3H).

The following example was prepared by a method analogous to the synthetic method described above for Example 80, by starting from Example 77, 4-fluoro-aniline (commercially available), and (2-acryloylamino-phenyl)-carbamic acid tert-butyl ester.

Example 80-2

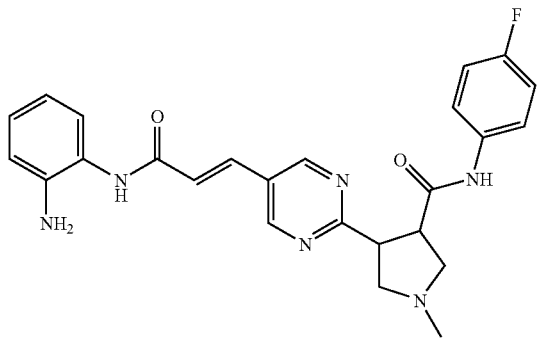

| Example | NMR and MS data |
|---|---|
| 80-2 | $^1$H NMR (CD$_3$OD, 400 MHz), 9.00 (s, 2H), 7.67-7.56 (m, 3H), 7.21 (d, 1H, J = 8.0 Hz), 7.07-7.01 (m, 4H), 6.87 (d, 1H, J = 8.0 Hz), 6.74 (t, 1H, J = 7.6 Hz), 4.15 (q, 1H, J = 7.6 Hz and J = 15.2 Hz), 3.68 (q, 1H, J = 7.6 Hz and J = 15.2 Hz), 3.28 (m, 1H), 3.22-3.11 (m, 2H), 3.05-3.00 (m, 1H), 2.47 (s, 3H). MS: calc'd 461 (MH+), exp 461 (MH+) |

Example 81

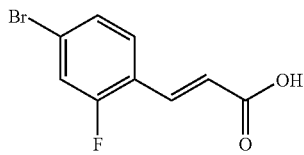

3-(4-Bromo-2-fluoro-phenyl)-acrylic acid

A mixture of 4-bromo-2-fluorobenzaldehyde (12.4 g, 61 mmol), malonic acid (12.7 g, 122 mmol) and 4-dimethylamino pyridine (0.75 g, 6.1 mmol) in 20 mL of DMF was heated at 100 degrees Celsius for 2 hrs. After cooling, the reaction mixture was diluted with 300 mL water, and filtered. The solid was collected, and triturated in hexane. The solid was collected and dried in vacuum to give 12.7 g (85%) of a white solid. MS: calc'd 243 (M–H), exp 243 (M–H).

Example 82

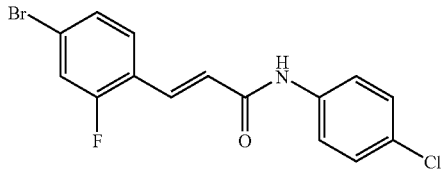

3-(4-Bromo-2-fluoro-phenyl)-N-(4-chloro-phenyl)-acrylamide

A mixture of 3-(4-bromo-2-fluoro-phenyl)-acrylic acid (12.7 g, 52 mmol), 4-chloroaniline (9.9 g, 78 mmol), HOBt (10.5 g, 78 mmol) and EDCI (15.0 g, 78 mmol) in 200 mL of dichloromethane was refluxed overnight, and the resulting mixture was washed with 1M NaOH solution, water and brine, dried over Na$_2$SO$_4$, and concentrated. Recrystallization of the residue from EtOAc/Hexane gave 15 g (82%) of white solid. MS: calc'd 354 (MH+), exp 354 (MH+). $^1$H NMR (CDCl$_3$, 400 MHz), 7.75 (d, 1H, J=15.6 Hz), 7.60 (d, 2H, J=8.8 Hz), 7.48 (s, 1H), 7.32-7.38 (m, 5H, J=7.6 Hz), 6.70 (d, 1H, J=15.6 Hz).

Example 83

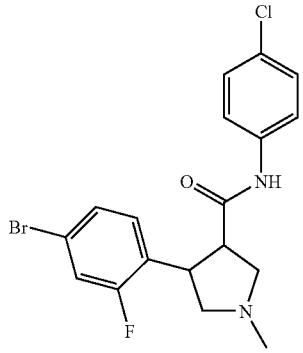

rac-(trans-3,4)-4-(4-Bromo-2-fluoro-phenyl)-1-methyl-pyrrolidine-3-carboxylic acid (4-chloro-phenyl)-amide A mixture of paraformaldehyde (15.3 g, 0.51 mol) and 3-(4-bromo-2-fluoro-phenyl)-N-(4-chloro-phenyl)-acrylamide (15 g, 42.5 mmol) was heated under reflux in toluene (150 mL), and sarcosine (15.2 g, 170 mmol, 4.0 equiv) was added in 4 portions over 4 hrs, the H$_2$O formed was removed with the aid of a Dean-Stark trap. After 4 hours, the cooled mixture was filtered. The filtrate was concentrated, and the residue was purified by chromatography on silica gel eluted with dichloromethane-methanol to give 7.0 g of 4-(4-bromo-2-fluoro-phenyl)-1-methyl-pyrrolidine-3-carboxylic acid (4-chloro-phenyl)-amide. Yield was 40%. MS: calc'd 411 (MH+), exp 411 (MH+). $^1$H NMR (CDCl$_3$, 400 MHz), 9.71

(s, 1H), 7.57 (d, 2H, J=8.8 Hz), 7.51 (t, 1H, J=7.6 Hz), 7.24 (t, 4H, J=8.8 Hz), 4.30 (q, 1H, J=8.8 Hz), 3.76-3.94 (m, 2H), 3.40-3.62 (m, 3H), 2.92 (s, 3H).

Example 84

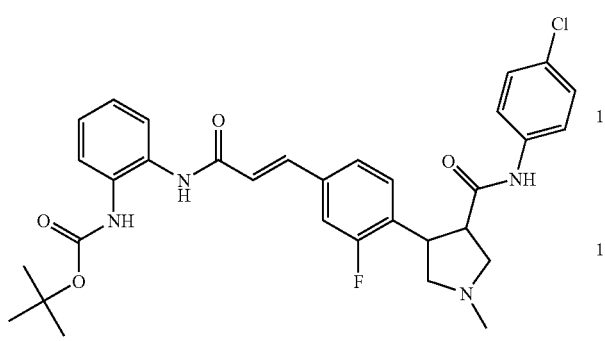

rac-[2-(3-{4-[(trans-3,4)-4-(4-Chloro-phenylcarbamoyl)-1-methyl-pyrrolidin-3-yl]-3-fluoro-phenyl}-acryloylamino)-phenyl]-carbamic acid tert-butyl ester A mixture of rac-(trans-3,4)-4-(4-bromo-2-fluoro-phenyl)-1-methyl-pyrrolidine-3-carboxylic acid (4-chloro-phenyl)-amide (7.0 g, 17.1 mmol), (2-acryloylamino-phenyl)-carbamic acid tert-butyl ester (4.7 g, 18 mmol), Pd$_2$(dba)$_3$ (1.25 g, 1.4 mmol), P(o-tolyl)$_3$ (0.83 g, 2.7 mmol) in DMF (80 mL) and TEA (12 mL, 85.5 mmol) was stirred at 100 degrees Celsius under N$_2$ in a sealed tube for 3 hours. The cooled mixture was partitioned between water and ethyl acetate. The organic phase was dried and concentrated. The residue was purified by chromatography on silica gel eluted by dichloromethane to give 7.0 g of [2-(3-{4-[4-(4-chloro-phenylcarbamoyl)-1-methyl-pyrrolidin-3-yl]-3-fluoro-phenyl}-acryloylamino)-phenyl]-carbamic acid tert-butyl ester, yield was 69%. MS: calc'd 593 (MH+), exp 593 (MH+).

Example 85

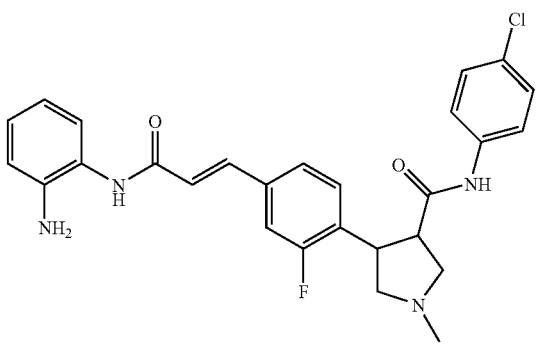

rac-(trans-3,4)-4-{4-[2-(2-Amino-phenylcarbamoyl)-vinyl]-2-fluoro-phenyl}-1-methyl-pyrrolidine-3-carboxylic acid (4-chloro-phenyl)-amide rac-[2-(3-{4-[(trans-3,4)-4-(4-Chloro-phenylcarbamoyl)-1-methyl-pyrrolidin-3-yl]-3-fluoro-phenyl}-acryloylamino)-phenyl]-carbamic acid tert-butyl ester (7.0 g, 11.8 mmol) was dissolved in 50 mL HCl/MeOH (1.25 M) and stirred at room temperature for 3 hrs. The reaction mixture was neutralized with NH$_3$/EtOH solution and purified by prep-HPLC to give 3.65 g of rac-(trans-3,4)-4-{4-[2-(2-amino-phenylcarbamoyl)-vinyl]-2-fluoro-phenyl}-1-methyl-pyrrolidine-3-carboxylic acid (4-chloro-phenyl)-amide with yield of 63%. MS: calc'd 493 (MH+), exp 493 (MH+). $^1$H NMR (d$_6$-DMSO, 400 MHz), 10.07 (s, 1H), 9.40 (s, 1H), 7.34-7.61 (m, 9H), 6.89-6.94 (m, 2H), 6.76 (d, 1H, J=8.0 Hz), 6.58 (t, 1H, J=7.6 Hz), 4.95 (s, 2H), 3.95 (q, 1H, J=7.2 Hz), 3.11-3.16 (m, 2H), 2.79-2.85 (m, 2H), 2.61 (t, 1H, J=7.2 Hz), 2.33 (s, 3H).

Compounds 85-2 through 85-9 described in the following tables were prepared by methods analogous to the synthetic methods described for previous examples (as indicated in Table 17) using analogous 2-fluoro-phenyl intermediates and other starting materials as indicated in Table 17.

TABLE 17

Structures, starting materials and method notes for Examples 85-2 to 85-9

| Example # | Structure | Starting Material(s) |
|---|---|---|
| 85-2 | ![structure] | 85-2a, commercially available; commercially available |

Method Notes: Synthesis of 85-2a proceeded analogously to that of Example 103 but starting with commercially available 4-bromo-2-fluoro-benzaldehyde and (carbethoxymethylene)-triphenylphosphorane to obtain 3-(4-bromo-2-fluoro-phenyl)-acrylic acid ethyl ester as described in Example 89. From 85-2a, 85-2 was obtained via synthetic methods analogous to Example 31.

TABLE 17-continued

Structures, starting materials and method notes for Examples 85-2 to 85-9

| Example # | Structure | Starting Material(s) |
|---|---|---|
| 85-3 | 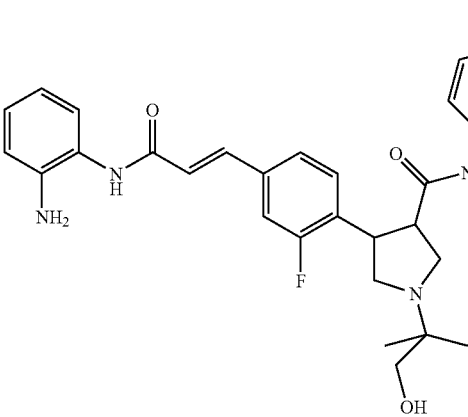 | 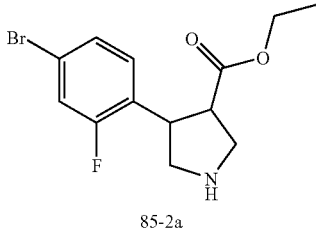 |

Method Notes: Synthesis of 85-2a proceeded as described for Example 85-2. From 85-2a, 85-3 was obtained via synthetic methods analogous to Example 26.

| 85-4 | 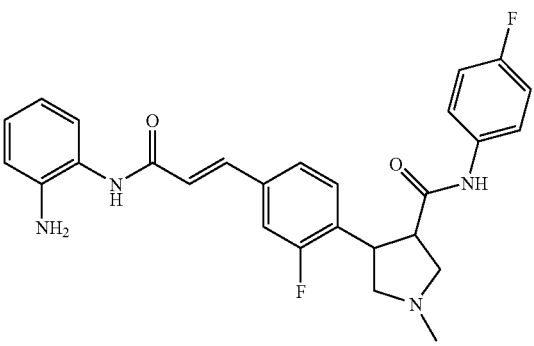 | Example 81, (2-acryloylamino-phenyl)-carbamic acid tert-butyl ester, 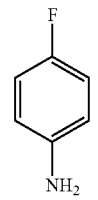 commercially available |

Method Notes: Analogous to Example 85

| 85-5 | 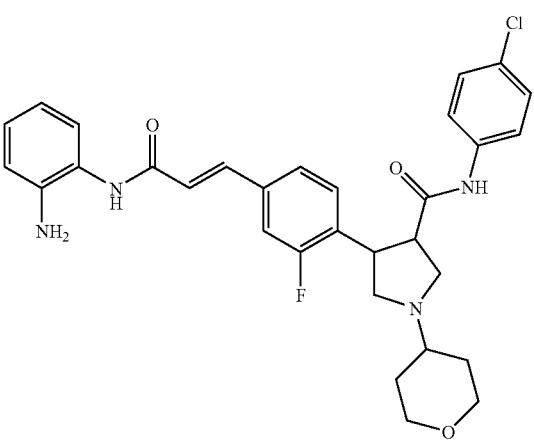 | 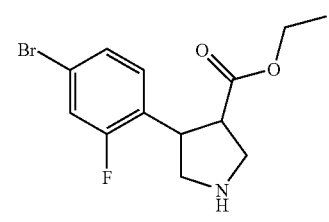 |

Method Notes: Synthesis of 85-2a proceeded as described for Example 85-2. From 85-2a, 85-5 was obtained via synthetic methods analogous to Example 16.

TABLE 17-continued

Structures, starting materials and method notes for Examples 85-2 to 85-9

| Example # | Structure | Starting Material(s) |
|---|---|---|
| 85-6 | 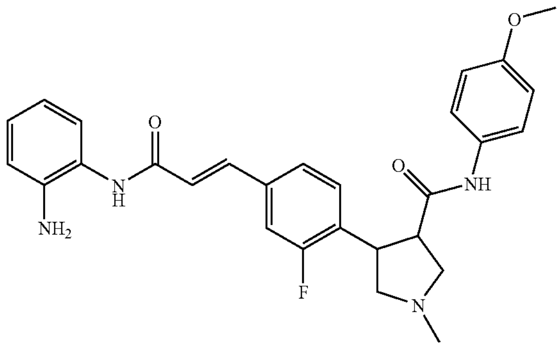 | Example 81, (2-acryloylamino-phenyl)-carbamic acid tert-butyl ester, 4-methoxyaniline commercially available |
| 85-7 | 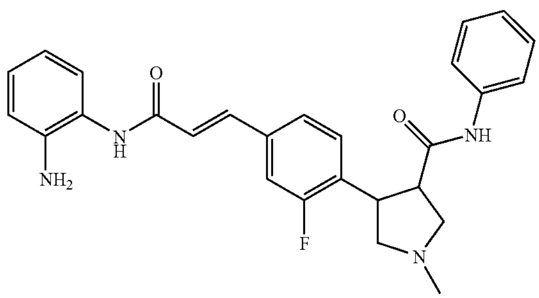 | Example 81, (2-acryloylamino-phenyl)-carbamic acid tert-butyl ester, aniline commercially available |
| 85-8 | 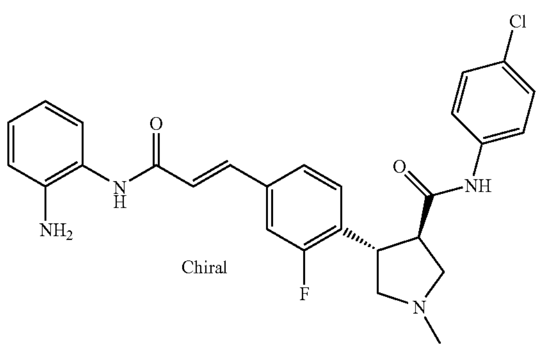 | Example 85 |
| 85-9 | 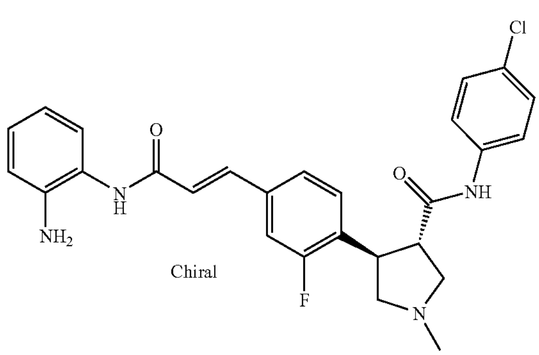 | Example 85 |

Method Notes for 85-6: Analogous to Example 85

Method Notes for 85-7: Analogous to Example 85

Method Notes for 85-8: Chiral separation

Method Notes for 85-9: Chiral separation

TABLE 18

MS and NMR data for examples 85-2 to 85-9

| Example # | MS and NMR data |
|---|---|
| 85-2 | $^1$H NMR (CD$_3$OD, 400 MHz), 7.51-7.62 (m, 4H), 7.40 (d, 1H, J = 8.0 Hz), 7.34 (d, 1H, J = 11.6 Hz), 7.27 (d, 2H, J = 8.8 Hz), 7.19 (d, 1H, J = 8.0 Hz), 7.04 (t, 1H, J = 7.2 Hz), 6.81-6.88 (m, 2H), 6.74 (t, 1H, J = 7.2 Hz), 3.98 (q, 1H, J = 7.2 Hz), 3.30 (m, 1H), 3.13-3.20 (m, 2H), 2.99-3.05 (m, 2H), 2.58 (q, 2H, J = 15.6 Hz), 1.25 (s, 6H)<br>MS: calc'd 551 (MH+), exp 551 (MH+) |
| 85-3 | $^1$H NMR (CD$_3$OD, 400 MHz), 7.52-7.64 (m, 4H), 7.42 (d, 1H, J = 8.4 Hz), 7.37 (d, 1H, J = 11.6 Hz), 7.28 (d, 2H, J = 8.8 Hz), 7.20 (d, 1H, J = 7.6 Hz), 7.05 (t, 1H, J = 6.8 Hz), 6.82-6.89 (m, 2H), 6.75 (t, 1H, J = 7.6 Hz), 3.93 (q, 1H, J = 8.0 Hz), 3.48 (s, 2H), 3.35 (m, 1H), 3.11-3.18 (m, 3H), 2.92 (broad m, 1H), 1.15 (s, 3H), 1.14 (s, 3H)<br>MS: calc'd 551 (MH+), exp 551 (MH+) |
| 85-4 | $^1$H NMR (d$_6$-DMSO, 400 MHz), 9.99 (s, 1H), 9.40 (s, 1H), 7.34-7.60 (m, 7H), 7.13 (t, 2H, J = 8.0 Hz), 6.77-6.94 (m, 2H), 6.76 (d, 1H, J = 7.6 Hz), 6.58 (t, 1H, J = 7.6 Hz), 4.95 (s, 2H), 3.95 (q, 1H, J = 6.8 Hz), 3.11-3.15 (m, 2H), 2.78-2.85 (m, 2H), 2.61 (m, 1H), 2.33 (s, 3H)<br>MS: calc'd 477 (MH+), exp 477 (MH+) |
| 85-5 | $^1$H NMR (CD$_3$OD, 400 MHz), 7.50-7.63 (m, 4H), 7.42 (d, 1H, J = 8.4 Hz), 7.36 (d, 1H, J = 11.6 Hz), 7.27 (d, 2H, J = 8.8 Hz), 7.19 (d, 1H, J = 7.6 Hz), 7.04 (t, 1H, J = 7.6 Hz), 6.82-6.88 (m, 2H), 6.74 (t, 1H, J = 7.2 Hz), 3.96-4.04 (m, 3H), 3.45 (t, 2H, J = 11.6 Hz), 3.15-3.27 (m, 3H), 2.96 (q, 2H, J = 8.0 Hz), 2.47 (m. 1H), 1.90 (d, 2H, J = 11.2 Hz), 1.59 (m, 2H)<br>MS: calc'd 563 (MH+), exp 563 (MH+) |
| 85-6 | $^1$H NMR (d$_6$-DMSO, 400 MHz), 9.79 (s, 1H), 9.41 (s, 1H), 7.34-7.56 (m, 7H), 6.75-6.94 (m, 4H), 6.75 (d, 1H, J = 8.0 Hz), 6.58 (t, 1H, J = 7.6 Hz), 4.95 (s, 2H), 3.94 (q, 1H, J = 6.4 Hz), 3.71 (s, 3H), 3.11 (m, 2H), 2.78-2.84 (m, 2H), 2.59 (m, 1H), 2.33 (s, 3H)<br>MS: calc'd 489 (MH+), exp 489 (MH+) |
| 85-7 | $^1$H NMR (d$_6$-DMSO, 400 MHz), 9.96 (s, 1H), 9.40 (s, 1H), 7.27-7.59 (m, 9H), 7.04 (t, 1H, J = 7.6 Hz), 6.91-6.94 (m, 2H), 6.76 (d, 1H, J = 8.0 Hz), 6.58 (t, 1H, J = 7.6 Hz), 4.95 (s, 2H), 3.98 (q, 1H, J = 6.8 Hz), 3.21 (m, 2H), 2.89-2.97 (m, 2H), 2.74 (m, 1H), 2.41 (s, 3H)<br>MS: calc'd 459 (MH+), exp 459 (MH+) |
| 85-8 | $^1$H NMR (d$_6$-DMSO, 400 MHz), 10.01 (s, 1H), 9.40 (s, 1H), 7.34-7.61 (m, 9H), 6.89-6.94 (m, 2H), 6.76 (d, 1H, J = 8.0 Hz), 6.58 (t, 1H, J = 7.6 Hz), 4.95 (s, 2H), 3.95 (q, 1H, J = 7.2 Hz), 3.11-3.16 (m, 2H), 2.79-2.85 (m, 2H), 2.61 (t, 1H, J = 7.2 Hz), 2.33 (s, 3H)<br>MS: calc'd 493 (MH+), exp 493 (MH+) |
| 85-9 | $^1$H NMR (d$_6$-DMSO, 400 MHz), 10.07 (s, 1H), 9.41 (s, 1H), 7.34-7.62 (m, 9H), 6.89-6.94 (m, 2H), 6.76 (d, 1H, J = 8.0 Hz), 6.58 (t, 1H, J = 7.6 Hz), 4.95 (s, 2H), 3.95 (q, 1H, J = 6.8 Hz), 3.11-3.16 (m, 2H), 2.79-2.85 (m, 2H), 2.59 (t, 1H, J = 7.2 Hz), 2.33 (s, 3H)<br>MS: calc'd 493 (MH+), exp 493 (MH+) |

Example 86

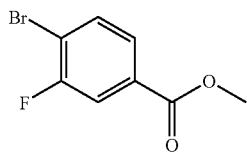

4-Bromo-3-fluoro-benzoic acid methyl ester

To a solution of 4-bromo-3-fluoro-benzoic acid (5.0 g, 22.9 mmol) in MeOH (60 mL) was added thionyl chloride (10 mL), This mixture was heated for about 5 h at 80 degrees Celsius until the starting material had been consumed, and then evaporated in vacuo to give white solid product (5.3 g, 100%).

Example 87

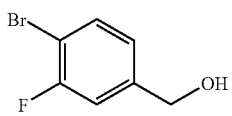

(4-Bromo-3-fluoro-phenyl)-methanol

To a solution of 4-bromo-3-fluoro-benzoic acid methyl ester (5.3 g, 22.9 mmol) in dry THF (60 mL) was added diisobutylaluminum hydride (30 mL) dropwise, This mixture was stirred overnight at room temperature until the starting material had been consumed, quenched with saturated aqueous potassium tartrate solution and extracted with ethyl acetate (3×50 mL). The combined organic layer was washed with brine, dried with Na$_2$SO$_4$, filtered, and evaporated to give white solid product (4.3 g, 92%).

Example 88

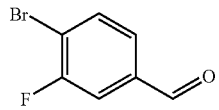

4-Bromo-3-fluoro-benzaldehyde

To a solution of (4-bromo-3-fluoro-phenyl)-methanol (4.3 g, 21 mmol) in CHCl$_3$ (50 mL) was added manganese dioxide (18.7 g, 210 mmol), and the resulting mixture was stirred overnight at room temperature until the starting material had been consumed. After filtration, the filtrate was concentrated in vacuo to give product (2.3 g, 55%).

Example 89

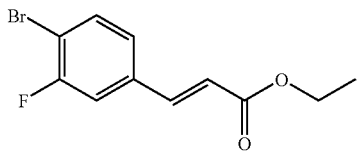

3-(4-Bromo-3-fluoro-phenyl)-acrylic acid ethyl ester

To a solution of (carbethoxymethylene)-triphenylphosphorane (4.2 g, 12 mmol) in CH$_2$Cl$_2$ at 10 degrees Celsius was added 4-bromo-3-fluoro-benzaldehyde (2.3 g, 11.4 mmol) dropwise over 30 minutes. This mixture was stirred for another 45 minutes at room temperature until the starting material had been consumed, and then the solvent was removed in vacuo. The crude product was purified by column chromatography (PET:EtOAc=1:1) to get desired product (2.69 g, 87%).

Example 90

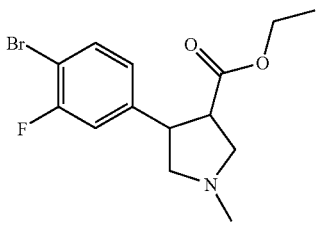

rac-(trans-3,4)-4-(4-Bromo-3-fluoro-phenyl)-1-methyl-pyrrolidine-3-carboxylic acid ethyl ester A mixture of 4-(4-bromo-3-fluoro-phenyl)-acrylic acid ethyl ester (2.69 g, 10.4 mmol), sarcosine (1.424 g, 20 mmol) and paraformaldehyde (3 g, 100 mmol) and 3 Angstrom molecular sieves in dry toluene under Ar was refluxed for 4 h with the aid of a Dean-Stark trap to remove water. Then the mixture was cooled and filtered. The solid was washed with ethyl acetate. The combined filtrate was concentrated in vacuo, and the residue was purified by flash chromatography over silica gel to afford the desired product (1.3 g, 40%).

Example 91

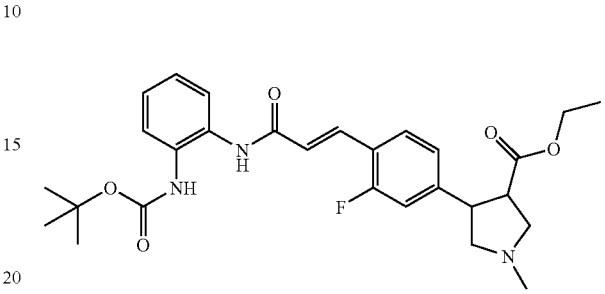

rac-(trans-3,4)-4-{4-[2-(2-tert-Butoxycarbonylamino-phenylcarbamoyl)-vinyl]-3-fluoro-phenyl}-1-methyl-pyrrolidine-3-carboxylic acid ethyl ester To a solution of rac-(trans-3,4)-4-(4-bromo-3-fluoro-phenyl)-1-methyl-pyrrolidine-3-carboxylic acid ethyl ester (1.3 g, 4 mmol), Pd$_2$(dba)$_3$ (183 mg, 0.2 mmol), tri-(o-tolyl)phosphine (72.8 mg, 0.2 mmol) and Et$_3$N (2 mL) in DMF (15 mL) was added (2-acryloylamino-phenyl)-carbamic acid tert-butyl ester (1.07 g, 4.1 mmol). This mixture was stirred at 100 degrees Celsius for 4 h until the starting material had been consumed, cooled, and filtered. The solution was poured into water (30 mL), extracted with ethyl acetate (3×30 mL), The combined organic layer was washed with brine, dried with Na$_2$SO$_4$, filtered, and evaporated. The crude product was purified by column chromatography (PET:EtOAc=1:1) to get yellow solid product (1.33 g, 67%). MS: calc'd 512 (MH+), exp 512 (MH+).

Example 92

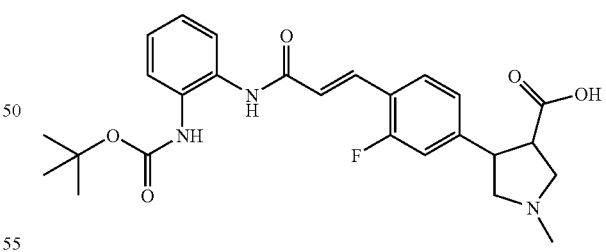

rac-(trans-3,4)-4-{4-[2-(2-tert-Butoxycarbonylamino-phenylcarbamoyl)-vinyl]-3-fluoro-phenyl}-1-methyl-pyrrolidine-3-carboxylic acid To a solution of rac-(trans-3,4)-4-{4-[2-(2-tert-butoxycarbonylamino-phenylcarbamoyl)-vinyl]-phenyl}-1-methyl-pyrrolidine-3-carboxylic acid ethyl ester (1.3 g, 2.68 mmol) in MeOH/H$_2$O (10 mL/10 mL) was added lithium hydroxide monohydrate (504 mg, 12.0 mmol). This mixture was stirred at room temperature overnight and then evaporated to remove most of the MeOH. The mixture was extracted with ethyl acetate (3×30 mL). The combined organic layer was washed with brine, dried with Na₂SO₄, filtered, and evaporated to get yellow solid product (1.2 g, 93%). MS: calc'd 484 (MH+), exp 484 (MH+).

Example 93

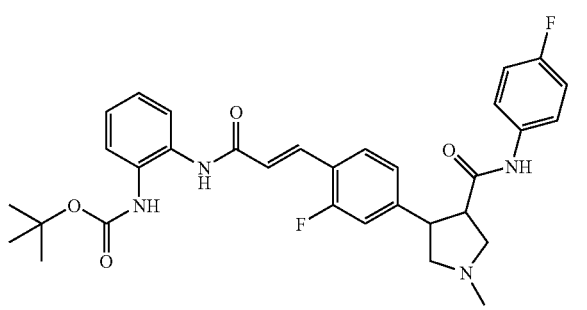

rac-[2-(3-{2-fluoro-[(trans-3,4)-4-(4-Fluoro-phenyl-carbamoyl)-1-methyl-pyrrolidin-3-yl]-phenyl}-acryloylamino)-phenyl]-carbamic acid tent-butyl ester To a solution of 4-{4-[2-(2-tert-butoxycarbonylamino-phenylcarbamoyl)-vinyl]-3-fluoro-phenyl}-1-methyl-pyrrolidine-3-carboxylic acid (300 mg, 0.52 mmol), HATU (217.7 mg, 0.572 mmol) and Et₃N (115.4 mg, 1.143 mmol) in DMF (10 mL) was added 4-fluoroaniline (63.4 mg, 0.572 mmol). The reaction mixture was stirred for 1 h at room temperature, diluted with dichloromethane (10 mL). The organic solution was washed with water (10 mL) and brine (10 mL), dried with Na₂SO₄, filtered, and evaporated in vacuo to obtain light yellow residue which was used in the next step without further purification.

Example 94

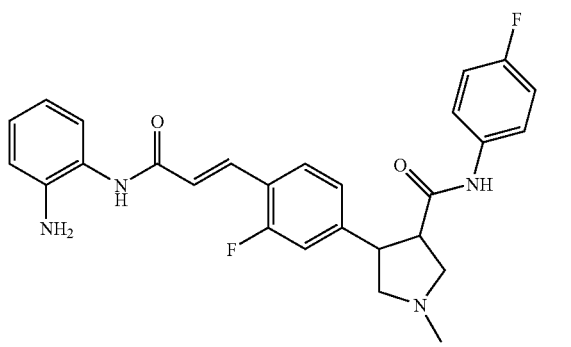

rac-(trans-3,4)-4-{4-[2-(2-Amino-phenylcarbamoyl)-vinyl]-3-fluoro-phenyl}-1-methyl-pyrrolidine-3-carboxylic acid (4-fluoro-phenyl)-amide Hydrochloric acid in methanol (1.25 M, 5 mL) was added to the rac-[2-(3-{4-[(trans-3,4)-4-(4-fluoro-phenylcarbamoyl)-1-methyl-pyrrolidin-3-yl]-phenyl}-acryloylamino)-phenyl]-carbamic acid tent-butyl ester residue, the resulted mixture was stirred for 3 h, and then NaHCO₃ was added to the reaction mixture. After filtration of solid, the crude mixture was purified by preparative HPLC to obtain light yellow solid. MS: calc'd (MH+) 477, exp (MH+) 477. ¹H NMR (d₆-DMSO, 400 MHz), 10.00 (s, 1H), 9.49 (s, 1H), 7.66-7.55 (m, 4H), 7.34-7.11 (m, 5H), 6.99-6.91 (m, 2H), 6.75 (d, 1H, J=7.6 Hz), 6.58 (t, 1H, J=7.6 Hz), 4.95 (s, 2H), 3.74 (m, 1H), 3.15-3.10 (m, 2H), 2.89 (m, 1H), 2.81 (m, 1H), 2.64 (m, 1H), 2.35 (s, 3H).

The following example was prepared by a method analogous to the synthetic method described above for Example 94, using Example 92 and 4-chloro-aniline (commercially available) as starting materials.

Example 94-2

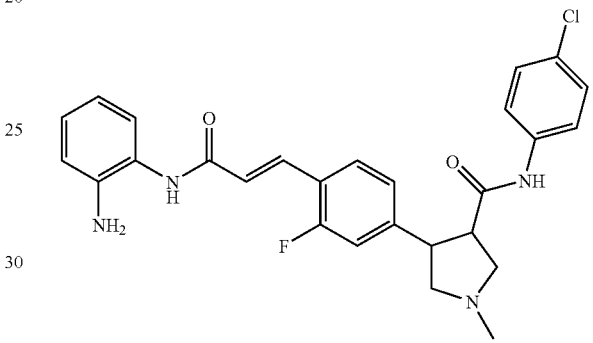

| Example # | MS and NMR data |
|---|---|
| 94-2 | ¹H NMR (d₆-DMSO, 400 MHz), 10.08 (s, 1H), 9.49 (s, 1H), 7.66-7.55 (m, 4H), 7.36-7.21 (m, 5H), 6.90-6.74 (m, 2H), 6.72 (d, 1H, J = 8.0 Hz), 6.58 (t, 1H, J = 7.6 Hz), 4.95 (s, 2H), 3.74 (m, 1H), 3.17-3.10 (m, 2H), 2.91-2.78 (m, 2H), 2.64 (m, 1H), 2.53 (s, 3H). MS: calc'd (MH+) 493, exp (MH+) 493. |

Example 95

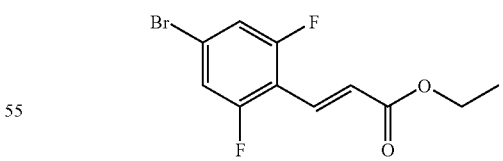

3-(4-Bromo-2,6-difluoro-phenyl)-acrylic acid ethyl ester

A mixture of 4-bromo-2,6-difluoro-benzaldehyde (1 g, 4.5 mmol), (carbethoxymethylene)-triphenyl-phosphorane (2 g, 5.7 mmol) in 30 mL of toluene was heated at reflux for 6 hours, and was evaporated to dryness. The solid was stirred in 200 mL of petroleum ether, and was filtered. The filtrate was evaporated to give the product as oil (1.2 g, yield 91%).

Example 96

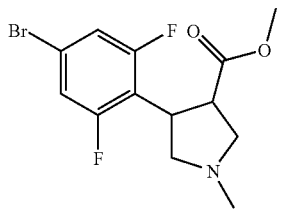

rac-(trans-3,4)-4-(4-Bromo-2,6-difluoro-phenyl)-1-methyl-pyrrolidine-3-carboxylic acid ethyl ester A mixture of sarcosine (1.3 g, 14.6 mmol), paraformaldehyde (3 g, 100 mmol), and 3-(4-bromo-2,6-difluoro-phenyl)-acrylic acid ethyl ester (1.2 g, 4.1 mmol) in toluene (50 mL) was heated under reflux, and the H₂O formed was removed with the aid of a Dean-Stark trap. After 6 hour, the cooled mixture was filtered. The filtrate was concentrated, and the residue was purified by chromatography on silica gel eluted with hexane-EtOAc to give 1.2 g of product (yield was 85%).

Example 97

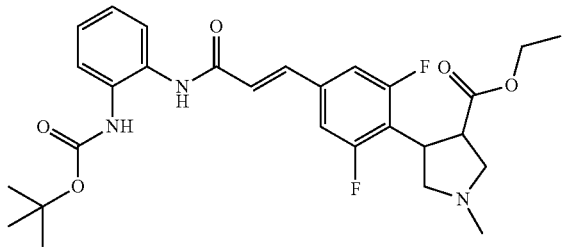

rac-(trans-3,4)-4-{4-[2-(2-tert-Butoxycarbonylamino-phenylcarbamoyl)-vinyl]-2,6-difluoro-phenyl}-1-methyl-pyrrolidine-3-carboxylic acid methyl ester A mixture of rac-(trans-3,4)-4-(4-bromo-2,6-difluoro-phenyl)-1-methyl-pyrrolidine-3-carboxylic acid ethyl ester (1.2 g, 3.5 mmol), (2-acryloylamino-phenyl)-carbamic acid tent-butyl ester (1 g, 3.8 mmol), Pd₂(dba)₃ (100 mg, 0.01 mmol), P(o-tolyl)₃ (100 mg, 0.33 mmol) in DMF (15 mL) and TEA (2 mL, 66 mmol) was stirred at 110 degrees Celsius under N₂ in a sealed tube overnight. LC-MS indicated that the reaction was completed. The cooled mixture was partitioned between water and ethyl acetate. The organic phase was dried and concentrated. The residue was purified by chromatography on silica gel eluted by dichloromethane to give 1.3 g of product (yield was 72%). MS: calc'd (MH+) 530, exp (MH+) 530.

Example 98

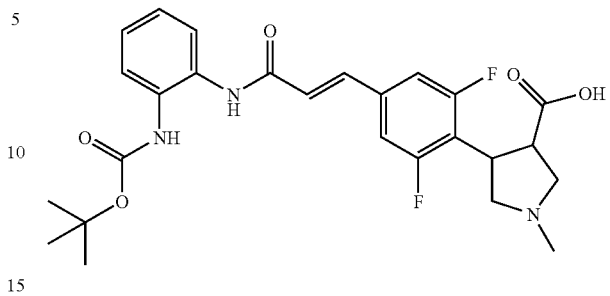

rac-(trans-3,4)-4-{4-[2-(2-tert-Butoxycarbonylamino-phenylcarbamoyl)-vinyl]-2,6-difluoro-phenyl}-1-methyl-pyrrolidine-3-carboxylic acid Lithium hydroxide monohydrate (0.84 g, 20 mmol) in water (20 mL) was added to a solution of rac-(trans-3,4)-4-{4-[2-(2-tert-butoxycarbonylamino-phenylcarbamoyl)-vinyl]-2,6-difluoro-phenyl}-1-methyl-pyrrolidine-3-carboxylic acid methyl ester (1.3 g, 2.45 mmol) in THF (20 mL), and the mixture was stirred at room temperature overnight. LC-MS indicated that the starting material was consumed. The mixture was adjusted to pH=6-8 with 6 N HCl. The solvent was removed to give crude product which was used in the next step without further purification.

Example 99

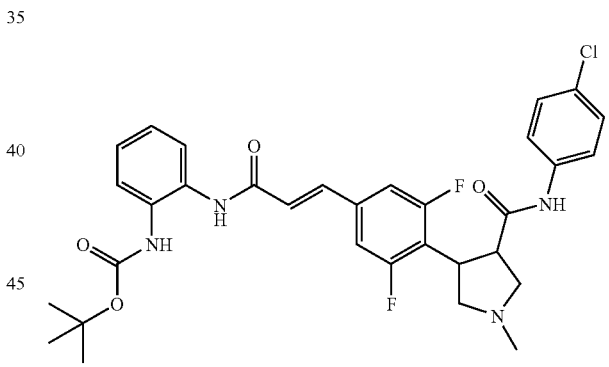

rac-[2-(3-{4-[(trans-3,4)-4-(4-Chloro-phenylcarbamoyl)-1-methyl-pyrrolidin-3-yl]-3,5-difluoro-phenyl}-acryloylamino)-phenyl]-carbamic acid tent-butyl ester HATU (13.3 g, 1.2 mmol) was added to a solution of rac-(trans-3,4)-4-{4-[2-(2-tert-butoxycarbonylamino-phenylcarbamoyl)-vinyl]-2,6-difluoro-phenyl}-1-methyl-pyrrolidine-3-carboxylic acid (crude material, 0.6 mmol) and 4-chloroaniline (0.2 g, 1.6 mmol) in TEA (0.3 mL) and dichloromethane (20 mL) at rt, and the mixture was stirred at rt for 3 hour. LC-MS indicated that the reaction was completed. The mixture was partitioned between water and dichloromethane. The organic phase was dried and concentrated. The residue was purified by chromatography on silica gel to give 200 mg of product (yield 54%). MS: calc'd (MH+) 611, exp (MH+) 611.

Example 100

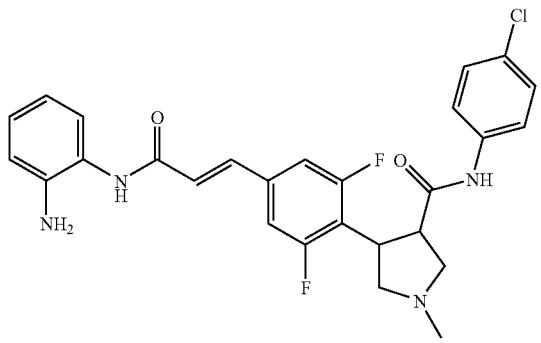

rac-(trans-3,4)-4-{4-[2-(2-Amino-phenylcarbamoyl)-vinyl]-2,6-difluoro-phenyl}-1-methyl-pyrrolidine-3-carboxylic acid (4-chloro-phenyl)-amide A solution of rac-[2-(3-{4-[(trans-3,4)-4-(4-chloro-phenylcarbamoyl)-1-methyl-pyrrolidin-3-yl]-3,5-difluoro-phenyl}-acryloylamino)-phenyl]-carbamic acid tent-butyl ester (200 mg, 0.32 mmol) in MeOH (1.25 M HCl, 10 mL) was stirred for 4 hours. LC-MS indicated that the reaction was completed. The solvent was removed and the residue was neutralized with TEA and purified by prep-HPLC to give 32 mg of product. MS: calc'd (MH+) 511, exp (MH+) 511. $^1$H NMR (CD$_3$OD, 400 MHz), 7.57 (d, 1H, J=15.6 Hz), 7.50 (d, 2H, J=8.4 Hz), 7.26 (d, 4H, J=8.4 Hz), 7.20 (d, 1H, J=7.6 Hz), 7.06 (t, 1H, J=7.2 Hz), 6.87 (m, 2H), 6.75 (t, 1H, J=7.2 Hz), 4.28 (m, 1H), 3.5-3.0 (m, 3H), 2.91 (m, 2H), 2.46 (s, 3H).

Example 101

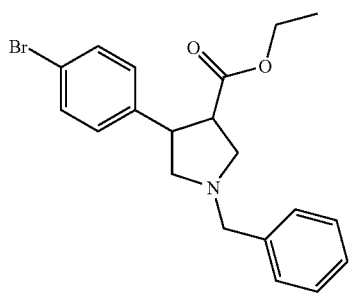

rac-(trans-3,4)-1-Benzyl-4-(4-bromo-phenyl)-pyrrolidine-3-carboxylic acid ethyl ester To a mixture of ethyl trans-4-bromo-cinnamate (0.95 g, 3.73 mmol) and N-(methoxymethyl) N-(trimethylsilylmethyl)benzylamine (1.06 g, 4.48 mmol) in dichloromethane (10 mL) was added orthoboric acid (23 mg, 0.37 mmol), and the mixture was stirred at room temperature for 2 days and heated at 45 degrees Celsius for two hours. The resulting mixture was concentrated in vacuo, and the crude product was purified by flash chromatography (PET:EtOAc=10:1) to get product as colorless oil (1.08 g, 71%). MS: calc'd 388 (MH+), exp 388 (MH+).

Example 102

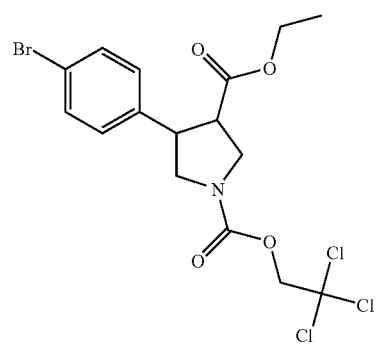

rac-(trans-3,4)-4-(4-Bromo-phenyl)-pyrrolidine-1,3-dicarboxylic acid 3-ethyl ester 1-(2,2,2-trichloro-ethyl)ester To a solution of rac-(trans-3,4)-1-benzyl-4-(4-bromo-phenyl) -pyrrolidine-3-carboxylic acid ethyl ester (3.97 g, 10.2 mmol) in acetonitrile (40 mL) was added K$_2$CO$_3$ (2.25 g, 16.3 mmol) and followed by 2,2,2-trichloroethyl chloroformate (3.03 g, 14.3 mmol), and the mixture was heated at 60 degrees Celsius for three hours. The mixture was diluted with ethyl acetate and filtered. The filtrate was concentrated in vacuo, and the crude product was purified by flash chromatography (Pet:EtOAc=10:1) to get product as colorless oil (3.2 g, 66.2%). MS: calc'd 472 (MH+), exp 472 (MH+).

Example 103

rac-(trans-3,4)-4-(4-Bromo-phenyl)-pyrrolidine-3-carboxylic acid ethyl ester

To a solution of rac-(trans-3,4)-4-(4-bromo-phenyl)-pyrrolidine-1,3-dicarboxylic acid 3-ethyl ester 1-(2,2,2-trichloro-ethyl)ester (3.2 g, 6.76 mmol) in acetic acid (15 mL) was added Zn (1.28 g, 19.6 mmol) under Ar, and the mixture was stirred for 3 h at room temperature. The resulting mixture was diluted with dichloromethane and filtered. The filtrate was concentrated in vacuo. The crude product (2.5 g) was obtained and used directly without further purification. MS: calc'd 298 (MH+), exp (MH+) 298.

Example 104

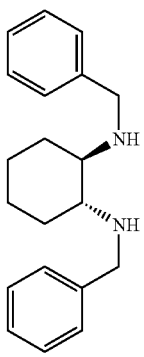

(R,R)-N,N'-Dibenzyl-cyclohexane-1,2-diamine

Benzaldehyde (12.72 g, 120 mmol) was added dropwise over a period of 2 minutes to a solution of (R,R)-cyclohexane-1,2-diamine (6.84 g, 60 mmol) in 100 mL of anhydrous MeOH at refluxing temperature. After stirring for 30 min, the solution was allowed to cool to room temperature and NaBH$_3$CN (4.8 g, 126 mmol) was added in portions. After the vigorous effervescence subsided down, the mixture was brought to refluxing and stirred for 20 min. The reaction was quenched by water and extracted with dichloromethane. The organic phase was dried and concentrated to give 16.95 g of crude product (yield 96%) which was used in the next step reaction without further purification.

Example 105

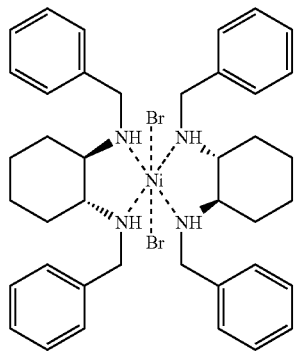

Ni(II)-bis[(R,R)-N,N'-dibenzylcyclohexane-1,2-diamine]Br$_2$

A mixture of 4.36 g (20 mmol) of NiBr$_2$ and 12.64 g (43 mmol) of (R,R)-N,N'-debenzylcyclohexane-1,2-diamine in 500 mL of acetonitrile were heated under reflux for 5 hrs. After removal of solvent, the residue was dissolved in dichloromethane and filtered through a fritted glass funnel. The solvent was evaporated off and the crude product was recrystallized from dichloromethane/acetonitrile to yield the title compound as a microcrystalline pale blue powder 10.5 g (yield 80%).

Example 106

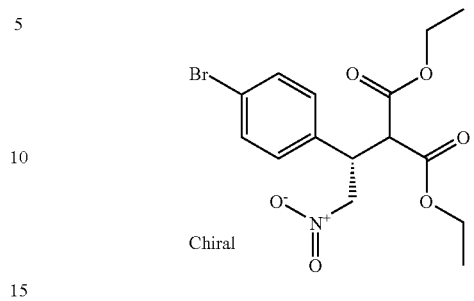

S-2-[1-(4-Bromo-phenyl)-2-nitro-ethyl]-malonic acid diethyl ester

A mixture of 4-bromo-benzaldehyde (55.5 g, 300 mmol), nitromethane (100 mL) and ammonium acetate (2.31 g, 30 mmol) in 150 mL of acetic acid was stirred at 100 degrees Celsius for 3 hrs. After 4-bromo-benzaldehyde was fully consumed by TLC check, the mixture was partitioned between water and ethyl acetate. The organic phase was washed with saturated sodium carbonate, dried and concentrated. The residue was recrystallized with acetonitrile/dichloromethane to get 52 g of product (yield 76%).

230 mL of toluene was added into a flask loaded with Ni(II)-bis[(R,R)-N,N'-dibenzylcyclohexane-1,2-diamine] Br$_2$ (3.61 g, 4.52 mmol), malonic acid diethyl ester (41.2 mL, 272 mmol), and 1-bromo-4-(2-nitro-propenyl)-benzene (51.64 g, 226 mmol), and the mixture was stirred at room temperature overnight. When the reaction was complete by TLC monitoring, the mixture was concentrated in vacuo. Recrystallization of crude product from petroleum ether/ethyl acetate gave 75 g of product (yield was 86%, >99% ee). MS: calc'd 388 (MH+), exp 388 (MH+).

Example 107

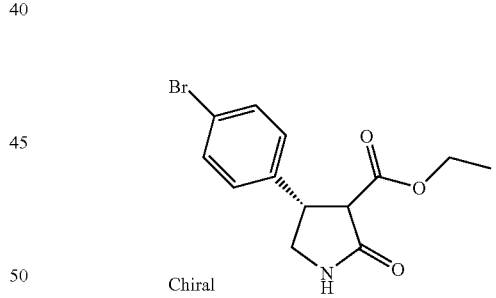

(4S)-4-(4-Bromo-phenyl)-2-oxo-pyrrolidine-3-carboxylic acid ethyl ester

A solution of S-2-[1-(4-Bromo-phenyl)-2-nitro-ethyl]-malonic acid diethyl ester (19.4 g, 50 mmol) in 50 ml, of methanol was added dropwise to a mixture of concentrated HCl (37%, 100 mL) and methanol (100 mL), and Zn powder was also added simultaneously in small portions, over a period of 30 minutes. After addition, the mixture was stirred at room temperature for 20 minutes. LC-MS indicated that the starting material was consumed. After removal of methanol in vacuo, the residue was extracted with ethyl acetate. The combined organic phase was treated with saturated sodium carbonate. After zinc salt was filtered off, the organic phase was separated, dried and concentrated. The crude product was purified through silica gel column to give 13 g of product (yield 83%). MS: calc'd 312 (MH+), exp 312 (MH+).

Example 108

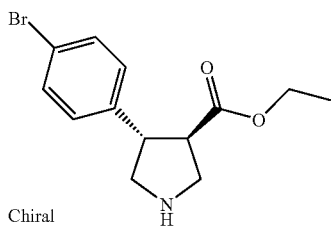

(3R,4S)-4-(4-Bromo-phenyl)-pyrrolidine-3-carboxylic acid ethyl ester

A solution of S-4-(4-bromo-phenyl)-2-oxo-pyrrolidine-3-carboxylic acid ethyl ester (12 g, 38.5 mmol) and trimethyloxonium tetrafluoroborate (6.83 g, 46.1 mmol) in 100 mL of anhydrous dichloromethane was stirred at room temperature overnight. The mixture was concentrated and the residue was dissolved in 100 mL of methanol. NaBH$_3$CN (3.4 g, 54 mmol) and 10 mg of bromocresol green were added to the solution. A solution of HCl in methanol (1.2 M) was added into the solution to keep the color yellow. The resulting mixture was stirred at room temperature for 4 hours before poured into saturated sodium carbonate and dichloromethane. The aqueous layer was extracted with dichloromethane. The combined organic phases were dried over sodium sulfate, and concentrated to give the crude product, which was purified by flash chromatography to give 7.2 g of product (yield 63%, trans/cis>9:1). MS: calc'd 298 (MH+), exp 298 (MH+). $^1$H NMR (CD$_3$OD, 400 MHz), 7.45 (d, 2H, J=8.4 Hz), 7.21 (d, 2H, J=8.4 Hz), 4.09 (t, 2H, J=7.2 Hz), 3.47-3.33 (m, 3H), 3.26-3.21 (m, 1H), 3.09-3.05 (m, 1H), 2.89-2.84 (m, 1H), 1.16 (t, 3H, J=7.2 Hz)

Example 109

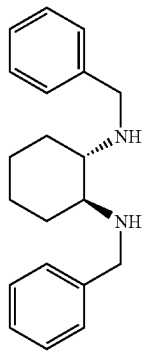

(S,S)-N,N'-Dibenzyl-cyclohexane-1,2-diamine

Benzaldehyde (6.36 g, 60 mmol) was added dropwise over a period of 2 minutes to a solution of (S,S)-cyclohexane-1,2-diamine (3.42 g, 30 mmol) in 50 mL of anhydrous MeOH at refluxing temperature. After stirring for 30 min, the solution was allowed to cool to room temperature and NaBH$_3$CN (2.4 g, 63 mmol) was added in portions. After the vigorous effervescence subsided down, the mixture was brought to refluxing and stirred for 20 min. The reaction was quenched by water and extracted with dichloromethane. The organic phase was dried and concentrated to give 8.5 g of crude product (yield 95%) which was used in the next step reaction without further purification.

Example 110

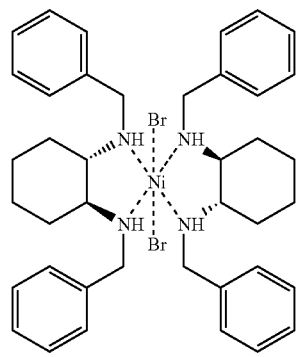

Ni(II)-bis[(S,S)-N,N'-dibenzylcyclohexane-1,2-diamine]Br$_2$

A mixture of 2.18 g (10 mmol) of NiBr$_2$ and 6.32 g (21.5 mmol) of (S,S)-N,N'-debenzylcyclohexane-1,2-diamine in 250 mL of acetonitrile were heated under reflux for 5 hrs. After removal of solvent, the residue was dissolved in dichloromethane and filtered through a fritted glass funnel. The solvent was evaporated off and the crude product was recrystallized from dichloromethane/acetonitrile to yield the title compound as a microcrystalline pale blue powder 5.3 g (yield 80%).

Example 111

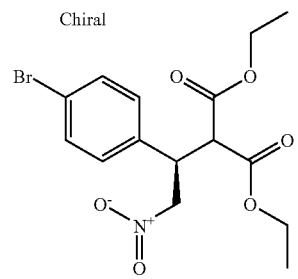

R-2-[1-(4-Bromo-phenyl)-2-nitro-ethyl]-malonic acid diethyl ester

A mixture of 4-bromo-benzaldehyde (55.5 g, 300 mmol), nitromethane (100 mL) and ammonium acetate (2.31 g, 30 mmol) in 150 mL of acetic acid was stirred at 100 degrees Celsius for three hours. After 4-bromo-benzaldehyde was fully consumed by TLC check, the mixture was partitioned between water and ethyl acetate. The organic phase was washed with saturated sodium carbonate, dried and concentrated. The residue was recrystallized with acetonitrile/dichloromethane to get 52 g of product (yield 76%).

230 ml, of toluene was added into a flask loaded with Ni(II)-bis[(S,S)-N,N'-dibenzylcyclohexane-1,2-diamine]Br$_2$ (3.61 g, 4.52 mmol), malonic acid diethyl ester (41.2 mL, 272 mmol), and 1-bromo-4-(2-nitro-propenyl)-benzene (51.64 g, 226 mmol), and the mixture was stirred at room temperature overnight. When the reaction was complete by TLC monitoring, the mixture was concentrated in vacuo. Recrystallization of crude product from petroleum ether/ethyl acetate gave 71.5 g of product (yield was 82%, >99% ee). MS: calc'd 388 (MH+), exp 388 (MH+).

Example 112

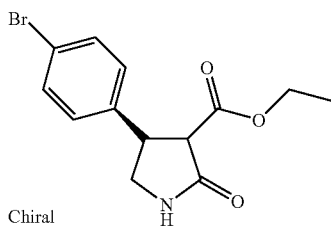

(4R)-4-(4-Bromo-phenyl)-2-oxo-pyrrolidine-3-carboxylic acid ethyl ester

A solution of R-2-[1-(4-bromo-phenyl)-2-nitro-ethyl]-malonic acid diethyl ester (19.4 g, 50 mmol) in 50 mL of methanol was added dropwise to a mixture of concentrated HCl (37%, 100 mL) and methanol (100 mL), and Zn powder was also added simultaneously in small portions, over a period of 30 minutes. After addition, the mixture was stirred at room temperature for 20 minutes. LC-MS indicated that the starting material was consumed. After removal of methanol in vacuo, the residue was extracted with ethyl acetate. The combined organic phase was treated with saturated sodium carbonate. After zinc salt was filtered off, the organic phase was separated, dried and concentrated. The crude product was purified through silica gel column to give 12.7 g of product (yield 81%). MS: calc'd 312 (MH+), exp 312 (MH+).

Example 113

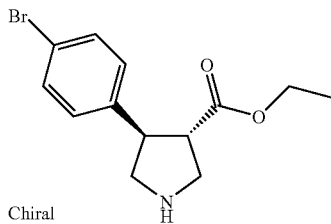

(3S,4R)-4-(4-Bromo-phenyl)-pyrrolidine-3-carboxylic acid ethyl ester

A solution of R-4-(4-bromo-phenyl)-2-oxo-pyrrolidine-3-carboxylic acid ethyl ester (12 g, 38.5 mmol) and trimethyloxonium tetrafluoroborate (6.83 g, 46.1 mmol) in 100 mL of anhydrous dichloromethane was stirred at room temperature overnight. The mixture was concentrated and the residue was dissolved in 100 mL of methanol. NaBH$_3$CN (3.4 g, 54 mmol) and 10 mg of bromocresol green were added to the solution. A solution of HCl in methanol (1.2M) was added into the solution to keep the color yellow. The resulting mixture was stirred at room temperature for 4 hours before poured into saturated sodium carbonate and dichloromethane. The aqueous layer was extracted with dichloromethane. The combined organic phases were dried over sodium sulfate, and concentrated to give crude product which was purified by flash chromatography to give 7.4 g of product (yield 65%, trans/cis>9:1). MS: calc'd 298 (MH+), exp (MH+) 298. $^1$H NMR (CD$_3$OD, 400 MHz), 7.45 (d, 2H, J=8.4 Hz), 7.21 (d, 2H, J=8.4 Hz), 4.09 (t, 2H, J=7.2 Hz), 3.47-3.33 (m, 3H), 3.26-3.21 (m, 1H), 3.09-3.05 (m, 1H), 2.89-2.84 (m, 1H), 1.16 (t, 3H, J=7.2 Hz).

The compounds of formula I and their pharmaceutically acceptable salts have valuable pharmacological properties. Specifically, these compounds are inhibitors of histone deacetylase (HDAC). The pharmacological properties of the compounds of this invention were confirmed by the following exemplified standard assays.

Example 114

HDAC Inhibition by Novel Compounds: HeLa Extract HDAC Fluorometric Assay

Novel compounds were tested for their ability to inhibit histone deacetylase using an in vitro deacetylation assay. The enzyme source for this assay was HeLa nuclear extract. The substrate consisted of a commercial product containing an acetylated lysine side chain (both HeLa extract and substrate are available commercially from BIOMOL Research Laboratories, Inc., Plymouth Meeting, Pa.). After deacetylation of the substrate by incubation with HeLa nuclear extract, subsequent exposure to a developing reagent produces a fluorophore that is directly proportional to the level of deacetylation. Using the substrate concentration at the K$_m$ for the HeLa nuclear extract, the deacetylation assay was performed in the presence of novel compounds at 30 micromolar and the percent enzyme inhibition relative to a known reference HDAC inhibitor (SNDX-275) was determined. The compounds of the instant invention described in the Examples and Tables above exhibit histone deacetylase inhibitory activity in the range of about 75% to 190% relative to the known reference compound. Inhibitory activity for specific representative compounds can be found in Table 19.

Example 115 p21 Reporter Gene Induction by Novel Compounds

The novel compounds of the present invention were tested for their ability to induce p21 gene expression using a reporter gene assay involving HeLa cells transfected with a p21 promoter-luciferase construct. The p21 promoter contained the Sp1/Sp3 binding site for HDAC but not the upstream p53 binding site. Briefly, the day before transfection, HeLa cells were seeded at 11,000 cells/well in a 96-well culture plate and incubated at 37 degrees Celsius in 5% CO$_2$ overnight. For transfection, the medium was removed and replaced with 100 microliters/well transfection media previously prepared as follows: 5 microliters serum-free DMEM, 0.15 microliters Fugene 6 reagent, 40 ng p21-luc, 10 ng GFP were mixed gently and incubated at room temperature for 30 minutes; then 98 microliters DMEM (with 10% FBS, 1% penicillin and streptomycin) was added to the DNA:Fugene 6 reagent complex and mixed gently. After incubating the cells for 24 hours at 37 degrees Celsius in 5% $CO_2$, fresh media and test compounds were added to the wells and the cells further incubated for 15 hours at 37 degrees Celsius in 5% $CO_2$. Cells were lysed by adding 80 microliters/well of a cell culture lysis reagent (Promega). 50 microliters of each lysate was taken for GFP detection using an excitation wavelength of 486 nm and detection at 527 nm. 100 microliters Luciferase assay reagent (Promega) was then added to every 20 microliters cell lysate for luminometer detection. The compounds of the instant invention described in the Examples and Tables above exhibit p21 induction activity in the range of about 25% to 300% relative to the known HDAC inhibitor (SNDX-275) at a concentration of 3 micromolar. Induction activity for specific representative compounds can be found in Table 19.

Example 116

Antiproliferative Activity Against Cancer Cell Lines by Novel Compounds

The novel compounds of the present invention were tested for their ability to inhibit growth of various cancer cell lines using in vitro growth inhibition assays described below.
MTS Assay
Cells were seeded in 96-well culture plates (200 microliters/well at different seeding concentrations depending on cell type) and incubated overnight at 37 degrees Celsius in 5% $CO_2$. After adding compound dilutions to the cells (DMSO concentration kept below 0.5%), the cells were incubated at 37 degrees Celsius in 5% $CO_2$ for 72 hours. The effects on proliferation were determined by addition of MTS reagent (Promega) according to the manufacturer's instruction, followed by incubation for 2 hours at 37 degrees Celsius in 5% $CO_2$, and finally recording the absorbance at 490 nm using an ELISA plate reader.
WST Assay
Similar to MTS assay except that the developer is the CCK-8 reagent (Dojindo) and the plate reader is set to 450 nm absorbance.

The compounds of the instant invention described in the Examples and Tables above inhibited growth of cancer cell lines with 72 hour $GI_{50}$ values in the range of about 400 nanomolar to greater than 6 micromolar. $GI_{50}$ and $GI_{90}$ values against SGC-7901 gastric cancer cells and SMMC-7721 liver cancer cells for specific representative compounds can be found in Table 19.

TABLE 19

Table 19. Biological activity data for selected examples from the present invention.

| Example # | HD RP30 | p21 RP3 | SGC GI50 | SGC GI90 | SMMC GI50 | SMMC GI90 |
|---|---|---|---|---|---|---|
| 5-2  | 1.73 | 2.51 | 0.38 | 1.13 | 0.66 | 1.98 |
| 5-8  | 1.95 | 2.10 | 0.31 | 1.14 | 0.78 | 3.96 |
| 5-19 | 1.63 | 2.62 | 0.49 | 1.79 | 0.67 | 1.75 |
| 5-20 | 1.62 | 0.35 | 0.50 | 1.30 | 0.77 | 1.62 |
| 5-27 | 1.61 | 1.96 | 0.28 | 1.12 | 0.57 | 1.60 |
| 5-28 | 1.70 | 3.53 | 0.31 | 1.73 | 0.76 | 2.01 |
| 5-29 | 1.65 | 2.07 | 0.32 | 1.04 | 0.64 | 1.39 |
| 5-30 | 1.97 | 1.84 | 0.34 | 1.56 | 0.71 | 2.34 |
| 5    | 1.61 | 2.54 | 0.39 | 1.70 | 0.65 | 1.95 |

TABLE 19-continued

Table 19. Biological activity data for selected examples from the present invention.

| Example # | HD RP30 | p21 RP3 | SGC GI50 | SGC GI90 | SMMC GI50 | SMMC GI90 |
|---|---|---|---|---|---|---|
| 5-32  | 1.58 | 2.73 | 0.41 | 2.04 | 0.71 | 2.42 |
| 5-33  | 1.49 | 1.66 | 0.42 | 1.62 | 0.87 | 2.21 |
| 11-2  | 1.64 | 2.25 | 0.42 | 1.99 | 0.70 | 1.69 |
| 11-3  | 1.62 | 2.47 | 0.32 | 1.62 | 0.68 | 2.20 |
| 11-4  | 1.70 | 2.82 | 0.37 | 1.71 | 0.64 | 1.81 |
| 16-2  | 1.36 | 2.22 | 0.41 | 1.17 | 0.75 | 1.87 |
| 11-6  | 1.79 | 1.96 | 0.35 | 1.08 | 0.92 | 3.04 |
| 16-15 | 1.51 | 1.94 | 0.29 | 1.24 | 0.72 | 2.02 |
| 16-16 | 2.03 | 1.53 | 0.34 | 0.89 | 0.70 | 1.62 |
| 16-17 | 1.53 | 2.31 | 0.44 | 1.89 | 0.90 | 2.45 |
| 16-20 | 1.90 | 1.88 | 0.45 | 1.23 | 0.83 | 2.96 |
| 21-6  | 1.48 | 1.67 | 0.40 | 1.21 | 0.80 | 2.52 |
| 21    | 1.09 | 1.77 | 0.42 | 1.38 | 0.91 | 2.63 |
| 21-15 | 1.47 | 2.52 | 0.60 | 2.95 | 1.34 | 3.32 |
| 26    | 1.38 | 2.61 | 0.29 | 1.04 | 0.64 | 1.53 |
| 31-8  | 1.48 | 2.30 | 0.54 | 1.38 | 0.76 | 2.09 |
| 36    | 1.75 | 1.62 | 0.49 | 1.53 | 0.96 | 3.29 |
| 36-5  | 1.70 | 2.15 | 0.31 | 1.08 | 0.65 | 1.84 |
| 73-2  | 1.36 | 1.54 | 0.49 | 2.01 | 1.44 | 4.52 |
| 85-4  | 1.84 | 1.92 | 0.47 | 2.40 | 1.20 | 3.40 |

HDAC (RP30) is the relative inhibitory potency compared with SNDX-275 at 30 micromolar;
p21 (RP3) is the relative induction potency compared with SNDX-275 at 3 micromolar.
$GI_{50}$ and $GI_{90}$ values are in units of micromolar.

The invention claimed is:
1. A 3,4-trans-isomer of a compound of formula (I)

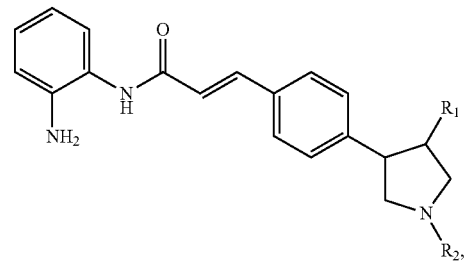

(I)

wherein
  $R^1$ —CO—NH—$R^3$, wherein $R^3$ is aryl or heteroaryl, unsubstituted or substituted once, twice or three times by halogen, lower alkyl, lower alkoxy, cyano, —$OCF_2H$, —$OCF_3$, trifluoromethyl, or cycloalkyl; and
  $R^2$ is lower alkyl, heterocyclyl, or heteroaryl, unsubstituted, or once, twice or three times substituted by halogen, phenyl, cyano, hydroxy, or lower alkoxy; or
a pharmaceutically acceptable salt, racemic mixture, enantiomer, or tautomeric form thereof.

2. A compound of formula (Ia)

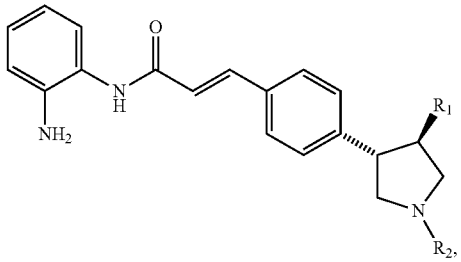

wherein
R¹ —CO—NH—R³, wherein R³ is aryl or heteroaryl, unsubstituted or substituted once, twice or three times by halogen, lower alkyl, lower alkoxy, cyano, —OCF₂H, —OCF₃, trifluoromethyl, or cycloalkyl; and
R² is lower alkyl, heterocyclyl, or heteroaryl, unsubstituted, or once, twice or three times substituted by halogen, phenyl, cyano, hydroxy, or lower alkoxy; or
a pharmaceutically acceptable salt, racemic mixture, enantiomer, or tautomeric form thereof.

3. A compound of formula (Ib)

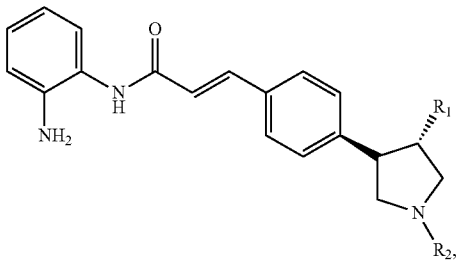

wherein
R¹ is —CO—NH—R³, wherein R³ is aryl or heteroaryl, unsubstituted or substituted once, twice or three times by halogen, lower alkyl, lower alkoxy, cyano, —OCF₂H, —OCF₃, trifluoromethyl, or cycloalkyl; and
R² is lower alkyl, heterocyclyl, or heteroaryl, unsubstituted, or once, twice or three times substituted by halogen, phenyl, cyano, hydroxy, or lower alkoxy; or
a pharmaceutically acceptable salt, racemic mixture, enantiomer, or tautomeric form thereof.

4. A compound of claim 1, wherein R³ is phenyl, unsubstituted or substituted once, twice or three times by halogen, lower alkyl, lower alkoxy, cyano, —OCF₂H, —OCF₃, trifluoromethyl, or cycloalkyl.

5. A compound of claim 1, wherein
R² is lower alkyl, unsubstituted or substituted by cyano, halogen, hydroxy; or is the group

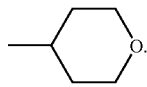

6. A compound of claim 1, selected from the group consisting of
rac-(trans-3,4)-4-{4-[(E)-2-(2-Amino-phenylcarbamoyl)-vinyl]-phenyl}-1-methyl-pyrrolidine-3-carboxylic acid (4-fluoro-3-methyl-phenyl)-amide;
rac-(trans-3,4)-4-{4-[(E)-2-(2-Amino-phenylcarbamoyl)-vinyl]-phenyl}-1-methyl-pyrrolidine-3-carboxylic acid m-tolylamide;
rac-(trans-3,4)-4-{4-[(E)-2-(2-Amino-phenylcarbamoyl)-vinyl]-phenyl}-1-methyl-pyrrolidine-3-carboxylic acid (4-chloro-3-methyl-phenyl)-amide; and
rac-(trans-3,4)-4-{4-[(E)-2-(2-Amino-phenylcarbamoyl)-vinyl]-phenyl}-1-methyl-pyrrolidine-3-carboxylic acid (3-chloro-4-fluoro-phenyl)-amide.

7. A compound of claim 1, selected from the group consisting of
rac-(trans-3,4)-4-{4-[(E)-2-(2-Amino-phenylcarbamoyl)-vinyl]-phenyl}-1-methyl-pyrrolidine-3-carboxylic acid (3-bromo-phenyl)-amide;
rac-(trans-3,4)-4-{4-[(E)-2-(2-Amino-phenylcarbamoyl)-vinyl]-phenyl}-1-methyl-pyrrolidine-3-carboxylic acid (4-fluoro-phenyl)-amide;
rac-(trans-3,4)-4-{4-[(E)-2-(2-Amino-phenylcarbamoyl)-vinyl]-phenyl}-1-methyl-pyrrolidine-3-carboxylic acid phenylamide;
rac-(trans-3,4)-4-{4-[(E)-2-(2-Amino-phenylcarbamoyl)-vinyl]-phenyl}-1-methyl-pyrrolidine-3-carboxylic acid (4-methoxy-phenyl)-amide;
rac-(trans-3,4)-4-{4-[(E)-2-(2-Amino-phenylcarbamoyl)-vinyl]-phenyl}-1-methyl-pyrrolidine-3-carboxylic acid p-tolylamide;
rac-(trans-3,4)-4-{4-[(E)-2-(2-Amino-phenylcarbamoyl)-vinyl]-phenyl}-1-methyl-pyrrolidine-3-carboxylic acid (4-bromo-phenyl)-amide;
rac-(trans-3,4)-4-{4-[(E)-2-(2-Amino-phenylcarbamoyl)-vinyl]-phenyl}-1-methyl-pyrrolidine-3-carboxylic acid (4-cyclopropyl-phenyl)-amide;
rac-(trans-3,4)-4-{4-[(E)-2-(2-Amino-phenylcarbamoyl)-vinyl]-phenyl}-1-methyl-pyrrolidine-3-carboxylic acid (4-difluoromethoxy-phenyl)-amide;
rac-(trans-3,4)-4-{4-[(E)-2-(2-Amino-phenylcarbamoyl)-vinyl]-phenyl}-1-methyl-pyrrolidine-3-carboxylic acid (3-methoxy-phenyl)-amide;
rac-(trans-3,4)-4-{4-[(E)-2-(2-Amino-phenylcarbamoyl)-vinyl]-phenyl}-1-methyl-pyrrolidine-3-carboxylic acid (3-bromo-4-fluoro-phenyl)-amide;
rac-(trans-3,4)-4-{4-[(E)-2-(2-Amino-phenylcarbamoyl)-vinyl]-phenyl}-1-methyl-pyrrolidine-3-carboxylic acid (2-fluoro-phenyl)-amide; and
rac-(trans-3,4)-4-{4-[(E)-2-(2-Amino-phenylcarbamoyl)-vinyl]-phenyl}-1-methyl-pyrrolidine-3-carboxylic acid (4-chloro-3-methoxy-phenyl)-amide.

8. A compound of claim 1, selected from the group consisting of
rac-(trans-3,4)-4-{4-[(E)-2-(2-Amino-phenylcarbamoyl)-vinyl]-phenyl}-1-methyl-pyrrolidine-3-carboxylic acid (2,4-difluoro-phenyl)-amide;
rac-(trans-3,4)-4-{4-[(E)-2-(2-Amino-phenylcarbamoyl)-vinyl]-phenyl}-1-methyl-pyrrolidine-3-carboxylic acid (3-cyano-phenyl)-amide;
rac-(trans-3,4)-4-{4-[(E)-2-(2-Amino-phenylcarbamoyl)-vinyl]-phenyl}-1-methyl-pyrrolidine-3-carboxylic acid (4-isopropyl-phenyl)-amide;
rac-(trans-3,4)-4-{4-[(E)-2-(2-Amino-phenylcarbamoyl)-vinyl]-phenyl}-1-methyl-pyrrolidine-3-carboxylic acid (3-chloro-4-methoxy-phenyl)-amide;
rac-(trans-3,4)-4-{4-[(E)-2-(2-Amino-phenylcarbamoyl)-vinyl]-phenyl}-1-methyl-pyrrolidine-3-carboxylic acid (3-fluoro-4-methoxy-phenyl)-amide;
(3R,4S)-4-{4-[(E)-2-(2-Amino-phenylcarbamoyl)-vinyl]-phenyl}-1-methyl-pyrrolidine-3-carboxylic acid (4-chloro-phenyl)-amide;
(3R,4S)-4-{4-[(E)-2-(2-Amino-phenylcarbamoyl)-vinyl]-phenyl}-1-methyl-pyrrolidine-3-carboxylic acid (4-fluoro-phenyl)-amide;

rac-(trans-3,4)-4-{4-[(E)-2-(2-Amino-phenylcarbamoyl)-vinyl]-phenyl}-1-cyanomethyl-pyrrolidine-3-carboxylic acid (4-chloro-phenyl)-amide;
rac-(trans-3,4)-4-{4-[(E)-2-(2-Amino-phenylcarbamoyl)-vinyl]-phenyl}-1-ethyl-pyrrolidine-3-carboxylic acid (4-chloro-phenyl)-amide;
rac-(trans-3,4)-4-{4-[(E)-2-(2-Amino-phenylcarbamoyl)-vinyl]-phenyl}-1-(2-fluoro-ethyl)-pyrrolidine-3-carboxylic acid (4-chloro-phenyl)-amide;
rac-(trans-3,4)-4-{4-[(E)-2-(2-Amino-phenylcarbamoyl)-vinyl]-phenyl}-1-(2-hydroxy-ethyl)-pyrrolidine-3-carboxylic acid (4-chloro-phenyl)-amide; and
rac-(trans-3,4)-4-{4-[(E)-2-(2-Amino-phenylcarbamoyl)-vinyl]-phenyl}-1-(2-fluoro-ethyl)-pyrrolidine-3-carboxylic acid (4-fluoro-phenyl)-amide.

9. A compound of claim 1, selected from the group consisting of
rac-(trans-3,4)-4-{4-[(E)-2-(2-Amino-phenylcarbamoyl)-vinyl]-phenyl}-1-(2-methoxy-ethyl)-pyrrolidine-3-carboxylic acid (4-chloro-phenyl)-amide;
rac-(trans-3,4)-4-{4-[(E)-2-(2-Amino-phenylcarbamoyl)-vinyl]-phenyl}-1-isopropyl-pyrrolidine-3-carboxylic acid (4-fluoro-phenyl)-amide;
rac-(trans-3,4)-4-{4-[(E)-2-(2-Amino-phenylcarbamoyl)-vinyl]-phenyl}-1-isopropyl-pyrrolidine-3-carboxylic acid (4-bromo-phenyl)-amide;
rac-(trans-3,4)-4-{4-[(E)-2-(2-Amino-phenylcarbamoyl)-vinyl]-phenyl}-1-isopropyl-pyrrolidine-3-carboxylic acid (4-chloro-phenyl)-amide;
rac-(trans-3,4)-4-{4-[(E)-2-(2-Amino-phenylcarbamoyl)-vinyl]-phenyl}-1-isopropyl-pyrrolidine-3-carboxylic acid (3-bromo-phenyl)-amide;
rac-(trans-3,4)-4-{4-[(E)-2-(2-Amino-phenylcarbamoyl)-vinyl]-phenyl}-1-tert-butyl-pyrrolidine-3-carboxylic acid (4-chloro-2-fluoro-phenyl)-amide;
rac-(trans-3,4)-4-{4-[(E)-2-(2-Amino-phenylcarbamoyl)-vinyl]-phenyl}-1-tert-butyl-pyrrolidine-3-carboxylic acid (4-bromo-phenyl)-amide;
rac-(trans-3,4)-4-{4-[(E)-2-(2-Amino-phenylcarbamoyl)-vinyl]-phenyl}-1-tert-butyl-pyrrolidine-3-carboxylic acid (4-difluoromethoxy-phenyl)-amide;
rac-(trans-3,4)-4-{4-[(E)-2-(2-Amino-phenylcarbamoyl)-vinyl]-phenyl}-1-tert-butyl-pyrrolidine-3-carboxylic acid (4-fluoro-phenyl)-amide;
rac-(trans-3,4)-4-{4-[(E)-2-(2-Amino-phenylcarbamoyl)-vinyl]-phenyl}-1-tert-butyl-pyrrolidine-3-carboxylic acid (4-chloro-phenyl)-amide;
rac-(trans-3,4)-4-{4-[(E)-2-(2-Amino-phenylcarbamoyl)-vinyl]-phenyl}-1-tert-butyl-pyrrolidine-3-carboxylic acid (4-cyano-phenyl)-amide; and
rac-(trans-3,4)-4-{4-[(E)-2-(2-Amino-phenylcarbamoyl)-vinyl]-phenyl}-1-(2-hydroxy-1,1-dimethyl-ethyl)-pyrrolidine-3-carboxylic acid (4-chloro-phenyl)-amide.

10. A compound of claim 1, selected from the group consisting of
(3R,4S)-4-{4-[(E)-2-(2-Amino-phenylcarbamoyl)-vinyl]-phenyl}-1-(2-hydroxy-1,1-dimethyl-ethyl)-pyrrolidine-3-carboxylic acid (4-chloro-phenyl)-amide;
rac-(trans-3,4)-4-{4-[(E)-2-(2-Amino-phenylcarbamoyl)-vinyl]-phenyl}-1-(2-hydroxy-1,1-dimethyl-ethyl)-pyrrolidine-3-carboxylic acid (4-difluoromethoxy-phenyl)-amide;
rac-(trans-3,4)-4-{4-[(E)-2-(2-Amino-phenylcarbamoyl)-vinyl]-phenyl}-1-(2-hydroxy-2-methyl-propyl)-pyrrolidine-3-carboxylic acid (4-chloro-phenyl)-amide;
rac-(trans-3,4)-4-{4-[(E)-2-(2-Amino-phenylcarbamoyl)-vinyl]-phenyl}-1-(2-hydroxy-2-methyl-propyl)-pyrrolidine-3-carboxylic acid (4-bromo-phenyl)-amide;
rac-(trans-3,4)-4-{4-[(E)-2-(2-Amino-phenylcarbamoyl)-vinyl]-phenyl}-1-(2-hydroxy-2-methyl-propyl)-pyrrolidine-3-carboxylic acid (4-difluoromethoxy-phenyl)-amide;
rac-(trans-3,4)-4-{4-[(E)-2-(2-Amino-phenylcarbamoyl)-vinyl]-phenyl}-1-(2-hydroxy-2-methyl-propyl)-pyrrolidine-3-carboxylic acid (4-chloro-phenyl)-amide;
rac-(trans-3,4)-4-{4-[(E)-2-(2-Amino-phenylcarbamoyl)-vinyl]-phenyl}-1-(tetrahydro-pyran-4-yl)-pyrrolidine-3-carboxylic acid (4-chloro-phenyl)-amide;
rac-(trans-3,4)-4-{4-[(E)-2-(2-Amino-phenylcarbamoyl)-vinyl]-phenyl}-1-(tetrahydro-pyran-4-yl)-pyrrolidine-3-carboxylic acid (4-bromo-phenyl)-amide;
rac-(trans-3,4)-4-{4-[(E)-2-(2-Amino-phenylcarbamoyl)-vinyl]-phenyl}-1-(tetrahydro-pyran-4-yl)-pyrrolidine-3-carboxylic acid (3-difluoromethoxy-phenyl)-amide;
rac-(trans-3,4)-4-{4-[(E)-2-(2-Amino-phenylcarbamoyl)-vinyl]-phenyl}-1-(tetrahydro-pyran-4-yl)-pyrrolidine-3-carboxylic acid (4-fluoro-phenyl)-amide; and
rac-(trans-3,4)-4-{4-[(E)-2-(2-Amino-phenylcarbamoyl)-vinyl]-phenyl}-1-(tetrahydro-pyran-4-yl)-pyrrolidine-3-carboxylic acid (4-difluoromethoxy-phenyl)-amide.

11. A compound of claim 3, selected from the group consisting of
(3S,4R)-4-{4-[(E)-2-(2-Amino-phenylcarbamoyl)-vinyl]-phenyl}-1-methyl-pyrrolidine-3-carboxylic acid (4-chloro-phenyl)-amide;
(3S,4R)-4-{4-[(E)-2-(2-Amino-phenylcarbamoyl)-vinyl]-phenyl}-1-methyl-pyrrolidine-3-carboxylic acid (4-fluoro-phenyl)-amide; and
(3S,4R)-4-{4-[(E)-2-(2-Amino-phenylcarbamoyl)-vinyl]-phenyl}-1-(2-hydroxy-1,1-dimethyl-ethyl)-pyrrolidine-3-carboxylic acid (4-chloro-phenyl)-amide.

12. A pharmaceutical composition comprising a therapeutically effective amount of a compound of claim 1.

* * * * *